(12) United States Patent
Young et al.

(10) Patent No.: US 9,944,654 B2
(45) Date of Patent: Apr. 17, 2018

(54) NARGENICIN COMPOUNDS AND USES THEREOF AS ANTIBACTERIAL AGENTS

(71) Applicant: Merck Sharp & Dohme Corp., Rahway, NJ (US)

(72) Inventors: Katherine Young, Metuchen, NJ (US); David B. Olsen, Landsdale, PA (US); Sheo B. Singh, Edison, NJ (US); Jing Su, Scotch Plains, NJ (US); Robert R. Wilkening, Maplewood, NJ (US); James M. Apgar, Highland, NJ (US); Dongfang Meng, Morganville, NJ (US); Dann Parker, Cranford, NJ (US); Mihir Mandal, Westfield, NJ (US); Lihu Yang, Edison, NJ (US); Ronald E. Painter, Piscataway, NJ (US); Qun Dang, Westfield, NJ (US); Takao Suzuki, Shanghai (CN)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 15/517,570

(22) PCT Filed: Oct. 21, 2015

(86) PCT No.: PCT/US2015/056627
§ 371 (c)(1),
(2) Date: Apr. 7, 2017

(87) PCT Pub. No.: WO2016/064982
PCT Pub. Date: Apr. 28, 2016

(65) Prior Publication Data
US 2017/0305924 A1    Oct. 26, 2017

(30) Foreign Application Priority Data

Oct. 22, 2014  (WO) ............... PCT/CN2014/089204

(51) Int. Cl.
| | |
|---|---|
| *C07D 493/08* | (2006.01) |
| *C07C 53/18* | (2006.01) |
| *C07C 309/06* | (2006.01) |
| *C07D 493/18* | (2006.01) |
| *C07F 7/18* | (2006.01) |

(52) U.S. Cl.
CPC ............ *C07D 493/08* (2013.01); *C07C 53/18* (2013.01); *C07C 309/06* (2013.01); *C07D 493/18* (2013.01); *C07F 7/1856* (2013.01)

(58) Field of Classification Search
CPC ..................................................... C07D 493/08
USPC ......................................................... 549/268
See application file for complete search history.

(56) References Cited

U.S. PATENT DOCUMENTS

| | | |
|---|---|---|
| 4,360,683 A | 11/1982 | Magerlein et al. |
| 4,448,970 A | 5/1984 | Magerlein |
| 4,605,624 A | 8/1986 | Celmer et al. |
| 2015/0148386 A1 | 5/2015 | Jang et al. |

FOREIGN PATENT DOCUMENTS

| | | |
|---|---|---|
| WO | WO2004014897 A1 | 2/2004 |
| WO | WO2004048350 A2 | 6/2004 |
| WO | WO2004048370 A1 | 6/2004 |
| WO | WO2005012270 A2 | 2/2005 |
| WO | WO2005058886 A1 | 6/2005 |
| WO | WO2005116023 A1 | 12/2005 |
| WO | WO2007133803 A2 | 11/2007 |
| WO | WO2008069619 A1 | 6/2008 |
| WO | WO2011139832 A2 | 11/2011 |
| WO | WO2016061772 A1 | 4/2016 |
| WO | WO2016064982 A1 | 4/2016 |

OTHER PUBLICATIONS

Celmer et al., Structure of Natural Antibiotic CP-47,444, Journal of the American Chemical Society, 1980, 4203-4209, 102:12.
Snyder et al., Biosynthesis of nargenicin and nodusmicin, Journal of the American Chemical Society, 1984, 787-789, 106(3).
Whaley et al., Nodusmicin: the structure of a new antibiotic, Tetrahedron Letters, 1980, 3659-3662, 21(38).

*Primary Examiner* — Taofiq A Solola
(74) *Attorney, Agent, or Firm* — Janet E. Fair; Catherine D. Fitch

(57) ABSTRACT

The present invention relates to novel nargenicin related compounds which can inhibit DnaE and have antibacterial, particularly antimycobacterial activity against *Mycobacterium tuberculosis*. The present invention also relates to method for inhibiting growth of mycobacterial cells as well as a method of treating mycobacterial infections by *Mycobacterium tuberculosis* by administering an antimycobacterially effective amount of nargenicin or a nargenicin-related compound and/or their pharmaceutically acceptable salts.

15 Claims, No Drawings

NARGENICIN COMPOUNDS AND USES THEREOF AS ANTIBACTERIAL AGENTS

CROSS-REFERENCE TO RELATED APPLICATIONS

This application is a U.S. National Phase application under 35 U.S.C. § 371 of PCT Application No. PCT/US15/056627, filed Oct. 21, 2015, which published as WO2016/064982 A1 on Apr. 28, 2016, and claims priority under 35 U.S.C. § 365(b) from PCT Application No. PCT/CN2014/089204, filed Oct. 22, 2014.

FIELD OF THE INVENTION

The present invention relates to novel nargenicin compounds useful for the treatment of bacterial infections, particularly mycobacterial infections. The invention also relates to methods of use of nargenicin compounds for the treatment of mycobacterial infections such as those caused by *Mycobacteria tuberculosis*.

BACKGROUND OF THE INVENTION

The nargenicins are a class of polyketide macrolide antibiotics with a tricyclic lactone containing a unique ether bridge. See Kallmerten, 1995, *Studies in Natural Products Chemistry* 17:283-310. The first nargenicin, nargenicin $A_1$, was originally isolated from *Nocardia argentinesis*. See Celmer et al., 1980, *J. Am. Chem. Soc.* 102:4203-4209. Nargenicin has been demonstrated to be effective towards gram-positive bacteria and, in particular, has been shown to have strong antibacterial activity against methicillin-resistant *Staphylococcus aureus*. See Sohng et al., 2008, *Arch Pharm Res* 31: 1339-1345 and Korean Patent Application No. KR2009093733A. It has also been contemplated for use as a treatment for neoplastic diseases and neurodegenerative diseases. See, e.g., Kim et al., 2009, *Biochem Pharmacol* 77:1694-1701, and Korean Patent Application No. KR2010071835A.

Other nargenicins, included, nargenicin $B_1$, nargenicin $B_2$, nargenicin $B_3$, and nargenicin $C_1$, are described in Magerlein et al., 1982, *J. Antibiotics* 35:254 and U.S. Pat. Nos. 4,436,747; 4,448,970; and 4,605,624.

Mycobacterium is a genus of bacterium, neither truly gram-positive nor truly gram-negative, including pathogens responsible for tuberculosis (*M. tuberculosis*) and leprosy (*M leprae*). Tuberculosis (TB), in particular, despite the availability of anti-TB drugs such as isoniazide and rifampin, is considered to be one of the world's deadliest diseases. According to World Health Organization, in 2012, there were 8.6 million new TB cases and 1.3 million TB deaths. See, Global tuberculosis report 2013 published by the World Health Organization. Complicating the TB epidemic is the rising tide of multi-drug-resistant strains, and the deadly association with HIV. People who are HIV-positive and infected with TB are 30 times more likely to develop active TB than people who are HIV-negative and TB is responsible for the death of one out of every three people with HIV/AIDS worldwide. See, e.g., Kaufmann et al., 1993, *Trends Microbiol.* 1:2-5 and Bloom et al., 1998, *N. Engl. J. Med.* 338:677-678.

Mycobacteria other than *M. tuberculosis* are increasingly found in opportunistic infections that plague the AIDS patient. Organisms from the *M avium-intracellulare* complex (MAC), especially serotypes four and eight, account for 68% of the mycobacterial isolates from AIDS patients. Enormous numbers of MAC are found (up to 1010 acid-fast bacilli per gram of tissue), and consequently, the prognosis for the infected AIDS patient is poor.

SUMMARY OF THE INVENTION

The present invention is directed to certain novel nargenicin compounds which are DnaE inhibitors and/or have antibacterial activity. The compounds, and their pharmaceutically acceptable salts, can be useful, for example, for the treatment of bacterial infections, for example, mycobacterial infections. More particularly, the present invention includes compounds of Formula I, or a pharmaceutically acceptable salt thereof:

(I)

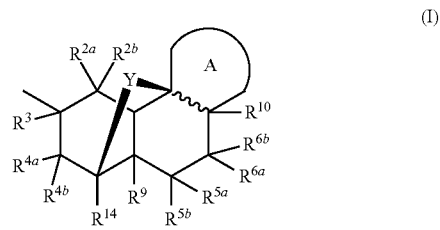

wherein

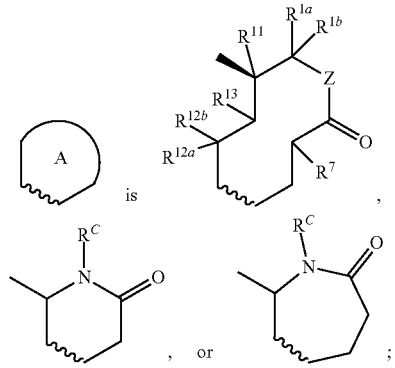

Y is O, $-NR^B$, S or $-SO_2$;
Z is O or $-NR^O$;
$R^O$ is H, $C_{1-6}$alkyl, $C_{3-6}$cycloalkyl, AryA, or HetA;
$R^{1a}$ is H, $C_{1-6}$alkyl, $C_{2-6}$alkenyl, $C_{3-6}$cycloalkyl, $-C(O)C_{1-6}$alkyl, AryA, or HetA,
  wherein the $R^{1a}$ alkyl is optionally substituted with halogen, $-NR^BR^C$; $=NOH$; $-OR^A$; -isoindoline-1,3-dione; or 1H-indene-1,3(2H)-dione;
$R^{1b}$ is H, $C_{1-6}$alkyl, or $C_{2-6}$alkenyl;
$R^A$ is H, $C_{1-6}$ alkyl, $C_{2-6}$ alkenyl, $C_{3-6}$ cycloalkyl, $-C(=O)C_{1-6}$alkyl, $-C(=O)C_{2-6}$alkenyl, $-C(=O)NHR^g$, $-C(=O)OR^g$, $-C(=O)C(=O)NHR^g$, $-C(=O)C(=O)OR^g$, AryA, HetA, $-C(=O)$-AryA, $-C(=O)$-HetA, $-C(=O)C(=O)$-HetA, $-SO_2OH$, or tert-butyl dimethylsilyl (TBDMS),
wherein
  any $R^A$ alkyl is optionally substituted with 1 or 2 substituents independently selected from halogen, $-NR^xR^y$, $-N^rR^xR^yR^z$, $-SCH_3$, AryA, and HetA; and
  any $R^A$ alkenyl is optionally substituted with AryA;
$R^g$ is H, $C_{1-8}$ alkyl, $C_{3-6}$ cycloalkyl, $-C(=O)CCl_3$, $-NR^xR^y$, $-NHC(=O)NR^xR^y$, $-NHC(=O)OCH_3$, AryA or —CH(CH$_2$-AryA)C(=O)NHCH(CH$_2$CH$_2$CH$_2$NHC(=NH)NH$_2$)C(=O)NH-AryA,
wherein the R$^g$ alkyl or R$^g$ cycloalkyl is optionally substituted by 1 to 3 —NR$^x$R$^y$, —N$^r$R$^x$R$^y$R$^z$, —N$^r$R$^x$R$^v$R$^w$ or —OH substituents or 1 substituent selected from C$_{1-6}$ alkoxy, —COOH, —C(=O)NR$^x$R$^y$, —SCH$_3$, —NR$^v$R$^w$, —S(O)$_2$NR$^x$R$^y$, AryA, and HetA;

R$^x$, R$^y$ and R$^z$ are independently H or C$_{1-6}$alkyl;

R$^v$ and R$^w$ are C$_{1-6}$alkyl substituted with 1 to 3 —OH substituents;

R$^B$ is H, C$_{1-6}$ alkyl, C$_{2-6}$ alkenyl, —(CH$_2$)$_{0-3}$C$_{3-6}$cycloalkyl, —C(=O)R$^b$, —C(=O)NHR$^b$, —C(=O)OR$^b$, C$_{1-6}$ alkoxy, —S(=O)$_2$R$^b$, —(CH$_2$)$_{0-3}$AryA, or —(CH$_2$)$_{0-3}$HetA;
wherein the R$^B$ alkyl is optionally substituted with —NR$^x$R$^y$ or —OH;

R$^C$ is H, C$_{1-6}$ alkyl, or C$_{3-6}$ cycloalkyl;

R$^b$ is C$_{1-6}$ alkyl, C$_{3-6}$ cycloalkyl, AryA, or HetA;

R$^{2a}$ is halogen, —NR$^B$R$^C$ or —OR$^{21}$;

R$^{2b}$ is H; or

R$^{2a}$ and R$^{2b}$ together form =O, or a 3- to 6-membered ring with 0, 1, or 2 heteroatom ring atoms selected from N, O and S;

R$^{21}$ is H, —C(=O)CH$_3$, —C(=O)NR$^x$R$^y$, —C(=O)NHCH$_2$CH$_2$N(CH$_3$)$_2$, —C(=O)NHC(=O)CCl$_3$, —C(=O)NH—C$_{3-6}$cycloalkyl, —C(=O)C(=O)OCH$_2$CH$_2$-HetA, or —C(=O)NHS(O)$_2$-AryA;

R$^3$ is H;

R$^{4a}$ is H, C$_{1-6}$hydroxyalkyl, C$_{2-6}$ alkenyl, —CH$_2$NO$_2$, cyano, —NR$^x$R$^y$, —NR$^x$(CH$_2$)$_{1-3}$AryA, —NR$^x$(CH$_2$)$_{1-3}$HetA, —NR$^x$(CH$_2$)$_{1-3}$NR$^x$R$^y$, —NR$^x$(CH$_2$)$_{1-3}$NR$^y$HetA, —NHC$_{1-6}$ alkyl, —NH-AryA, —NH-HetA, —NHC$_{1-6}$alkyl-R$^z$, —NHC(=O)C$_{1-6}$alkyl, —OH, —O—C$_{1-6}$alkyl, —O-AryA, —O-HetA, —OCH$_2$-HetA, —OCH$_2$-AryA, —OC(=O)CH$_3$, —OC(=O)NH$_2$, —OC(=O)-AryA, —OC(=O)-HetA, —SO$_2$OH, AryA, or HetA;

R$^{4b}$ is H; or

R$^3$ and R$^{4a}$ together form a bond; or

R$^{4a}$ and R$^{4b}$ together form =O;

R$^z$ is NR$^x$R$^y$, —NH—C$_{3-6}$cycloalkyl, disulfanylC$_{1-6}$alkylamine, AryA, or HetA; or R$^{5a}$ is H, —C$_{1-6}$ alkyl, OH, or AryA;

R$^{5b}$ is H; or

R$^{5a}$ and R$^{5b}$ together form =O or =C;

R$^{6a}$ is H, —C$_{1-6}$ alkyl, OH, or AryA;

R$^{6b}$ is H; or

R$^{6a}$ and R$^{6b}$ together form =O or =C; or

R$^{5a}$ and R$^{6a}$ together form a bond or together with the atoms to which they are attached form an oxirane; a cyclopropyl ring optionally substituted with one or two substituents independently selected from F, Cl, and C(=O)OC$_{1-6}$alkyl; a cyclopentyl ring optionally substituted with —OR$^D$; an oxetanyl ring; a pyrrolidinyl ring, wherein the pyrrolidinyl ring is substituted with R$^B$; or an isoxazolidinyl ring, wherein the isoxazolidinyl ring is substituted with R$^b$;

R$^D$ is H, C$_{1-6}$ alkyl, C(=O)R$^b$, or C(=O)NHR$^b$;

R$^7$ is —OR$^8$ or NR$^B$R$^C$;

R$^8$ is H or C$_{1-6}$alkyl;

R$^9$, R$^{10}$ and R$^{11}$ are independently H, CH$_3$, or —OH;

R$^{12a}$ is CH$_3$ or CH$_2$OH;

R$^{12b}$ and R$^{13}$ are H, or together form a bond, or together with the atoms to which they are connected form a cyclopropyl ring;

R$^{14}$ is H or C$_{1-6}$ alkyl;

AryA is
1) a 4- to 6-membered monocyclic aromatic ring with 0, 1, 2, 3 or 4 ring atoms independently selected from N, N as a quaternary salt, O and S, optionally substituted with 1 to 3 substituents independently selected from halogen, C$_1$-C$_6$ alkyl, C$_1$-C$_6$haloalkyl, C$_1$-C$_6$hydroxyalkyl, C$_1$-C$_6$ aminoalkyl, C$_1$-C$_6$ alkoxy, cyano, —(CH$_2$)$_{0-3}$NR$^x$R$^y$, (CH$_2$)$_{0-3}$N$^r$R$^x$R$^y$R$^z$, —OH, CH=CHC(=O)OC$_{1-6}$alkyl, —C(=O)R$^b$, (CH$_2$)$_{0-1}$C(=O)NH$_2$, —C(=O)NHR$^b$, —C(=O)OH, —C(=O)OR$^b$, —NHC(=O)C$_{1-6}$alkyl, —NHC(=O)-AryB, —NO$_2$, —OC(=O)C$_{1-6}$alkyl, =O, —S(=O)$_2$R$^b$, —(CH$_2$)$_{0-3}$AryB, and (CH$_2$)$_{0-3}$HetB; or
2) a 7- to 11-membered bicyclic aromatic ring with 0, 1, 2 or 3 N, or N as a quaternary salt, ring atoms optionally substituted with 1 to 3 substituents independently selected from halogen, C$_1$-C$_6$ alkyl, C$_1$-C$_6$ haloalkyl, C$_1$-C$_6$ hydroxyalkyl, C$_1$-C$_6$ aminoalkyl, C$_1$-C$_6$ alkoxy, cyano, —(CH$_2$)$_{0-3}$NR$^x$R$^y$, —(CH$_2$)$_{0-3}$N$^r$R$^x$R$^y$R$^z$, —OH, —CH=CHC(=O)OC$_{1-6}$alkyl, —C(=O)R$^b$, —(CH$_2$)$_{0-1}$C(=O)NH$_2$, —C(=O)NHR$^b$, —C(=O)OH, —C(=O)OR$^b$, —NHC(=O)C$_{1-6}$alkyl, —NHC(=O)-AryB, —NO$_2$, —OC(=O)C$_{1-6}$alkyl, =O, —S(=O)$_2$R$^b$, —(CH$_2$)$_{0-3}$AryB, and —(CH$_2$)$_{0-3}$HetB;

HetA is
1) a 4- to 6-membered saturated or monounsaturated monocyclic ring with 1 or 2 heteroatom ring atoms independently selected from N, N as a quaternary salt, O and S, optionally substituted with 1 or 2 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, cyano, —(CH$_2$)$_{0-3}$NR$^x$R$^y$, —(CH$_2$)$_{0-3}$N$^r$R$^x$R$^y$R$^z$, —OH, —(CH$_2$)$_{0-1}$C(O)NH$_2$, —(CH$_2$)$_{0-1}$C(=O)NHR$^b$, —(CH$_2$)$_{0-1}$C(=O)NH(CH$_2$)$_2$NHC(=O)OCH$_2$-AryB, —(CH$_2$)$_3$N$_3$, —C(=O)R$^b$, —C(=O)OR$^b$, —S(=O)$_2$R$^b$, (CH$_2$)$_{0-3}$AryB, and —(CH$_2$)$_{0-3}$HetB; or
2) a 7- to 11-membered saturated or monounsaturated bicyclic ring with 1, 2, or 3 heteroatom ring atoms independently selected from N, N as a quaternary salt, O and S, optionally substituted with 1 or 2 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, cyano, —(CH$_2$)$_{0-3}$NR$^x$R$^y$, —(CH$_2$)$_{0-3}$N$^r$R$^x$R$^y$R$^z$, —OH, —(CH$_2$)$_{0-1}$C(=O)NH$_2$, —(CH$_2$)$_{0-1}$C(=O)NHR$^b$, —(CH$_2$)$_{0-1}$C(=O)NH(CH$_2$)$_2$NHC(=O)OCH$_2$-AryB, —(CH$_2$)$_3$N$_3$, —C(=O)R$^b$, —C(=O)OR$^b$, —S(=O)$_2$R$^b$, —(CH$_2$)$_{0-3}$AryB, and —(CH$_2$)$_{0-3}$HetB;

AryB is
1) a 4- to 6-membered monocyclic aromatic ring with 0, 1, 2, or 3 ring atoms independently selected from N, N as a quaternary salt, O and S, optionally substituted with 1 to 3 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, cyano, —NH$_2$, —OH, —(CH$_2$)$_{0-3}$C(=O)NR$^x$R$^y$, —(CH$_2$)$_{1-3}$SO$_2$NR$^x$R$^y$, —CH=CHC(=O)OC$_{1-6}$alkyl, —NHC(=O)C$_{1-6}$alkyl, —NO$_2$, —N$^r$(O)OH, —OC(=O)C$_{1-6}$alkyl, and —C(=O)OC$_{1-6}$alkyl; or
2) a 7- to 11-membered bicyclic aromatic ring with 1, 2 or 3 N, or N as a quaternary salt, ring atoms optionally substituted with 1 to 3 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, cyano, NH$_2$, —OH, —(CH$_2$)$_{0-3}$C(=O)NR$^x$R$^y$, (CH$_2$)$_{1-3}$SO$_2$NR$^x$R$^y$, —CH=CHC(=O)OC$_{1-6}$alkyl, NHC(=O)C$_{1-6}$alkyl, NO$_2$, —OC(=O)C$_{1-6}$alkyl, and C(=O)OC$_{1-6}$alkyl;

HetB is
1) a 4- to 6-membered saturated or monounsaturated monocyclic ring with 1 or 2 heteroatom ring atoms independently selected from N, N as a quaternary salt, O and S, optionally substituted with 1 or 2 substituents independently selected from halogen, $C_1$-$C_6$ alkyl, $C_1$-$C_6$ hydroxyalkyl, $C_1$-$C_6$ aminoalkyl, $C_1$-$C_6$ alkoxy, —$(CH_2)_{0-3}$C(=O)$NR^xR^y$, cyano, —$NH_2$, —OH, and —$(CH_2)_{0-3}$HetC; or
2) a 7- to 11-membered saturated or monounsaturated bicyclic ring with 1, 2, or 3 heteroatom ring atoms independently selected from N, N as a quaternary salt, O and S, optionally substituted with 1 or 2 substituents independently selected from halogen, $C_1$-$C_6$ alkyl, $C_1$-$C_6$ hydroxyalkyl, $C_1$-$C_6$ aminoalkyl, $C_1$-$C_6$ alkoxy, —$(CH_2)_{0-3}$—C(=O)$NR^xR^y$, cyano, —$NH_2$, —OH, and —$(CH_2)_{0-3}$HetC;

HetC is
1) a 4- to 6-membered saturated or monounsaturated monocyclic ring with 1 or 2 heteroatom ring atoms independently selected from N, N as a quaternary salt, O and S; or
2) a 7- to 11-membered saturated or monounsaturated bicyclic ring with 1, 2, or 3 heteroatom ring atoms independently selected from N, N as a quaternary salt, O and S;

with the proviso
that the compound is not nodusmicin, and
that when

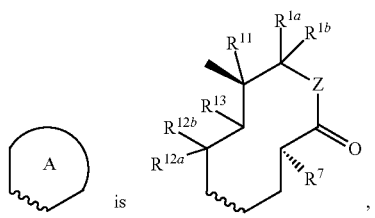
is

Y and Z are O;
$R^{1b}$, $R^{2b}$, $R^9$, $R^{10}$, $R^{11}$ and $R^{14}$ are H;
$R^{2a}$ is —OH;
$R^{4a}$ is —OC(=O)-pyrrolyl;
$R^{5a}$ and $R^{6a}$ together form a bond;
$R^{12b}$ and $R^{13}$ together form a bond;
$R^7$ is —OH or —$OCH_3$;
$R^{12a}$ is —$CH_3$;
then $R^{1a}$ is not ethyl optionally substituted with: —OH; $C_{1-6}$alkoxy; hydroxyl and methoxy; amine or amine substituted with $C_{1-3}$ alkyl; or =NOH.

The present invention also relates to a pharmaceutical composition for treating a bacterial infection in a subject, particularly an *M tuberculosis* infection, comprising a compound of the invention and a pharmaceutically acceptable carrier, diluent or excipient.

The present invention is also directed to 1) methods of treating tuberculosis in a subject in need of treatment thereof, comprising administering to the subject an effective amount of a nargenicin compound; and 2) uses of a nargenicin compound for the treatment of tuberculosis.

Embodiments, sub-embodiments, aspects and features of the present invention are either further described in or will be apparent from the ensuing description, examples and appended claims.

DETAILED DESCRIPTION OF THE INVENTION

The present invention is based, in part, on the surprising result that nargenicin, previously known to be narrowly active against gram-positive bacteria, is cidal against mycobacteria and, therefore, potentially useful in treating tuberculosis. Nargenicins were originally developed for use in treating gram-positive bacterial infections, particularly, methicillin-resistant *S. aureus* infections. Nargenicins have also been reported to have potential activity for neoplastic diseases and neurogenerative diseases. The target for nargenicins appears to be DnaE, a homolog of the *E. coli* holoenzyme alpha subunit. As shown in the Examples, in vitro MIC testing of nargenicin compounds against a variety of aerobic bacteria revealed excellent potency.

In one aspect, the present invention includes compounds of Formula I, wherein the compounds are suitable for use for the treatment of bacterial infections, particularly mycobacterial infections. In this aspect, a compound of the invention does not include any of the compounds disclosed in Megerlein et al., 1982, *J. Antibiotics* 35:254-255; Kallmerten, 1995, *Studies in Natural Products Chemistry* 17:283-310; and U.S. Pat. Nos. 4,148,883; 4,448,970; and 4,605,624 including, but not limited to, Nargenicin $A_1$ (see Example 145), 18-deoxynargenicin $A_1$, 18-deoxy-18-oxonargenicin $A_1$, 18-chloro-18-deoxynargenicin $A_1$, 18-azido-18-deoxynargenicin $A_1$, 18-O-thiocarbonyl-1'-imidazolenargenicin $A_1$, Nargenicin $B_1$, Nargenicin $B_2$, Nargenicin $B_3$, Nargenicin $C_1$, and nodusmicin. Representative structures include:

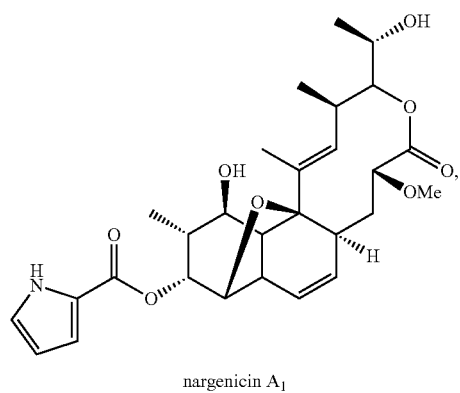

nargenicin $A_1$

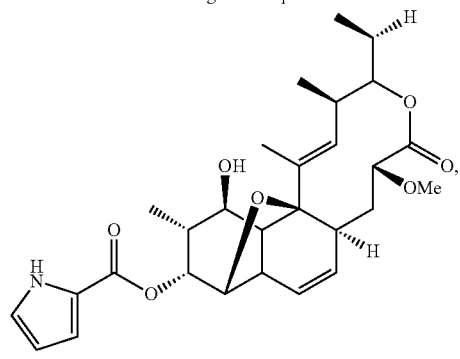

18-deoxynargenicin $A_1$

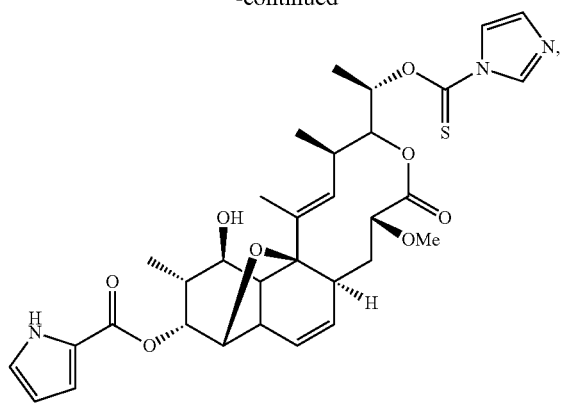

18-O-thiocarbonyl-1′-imidazolenargenicin A1

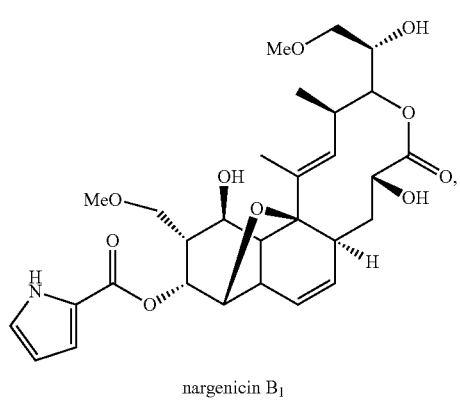

nargenicin B₁

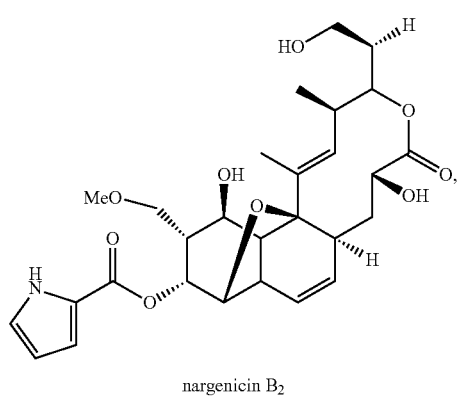

nargenicin B₂

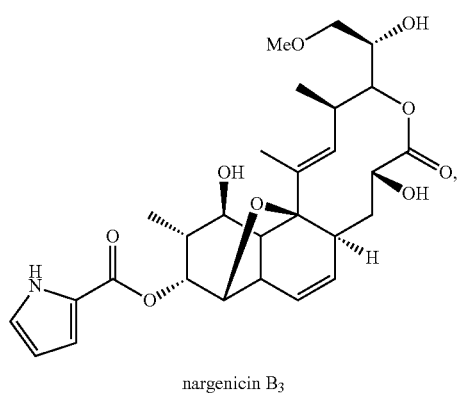

nargenicin B₃

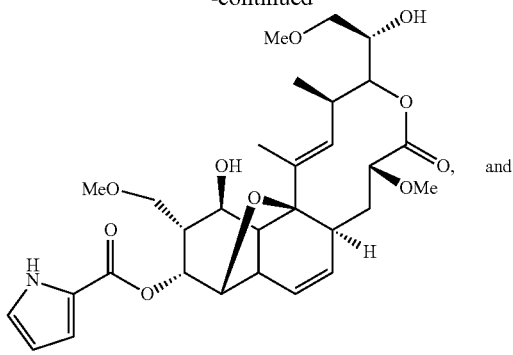

nargenicin C₁

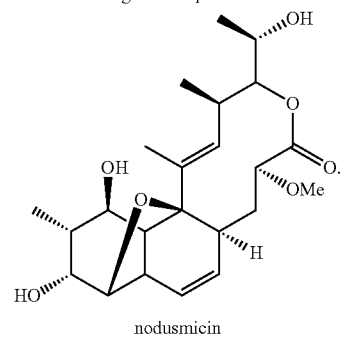

nodusmicin

However, as will be described in greater detail below, such compounds are nargenicin compounds which can be used in the methods of the invention.

In a first embodiment of the invention, the compound is a compound of formula I, or a pharmaceutically acceptable salt thereof, wherein Y is O, and the other groups are as provided in the general formula for formula I.

In a second embodiment of the invention, the compound has the formula

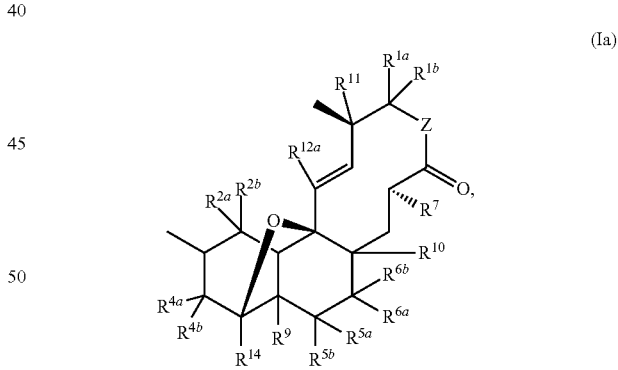

(Ia)

or a pharmaceutically acceptable salt thereof, wherein Z is O or NH and the other groups are as provided in the general formula I above or as in the first embodiment.

In a third embodiment of the invention, the compound is a compound of formula I or Ia, or a pharmaceutically acceptable salt thereof, wherein $R^{1a}$ is H; $C_{1-6}$ alkyl, $C_{2-6}$ alkenyl, —CH(CH₃)NH-cyclopropyl, —CH(CH₃)=NOH, —CH(CH₃)OR$^d$, —CH(CH₃)-1H-indene-1,3(2H)-dione, —CH(CH₃)-isoindoline-1,3-dione, —C(=O)C$_{1-6}$alkyl, or AryA;

$R^{1b}$ is H;

$R^4$ is H, $C_{1-6}$alkyl, —C(=O)C$_{1-6}$alkyl, —C(=O)NHR$^g$, —C(=O)OR$^g$, —C(=O)C(=O)NHR$^g$, —C(=O)C (=O)OR$^g$, —C(=O)-AryA, —C(=O)-HetA, —C(=O)C(=O)-HetA, —SO$_2$OH, or tert-butyl dimethylsilyl;
wherein the R$^4$ alkyl is optionally substituted with one or two substituents independently selected from halogen, —SCH$_3$, AryA, and HetA; and R$^g$ is H, —C$_{1-8}$ alkyl, C$_{3-6}$ cycloalkyl, —C(=O)CCl$_3$, NR$^x$R$^y$, —NHC(=O)NR$^x$R$^y$, —NHC(=O)OCH$_3$, AryA or —CH(CH$_2$-AryA)C(=O)NHCH(CH$_2$CH$_2$CH$_2$NHC=NHNH$_2$)C(=O)NH-AryA, wherein the R$^g$ alkyl is optionally substituted by 1 to 3 —NR$^x$R$^y$, —N$^t$R$^x$R$^y$R$^z$, N$^t$R$^x$R$^y$R$^w$ or —OH substituents or 1 substituent selected from C$_{1-6}$ alkoxy, —COOH, —C(=O)NR$^x$R$^y$, —SCH$_3$, —NR'R$^w$, AryA, and HetA, and the other groups are as provided in the general formula I above, or as in the first or second embodiment.

In a fourth embodiment of the invention, the compound is a compound of formula Ib, or a pharmaceutically acceptable salt thereof, (Ib)

wherein
R$^{2a}$ is halogen or —OR$^{2'}$;
R$^{2b}$ is H; or
R$^{2a}$ and R$^{2b}$ together form =O;
R$^{2'}$ is H, —C(=O)CH$_3$, C(=O)NR$^x$R$^y$, —C(=O)NHCH$_2$CH$_2$N(CH$_3$)$_2$, —C(=O)NHC(=O)CCl$_3$, —C(=O)NHC$_{3-6}$cycloalkyl, —C(=O)C(=O)OCH$_2$CH$_2$-HetA, or —C(=O)NHS(O)$_2$AryA;
R$^{5a}$ is H or OH;
R$^{5b}$ is H; or
R$^{5a}$ and R$^{5b}$ together form =O or =C;
R$^{6a}$ is H or OH;
R$^{6b}$ is H; or
R$^{6a}$ and R$^{6b}$ together form =O or =C; or
R$^{5a}$ and R$^{6a}$ together form a bond or together with the atoms to which they are attached form an oxirane;
R$^7$ is —OR$^8$;
R$^8$ is H or C$_{1-6}$alkyl;
AryA is
1) a 5- to 6-membered monocyclic aromatic ring with 0, 1, or 2 ring atoms independently selected from N, N as a quaternary salt, O and S, or 4 N ring atoms, optionally substituted with 1 to 3 substituents independently selected from halogen, C$_1$-C$_6$ alkyl, C$_1$-C$_6$ haloalkyl, cyano, —(CH$_2$)$_{0-3}$NR$^x$R$^y$, —OH, —CH=CHC(=O)OC$_{1-6}$alkyl, C(=O)C$_{1-6}$alkyl, —C(=O)NH$_2$, —C(=O)OH, —NHC(=O)C$_{1-6}$alkyl, —NHC(=O)AryB, —OC(=O)C$_{1-6}$alkyl, =O, —(CH$_2$)$_{0-1}$AryB, and —CH$_2$HetB; or
2) a 10-membered bicyclic aromatic ring with 0 N ring atoms;

HetA is
1) a 5- to 6-membered saturated or monounsaturated monocyclic ring with 1 or 2 heteroatom ring atoms independently selected from N, N as a quaternary salt, and O, optionally substituted with 1 substituent selected from C$_1$-C$_6$ alkyl, —OH, and =O; or
2) a 8-membered saturated bicyclic ring with 2 N, or N as a quaternary salt, ring atoms, optionally substituted with 1 substituent selected from C$_1$-C$_6$ alkyl, —CH$_2$C(=O)NH$_2$, —(CH$_2$)C(=O)NH(CH$_2$)$_2$NHC(=O)OCH$_2$AryB, —(CH$_2$)$_3$N$_3$, and —(CH$_2$)$_3$HetB;

AryB is
a 5- to 6-membered monocyclic aromatic ring with 0 or 1 ring atoms selected from N, N as a quaternary salt, and S, optionally substituted with 1 substituent selected from C$_1$-C$_6$ alkyl, —C(=O)NH$_2$, —NO$_2$, —N$^t$—(O)OH, —OC(=O)C$_{1-6}$alkyl, and —C(=O)OC$_{1-6}$alkyl;

HetB is
a 8-membered saturated bicyclic ring with 2 N, or N as a quaternary salt, ring atoms, optionally substituted with 1 substituent selected from C$_1$-C$_6$ alkyl, —CH$_2$C(=O)NH$_2$, and —(CH$_2$)$_3$HetC; and HetC is
a 8-membered saturated bicyclic ring with 2 N, or N as a quaternary salt, ring atoms, and the other groups are as provided in the general formula I above, or as in any of the first through third embodiments.

In a fifth embodiment of the invention, the compound is a compound of formula I, Ia, or Ib, or a pharmaceutically acceptable salt thereof, wherein AryA is
1) a monocyclic ring selected from furanyl, imidazolyl, pyrazolyl, pyrrolyl, phenyl, pyridinyl, tetrazolyl, thiazolyl, or thiophenyl, wherein any N ring atom in the monocyclic ring is optionally in the form of a quaternary salt, and wherein the monocyclic ring is optionally substituted with 1 to 3 substituents independently selected from halogen, C$_1$-C$_6$ alkyl, C$_1$-C$_6$ haloalkyl, cyano, —(CH$_2$)$_{0-1}$—NR$^x$R$^y$, —OH, —CH=CHC(=O)OC$_{1-6}$alkyl, —C(=O)C$_{1-6}$alkyl, —C(=O)NH$_2$, —C(=O)OH, —NHC(=O)C$_{1-6}$alkyl, —NHC(=O)AryB, —OC(=O)C$_{1-6}$alkyl, =O, —(CH$_2$)$_{0-1}$AryB, and —CH$_2$HetB; or
2) naphthalenyl;

HetA is
1) a monocyclic ring selected from morpholinyl, piperazinyl, piperidinyl, pyrrolidinyl, wherein the monocyclic ring is optionally substituted with 1 substituent selected from C$_1$-C$_6$ alkyl, —OH, and =O; or
2) 1,4-diazabicyclo[2.2.2]octane, optionally substituted with 1 substituent selected from C$_1$-C$_6$ alkyl, —CH$_2$C(=O)NH$_2$, —(CH$_2$)C(=O)NH(CH$_2$)$_2$NHC(=O)OCH$_2$-AryB, —(CH$_2$)$_3$N$_3$, and —(CH$_2$)$_3$HetB;

AryB is a monocyclic ring selected from phenyl, pyridinyl, pyrrolyl, thiophenyl, wherein any N ring atom in the monocyclic ring is optionally in the form of a quaternary salt, and wherein the monocyclic ring is optionally substituted with 1 substituent selected from C$_1$-C$_6$ alkyl, —C(=O)NH$_2$, —NO$_2$, —N(O)OH, and —C(=O)OC$_{1-6}$alkyl;

HetB is 1,4-diazabicyclo[2.2.2]octane, optionally substituted with 1 substituent selected from C$_1$-C$_6$ alkyl, —CH$_2$C(=O)NH$_2$, and —(CH$_2$)$_3$HetC; and HetC is 1,4-diazabicyclo[2.2.2]octane;

and the other groups are as provided in the general formula I above, or as in any of the first through fourth embodiments.
In a sixth embodiment of the invention, the compound is a compound of formula I, Ia, or Ib, or a pharmaceutically acceptable salt thereof, wherein
$R^{4a}$ is H, —NH$_2$, —OH, cyano,
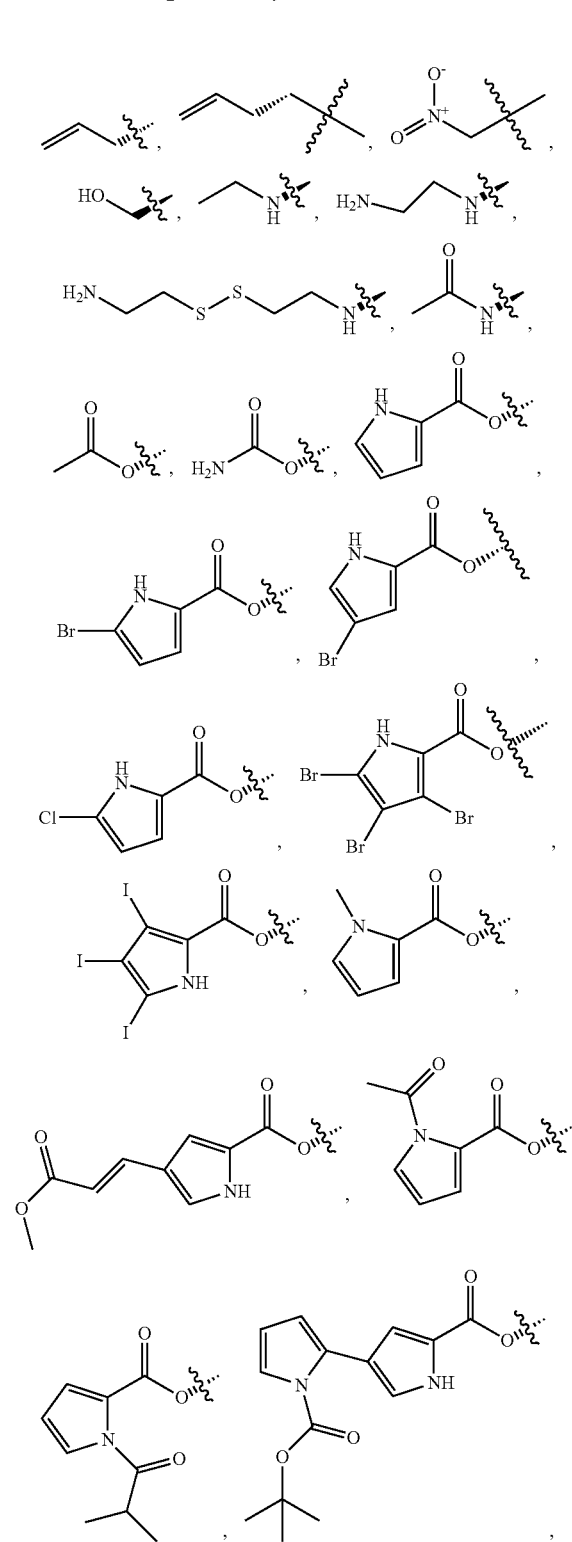
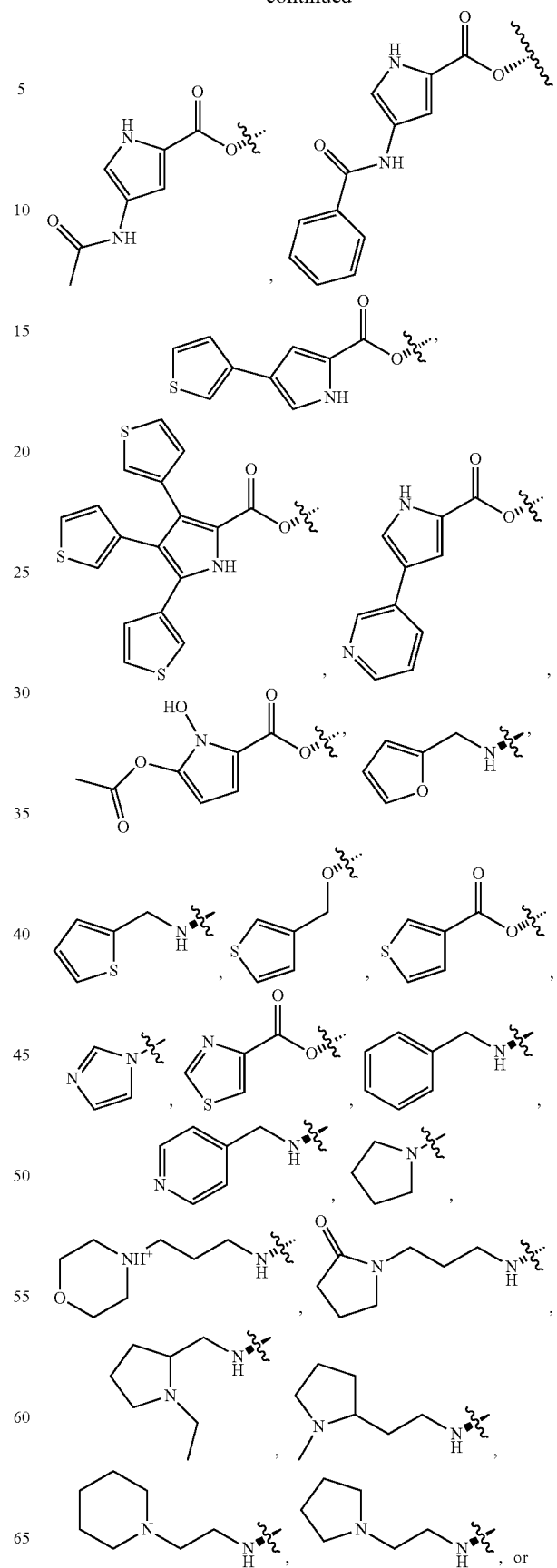

13

-continued

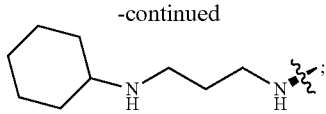

$R^{4b}$ is H; or $R^{4a}$ and $R^{4b}$ together form =O;

and the other groups are as provided in the general formula I above, or as in any of the first through fifth embodiments.

In a seventh embodiment of the invention, the compound is a compound of formula I, Ia, or Ib, or a pharmaceutically acceptable salt thereof, wherein $R^{2a}$ is —OH, F,

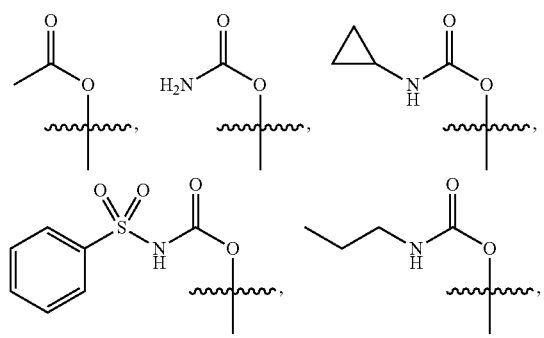

14

-continued

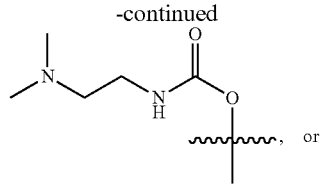

, or

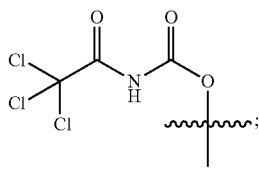

;

$R^{2b}$ is H; or $R^{2a}$ and $R^{2b}$ together form =O;

and the other groups are as provided in the general formula I above, or as in any of the first through sixth embodiments.

In an eighth embodiment of the invention, the compound is a compound of formula I, or a pharmaceutically acceptable salt thereof, wherein $R^{1a}$ is H, methyl, ethyl, phenyl,

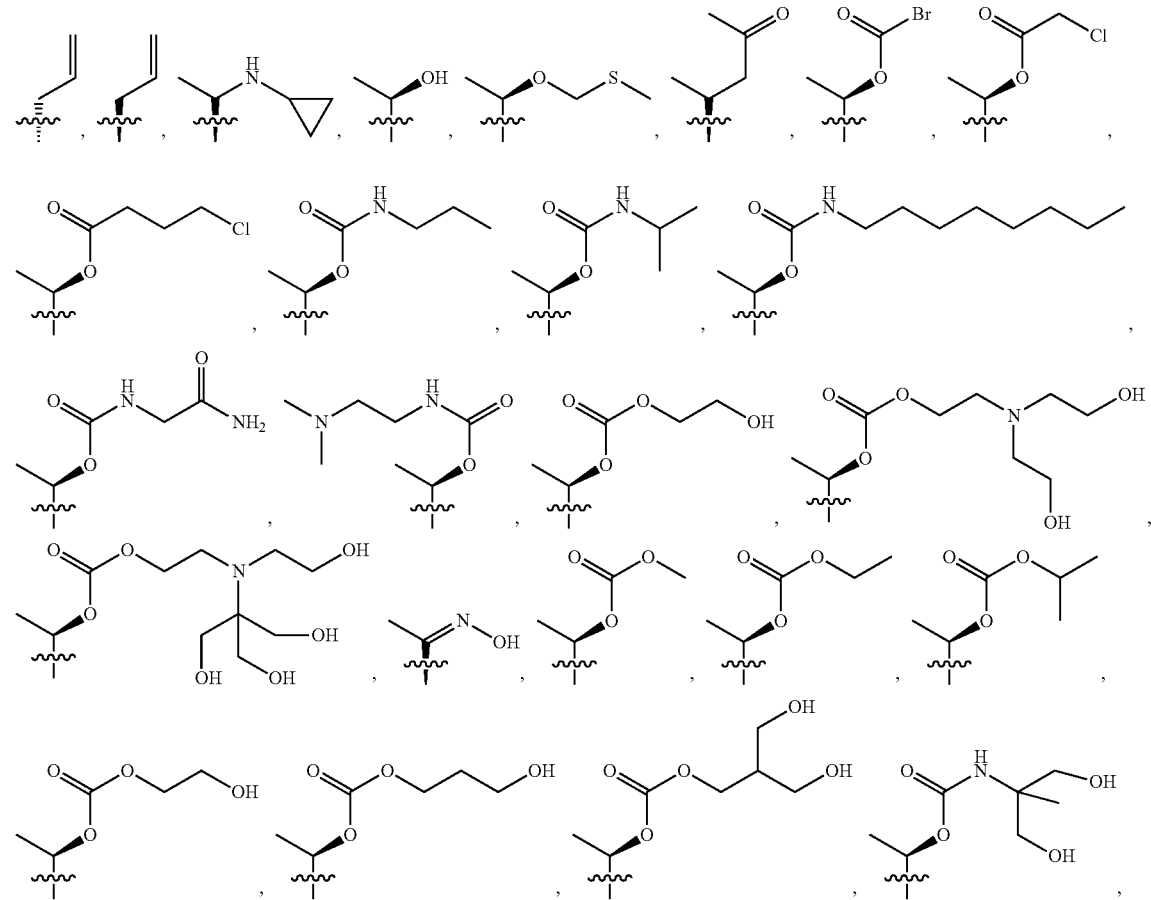

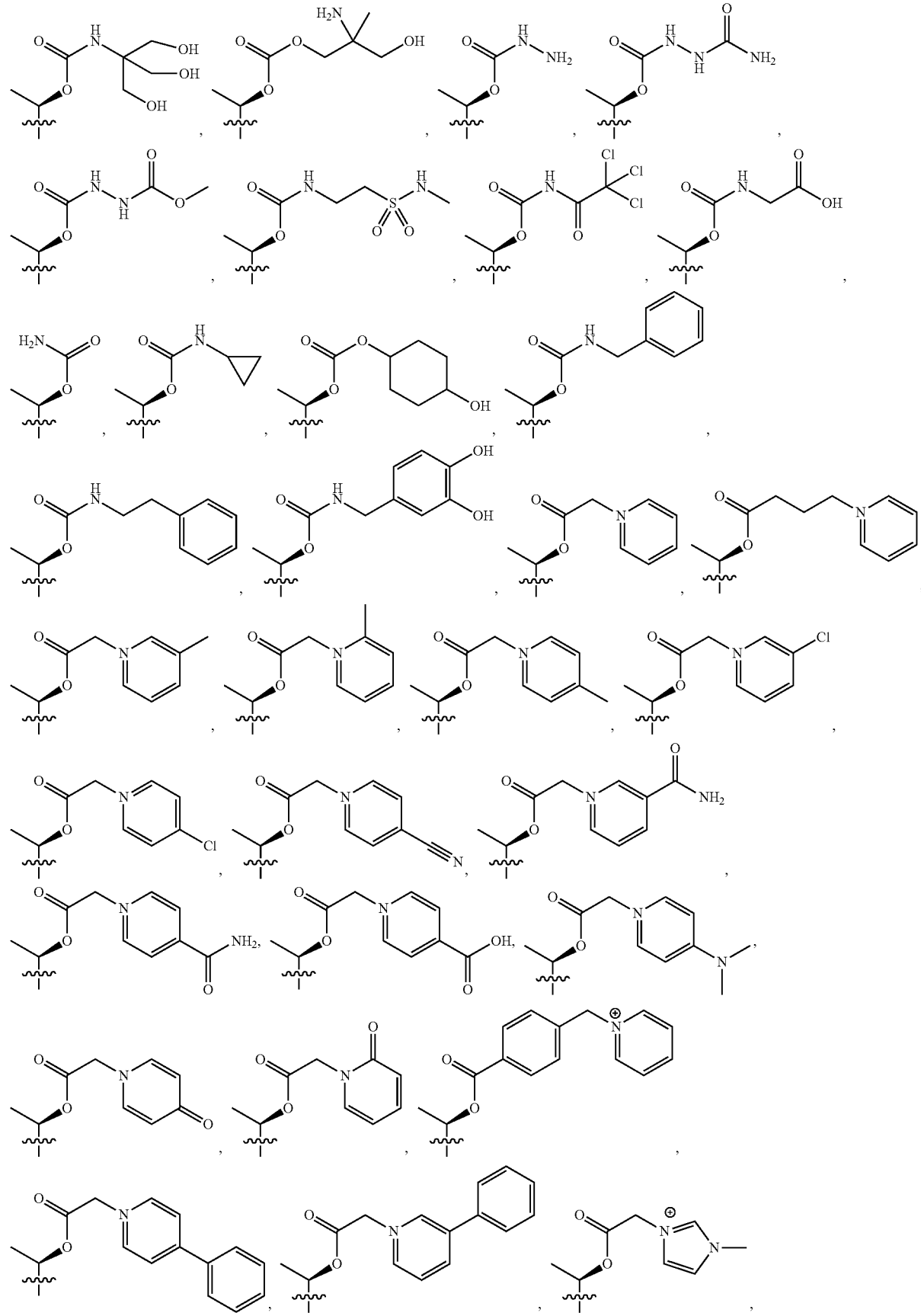

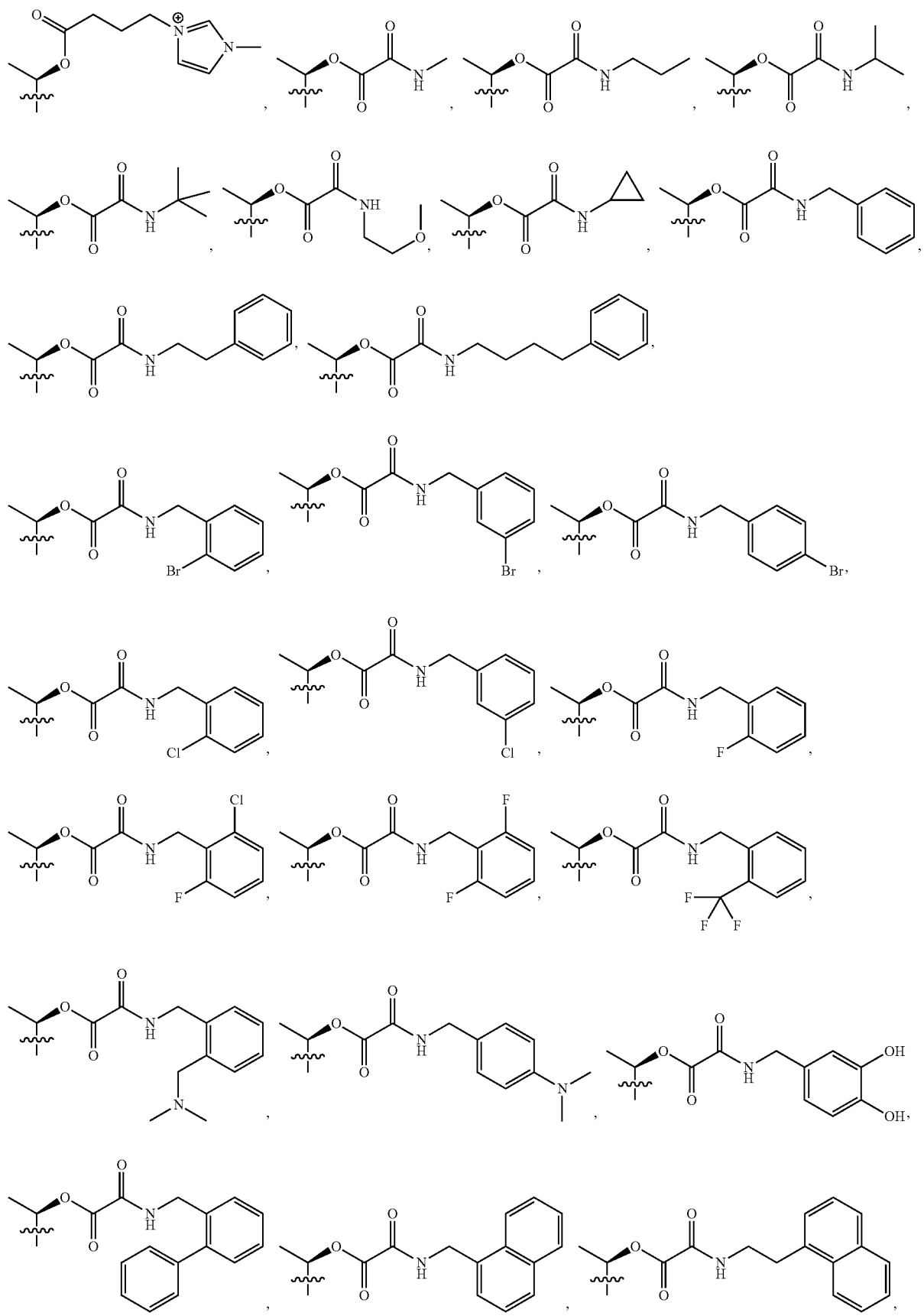

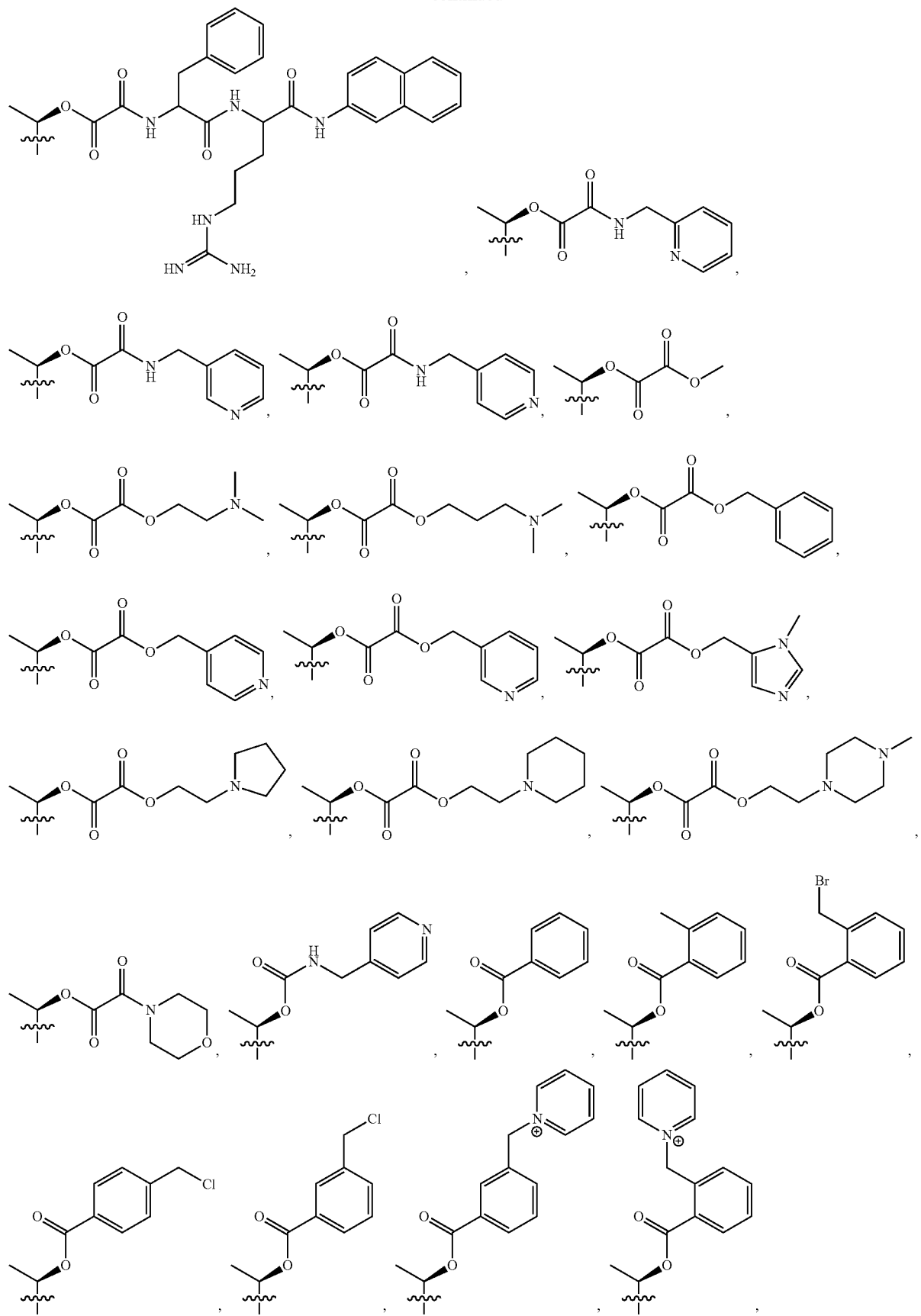

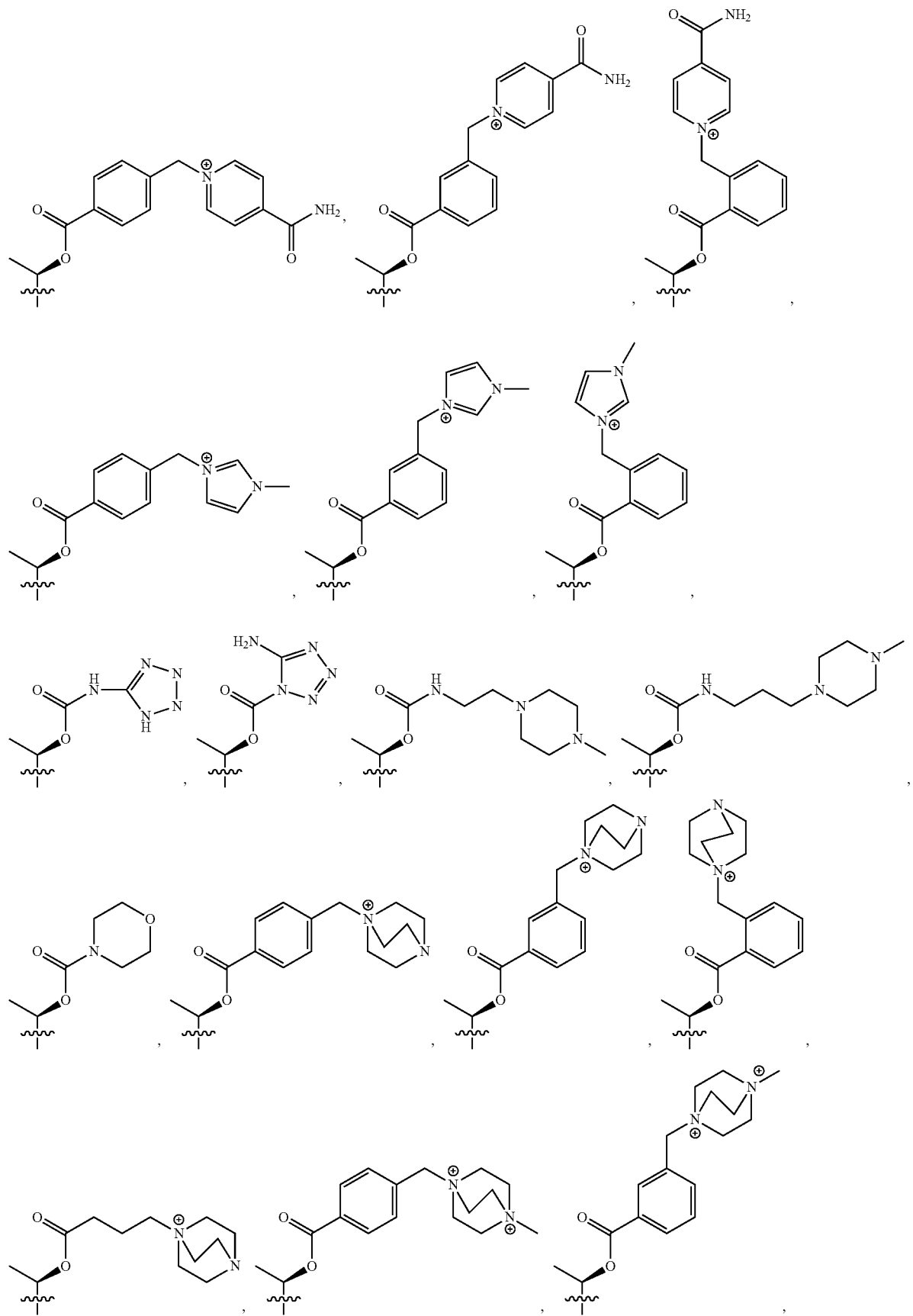

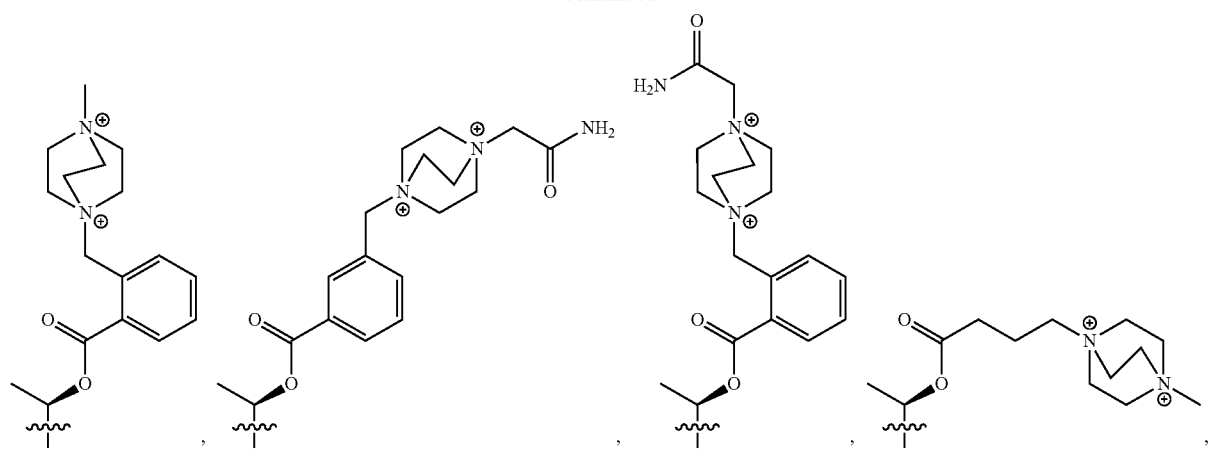
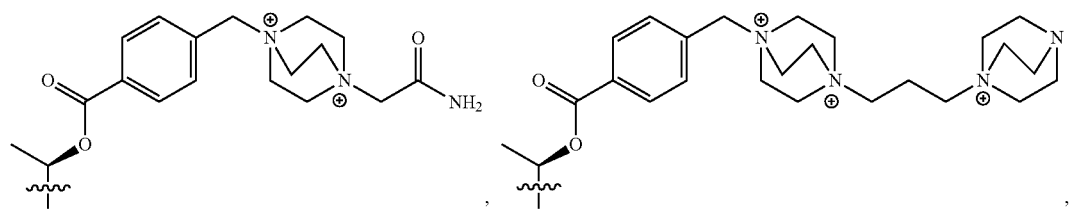
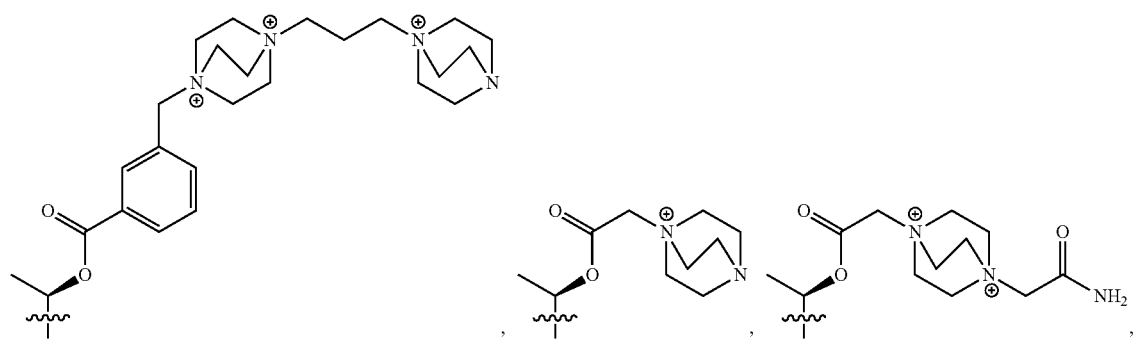
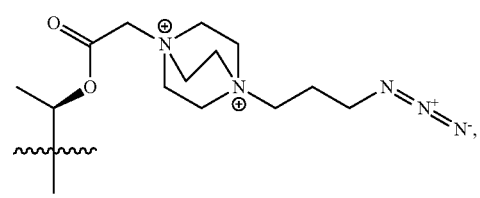
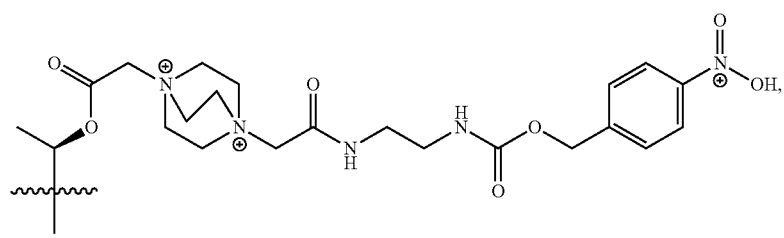

-continued

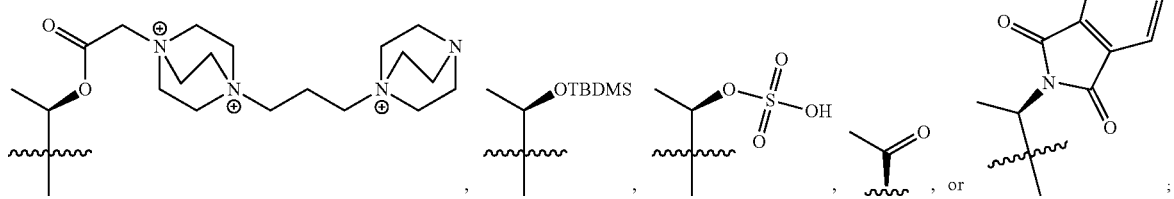

and
R$^{1b}$ is H.

In a ninth embodiment of the invention, the compound is a compound of formula Ic, or a pharmaceutically acceptable salt thereof,

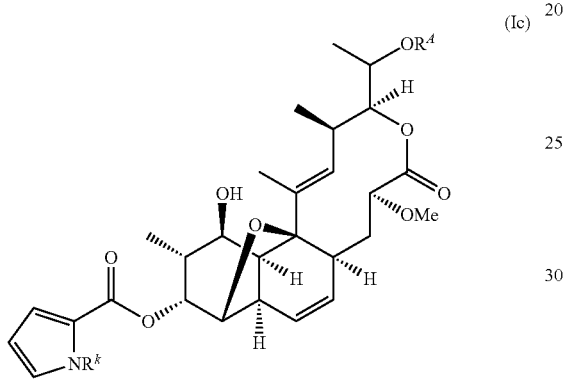

(Ic)

wherein
R$^A$ is H, C$_{1-6}$ alkyl, C$_{2-6}$ alkenyl, C$_{3-6}$ cycloalkyl, —C(=O)C$_{1-6}$alkyl, —C(=O)NHR$^g$, —C(=O)OR$^g$, —C(=O)C(=O)NHR$^g$, —C(=O)C(=O)OR$^g$, AryA, HetA, —C(=O)-AryA, or —C(=O)C(=O)-HetA;
wherein
any R$^A$ alkyl is optionally substituted with 1 or 2 substituents independently selected from halogen, —NR$^x$R$^y$, —N$^+$R$^x$R$^y$R$^z$, —SCH$_3$, AryA, and HetA; and the R$^A$ alkenyl is optionally substituted with AryA;
R$^b$ is C$_{1-6}$ alkyl, C$_{3-6}$ cycloalkyl, AryB, or HetB;
R$^g$ is H, C$_{1-8}$ alkyl, C$_{3-6}$ cycloalkyl, —C(=O)CCl$_3$, —NR$^x$R$^y$, —NHC(=O)NR$^x$R$^y$, —NHC(=O)OCH$_3$, or AryA, wherein the R$^g$ alkyl or R$^g$ cycloalkyl is optionally substituted by 1 to 3 —NR$^x$R$^y$, —N$^+$R$^x$R$^y$R$^z$, —N$^+$R$^x$R$^y$R$^w$ or —OH substituents or 1 substituent selected from C$_{1-6}$alkoxy, —COOH, —C(=O)NR$^x$R$^y$, —SCH$_3$, —NR$^y$R$^w$, —S(O)$_2$NR$^x$R$^y$, AryA, and HetA;
R$^k$ is H, —CH$_3$, —C(=O)C$_{1-6}$alkyl, —CH=CHC(=O)OCH$_3$, or —OH;
R$^x$, R$^y$ and R$^z$ are independently H or C$_{1-6}$alkyl;
R$^v$ and R$^w$ are C$_{1-6}$alkyl substituted with 1 to 3 —OH substituents;
AryA is
1) a 4- to 6-membered monocyclic aromatic ring with 0, 1, 2, or 3 ring atoms independently selected from N, N as a quaternary salt, O and S, optionally substituted with 1 to 3 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, cyano, —NH$_2$, —OH, —CH=CHC(=O)OC$_{1-6}$alkyl, —C(=O)R$^b$, —C(=O)NHR$^b$, —C(=O)OR$^b$, —NHC(=O)C$_{1-6}$alkyl, —NHC(=O)-AryB, —NO$_2$, —OC(=O)C$_{1-6}$alkyl, —S(=O)$_2$R$^b$, —(CH2)$_{0-3}$AryB, and —(CH2)$_{0-3}$HetB; or
2) a 7- to 11-membered bicyclic aromatic ring with 1, 2 or 3 N, or N as a quaternary salt, ring atoms optionally substituted with 1 to 3 substituents independently selected from C$_1$-C$_6$ alkyl, C$_1$-C$_6$ hydroxyalkyl, C$_1$-C$_6$ aminoalkyl, C$_1$-C$_6$ alkoxy, cyano, —NH$_2$, —OH, —C(=O)R$^b$, —C(=O)NHR$^b$, —C(=O)OR$^b$, —S(=O)$_2$R$^b$, —(CH2)$_{0-3}$AryB, and —(CH$_2$)$_{0-3}$HetB;
HetA is
1) a 4- to 6-membered saturated or monounsaturated monocyclic ring with 1 or 2 heteroatom ring atoms independently selected from N, N as a quaternary salt, O and S, optionally substituted with 1 or 2 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, cyano, —NH$_2$, —OH, —(CH$_2$)$_{0-1}$C(=O)NR$^b$, —C(=O)R$^b$, —C(=O)OR$^b$, —S(=O)$_2$R$^b$, —(CH$_2$)$_{0-3}$AryB, and —(CH$_2$)$_{0-3}$HetB; or
2) a 7- to 11-membered saturated or monounsaturated bicyclic ring with 1, 2, or 3 heteroatom ring atoms independently selected from N, N as a quaternary salt, O and S, optionally substituted with 1 or 2 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, cyano, —NH$_2$, —OH, —(CH$_2$)$_{0-1}$C(=O)NR$^b$, —C(=O)R$^b$, —C(=O)OR$^b$, —S(=O)$_2$R$^b$, —(CH2)$_{0-3}$AryB, and —(CH2)$_{0-3}$HetB;
AryB is
1) a 4- to 6-membered monocyclic aromatic ring with 0, 1, 2, or 3 ring atoms independently selected from N, N as a quaternary salt, O and S, optionally substituted with 1 to 3 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, cyano, —NH$_2$, —OH, —(CH$_2$)$_{1-3}$C(=O)NR$^x$R$^y$, —(CH$_2$)$_{1-3}$SO$_2$NR$^x$R$^y$, —CH=CHC(=O)OC$_{1-6}$alkyl, —NHC(=O)C$_{1-6}$alkyl, —NO$_2$, —N$^+$(O)OH, and —OC(=O)C$_{1-6}$alkyl; or
2) a 7- to 11-membered bicyclic aromatic ring with 1, 2 or 3 N, or N as a quaternary salt, ring atoms optionally substituted with 1 to 3 substituents independently selected from C$_1$-C$_6$ alkyl, C$_1$-C$_6$ hydroxyalkyl, C$_1$-C$_6$ aminoalkyl, C$_1$-C$_6$ alkoxy, cyano, —NH$_2$, and —OH;
HetB is
1) a 4- to 6-membered saturated or monounsaturated monocyclic ring with 1 or 2 heteroatom ring atoms independently selected from N, N as a quaternary salt, O and S, optionally substituted with 1 or 2 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, cyano, —NH$_2$, and —OH; or 2) a 7- to 11-membered saturated or monounsaturated bicyclic ring with 1, 2, or 3 heteroatom ring atoms independently selected from N, N as a quaternary salt, O and S, optionally substituted with 1 or 2 substituents independently selected from halogen, $C_1$-$C_6$ alkyl, $C_1$-$C_6$ hydroxyalkyl, $C_1$-$C_6$ aminoalkyl, $C_1$-$C_6$ alkoxy, cyano, —$NH_2$, and —OH;

and the other groups are as provided in the general formula I above, or as in any of the first through eighth embodiments.

In a tenth embodiment of the invention, the compound is a compound of formula Ic, or a pharmaceutically acceptable salt thereof, wherein $R^A$ is H, $C_{1-6}$alkyl-HetA, —C(=O)AryA, or —C(=O)C(=O)HetA;

and the other groups are as provided in the general formula I above, or as in any of the first through ninth embodiments. In one aspect of this embodiment, $R^A$ is —C(=O)AryA, wherein AryA is phenyl substituted by —$CH_2$-AryB. In one subaspect of the aspect, AryB is pyridinyl or imidazolyl, wherein a N ring atom is optionally in the form of a quaternary salt, and wherein AryB is optionally substituted with —$CH_3$. In another aspect of this embodiment, $R^A$ is —$C_{1-6}$alkyl-HetA or —C(=O)C(=O)HetA. In one subaspect of this embodiment, HetA is morpholinyl or 1,4-diazabicyclo[2.2.2]octane.

In an eleventh embodiment of the invention, the compound is a compound of formula Ic, or a pharmaceutically acceptable salt thereof, wherein $R^k$ is H or —C(=O)$C_{1-6}$alkyl, and the other groups are as provided in the general formula I above, or as in any of the first through tenth embodiments.

In a twelfth embodiment of the invention, the compound of the invention is selected from the exemplary species depicted in EXAMPLES 1 to 142 and 145 to 213 shown below, and pharmaceutically acceptable salts thereof.

In a thirteenth embodiment of the invention, the compound of the invention is selected from the exemplary species depicted in EXAMPLES 90, 94, 100, 108, 109, 118, and 204 shown below, and pharmaceutically acceptable salts thereof.

Representative formulas where $R^{1a}$ contains a HetA group include:

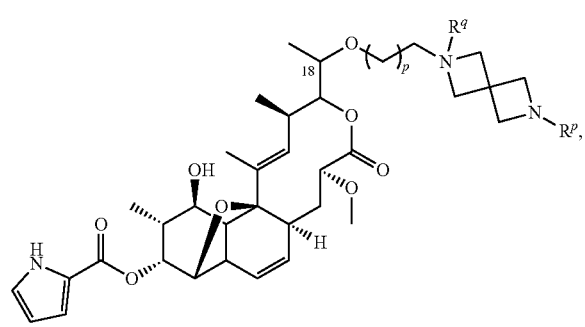

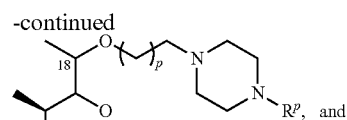

-continued

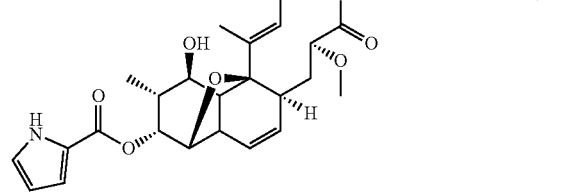

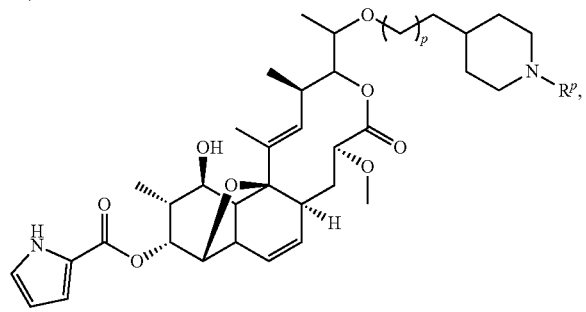

where p is 1 to 4, RP includes any of the substutitions for HetA, and Rq is H or —$CH_3$.

Reference to different embodiments with respect to Formula I compounds, specifically includes different embodiments of Formula I such as Formula Ia, Ib, and Ic, sub-embodiments of Formula Ia, Ib, and Ic, other embodiments provided herein, and individual compounds described herein.

Other embodiments of the present invention include the following:

(a) A pharmaceutical composition comprising an effective amount of a compound of Formula I, Ia, Ib, or Ic, as defined above, or a pharmaceutically acceptable salt thereof, and a pharmaceutically acceptable carrier.

(b) The pharmaceutical composition of (a), further comprising a second compound, wherein the second compound is an antibiotic.

(c) The pharmaceutical composition of (b), wherein the second compound is amikacin, para-aminosalicylic acid, capreomycin, cycloserine, ethionamide, ethambutol, isoniazid, levofloxacin, moxifloxacin, pyrazinamide, rifabutin, rifampin, rifapentine, or streptomycin.

(d) A pharmaceutical composition comprising (i) a compound of formula I, Ia, Ib, or Ic, or a pharmaceutically acceptable salt thereof, and (ii) a second compound, wherein the second compound is an antibiotic, wherein the compound of formula I, Ia, Ib, or Ic, and the second compound are each employed in an amount that renders the combination effective for inhibiting DnaE, or for treating or preventing bacterial infection.

(e) The combination of (d), wherein the second compound is amikacin, para-aminosalicylic acid, capreomycin, cycloserine, ethionamide, ethambutol, isoniazid, levofloxacin, moxifloxacin, pyrazinamide, rifabutin, rifampin, rifapentine, or streptomycin.

(f) A method for inhibiting DnaE and/or treating a bacterial infection which comprises administering to a subject in need of such treatment an effective amount of a compound of Formula I, Ia, Ib, or Ic, or a pharmaceutically acceptable salt thereof.

(g) A method for preventing and/or treating a bacterial infection which comprises administering to a subject in need of such treatment an effective amount of a compound of Formula I, Ia, Ib, or Ic, or a pharmaceutically acceptable salt thereof.

(h) A method for treating a bacterial infection which comprises administering to a subject in need of such treatment a therapeutically effective amount of the composition of (a), (b), (c), (d), or (e).

(i) The method of treating a bacterial infection as set forth in (f), (g), or (h), wherein the bacterial infection is due to *Escherichia* spp., or *Pseudomonas* spp., *Staphylococcus* spp., or *Streptococcus* spp.

(j) A method for preventing and/or treating a mycobacterial infection which comprises administering to a subject in need of such treatment an effective amount of a composition comprising a nargenicin compound, or a pharmaceutically acceptable salt thereof.

(k) The method of treating a mycobacterial infection as set forth in (j), wherein the mycobacterial infection is due to *M. tuberculosis*.

(l) The method of treating a mycobacterial infection as set forth in (j), wherein the composition is a composition of (a), (b), (c), (d), or (e).

The present invention also includes a compound of Formula I, Ia, Ib, or Ic, or a pharmaceutically acceptable salt thereof, (i) for use in, (ii) for use as a medicament for, or (iii) for use in the preparation (or manufacture) of a medicament for, medicine or inhibiting DnaE or treating bacterial infection, particularly a mycobacterial infection. In these uses, the compounds of the present invention can optionally be employed in combination with one or more second therapeutic agents including amikacin, para-aminosalicylic acid, capreomycin, cycloserine, ethionamide, ethambutol, isoniazid, levofloxacin, moxifloxacin, pyrazinamide, rifabutin, rifampin, rifapentine, or streptomycin.

Additional embodiments of the invention include the pharmaceutical compositions, combinations and methods set forth in (a)-(l) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (l) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its salt and a pharmaceutically acceptable carrier and optionally one or more excipients, it is understood that the term "substantially pure" is in reference to a compound of Formula I or its salt per se; i.e., the purity of the active ingredient in the composition.

Definitions:

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent.

"About", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation of ±1%, 2%, 3%, 4%, 5%, 10%, or 20%.

"Aromatic ring system", as exemplified herein, by AryA, AryB and AryC, means monocyclic, bicyclic or tricyclic aromatic ring or ring system containing 5-14 ring atoms, wherein at least one of the rings is aromatic. Aromatic ring systems, as used herein, encompass aryls and heteroaryls. The term may be used to describe a carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In another example, a heteromonocyclic ring is fused through two ring atoms to a phenyl or 5-6-membered heteroaryl containing 1, 2, or 3 heteroatoms selected from N, O, and S.

"Aryl" means a monocyclic, bicyclic or tricyclic carbocyclic aromatic ring or ring system containing 6-14 carbon atoms, wherein at least one of the rings is aromatic. Examples of aryl include phenyl and naphthyl.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, and the like.

"Drug resistant" means, in connection with a Mycobacterium, a Mycobacterium which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs.

"Halogen" includes fluorine, chlorine, bromine and iodine.

"Heteroaryl" means monocyclic, bicyclic or tricyclic ring or ring system containing 5-14 carbon atoms and containing at least one ring heteroatom selected from N, NH, a N as a quaternary salt, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzopyrazolyl, benzofuranyl, benzothiophenyl (including S-oxide and dioxide), benzotriazolyl, furo(2,3-b)pyridyl, quinolyl, indolyl, isoquinolyl, quinazolinyl, dibenzofuranyl, and the like. In one embodiment of the present invention, heteroaryl is selected from: pyridine, pyrimidine, thiazole, benzimidazole, benzthiazole, benzoxazole, and benzisoxazole. In another embodiment of the present invention, heteroaryl is pyridine. Examples of bicyclic rings (which are contemplated in the definition of AryA) include

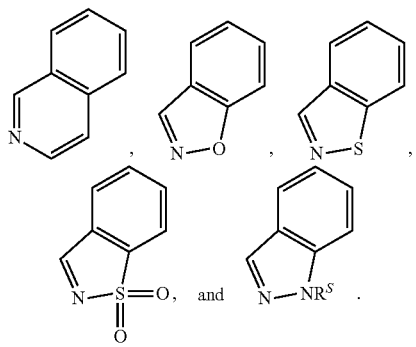

"Heterocycle", as exemplified herein by HetA, HetB and HetC, means monocyclic, bicyclic or tricyclic saturated or monounsaturated ring or ring system containing 5-14 carbon atoms and containing at least one ring heteroatom selected from N, NH, a N as a quaternary salt, S (including SO and $SO_2$) and O. When a heterocycle contains two rings, the rings may be fused, bridged or spirocyclic. Examples of monocyclic heterocycle rings include piperazine, piperidine, and morpholine. Examples of bicyclic heterocycle rings include 1,4-diazabicyclo[2,2,2]octane and 2,6-diazaspiroheptane.

"Nargenicin compound" refers to a class of structurally related compounds having tricyclic lactone containing a unique ether bridge and analogs thereof including whether the bridge is an amine. As used herein, nargenicin compounds include any of the compounds disclosed in Megerlein et al., 1982, J. Antibiotics 35:254-255; Kallmerten, 1995, Studies in Natural Products Chemistry 17:283-310; and U.S. Pat. Nos. 4,148,883; 4,448,970; and 4,605,624 including, but not limited to, Nargenicin $A_1$, 18-deoxynargenicin $A_1$, 18-deoxy-18-oxonargenicin $A_1$, 18-chloro-18-deoxynargenicin $A_1$, 18-azido-18-deoxynargenicin $A_1$, 18-O-thiocarbonyl-1'-imidazolenargenicin $A_1$, Nargenicin $B_1$, Nargenicin $B_2$, Nargenicin $B_3$, Nargenicin $C_1$, and nodusmicin. Nargenicin compounds also includes any of the compounds encompassed by formulas I, Ia, Ib, or Ic.

"Oxo" means an oxygen atom connected to another atom by a double bond and is can be represented "=O".

"Tuberculosis" comprises disease states usually associated with infections caused by mycobacteria species comprising M tuberculosis complex. The term "tuberculosis" is also associated with mycobacterial infections caused by mycobacteria other than M. tuberculosis (MOTT). Other mycobacterial species include M. avium-intracellulare, M kansarii, M. fortuitum, M. chelonae, M. leprae, M africanum, and M microti, M avium paratuberculosis, M. intracellulare, M. scrofulaceum, M. xenopi, M. marinum, and M ulcerans.

As used herein,

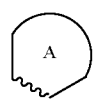

represents a cyclic ring where the wavy line indicates the attachment to the remainder of the molecule and is a single bond.

Another embodiment of the present invention is a compound of Formula I, or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers.

With respect to a compound of the invention which has one or more asymmetric centers and can occur as mixtures of stereoisomers, a substantially pure compound can be either a substantially pure mixture of the stereoisomers or a substantially pure individual diastereomer or enantiomer. All isomeric forms of these compounds, whether individually or in mixtures, are within the scope of the present invention.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described last, preceded by the adjacent functionality toward the point of attachment.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

When a group, e.g., $C_{1-8}$ alkyl, is indicated as being substituted, such substitutions can also occur where such group is part of a larger substituent, e.g., —$C_{1-8}$alkyl-$C_{3-7}$cycloalkyl and —$C_{1-8}$alkyl-aryl.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the EXAMPLES herein using appropriate isotopically-enriched reagents and/or intermediates.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_{1-6}$ when used with a chain, for example an alkyl chain, means that the chain can contain 1, 2, 3, 4, 5 or 6 carbon atoms. It also includes all ranges contained therein including $C_{1-5}$, $C_{1-4}$, $C_{1-3}$, $C_{1-2}$, $C_{2-6}$, $C_{3-6}$, $C_{4-6}$, $C_{5-6}$, and all other possible combinations.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

The term "compound" refers to the free compound and, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). A pharmaceutically acceptable salt can be formed, for example, by treating the compound of the invention (e.g., a compound of Formula I) with one molar equivalent of a mild base (e.g., sodium carbonate, sodium bicarbonate, potassium bicarbonate, or sodium acetate). In this case, M is a cation, such as $Na^+$ in the event of treatment with a sodium base.

The compounds of the invention can also be employed in the form of a prodrug. For example, the hydrogen in —COOH be replaced with any the following groups: $C_{1-6}$ alkyl, $C_{3-6}$ cycloalkyl, —$C_{1-6}$alkyl-$C_{3-6}$cycloalkyl, $C_{3-7}$ cycloheteroalkyl, —$C_{1-6}$alkyl-$C_{3-7}$cycloheteroalkyl, aryl, —$C_{1-10}$alkyl-aryl, heteroaryl, and —$C_{1-10}$ alkyl-heteroaryl. Any $C_{1-6}$ alkyl, $C_{3-6}$ cycloalkyl, or $C_{3-7}$ cycloheteroalkyl can also be substituted. Any aryl or heteroaryl can also be substituted as indicated.

As set forth above, the present invention includes pharmaceutical compositions comprising a compound of Formula I of the present invention, optionally one or more other active components, and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula I, or a pharmaceutically acceptable salt thereof. The term "subject" (or, alternatively, "patient") as used herein refers to an animal, preferably a mammal, most preferably a human, who has been the object of treatment, observation or experiment. The term "administration" and variants thereof (e.g., "administering" a compound) in reference to a compound of Formula I mean providing the compound, or a pharmaceutically acceptable salt thereof, to the individual in need of treatment. When a compound or a salt thereof is provided in combination with one or more other active agents, "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" as used herein with respect to a nargenicin compound means the amount of active compound sufficient to inhibit DnaE and/or cause a bacteriocidal or bacteriostatic effect. In one embodiment, the effective amount is a "therapeutically effective amount" meaning the amount of active compound that can overcome bacterial drug resistance and which is sufficient to inhibit bacterial replication and/or result in bacterial killing. When the active compound (i.e., active ingredient) is administered as the salt, references to the amount of active ingredient are to the free acid or free base form of the compound.

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington —The Science and Practice of Pharmacy, $21^{st}$ edition, 2006. In one embodiment, compounds of the invention are administered intravenously in a hospital setting. In another embodiment, administration is oral in the form of a tablet or capsule or the like. The dosage of the compounds of the invention and of their pharmaceutically acceptable salts may vary within wide limits and should naturally be adjusted, in each particular case, to the individual conditions and to the pathogenic agent to be controlled. In general, for a use in the treatment of bacterial infections, the daily dose may be between 0.005 mg/kg to 100 mg/kg, 0.01 mg/kg to 10 mg/kg, 0.05 mg/kg to 5 mg/kg, 0.05 mg/kg to 1 mg/kg.

In some embodiments, the compound of the invention is provided in a pharmaceutical formulation for oral, intravenous, intramuscular, nasal, or topical administration. Thus, in some embodiments, the formulation can be prepared in a dosage form, such as but not limited to, a tablet, capsule, liquid (solution or suspension), suppository, ointment, cream, or aerosol. In some embodiments, the presently disclosed subject matter provides such compounds and/or formulations that have been lyophilized and that can be reconstituted to form pharmaceutically acceptable formulations for administration, for example, as by intravenous or intramuscular injection.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing infection in a subject, and a method for the prophylaxis (i.e., preventing) of infection, such as in a subject that has been exposed to a microbe as disclosed herein or that has an expectation of being exposed to a microbe as disclosed herein.

Infections that may be treatable by the compounds of the invention can be caused by a variety of microbes, including fungi, algae, protozoa, bacteria, and viruses. In some embodiments, the infection is a bacterial infection. Exemplary microbial infections that may be treated by the methods of the invention include, but are not limited to, infections caused by one or more of *Staphylococcus aureaus, Enterococcus faecalis, Bacillus anthracis*, a *Streptococcus* species (e.g., *Streptococcus pyogenes* and *Streptococcus pneumoniae*), *Escherichia coli, Pseudomonas aeruginosa, Burkholderia cepacia*, a *Proteus* species (e.g., *Proteus mirabilis* and *Proteus vulgaris*), *Klebsiella pneumoniae, Acinetobacter baumannii, Strenotrophomonas maltophillia, Mycobacterium tuberculosis, Mycobacterium bovis*, other mycobacteria of the tuberculosis complex, and non-tuberculous mycobacteria, including *Mycobacterium ulcerans*.

In certain embodiments, the infection is an infection of a gram-positive bacterium. In some embodiments, the infection is selected from a mycobacterial infection, a *Bacillus anthracis* infection, an *Enterococcus faecalis* infection, and a *Streptococcus pneumoniae* infection.

In some embodiments, the compound of Formula (I) is administered prophylactically to prevent or reduce the incidence of one of: (a) a *Mycobacterium tuberculosis* infection in a subject at risk of infection; (b) a recurrence of a *Mycobacterium tuberculosis* infection; and (c) combinations thereof. In some embodiments, the compound of Formula (I) is administered to treat an existing *Mycobacterium tuberculosis* infection. In some embodiments, the compound of Formula (I) is administered to treat an infection of a multi-drug resistant strain of *Mycobacterium tuberculosis* (i.e., a strain that is resistant to two or more previously known anti-tuberculosis drugs, such as isoniazid, ethambutol, rifampicin, kanamycin, capreomycin, linezolid, and streptomycin). In some embodiments, the compound of Formula (I) has a minimum inhibitory concentration (MIC) against *Mycobacterium tuberculosis* of 25 µg/mL or less. In some embodiments, the compound of Formula (I) is administered to treat an infection of a multi-drug resistant strain of *Mycobacterium tuberculosis*.

Thus, the methods of the presently disclosed subject matter can be useful for treating tuberculosis in that they inhibit the onset, growth, or spread of a TB infection, cause regression of the TB infection, cure the TB infection, or otherwise improve the general well-being of a subject afflicted with, or at risk of, contracting tuberculosis.

Subjects suffering from an *M. tuberculosis* or other tuberculosis-related infection can be determined via a number of techniques, e.g., sputum smear, chest X-ray, tuberculin skin test (i.e., Mantoux test or PPD test) and/or the presence of other clinical symptoms (e.g., chest pain, coughing blood, fever, night sweats, appetite loss, fatigue, etc.). If desired, bacterial RNA, DNA or proteins can be isolated from a subject believed to be suffering from TB and analyzed via methods known in the art and compared to known nucleic or amino acid sequences of bacterial RNA, DNA or protein.

In some embodiments, the compound of Formula I, Ia, Ib, or Ic has a minimum inhibitory concentration (MIC) against *Mycobacterium tuberculosis* of 25 μg/mL or less. MICs can be determined via methods known in the art, for example, as described in Hurdle et al., 2008, *J. Antimicrob. Chemother.* 62:1037-1045.

In some embodiments, the methods of the invention further comprise administering to the subject an additional therapeutic compound. In some embodiments, the compound of the invention is administered to the subject before, after, or at the same time as one or more additional therapeutic compounds. In some embodiments, the additional therapeutic compound is an antibiotic. In some embodiments, the additional therapeutic compound is an anti-tuberculosis therapeutic. In some embodiments, the additional therapeutic compound is selected from the group comprising isoniazid, ethambutol, rifampicin, kanamycin, capreomycin, linezolid, and streptomycin.

The invention thus provides in a further aspect, a combination comprising a compound of Formula I, or a pharmaceutically acceptable salt thereof, together with one or more additional therapeutic agents. Examples of such one or more additional therapeutic agents are anti-tuberculosis agents including, but not limited to, amikacin, aminosalicylic acid, capreomycin, cycloserine, ethambutol, ethionamide, isoniazid, kanamycin, pyrazinamide, rifamycins (such as rifampin, rifapentine and rifabutin), streptomycin, clarithromycin, azithromycin, oxazolidinones and fluoroquinolones (such as ofloxacin, ciprofloxacin, moxifloxacin and gatifloxacin). Such chemotherapy is determined by the judgment of the treating physician using preferred drug combinations. "First-line" chemotherapeutic agents used to treat a *Mycobacterium tuberculosis* infection that is not drug resistant include isoniazid, rifampin, ethambutol, streptomycin and pyrazinamide. "Second-line" chemotherapeutic agents used to treat a *Mycobacterium tuberculosis* infection that has demonstrated drug resistance to one or more "first-line" drugs include ofloxacin, ciprofloxacin, ethionamide, aminosalicylic acid, cycloserine, amikacin, kanamycin and capreomycin. In addition to the aforementioned, there are a number of new anti-tuberculosis therapeutic agents emerging from clinical studies that may also be employed as the one or more additional therapeutic agents in a combination with a compound of Formula I, including, but not limited to, TMC-207, OPC-67683, PA-824, LL-3858 and SQ-109.

Thus, the other antibiotic which may be combined with the compounds of formula I, Ia, Ib, or Ic are for example rifampicin (=rifampin); isoniazid; pyrazinamide; amikacin; ethionamide; moxifloxacin; ethambutol; streptomycin; para-aminosalicylic acid; cycloserine; capreomycin; kanamycin; thioacetazone; PA-824; quinolones/fluoroquinolones such as for example ofloxacin, ciprofloxacin, sparfloxacin; macrolides such as for example clarithromycin, clofazimine, amoxycillin with clavulamic acid; rifamycins; rifabutin; rifapentine.

In a further aspect, the one or more additional therapeutic agent is, for example, an agent useful for the treatment of tuberculosis in a mammal, therapeutic vaccines, anti-bacterial agents, anti-viral agents; antibiotics and/or agents for the treatment of HIV/AIDS. Examples of such therapeutic agents include isoniazid (INH), ethambutol, rifampin, pirazinamide, streptomycin, capreomycin, ciprofloxacin and clofazimine.

In one aspect, the one or more additional therapeutic agent is a therapeutic vaccine. A compound of Formula I, or a pharmaceutically acceptable salt thereof, may thus be administered in conjunction with vaccination against mycobacterial infection, in particular vaccination against *Mycobacterium tuberculosis* infection. Existing vaccines against mycobacterial infection include Bacillus Calmette Guerin (BCG). Vaccines currently under development for the treatment, prophylaxis or amelioration of mycobacterial infection include: modified BCG strains which recombinantly express additional antigens, cytokines and other agents intended to improve efficacy or safety; attenuated mycobacteria which express a portfolio of antigens more similar to *Mycobacterium tuberculosis* than BCG; and subunit vaccines. Subunit vaccines may be administered in the form of one or more individual protein antigens, or a fusion or fusions of multiple protein antigens, either of which may optionally be adjuvanted, or in the form of a polynucleotide encoding one or more individual protein antigens, or encoding a fusion or fusions of multiple protein antigens, such as where the polynucleotide is administered in an expression vector. Examples of subunit vaccines include, but are not limited to: M72, a fusion protein derived from the antigens Mtb32a and Mtb39; HyVac-1, a fusion protein derived from antigen 85b and ESAT-6; HyVac-4, a fusion protein derived from antigen 85b and Tb10.4; MVA85a, a modified vaccinia virus Ankara expressing antigen 85a; and Aeras-402, adenovirus 35 expressing a fusion protein derived from antigen 85a, antigen 85b and Tb10.4.

Abbreviations employed herein include the following: ACN=acetonitrile; $CDCl_3$=deuterated chloroform; DABCO=1,4-diazabicyclo[2.2.2]octane; DCE=1,2-dichloroethane; DCM=dichloromethane; DMAP=4-dimethylaminopyridine or N,N-dimethylaminopyridine; DME=dimethyl ether; DMF=N,N-dimethylformamide; DMSO=dimethyl sulfoxide; Et=ethyl; EtOAc=ethyl acetate; $H_2$=hydrogen gas, HPLC=high-performance liquid chromatography; LC-MS=liquid chromatography/mass spectrometry; Me=methyl; MeCN=acetonitrile; MEOH=methanol; MHBII=Mueller Hinton Broth type II; MIC=minimum inhibitory concentration; MW=molecular weight; NBS=N-Bromosuccinimide; MS=mass spectrometry; Pd-C=palladium on carbon; RT=room temperature; TEA=triethylamine; TFA=trifluoroacetic acid; THF=tetrahydrofuran; TBDMS=tert-butyl dimethylsilyl; TSB=trypticase soy broth.

The compounds disclosed herein can be prepared according to the following reaction schemes and EXAMPLES, or modifications thereof, using readily available starting materials, reagents and conventional synthesis procedures. In these reactions, it is also possible to make use of variations which are themselves known to those of ordinary skill in this art, but are not mentioned in greater detail. Furthermore, other methods for preparing compounds disclosed herein will be readily apparent to the person of ordinary skill in the art in light of the following reaction schemes and EXAMPLES.

Scheme 1
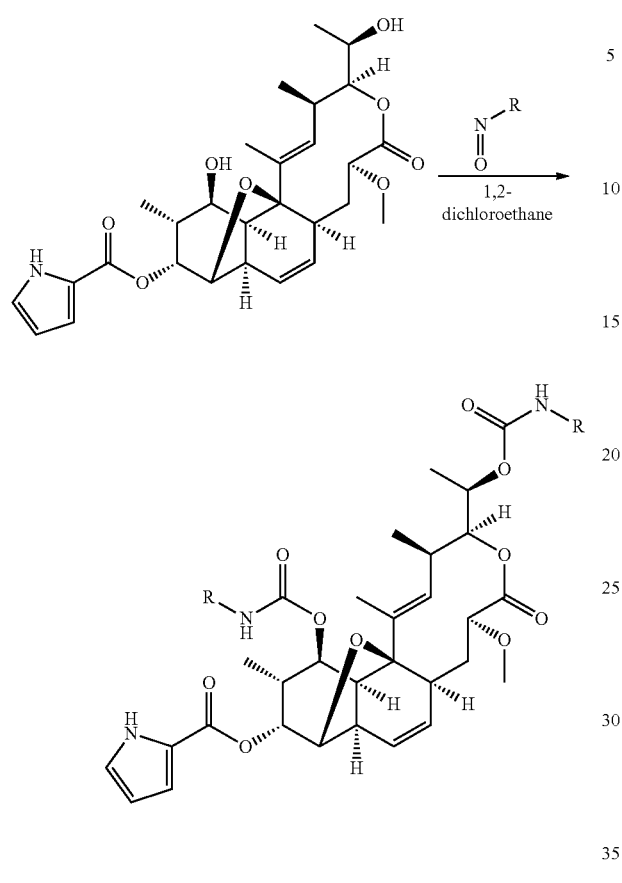
Scheme 2
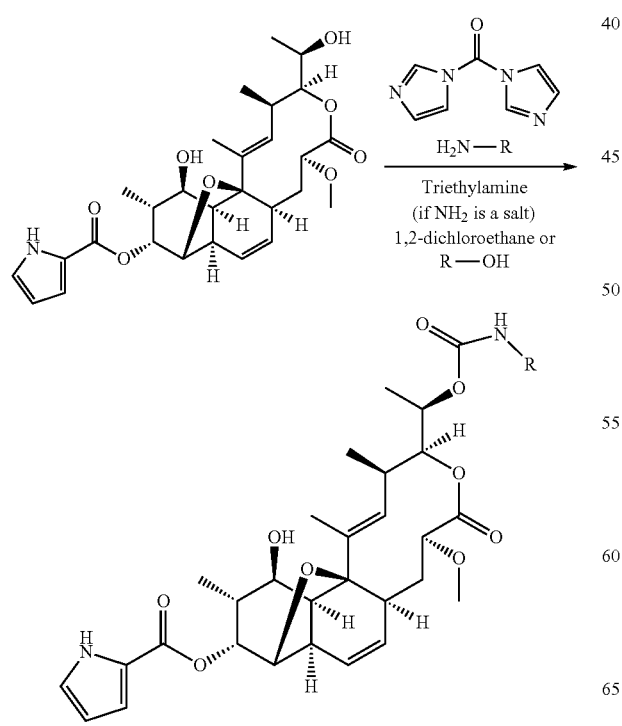
Scheme 3
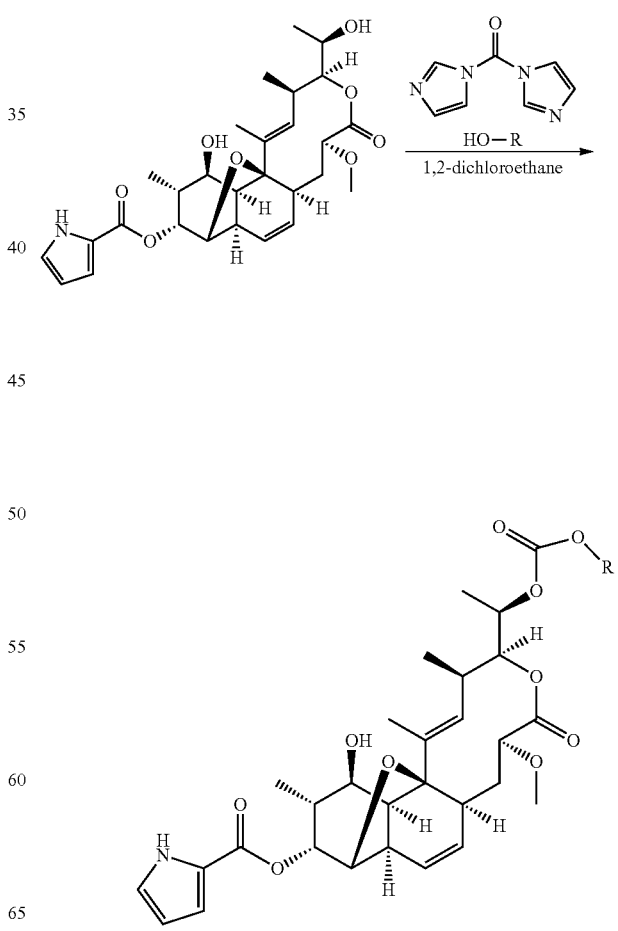

Scheme 4
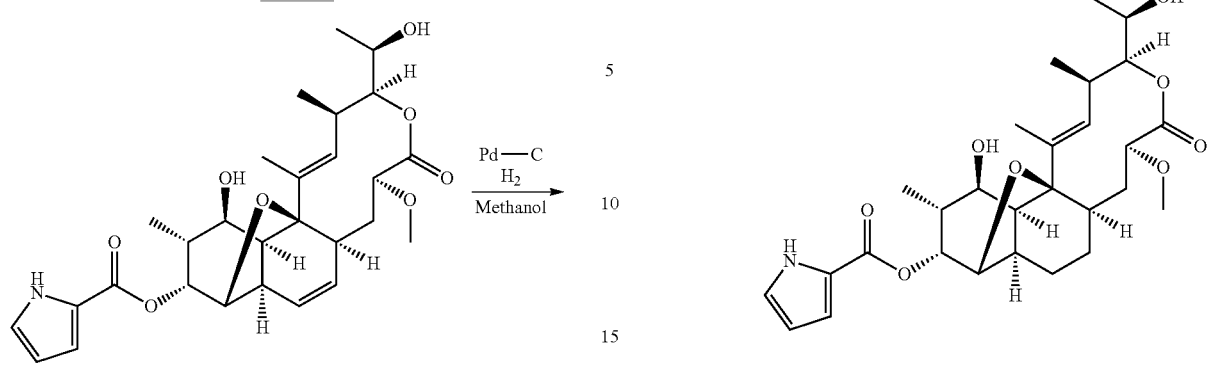
Scheme 5
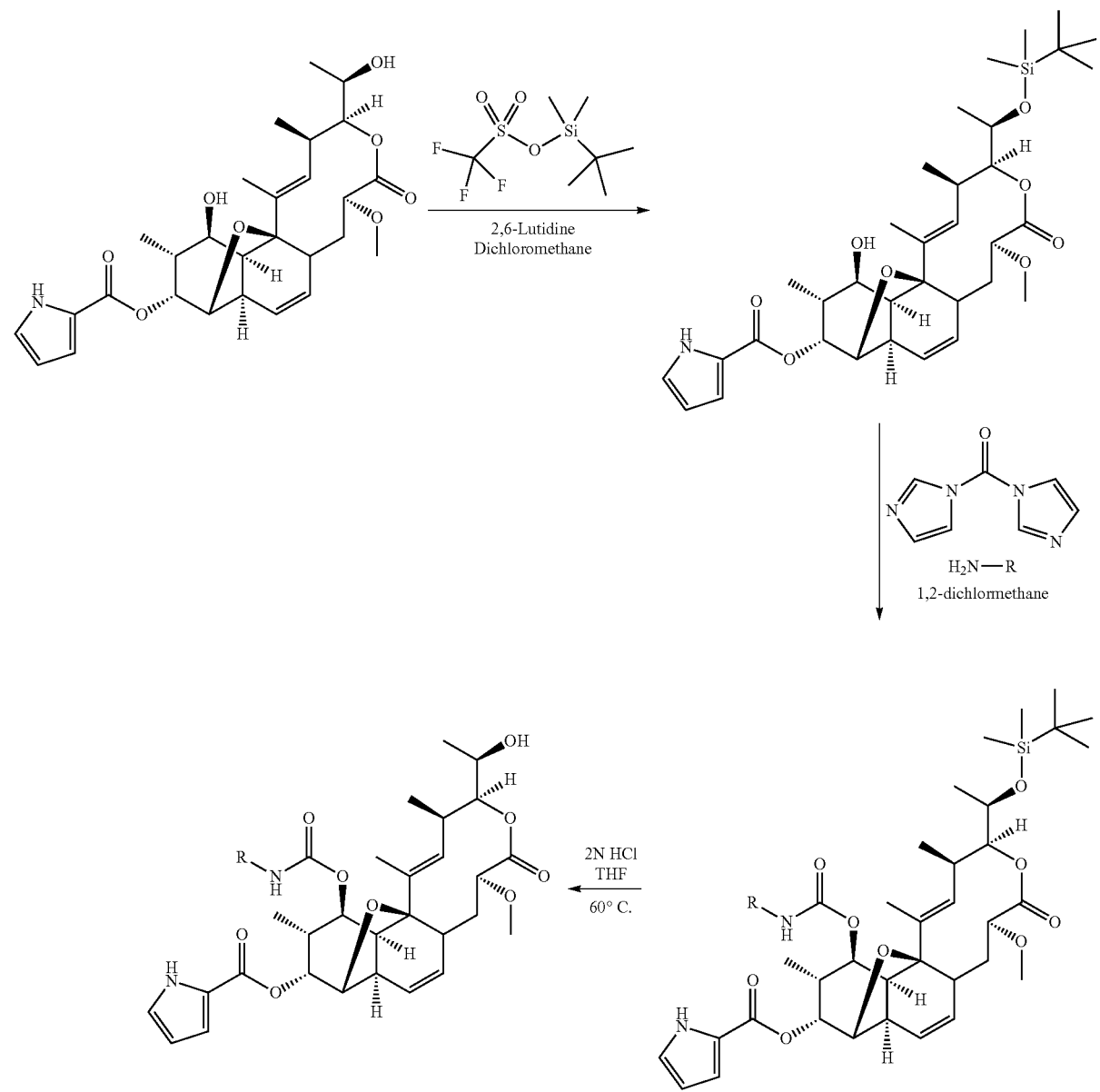

Scheme 6
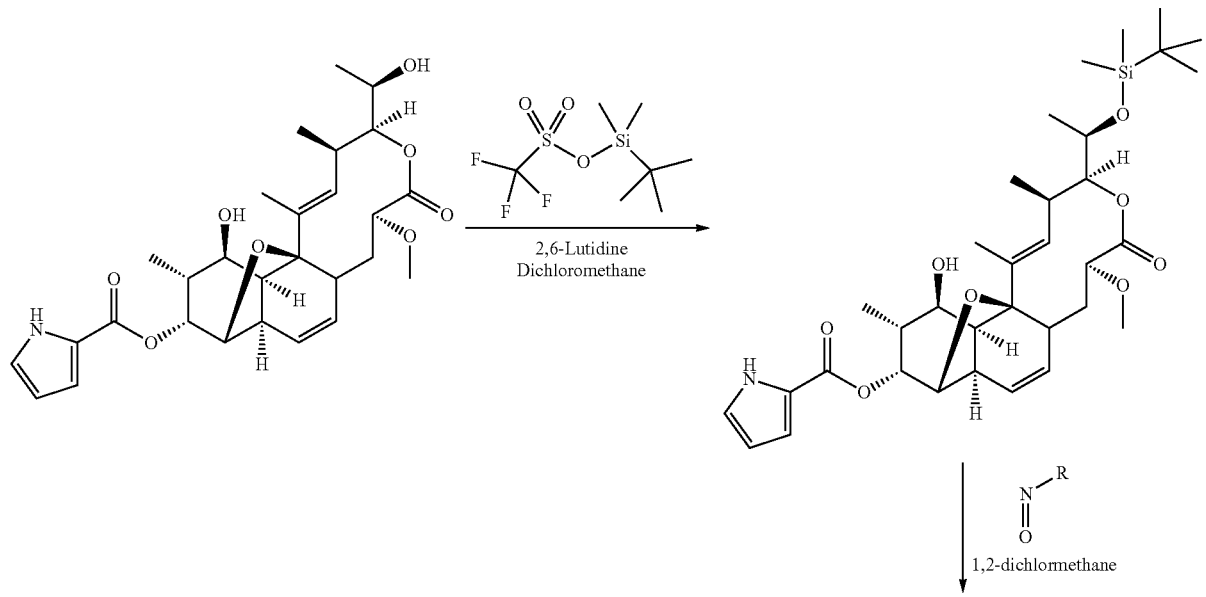
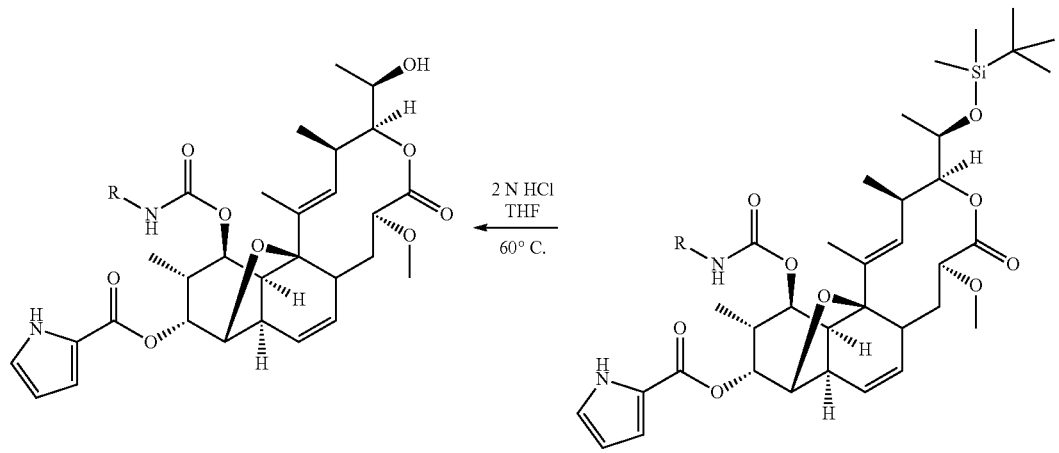
Scheme 7
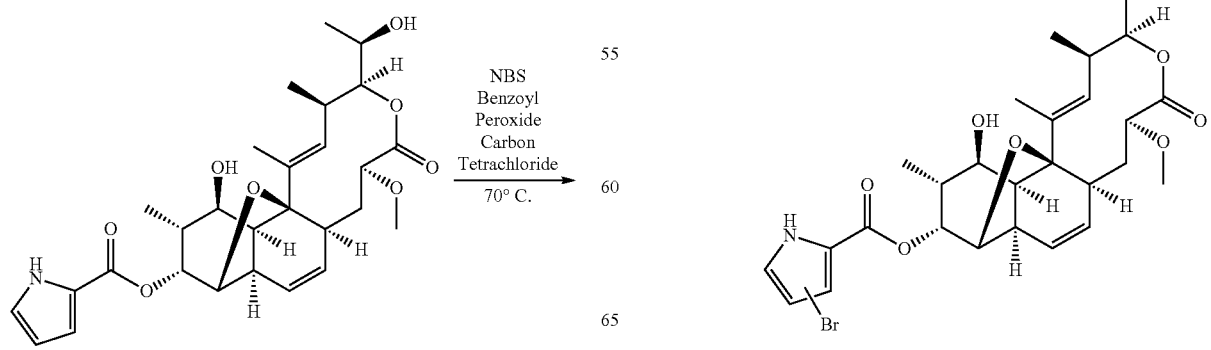

Scheme 8
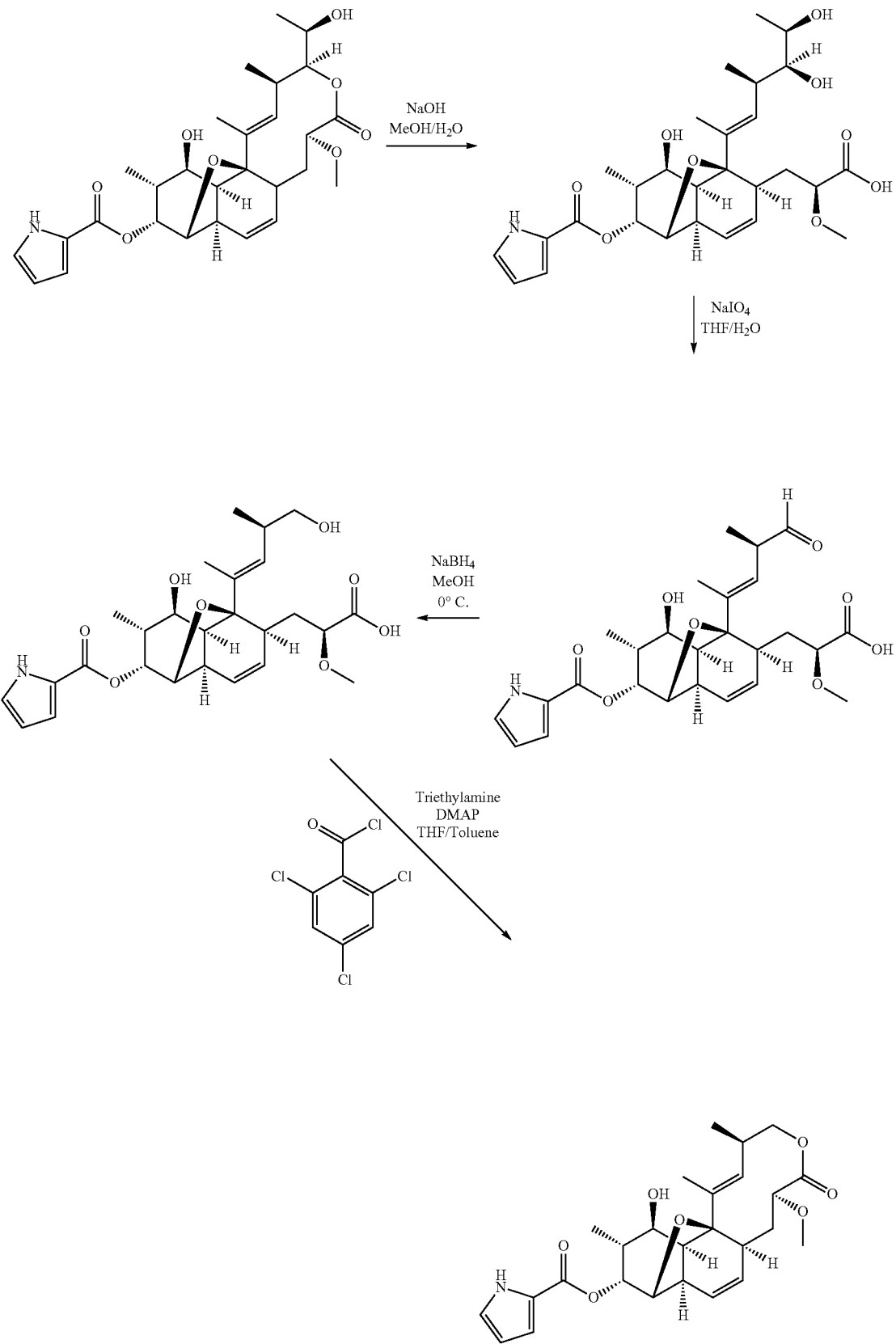

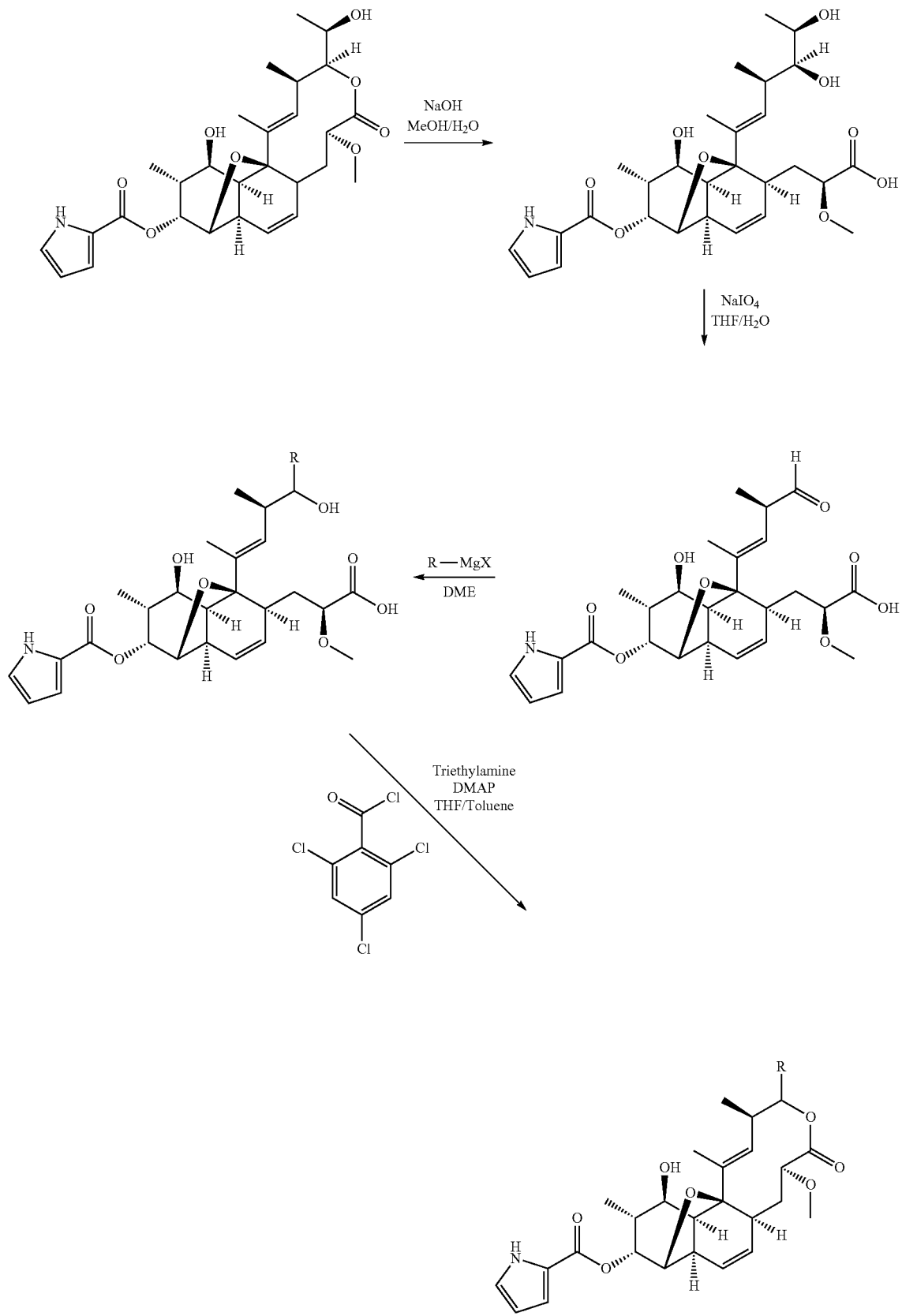
Scheme 9

Scheme 10
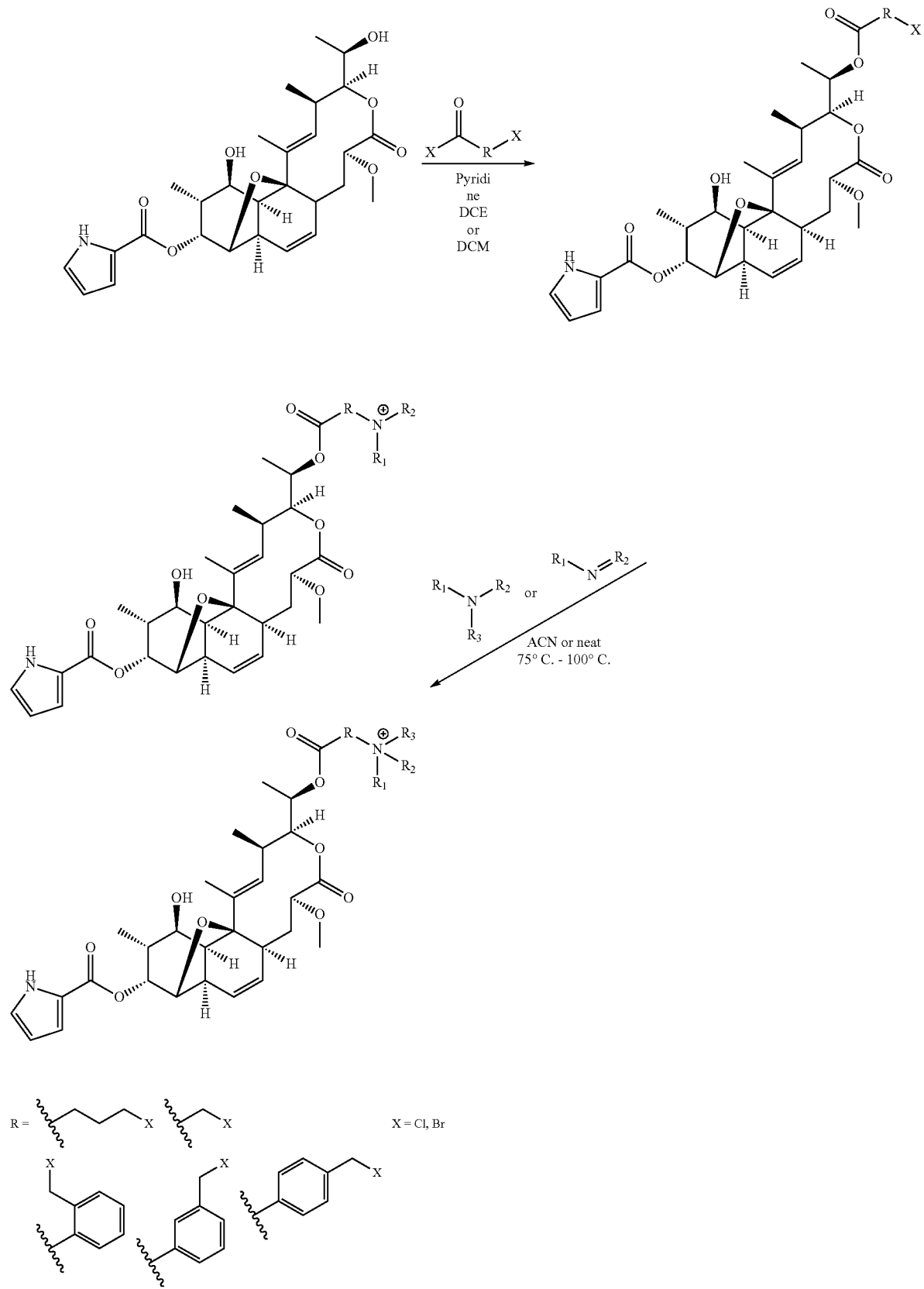

Scheme 11

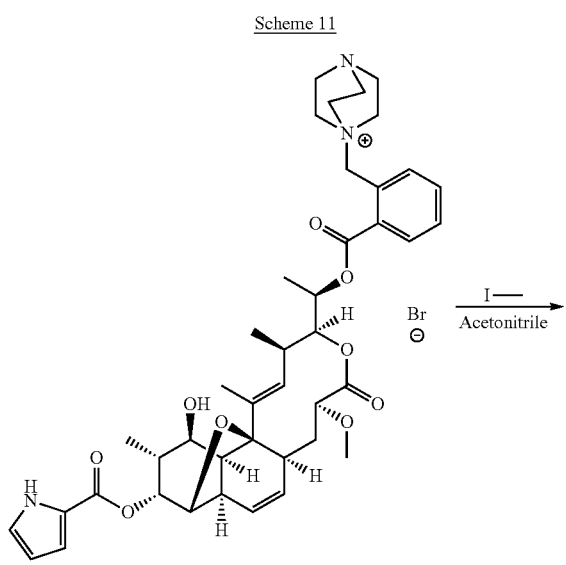

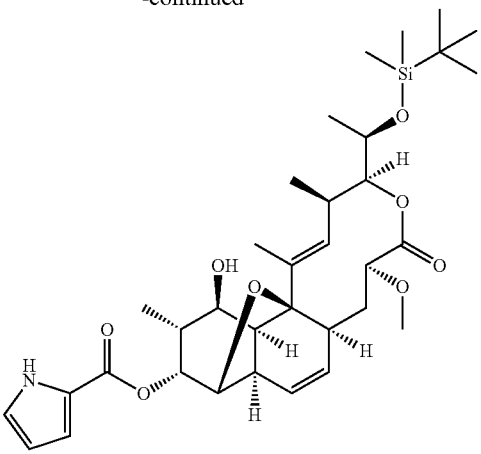

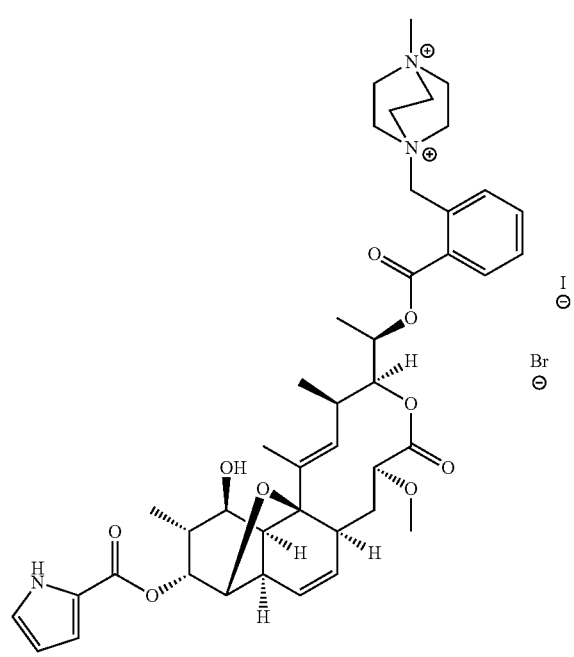

Intermediate 1

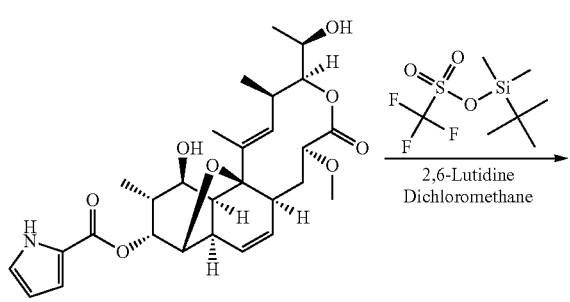

(3R,4S,7S,10aR,11R,12R,13R,14R,14aS,14bS,E)-4-((R)-1-((tert-butyldimethylsilyl)oxy)ethyl)-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate.

2,6-Lutidine (0.11 ml, 0.944 mmol) and tert-butyldimethylsilyltrifluoromethanesulfonate (0.15 ml, 0.653 mmol) were added to a stirred solution of Nargenicin (160.0 mg, 0.310 mmol) in dichloromethane (2.0 ml), that had been degassed and placed under nitrogen. The reaction mixture was a light amber solution that was stirred at room temperature. After 1 hour, the reaction mixture was evaporated under reduced pressure before being partitioned between dichloromethane (20 ml) and water (20 ml). The aqueous layer was extracted with dichloromethane (1×20 ml). The organic layers were combined, dried over magnesium sulfate, filtered, and evaporated under reduced pressure to give a yellow oil. The oil was taken up in dichloromethane and purified by normal phase chromatography on an ISCO companion, eluting with 20% ethyl acetate/hexanes for 2 minutes followed by a 20%-40% ethyl acetate/hexanes gradient. The product fractions were combined, evaporated, and the resulting residue was lyophilized from benzene to give the title compound as a white solid. $C_{34}H_{51}NO_8Si^1H$ NMR δ (ppm) $CDCl_3$: 9.07 (s, 1 H); 7.00 (td, J=2.7, 1.4 Hz, 1 H); 6.89 (ddd, J=3.8, 2.4, 1.4 Hz, 1 H); 6.29 (dt, J=3.8, 2.6 Hz, 1 H); 5.86 (ddd, J=9.3, 6.8, 1.7 Hz, 1 H); 5.59 (dd, J=9.3, 3.2 Hz, 1 H); 5.54 (d, J=7.0 Hz, 1 H); 5.14 (t, J=5.0 Hz, 1 H); 4.23 (d, J=4.9 Hz, 1 H); 4.13 (dq, J=8.1, 6.1 Hz, 1 H); 3.72 (dd, J=11.6, 4.2 Hz, 1 H); 3.67 (ddd, J=10.9, 7.2, 2.8 Hz, 1 H); 3.31 (s, 3 H); 3.04-3.07 (m, 1 H); 2.50-2.55 (m, 4 H); 2.31-2.37 (m, 2 H); 1.83 (s, 3 H); 1.38-1.43 (m, 2 H); 1.25 (d, J=7.0 Hz, 3 H); 1.22 (d, J=6.1 Hz, 3 H); 0.99 (d, J=6.8 Hz, 3 H); 0.92 (s, 9 H); 0.13 (s, 3 H); 0.13 (s, 3 H).

Intermediate 2

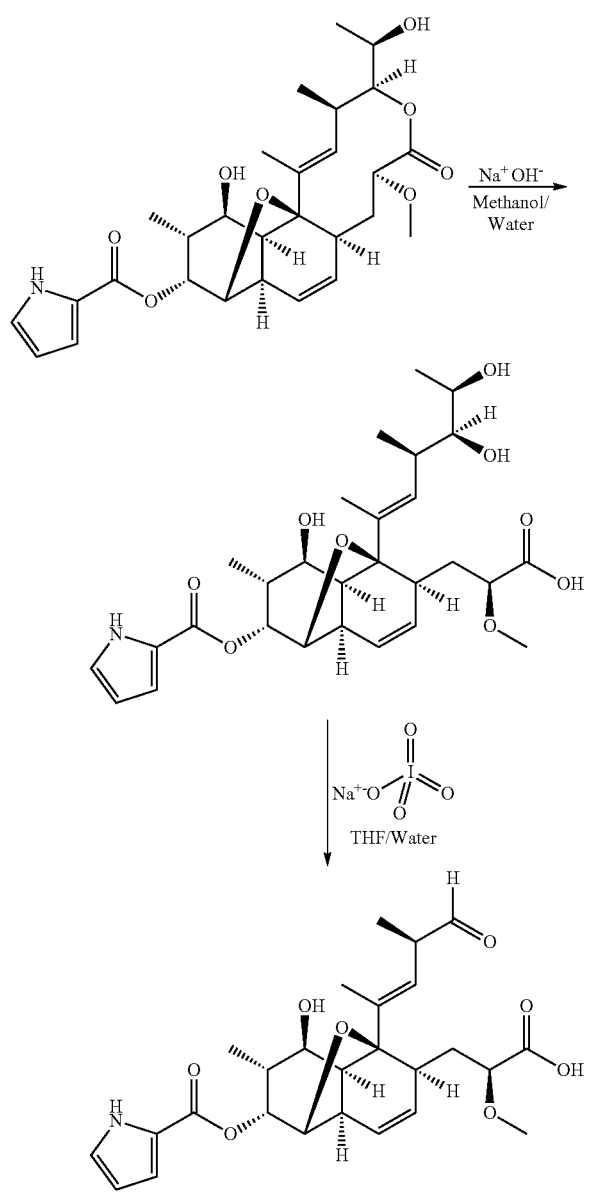

(S)-3-((1S,2S,4aR,5R,6R,7R,8R,8aS)-6-((1H-pyr-role-2-carbonyl)oxy)-8-hydroxy-7-methyl-1((R,E)-4-methyl-5-oxopent-2-en-2-yl)-1,2,4a,5,6,7,8,8a-octahydro-1,5-epoxynaphthalen-2-yl)-2-methoxypropanoic acid (S)-3-((1S,2S,4aR,5R,6R,7R,8R,8aS)-6-((1H-pyr-role-2-carbonyl)oxy)-1-((4R,5S,6R,E)-5,6-dihy-droxy-4-methylhept-2-en-2-yl)-8-hydroxy-7-methyl-1,2,4a,5,6,7,8,8a-octahydro-1,5-epoxynaphthalen-2-yl)-2-methoxypropanoic acid 5N sodium hydroxide (0.3 ml, 1.500 mmol) was added to a stirred solution of Nargenicin (0.56 g, 1.086 mmol) in methanol (5.25 ml) and water (5.25 ml). The addition of the sodium hydroxide resulted in the formation of a white precipitate, which quickly dissolved to give a pale yellow solution that was stirred at room temperature. After 1 hour, the reaction mixture was acidified to a pH of 2 with 2N HCl. The reaction mixture was concentrated under reduced pressure to about 1-2 ml before partitioning between ethyl acetate (50 ml) and water (50 ml). A few mls of brine were added to improve the separation of the layers. The aqueous layer was extracted with ethyl acetate (3×30 ml). The organic layers were combined, dried over sodium sulfate, filtered, and evaporated under reduced pressure. The resulting residue was lyophilized from ethanol and benzene to give the desired product as a white solid, which was used in the next step withou further purification. LC-MS: calculated for $C_{28}H_{39}NO_9$ 533.26 observed m/e: 534.13 (M+H) (Rt 1.74/4 min).

(S)-3-((1S,2S,4aR,5R,6R,7R,8R,8aS)-6-((1H-pyr-role-2-carbonyl)oxy)-8-hydroxy-7-methyl-1-((R,E)-4-methyl-5-oxopent-2-en-2-yl)-1,2,4a,5,6,7,8,8a-octahydro-1,5-epoxynaphthalen-2-yl)-2-methoxypropanoic acid Sodium periodate (138.3 mg, 0.647 mmol) was added to a stirred solution of (S)-3-((1S,2S,4aR,5R,6R,7R,8R,8aS)-6-((1H-pyrrole-2-carbonyl)oxy)-1-((4R,5S,6R,E)-5,6-dihy-droxy-4-methylhept-2-en-2-yl)-8-hydroxy-7-methyl-1,2,4a,5,6,7,8,8a-octahydro-1,5-epoxynaphthalen-2-yl)-2-methoxypropanoic acid (264.2 mg, 0.495 mmol) in tetrahydrofuran (3.96 ml) and water (0.99 ml). The reaction mixture was a colorless solution that was stirred at room temperature. After 1.5 hours, the reaction mixture was partitioned between ethyl acetate (50 ml) and a 0.1 M aqueous sodium bisulfite solution (30 ml). The aqueous layer was extracted with ethyl acetate (3×30 ml). The organic layers were combined, dried over sodium sulfate, filtered, and evaporated under reduced pressure. The resulting residue was lyophlized from ethanol and benzene to give the title compound as a yellow solid, which was used in the next reaction without further purification. LC-MS: calculated for $C_{26}H_{33}NO_8$ 487.22 observed m/e: 488.09 (M+H)$^+$ (Rt 1.78/4 min); $^1$H NMR δ (ppm) CD$_3$OD: 11.27 (s, 1 H); 9.50 (d, J=1.8 Hz, 1 H); 6.96-6.97 (m, 1 H); 6.85-6.86 (m, 1 H); 6.18-6.20 (m, 1 H); 5.91 (dd, J=9.6, 6.8 Hz, 1 H); 5.62-5.69 (m, 2 H); 5.06 (t, J=5.0 Hz, 1 H); 4.30-4.38 (m, 1 H); 4.17 (d, J=4.8 Hz, 1 H); 3.80-3.84 (m, 1 H); 3.66 (dd, J=10.9, 2.8 Hz, 1 H); 3.33 (s, 3 H); 2.60-2.70 (m, 3 H); 2.49 (t, J=3.3 Hz, 1 H); 1.70 (d, J=7.3 Hz, 3 H); 1.40-1.45 (m, 1 H); 1.16-1.19 (m, 1 H); 1.00 (d, J=6.8 Hz, 3 H); 0.89 (d, J=6.9 Hz, 3 H).

Intermediate 3

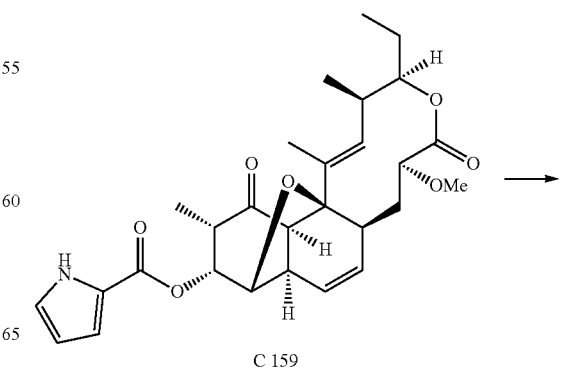

C 159

55
-continued

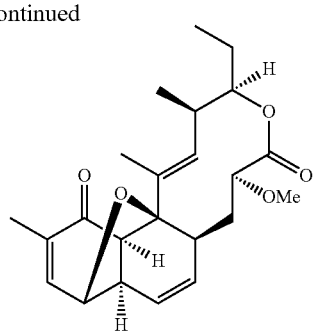

Intermediate 3

(3R,4R,7S,8aS,10aR,11R,14aR,14bS,E)-4-ethyl-7-methoxy-1,3,13-trimethyl-3,4,8,8a,10a,11-hexahydro-11,14b-epoxynaphtho[2,1-e]oxecine-6,14(7H,14aH)-dione To a mixture of (3R,4R,7S,8aS,10aR,11R,12R,13S,14aR,14bS,E)-4-ethyl-7-methoxy-1,3,13-trimethyl-6,14-dioxo-3,4,6,7,8,8a,10a,11,12,13,14,14a-dodecahydro-11,14b-epoxynaphtho[2,1-e]oxecin-12-yl 1H-pyrrole-2-carboxylate (C 159, described in Example 159; 26 mg, 0.05 mmol) in toluene (0.5 mL) was added pyrrolidine (17 μL, 0.2 mmol) and acetic acid (12 μL, 0.2 mmol) and the resulting mixture was stirred at room temperature overnight. The reaction was then heated to 50° C. for four hours. After cooling to room temperature, the reaction mixture was purified by preparative thin layer chromatography (4:1 Hexanes:Ethyl Acetate) to give the Intermediate Compound (3R,4R,7S,8aS,10aR,11R,14aR,14bS,E)-4-ethyl-7-methoxy-1,3,13-trimethyl-3,4,8,8a,10a,11-hexahydro-11,14b-epoxynaphtho[2,1-e]oxecine-6,14(7H,14aH)-dione (0.03 mmol).

1H NMR (500 MHz, CD$_3$OD): δ 7.18-7.19 (m, 1 H), 5.89-5.93 (m, 1 H), 5.69 (dd, 1 H), 5.35 (d, 1 H), 5.11 (ddd, 1 H), 4.50 (d, 1 H), 3.68 (dd, 1 H), 3.46 (t, 1 H), 3.29 (s, 3 H), 3.21 (s, 1 H), 3.18 (t, 1 H), 2.78 (d, 1 H), 2.60-2.63 (m, 1 H), 2.45 (ddd, 1 H), 1.65 (d, 3 H), 1.60 (s, 3 H), 1.50-1.54 (m, 1 H), 1.01 (d, 3 H), 0.93-0.96 (m, 3 H).

EXAMPLES

Example 1

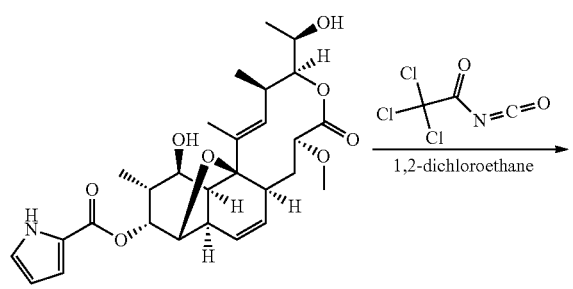

56
-continued

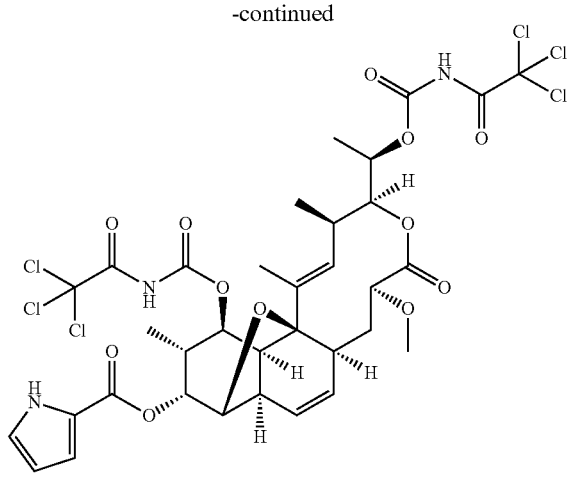

(3R,4S,7S,8aS,10aR,11R,12R,13R,14R,14aS,14bS,E)-7-methoxy-1,3,13-trimethyl-6-oxo-14-(((2,2,2-trichloroacetyl)carbamoyl)oxy)-4-((R)-1-(((2,2,2-trichloroacetyl)carbamoyl)oxy)ethyl)-3,4,6,7,8,8a,10a,11,12,13,14,14a-dodecahydro-11,14b-epoxynaphtho[2,1-e]oxecin-12-yl 1H-pyrrole-2-carboxylate.

Trichloroacetyl isocyanate (0.6 μl, 4.85 μmol) was added to a stirred solution of Nargenicin (2.5 mg, 4.85 μmol) in 1,2-dichloroethane (0.25 ml). The reaction mixture was a colorless solution that was stirred at room temperature. After 1 hour, the reaction mixture was evaporated under reduced pressure. The resulting residue was purified on a Waters Sunfire C18, 30×150 mm column, eluting with Acetonitrile/Water +0.1% TFA at 20 ml/min using a 12 minute 20-100% Acetonitrile/Water gradient followed by a 6 minute Acetonitrile flush. The product fractions were combined, evaporated under reduced pressure, and lyophilized from benzene to give the title compound as a white solid. LC-MS: calculated for $C_{34}H_{37}Cl_6N_3O_{12}$ 891.05 observed m/e: 892.17 (M+H)$^+$ (Rt 2.62/4 min); $^1$H NMR δ (ppm) CD$_3$OD: 11.41 (s, 1 H); 6.99 (td, J=2.6, 1.4 Hz, 1 H); 6.92 (dt, J=3.6, 1.8 Hz, 1 H); 6.21 (dt, J=3.7, 2.3 Hz, 1 H); 5.94 (ddd, J=9.4, 7.0, 1.7 Hz, 1 H); 5.63 (dd, J=9.4, 3.0 Hz, 1 H); 5.58 (d, J=8.7 Hz, 1 H); 5.38 (t, J=6.6 Hz, 1 H); 5.24-5.28 (m, 1 H); 5.14 (t, J=4.9 Hz, 1 H); 4.21 (d, J=4.9 Hz, 1 H); 3.72 (dd, J=11.5, 3.7 Hz, 1 H); 3.17-3.23 (m, 1 H); 2.87 (d, J=2.5 Hz, 1 H); 2.82 (d, J=7.1 Hz, 1 H); 2.66-2.72 (m, 1 H); 2.51 (ddd, J=15.1, 11.6, 4.2 Hz, 1 H); 2.34 (s, 1 H); 1.61 (s, 3 H); 1.43 (d, J=6.3 Hz, 3 H); 1.39 (dt, J=15.2, 3.3 Hz, 1H); 1.19 (d, J=7.1 Hz, 3 H); 0.94 (d, J=6.8 Hz, 3 H).

Example 2

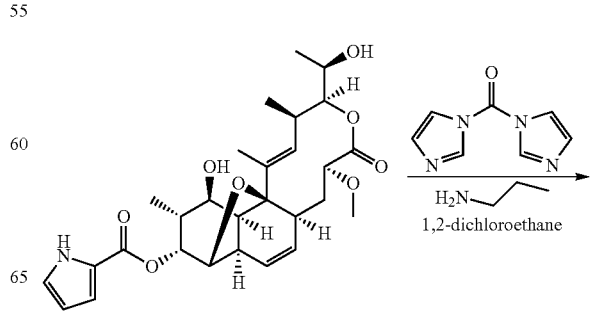

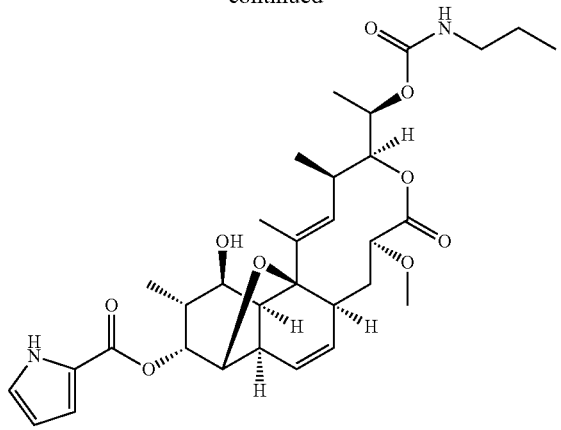

(3R,4S,7S,8aS,10aR,11R,12R,13R,14R,14aS,14bS,E)-14-hydroxy-7-methoxy-1,3,13-trimethyl-6-oxo-4-((R)-1-((propylcarbamoyl)oxy)ethyl)-3,4,6,7,8,8a,10a,11,12,13,14,14a-dodecahydro-11,14b-epoxynaphtho[2,1-e]oxecin-12-yl 1H-pyrrole-2-carboxylate N,N'-Carbonyldiimidazole (1.3 mg, 8.02 μmol) was added to a stirred solution of Nargenicin (4.0 mg, 7.76 μmol) in 1,2-dichloroethane (0.25 ml). The reaction mixture was a colorless solution that was stirred at room temperature. After 5.5 hours, N-propylamine (3 μl, 0.037 mmol) was added to the reaction mixture. After an additional 16 hours, the reaction mixture was evaporated and the resulting residue was placed under high vacuum. The residue was purified on a Waters Sunfire C18, 30×150 mm column, eluting with Acetonitrile/Water +0.1% TFA at 20 ml/min using a 17 minute 20-100% Acetonitrile/Water gradient followed by a 2 minute Acetonitrile flush. The product fractions were combined, evaporated under reduced pressure, and lyophilized from ethanol and benzene to give the title compound as a white solid. LC-MS: calculated for $C_{32}H_{44}N_2O_9$ 600.30 observed m/e: 601.27 (M+H)$^+$ (Rt 2.24/4 min); $^1$H NMR δ (ppm) CD$_3$OD: 11.28 (s, 1 H); 6.97 (td, J=2.7, 1.5 Hz, 1 H); 6.86 (ddd, J=3.6, 2.4, 1.5 Hz, 1 H); 6.19 (dt, J=3.7, 2.3 Hz, 1 H); 5.90 (ddd, J=9.4, 7.0, 1.7 Hz, 1 H); 5.59 (dd, J=9.4, 3.0 Hz, 1 H); 5.45 (d, J=7.5 Hz, 1 H); 5.29 (t, J=7.1 Hz, 1 H); 5.02 (t, J=4.9 Hz, 1 H); 4.96-5.00 (m, 1 H); 4.12 (d, J=4.9 Hz, 1 H); 3.66-3.71 (m, 2 H); 3.28 (s, 3 H); 3.05-3.09 (m, 3 H); 2.60 (d, J=7.0 Hz, 1 H); 2.46-2.52 (m, 2 H); 2.30-2.34 (m, 2 H); 1.77 (s, 3 H); 1.45-1.50 (m, 2 H); 1.31-1.37 (m, 2 H); 1.26 (d, J=6.5 Hz, 3 H); 1.15 (d, J=7.2 Hz, 3 H); 0.89-0.92 (m, 6 H).

Examples 3-25

Examples 3-25 were generally prepared according to the methods in Example 2.

| Examples | Structure | [M + H]+ |
|---|---|---|
| 3 | 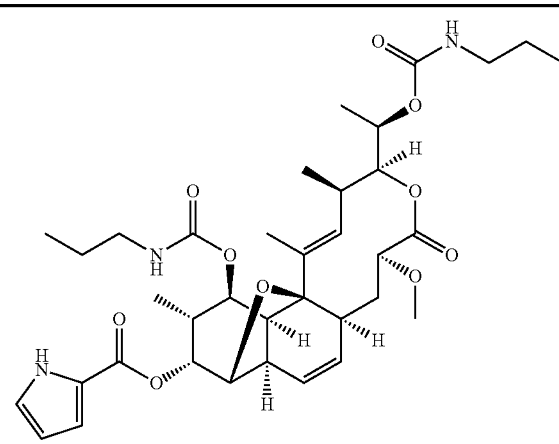 | 686.37 |
| 4 | 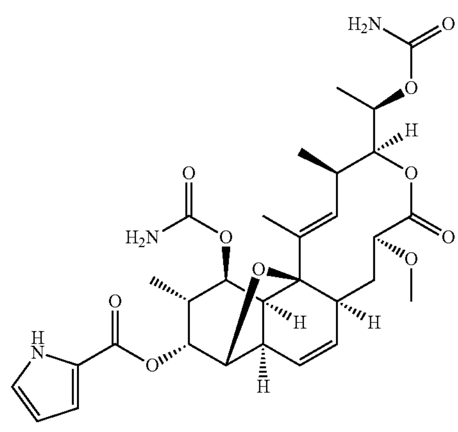 [SMILES: CO[C@H]1C[C@H]2C=C[C@H]3[C@H]4O[C@]2(/C(C)=C/[C@@H](C)[C@@H]([C@@H](C)OC(N)=O)OC1=O)[C@@H]3[C@H](OC(N)=O)[C@@H](C)[C@H]4OC(=O)c1ccc[nH]1] | 602.24 |

-continued
| Examples | Structure | [M + H]+ |
|---|---|---|
| 5 | 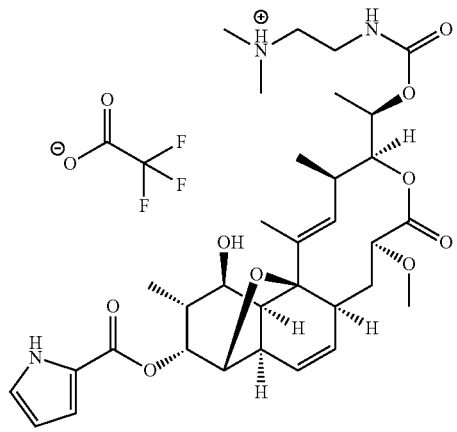 | 630.30 |
| 6 | 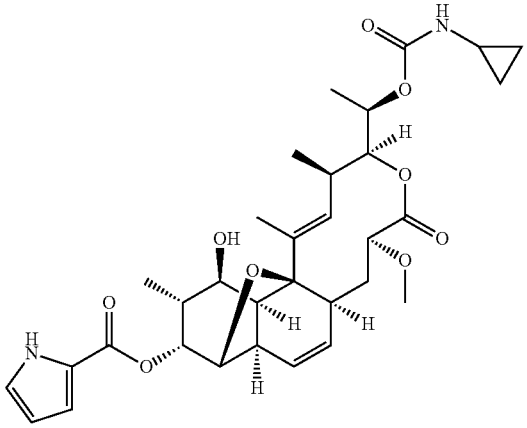 [SMILES: CO[C@H]1C[C@H]2C=C[C@H]3[C@H]4O[C@]2(/C(C)=C/[C@@H](C)[C@@H]([C@@H](C)OC(=O)NC2CC2)OC1=O)[C@@H]3[C@H](O)[C@@H](C)[C@H]4OC(=O)c1ccc[nH]1] | 599.28 |
| 7 | 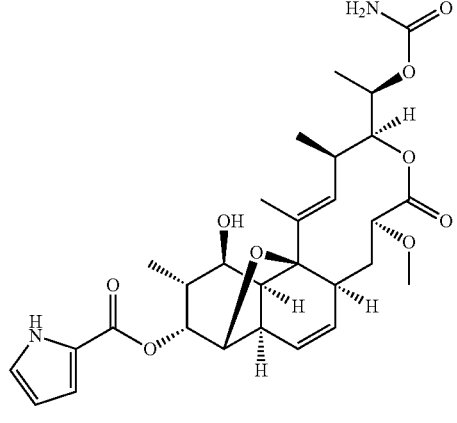 [SMILES: CO[C@H]1C[C@H]2C=C[C@H]3[C@H]4O[C@]2(/C(C)=C/[C@@H](C)[C@@H]([C@@H](C)OC(N)=O)OC1=O)[C@@H]3[C@H](O)[C@@H](C)[C@H]4OC(=O)c1ccc[nH]1] | [M + Na] 581.22 |

| Examples | Structure | [M + H]+ |
|---|---|---|
| 8 | 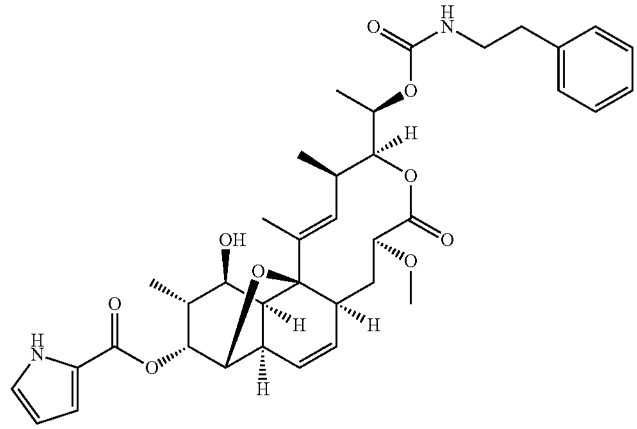 [SMILES: CO[C@H]1C[C@H]2C=C[C@H]3[C@H]4O[C@]2(/C(C)=C/[C@@H](C)[C@@H]([C@@H](C)OC(=O)NCCc2ccccc2)OC1=O)[C@@H]3[C@H](O)[C@@H](C)[C@H]4OC(=O)c1ccc[nH]1] | 663.33 |
| 9 | 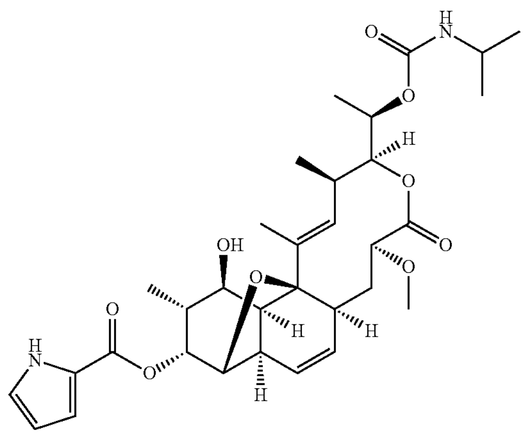 [SMILES: CO[C@H]1C[C@H]2C=C[C@H]3[C@H]4O[C@]2(/C(C)=C/[C@@H](C)[C@@H]([C@@H](C)OC(=O)NC(C)C)OC1=O)[C@@H]3[C@H](O)[C@@H](C)[C@H]4OC(=O)c1ccc[nH]1] | 601.30 |
| 10 | 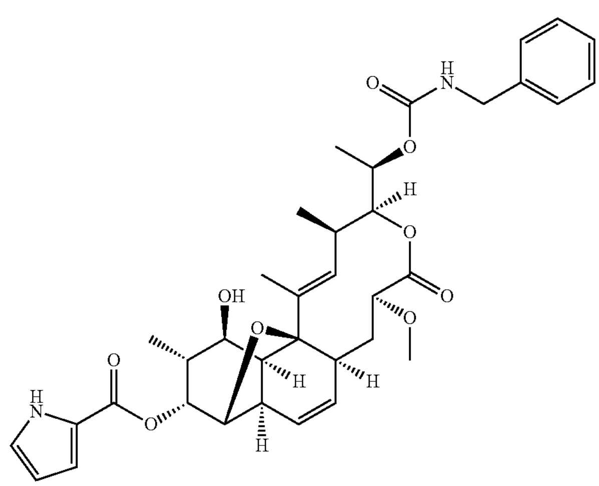 [SMILES: CO[C@H]1C[C@H]2C=C[C@H]3[C@H]4O[C@]2(/C(C)=C/[C@@H](C)[C@@H]([C@@H](C)OC(=O)NCc2ccccc2)OC1=O)[C@@H]3[C@H](O)[C@@H](C)[C@H]4OC(=O)c1ccc[nH]1] | 649.34 |

-continued

| Examples | Structure | [M + H]+ |
|---|---|---|
| 11 | 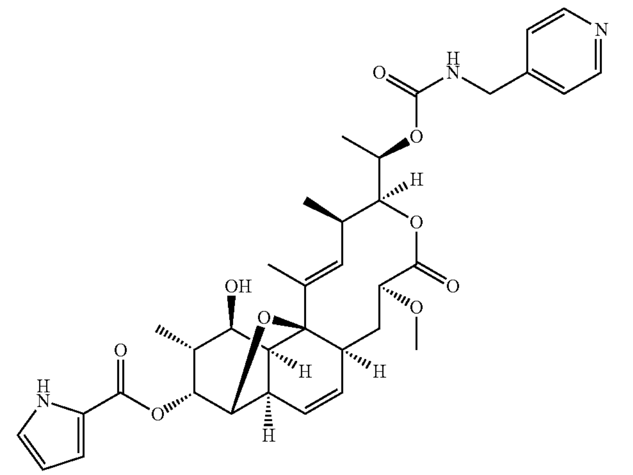 [SMILES: CO[C@H]1C[C@H]2C=C[C@H]3[C@H]4O[C@]2(/C(C)=C/[C@@H](C)[C@@H]([C@@H](C)OC(=O)NCc2ccncc2)OC1=O)[C@@H]3[C@H](O)[C@@H](C)[C@H]4OC(=O)c1ccc[nH]1] | 650.31 |
| 12 | | [M + Na] 639.52 | t-butyl ester was deblocked to the acid in 1:1 dichloromethane/trifluoroacetic acid

| | | |
|---|---|---|
| 13 | | [M + Na] 702.22 |

5 equivalents of triethylamine were used in this reaction.

| Examples | Structure | [M + H]+ |
|---|---|---|
| 14 | 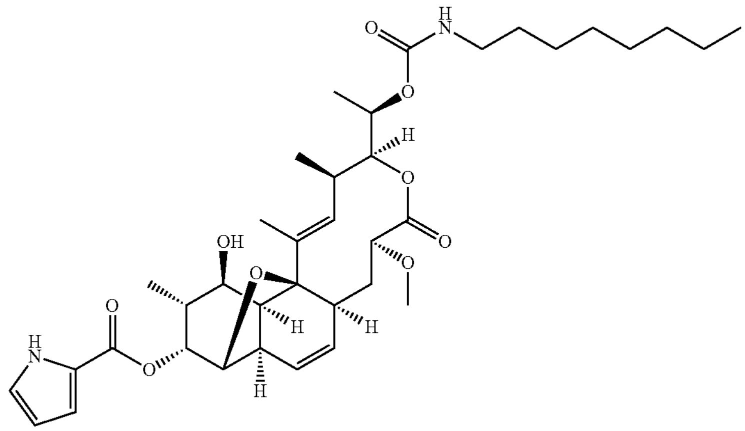 [SMILES: CCCCCCCCNC(=O)O[C@H](C)[C@H]1OC(=O)[C@@H](OC)C[C@H]2C=C[C@H]3[C@H]4O[C@]2(/C(C)=C/[C@H]1C)[C@@H]3[C@H](O)[C@@H](C)[C@H]4OC(=O)c1ccc[nH]1] | 671.32 |
| 15 | 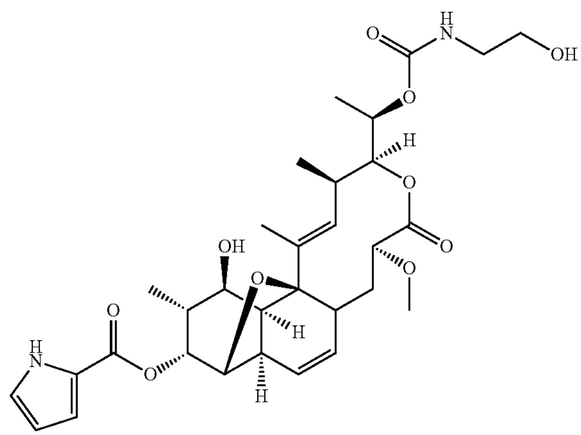 [SMILES: CO[C@H]1CC2C=C[C@H]3[C@H]4O[C@]2(/C(C)=C/[C@@H](C)[C@@H]([C@@H](C)OC(=O)NCCO)OC1=O)[C@@H]3[C@H](O)[C@@H](C)[C@H]4OC(=O)c1ccc[nH]1] | 603.22 |
| 16 | 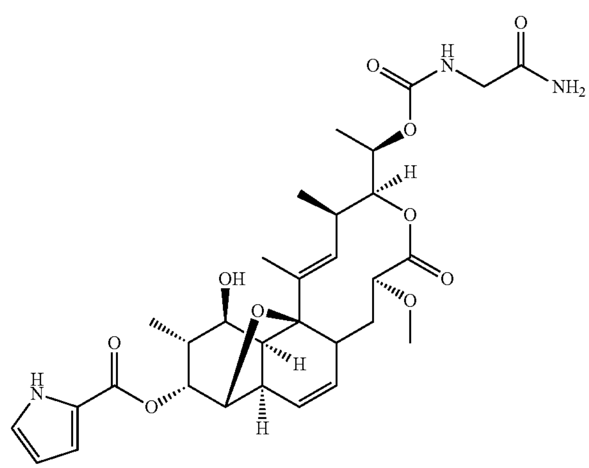 [SMILES: CO[C@H]1CC2C=C[C@H]3[C@H]4O[C@]2(/C(C)=C/[C@@H](C)[C@@H]([C@@H](C)OC(=O)NCC(N)=O)OC1=O)[C@@H]3[C@H](O)[C@@H](C)[C@H]4OC(=O)c1ccc[nH]1] | [M + Na] 638.18 |

5 equivalents of triethylamine were used in this reaction. The reaction mixture was evaporated and methanol was used as the solvent for the amine displacement of the imidazole ester.

| Examples | Structure | [M + H]+ |
|---|---|---|
| 17 | 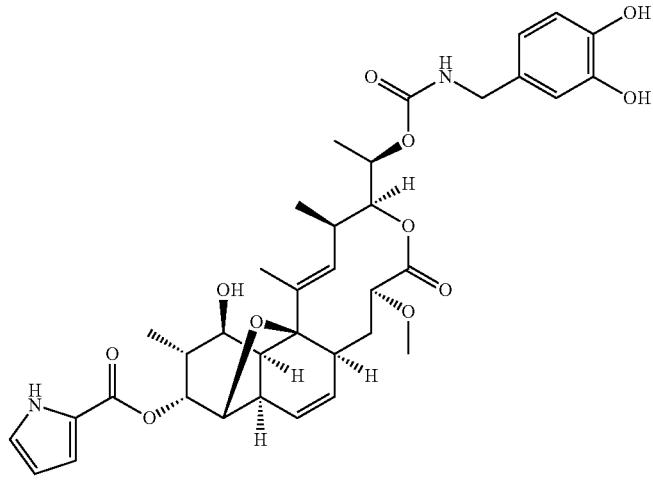 [SMILES: CO[C@H]1C[C@H]2C=C[C@H]3[C@H]4O[C@]2(/C(C)=C/[C@@H](C)[C@@H]([C@@H](C)OC(=O)NCc2ccc(O)c(O)c2)OC1=O)[C@@H]3[C@H](O)[C@@H](C)[C@H]4OC(=O)c1ccc[nH]1] | 681.19 |
5 equivalents of triethylamine were used in this reaction. The reaction mixture was evaporated and methanol was used as the solvent for the amine displacement of the imidazole ester.
| | | |
|---|---|---|
| 18 | 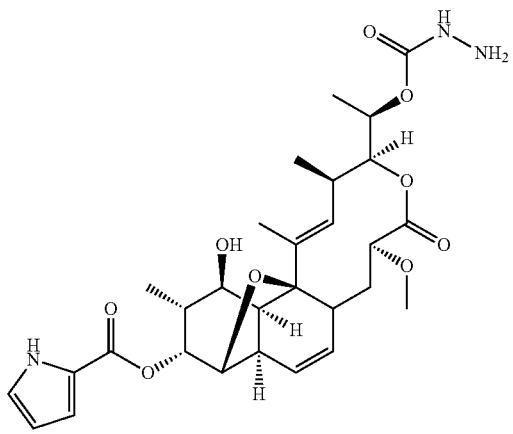 [SMILES: CO[C@H]1CC2C=C[C@H]3[C@H]4O[C@]2(/C(C)=C/[C@@H](C)[C@@H]([C@@H](C)OC(=O)NN)OC1=O)[C@@H]3[C@H](O)[C@@H](C)[C@H]4OC(=O)c1ccc[nH]1] | 574.18 |
| 19 | 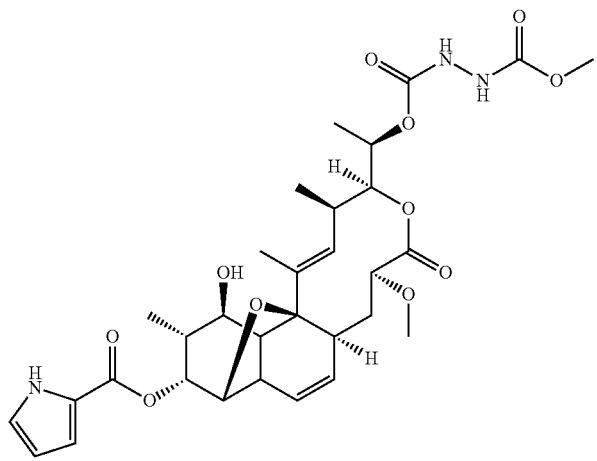 [SMILES: COC(=O)NNC(=O)O[C@H](C)[C@H]1OC(=O)[C@@H](OC)C[C@H]2C=CC3C4[C@H](O)[C@@H](C)[C@@H](OC(=O)c5ccc[nH]5)[C@@H]3O[C@]42/C(C)=C/[C@H]1C] | 614.25 |

| Examples | Structure | [M + H]+ |
|---|---|---|
| 20 | 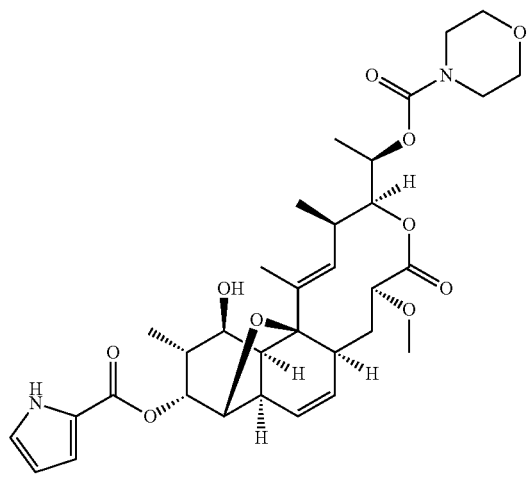 [SMILES: CO[C@H]1C[C@H]2C=C[C@H]3[C@H]4O[C@]2(/C(C)=C/[C@@H](C)[C@@H]([C@@H](C)OC(=O)N2CCOCC2)OC1=O)[C@@H]3[C@H](O)[C@@H](C)[C@H]4OC(=O)c1ccc[nH]1] | 629.28 |
| 21 | 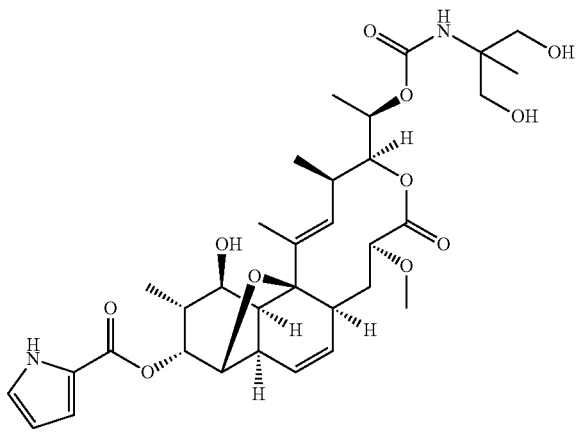 [SMILES: CO[C@H]1C[C@H]2C=C[C@H]3[C@H]4O[C@]2(/C(C)=C/[C@@H](C)[C@@H]([C@@H](C)OC(=O)NC(C)(CO)CO)OC1=O)[C@@H]3[C@H](O)[C@@H](C)[C@H]4OC(=O)c1ccc[nH]1] | 647.31 |
The reaction mixture was evaporated and ethanol was used as the solvent for the amine displacement of the imidazole ester.
| | | |
|---|---|---|
| 22 | 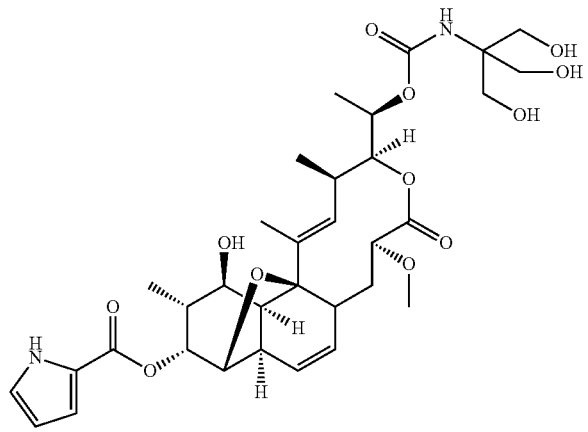 [SMILES: CO[C@H]1CC2C=C[C@H]3[C@H]4O[C@]2(/C(C)=C/[C@@H](C)[C@@H]([C@@H](C)OC(=O)NC(CO)(CO)CO)OC1=O)[C@@H]3[C@H](O)[C@@H](C)[C@H]4OC(=O)c1ccc[nH]1] | 663.29 |
The reaction mixture was evaporated and isopropanol was used as the solvent for the amine displacement of the imidazole ester and the reaction mixture was heated at 50 °C. for 3 days.

| Examples | Structure | [M + H]+ |
|---|---|---|
| 23 | 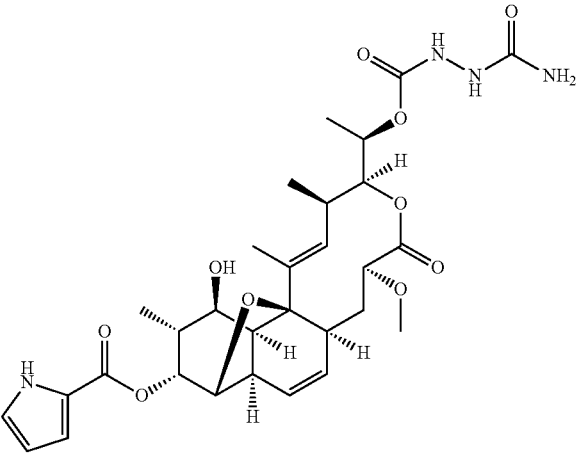 [SMILES: CO[C@H]1C[C@H]2C=C[C@H]3[C@H]4O[C@]2(/C(C)=C/[C@@H](C)[C@@H]([C@@H](C)OC(=O)NNC(N)=O)OC1=O)[C@@H]3[C@H](O)[C@@H](C)[C@H]4OC(=O)c1ccc[nH]1] | [M + 23] 639.28 |
6 equivalents of triethylamine were used in this reaction. The reaction mixture was evaporated and isopropanol was used as the solvent for the amine displacement of the imidazole ester and the reaction mixture was heated at 50 °C. for 1 day.
| | | |
|---|---|---|
| 24 | 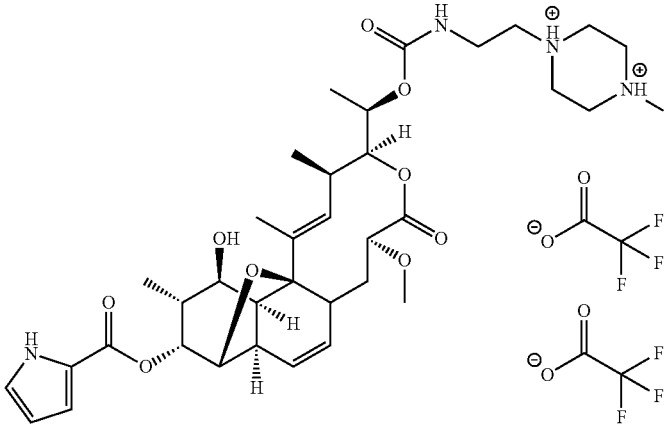 | 685.35 |
| 25 | 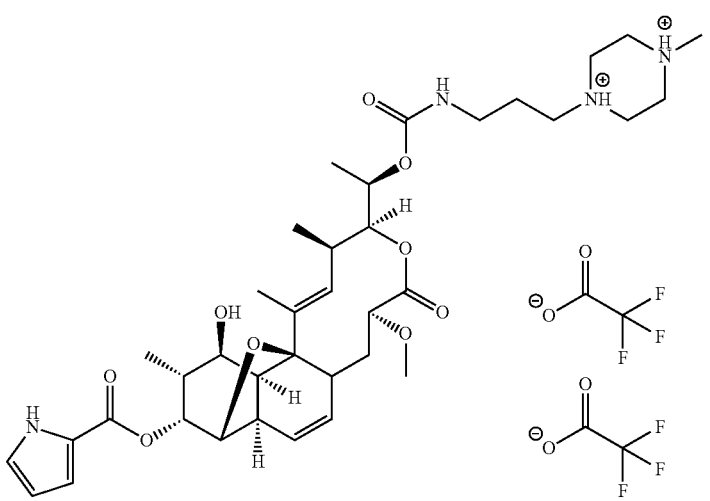 | 699.36 |

Example 26

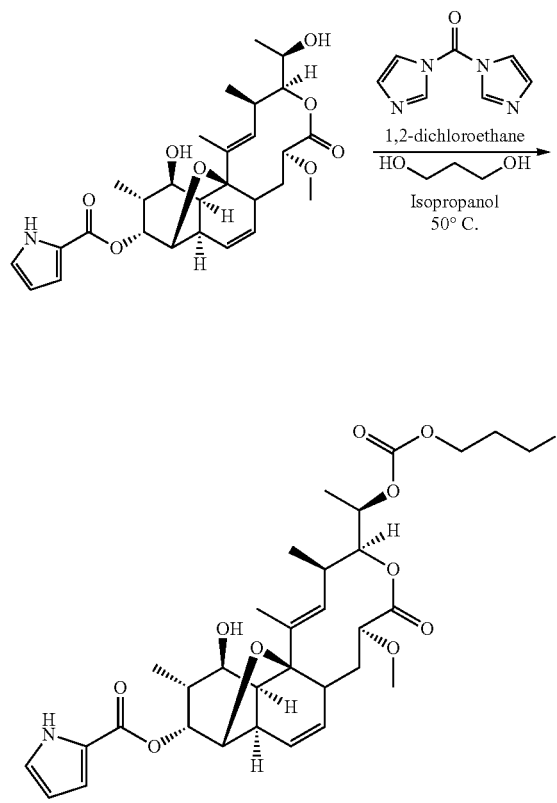

(3R,4S,7S,10aR,11R,12R,13R,14R,14aS,14bS,E)-14-hydroxy-4-((R)-1-(((3-hydroxypropoxy)carbonyl)oxy)ethyl)-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate N,N'-carbonyldiimidazole (5.7 mg, 0.035 mmol) was added to a stirred solution of Nargenicin (8.9 mg, 0.017 mmol) in 1,2-dichloroethane (0.35 ml). The reaction mixture was a colorless solution that was stirred at room temperature. After 1.5 hours, the reaction mixture was evaporated to give a colorless residue, which was dissolved in isopropanol (0.35 ml) to give a colorless solution. 1,3-propanediol (0.02 ml, 0.277 mmol) was added to the reaction mixture, which was heated to 50° C. After 4 days, the reaction mixture was cooled to room temperature and evaporated. The resulting residue was purified on a Waters Sunfire C18, 30×150 mm column, eluting with Acetonitrile/Water +0.1% TFA at 20 ml/min using a 17 minute 20-100% Acetonitrile/Water gradient followed by a 2 minute Acetonitrile flush. The product fractions were combined, evaporated under reduced pressure, and lyophilized from ethanol and benzene to give the title compound as a white solid. LC-MS: calculated for $C_{32}H_{43}NO_{11}$ 617.28 observed m/e: 640.52 (M+Na) (Rt 1.90/4 min); $^1$H NMR δ (ppm) CD$_3$OD: 11.28 (s, 1 H); 6.97 (td, J=2.7, 1.5 Hz, 1 H); 6.86 (dt, J=3.7, 1.9 Hz, 1 H); 6.19 (dt, J=3.7, 2.4 Hz, 1 H); 5.90 (ddd, J=9.4, 6.9, 1.8 Hz, 1 H); 5.59 (dd, J=9.4, 3.0 Hz, 1 H); 5.46 (dd, J=8.1, 1.5 Hz, 1 H); 5.29 (t, J=6.7 Hz, 1 H); 4.98-5.04 (m, 2 H); 4.25 (t, J=6.4 Hz, 2 H); 4.12 (d, J=4.9 Hz, 1 H); 3.66-3.71 (m, 2 H); 3.63 (t, J=6.2 Hz, 2 H); 3.28 (s, 3 H); 3.12 (h, J=7.2 Hz, 1 H); 2.60 (d, J=7.0 Hz, 1 H); 2.50 (ddd, J=15.1, 11.6, 4.1 Hz, 1 H); 2.46 (d, J=2.6 Hz, 1 H); 2.28-2.33 (m, 2 H); 1.87 (p, J=6.3 Hz, 2 H); 1.77 (s, 3 H); 1.33-1.36 (m, 3 H); 1.16 (d, J=7.1 Hz, 3 H); 0.92 (d, J=6.9 Hz, 3 H).

Examples 27-36

Examples 27-36 were generally prepared according to the methods in Example 26.

| Example | Structure | [M + H]+ |
|---|---|---|
| 27 | 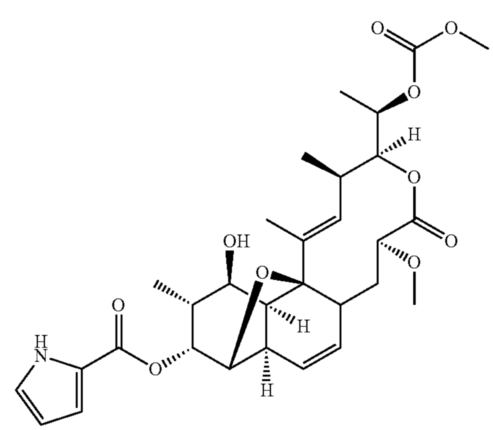 [SMILES: COC(=O)O[C@H](C)[C@H]1OC(=O)[C@@H](OC)CC2C=C[C@H]3[C@H]4O[C@]2(/C(C)=C/[C@H]1C)[C@@H]3[C@H](O)[C@@H](C)[C@H]4OC(=O)c1ccc[nH]1] | [M + Na] 596.18 |

-continued
| Example | Structure | [M + H]+ |
|---|---|---|
| 28 | 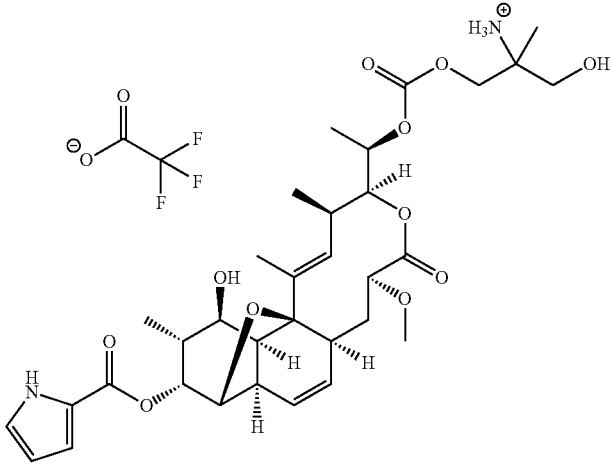 [SMILES: CO[C@H]1C[C@H]2C=C[C@H]3[C@H]4O[C@]2(/C(C)=C/[C@@H](C)[C@@H]([C@@H](C)OC(=O)OCC(C)([NH3+])CO)OC1=O)[C@@H]3[C@H](O)[C@@H](C)[C@H]4OC(=O)c1ccc[nH]1 ; O=C([O-])C(F)(F)F] | 647.29 |
| 29 | 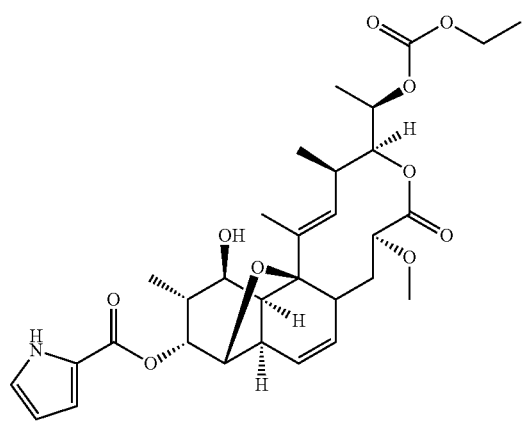 [SMILES: CCOC(=O)O[C@H](C)[C@H]1OC(=O)[C@@H](OC)CC2C=C[C@H]3[C@H]4O[C@]2(/C(C)=C/[C@H]1C)[C@@H]3[C@H](O)[C@@H](C)[C@H]4OC(=O)c1ccc[nH]1] | [M + Na] 610.18 |
| 30 | 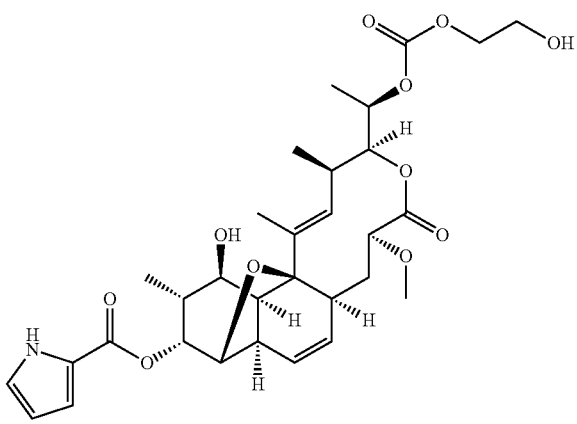 [SMILES: CO[C@H]1C[C@H]2C=C[C@H]3[C@H]4O[C@]2(/C(C)=C/[C@@H](C)[C@@H]([C@@H](C)OC(=O)OCCO)OC1=O)[C@@H]3[C@H](O)[C@@H](C)[C@H]4OC(=O)c1ccc[nH]1] | [M + Na] 626.22 |

-continued

| Example | Structure | [M + H]+ |
|---|---|---|
| 31 | 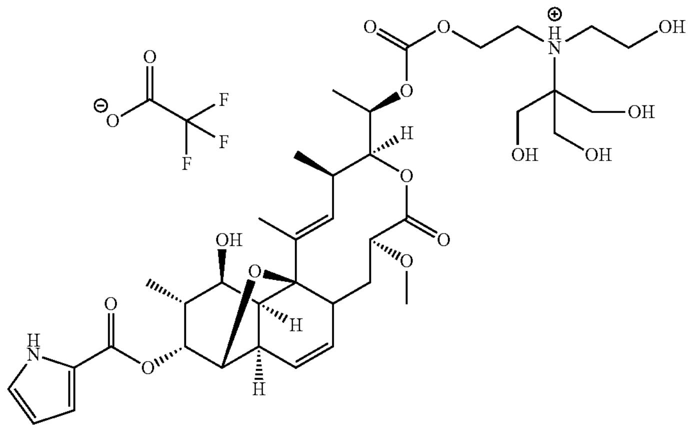 | 751.76 |
| 32 | 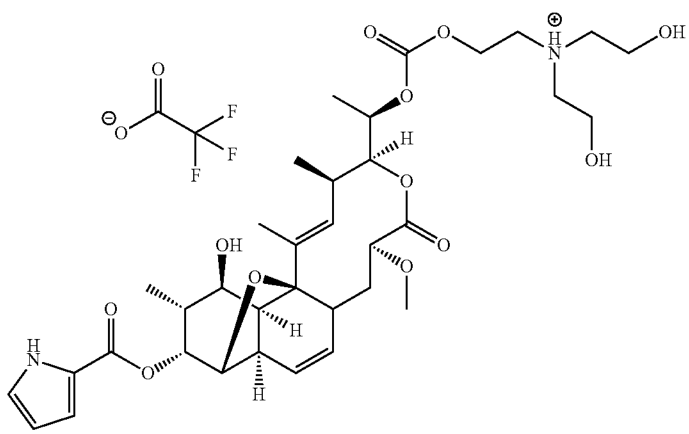 | 691.67 |
| 33 | 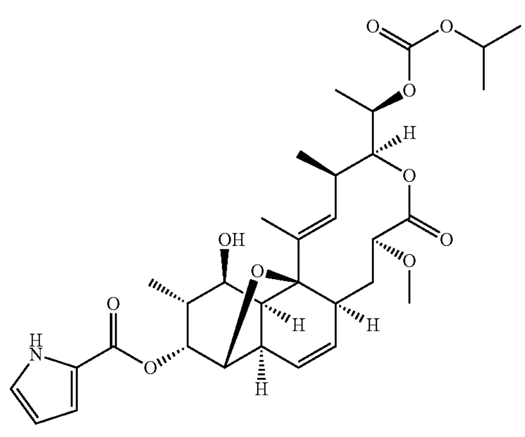 [SMILES: CO[C@H]1C[C@H]2C=C[C@H]3[C@H]4O[C@]2(/C(C)=C/[C@@H](C)[C@@H]([C@@H](C)OC(=O)OC(C)C)OC1=O)[C@@H]3[C@H](O)[C@@H](C)[C@H]4OC(=O)c1ccc[nH]1] | [M + Na] 624.28 |

-continued

| Example | Structure | [M + H]+ |
|---------|-----------|----------|
| 34 | Isomer A | [M + Na] 680.28 |
| 35 | Isomer B | [M + Na] 680.30 |
| 36 | 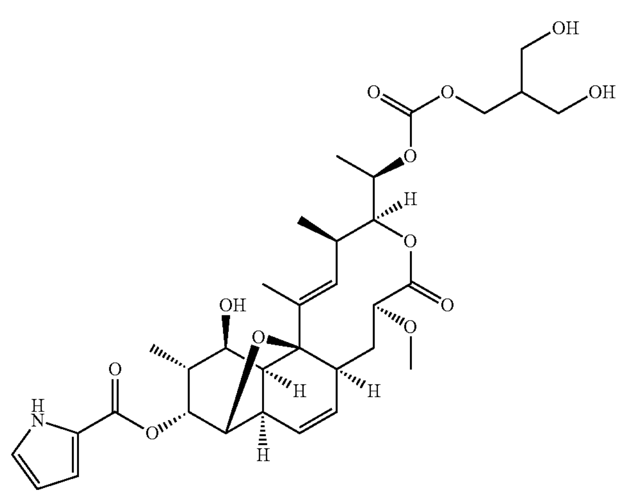 [SMILES: CO[C@H]1C[C@H]2C=C[C@H]3[C@H]4O[C@]2(/C(C)=C/[C@@H](C)[C@@H]([C@@H](C)OC(=O)OCC(CO)CO)OC1=O)[C@@H]3[C@H](O)[C@@H](C)[C@H]4OC(=O)c1ccc[nH]1] | [M + Na] 670.21 |

Example 37

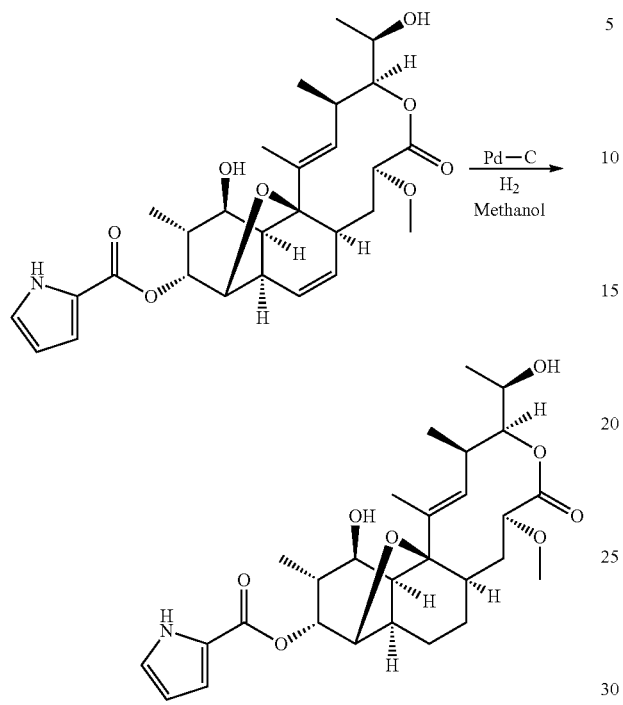

(3R,4S,7S,8aR,10aR,11R,12R,13R,14R,14aS,14bS,
E)-14-hydroxy-4-((R)-1-hydroxyethyl)-7-methoxy-
1,3,13-trimethyl-6-oxo-3,4,6,7,8,8a,9,10,10a,11,12,
13,14,14a-tetradecahydro-11,14b-epoxynaphtho[2,1-
e]oxecin-12-yl 1H-pyrrole-2-carboxylate Nargenicin (3.9 mg, 7.56 μmol), palladium on carbon (0.8 mg, 0.752 μmol), and methanol (0.5 ml) were combined in a 5 ml flask. The reaction mixture was degassed (3×) and purged with hydrogen before being placed under a hydrogen balloon. After 2 hours, the hydrogen balloon was removed and the reaction mixture was degassed (2×). The reaction mixture was filtered (0.45 μm syringe filter) and diluted with methanol before being purified on a Waters Sunfire C18, 30×150 mm column, eluting with Acetonitrile/Water +0.1% TFA at 20 ml/min using a 17 minute 20-100% Acetonitrile/Water gradient followed by a 2 minute Acetonitrile flush. The product fractions were combined, evaporated under reduced pressure, and lyophilized from ethanol and benzene to give the title compound as a white solid. LC-MS: calculated for $C_{28}H_{39}NO_8$ 517.27 observed m/e: 540.20 (M+Na) (Rt 1.90/4 min); $^1$H NMR δ (ppm) $CD_3OD$: 6.96 (dd, J=2.5, 1.5 Hz, 1 H); 6.84 (dd, J=3.7, 1.5 Hz, 1 H); 6.18 (dd, J=3.7, 2.5 Hz, 1 H); 5.43 (d, J=9.0 Hz, 1 H); 5.05 (t, J=4.9 Hz, 1 H); 4.08 (d, J=4.9 Hz, 1 H); 3.97-4.01 (m, 1 H); 3.70 (dd, J=6.6, 3.7 Hz, 1 H); 3.63 (dd, J=10.9, 2.6 Hz, 1 H); 3.26 (s, 3 H); 3.19-3.24 (m, 1 H); 2.34-2.39 (m, 2 H); 2.24 (d, J=2.6 Hz, 1 H); 2.08-2.13 (m, 1 H); 1.85 (s, 3 H); 1.78-1.82 (m, 1 H); 1.59-1.73 (m, 4 H); 1.27-1.31 (m, 2 H); 1.24 (d, J=6.2 Hz, 3 H); 1.15 (d, J=7.0 Hz, 3 H); 0.91 (d, J=6.9 Hz, 3 H).

Example 38

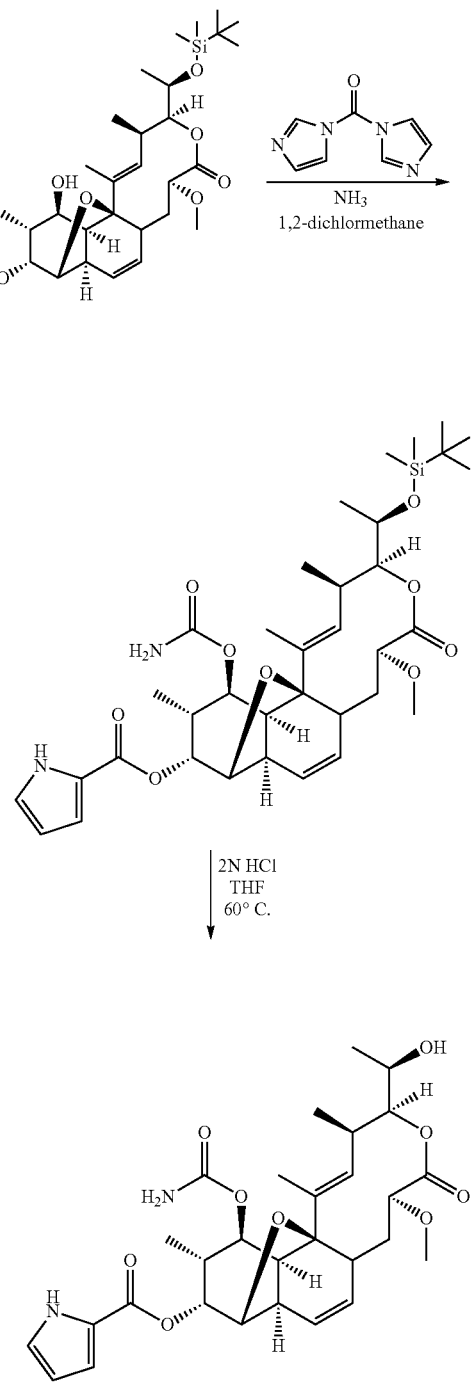

(3R,4S,7S,10aR,11R,12R,13R,14R,14aS,14bS,E)-
14-(carbamoyloxy)-4-((R)-1-hydroxyethyl)-7-
methoxy-1,3,13-trimethyl-6-oxo-3,4,6,7,8,8a,10a,11,
12,13,14,14 a-dodecahydro-11,14b-epoxynaphtho[2,
1-e]oxecin-12-yl 1H-pyrrole-2-carboxylate N,N'-carbonyldiimidazole (13.0 mg, 0.080 μmol) was added to a stirred solution of (3R,4S,7S,10aR,11R,12R,13R, 14R,14aS,14bS,E)-4-((R)-1-((tert-butyldimethylsilyl)oxy)

ethyl)-14-hydroxy-7-methoxy-1,3,13-trimethyl-6-oxo-3,4, 6,7,8,8a,10a,11,12,13,14,14a-dodecahydro-11,14b-epoxynaphtho[2,1-e]oxecin-12-yl 1H-pyrrole-2-carboxylate (6.9 mg, 10.95 μmol) in 1,2-dichloroethane (0.25 ml). The reaction mixture was a colorless solution that was stirred at room temperature. After 3 hours, ammonia was blown into the reaction mixture for 1 minute. After another 17.5 hours, additional 1,2-dichloroethane (0.1 ml) was added and ammonia was blown into the reaction mixture for 1 minute. After an additional 22 hours, the reaction mixture was evaporated under reduced pressure. The resulting residue was dissolved in tetrahydrofuran (0.6 ml) and 2N HCl (0.1 ml) was added to the resulting solution. The reaction mixture was heated to 60° C. After 5 hours, the reaction mixture was cooled to room temperature and evaporated under reduced pressure. The residue was dissolved in methanol and purified on a Waters Sunfire C18, 30×150 mm column, eluting with Acetonitrile/Water +0.1% TFA at 20 ml/min using a 17 minute 20-100% Acetonitrile/Water gradient followed by a 2 minute Acetonitrile flush. The product fractions were combined, evaporated under reduced pressure, and lyophilized from ethanol and benzene to give the title compound as a white solid. LC-MS: calculated for $C_{29}H_{38}N_2O_9$ 558.26 observed m/e: 559.16 (M+Na) (Rt 1.96/4 min); $^1$H NMR δ (ppm) CD$_3$OD: 11.35 (s, 1 H); 6.98 (td, J=2.7, 1.5 Hz, 1 H); 6.90 (dt, J=3.7, 1.9 Hz, 1 H); 6.20 (dt, J=3.7, 2.4 Hz, 1 H); 5.91 (ddd, J=9.4, 7.0, 1.7 Hz, 1 H); 5.61 (dd, J=9.4, 3.0 Hz, 1 H); 5.48 (dd, J=7.3, 1.5 Hz, 1 H); 5.14 (t, J=7.1 Hz, 1 H); 5.07 (t, J=4.9 Hz, 1 H); 4.65 (dd, J=11.6, 2.6 Hz, 1 H); 4.17 (d, J=4.9 Hz, 1 H); 4.01 (dq, J=8.6, 6.2 Hz, 1 H); 3.72 (dd, J=11.4, 4.2 Hz, 1 H); 3.28 (s, 3 H); 3.05-3.11 (m, 1 H); 2.73 (d, J=7.0 Hz, 1 H); 2.66 (d, J=2.5 Hz, 1 H); 2.54-2.60 (m, 1 H); 2.47 (ddd, J=15.0, 11.4, 3.9 Hz, 1 H); 2.28 (s, 1 H); 1.71 (s, 3 H); 1.35 (dt, J=15.0, 3.8 Hz, 1 H); 1.24 (d, J=7.1 Hz, 3 H); 1.21 (d, J=6.2 Hz, 3 H); 0.86 (d, J=6.8 Hz, 3 H).

Example 39

Example 39 was generally prepared according to the methods in Example 38.

| Examples | Structure | [M + H]+ |
|---|---|---|
| 39 | 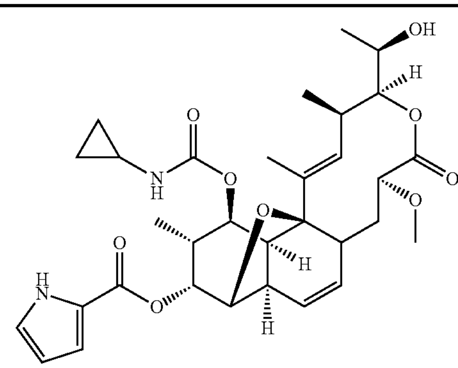 | 599.24 |

Example 40

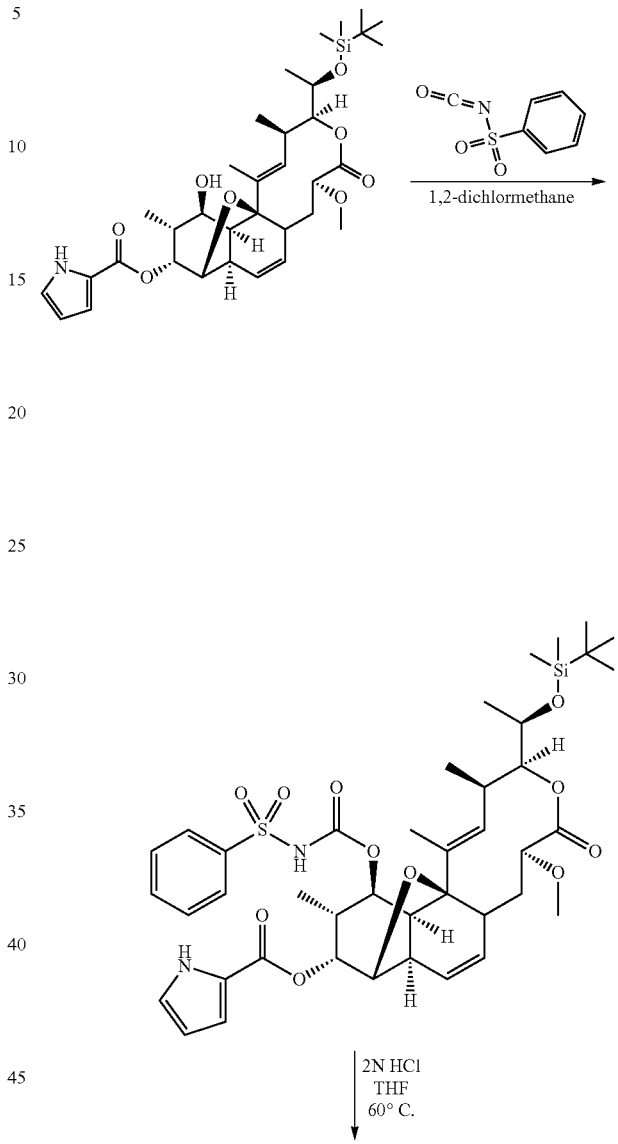

-continued

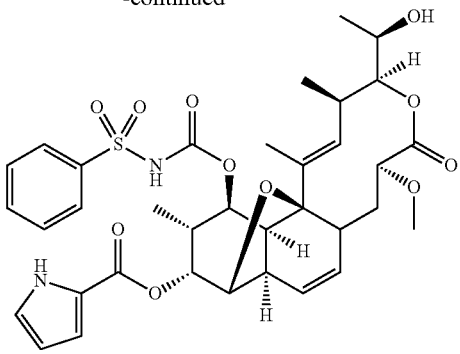

(3R,4S,7S,10aR,11R,12R,13R,14R,14aS,14bS,E)-4-((R)-1-hydroxyethyl)-7-methoxy-1,3,13-trimethyl-6-oxo-14-(((phenylsulfonyl)carbamoyl)oxy)-3,4,6,7,8,8a,10a,11,12,13,14,14a-dodecahydro-11,14b-epoxynaphtho[2,1-e]oxecin-12-yl 1H-pyrrole-2-carboxylate Benzenesulfonyl isocyanate (10 μl, 0.075 mmol) was added to a stirred solution of (3R,4S,7S,10aR,11R,12R,13R,14R,14aS,14bS,E)-4-((R)-1-(((tert-butyldimethylsilyl)oxy)ethyl)-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate (4.9 mg, 7.78 μmol) in 1,2-dichloroethane (0.25 ml). After 1.5 hours, the reaction mixture was evaporated to give a white residue. The residue was dissolved in 0.4 ml tetrahydrofuran before adding 0.08 ml 2N HCl. The resulting solution was heated at 60° C. After 3.5 hours, the reaction mixture was cooled to room temperature before being evaporated under reduced pressure to give a white residue. The residue (loaded in methanol) was purified on a Waters Sunfire C18, 30×150 mm column, eluting with Acetonitrile/Water +0.1% TFA at 20 ml/min using a 17 minute 20-100% Acetonitrile/Water gradient followed by a 2 minute Acetonitrile flush. The product fractions were combined, evaporated under reduced pressure, and lyophilized from ethanol and benzene to give the title compound as a white solid. LC-MS: calculated for $C_{35}H_{42}N_2O_{11}S$ 698.25 observed m/e: 699.26 (M+H)$^+$ (Rt 2.24/4 min); $^1$H NMR δ (ppm) CD$_3$OD: 11.37 (s, 1 H); 7.99-8.00 (m, 1 H); 7.98-7.99 (m, 1 H); 7.69-7.72 (m, 1 H); 7.59-7.62 (m, 2 H); 6.98 (td, J=2.7, 1.5 Hz, 1 H); 6.90 (ddd, J=3.7, 2.4, 1.5 Hz, 1 H); 6.21 (dt, J=3.7, 2.4 Hz, 1 H); 5.89 (ddd, J=9.3, 7.0, 1.7 Hz, 1 H); 5.60 (dd, J=9.3, 3.1 Hz, 1 H); 5.47 (dd, J=7.3, 1.4 Hz, 1 H); 5.13 (dd, J=8.6, 6.0 Hz, 1 H); 5.06 (t, J=4.9 Hz, 1 H); 4.64 (dd, J=11.5, 2.6 Hz, 1 H); 4.16 (d, J=4.9 Hz, 1 H); 3.99-4.04 (m, 1 H); 3.71 (dd, J=11.5, 4.2 Hz, 1 H); 3.29 (s, 3 H); 3.03-3.10 (m, 1 H); 2.71 (d, J=7.0 Hz, 1 H); 2.64 (d, J=2.5 Hz, 1 H); 2.52-2.59 (m, 1 H); 2.44 (ddd, J=15.0, 11.5, 3.8 Hz, 1 H); 2.16-2.18 (m, 1 H); 1.45 (s, 3 H); 1.30-1.36 (m, 1 H); 1.26 (d, J=7.1 Hz, 3 H); 1.24 (d, J=6.2 Hz, 3 H); 0.79 (d, J=6.8 Hz, 3 H).

Example 41

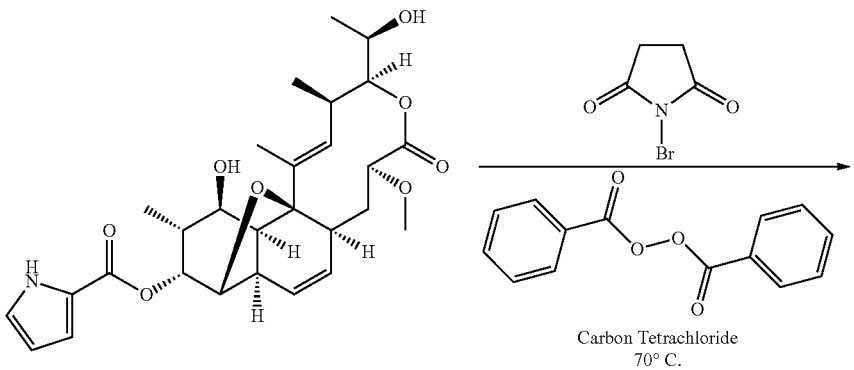

Carbon Tetrachloride
70° C.

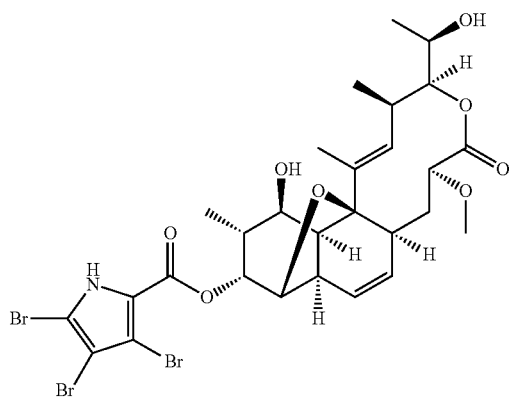

(3R,4S,7S,8aS,10aR,11R,12R,13R,14R,14aS,14bS,E)-14-hydroxy-4-((R)-1-hydroxyethyl)-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 3,4,5-tribromo-1H-pyrrole-2-carboxylate N-bromosuccinimide (2.5 mg, 0.014 mmol) and benzoyl peroxide (1.1 mg, 4.54 μmol) were added to a stirred suspension of Nargenicin (6.1 mg, 0.012 mmol) in carbon tetrachloride (0.25 ml). The reaction mixture was an opaque suspension that was heated to 70° C. After 5 hours, the reaction mixture was cooled to room temperature and evaporated under reduced pressure. The resulting residue (loaded in methanol) was purified on a Waters Sunfire C18, 30×150 mm column, eluting with Acetonitrile/Water +0.1% TFA at 20 ml/min using a 17 minute 20-100% Acetonitrile/Water gradient followed by a 2 minute Acetonitrile flush. The product fractions were combined, evaporated under reduced pressure, and lyophilized from ethanol and benzene to give the title compound as a white solid. $C_{28}H_{34}Br_3NO_8$ $^1$H NMR δ (ppm) CD$_3$OD: 5.89 (ddd, J=9.4, 6.9, 1.7 Hz, 1 H); 5.60 (dd, J=9.3, 3.1 Hz, 1 H); 5.43 (dd, J=7.1, 1.5 Hz, 1 H); 5.13 (t, J=4.9 Hz, 1 H); 4.11 (d, J=4.9 Hz, 1 H); 3.98 (dq, J=8.7, 6.1 Hz, 1 H); 3.75 (dd, J=11.0, 2.7 Hz, 1 H); 3.71 (dd, J=11.4, 4.3 Hz, 1 H); 3.62-3.64 (m, 1 H); 3.28 (s, 3 H); 3.04-3.10 (m, 1 H); 2.73 (d, J=7.0 Hz, 1 H); 2.44-2.49 (m, 2 H); 2.33-2.39 (m, 1 H); 2.28-2.29 (m, 1 H); 1.81 (s, 3 H); 1.34 (dt, J=14.9, 4.1 Hz, 1 H); 1.24 (d, J=7.1 Hz, 3 H); 1.20 (d, J=6.2 Hz, 3 H); 0.94 (d, J=6.9 Hz, 3 H).

Examples 42-46

Examples 42-46 were generally prepared according to the methods in Example 41.

| Examples | Structure | $^1$H NMR δ (ppm) CD$_3$OD or [M + H]+ |
|---|---|---|
| 42 | 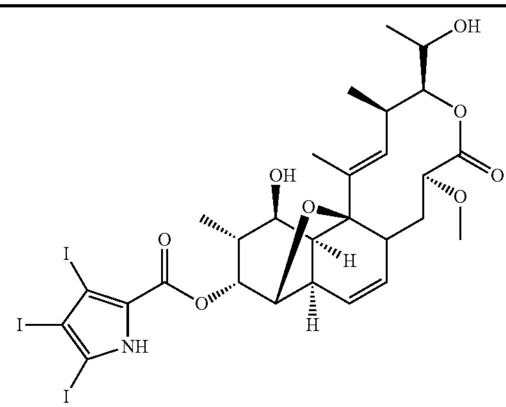 | M + 1-H$_2$O = 876.98 |
| 43 | 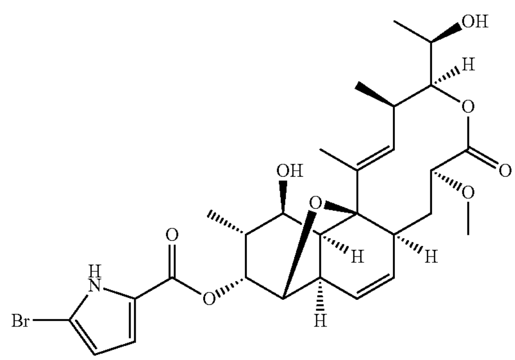 | 6.80 (d, J = 3.9 Hz, 1 H); 6.17 (d, J = 3.9 Hz, 1 H); 5.90 (ddd, J = 9.4, 7.0, 1.6 Hz, 1 H); 5.60 (dd, J = 9.4, 3.0 Hz, 1 H); 5.43 (dd, J = 7.1, 1.5 Hz, 1 H); 5.12 (t, J = 7.4 Hz, 1 H); 5.02 (t, J = 4.9 Hz, 1 H); 4.10 (d, J = 4.8 Hz, 1 H); 3.98 (dq, J = 8.7, 6.2 Hz, 1 H); 3.71 (dd, J = 11.4, 4.3 Hz, 1 H); 3.68 (dd, J = 11.2, 2.7 Hz, 1 H); 3.62-3.63 (m, 1 H); 3.28 (s, 3 H); 3.03-3.09 (m, 1 H); 2.60 (d, J = 6.8 Hz, 1 H); 2.44-2.49 (m, 2 H); 2.28-2.34 (m, 1 H); 1.81 (s, 3 H); 1.34 (dt, J = 14.9, 4.1 Hz, 1 H); 1.24 (d, J = 7.1 Hz, 3 H); 1.20 (d, J = 6.2 Hz, 3 H); 0.91 (d, J = 6.9 Hz, 3 H). |
| | isolated from the reaction described in Example 41 | |
| 44 | 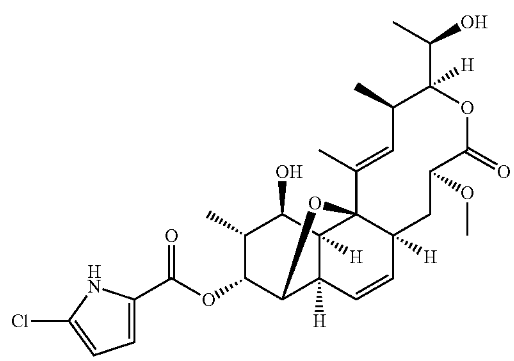 [SMILES: CO[C@H]1C[C@H]2C=C[C@H]3[C@H]4O[C@]2(/C(C)=C/[C@@H](C)[C@@H]([C@@H](C)O)OC1=O)[C@@H]3[C@H](O)[C@@H](C)[C@H]4OC(=O)c1ccc(Br)[nH]1] | M + 23 = 572 |

| Examples | Structure | ¹H NMR δ (ppm) CD₃OD or [M + H]+ |
|---|---|---|
| 46 | (structure shown) isolated from the reaction described in Example 41 | 11.68 (s, 1 H); 6.97-6.98 (m, 1 H); 6.81-6.82 (m, 1 H); 5.90 (ddd, J = 9.4, 7.0, 1.7 Hz, 1 H); 5.60 (dd, J = 9.3, 3.1 Hz, 1 H); 5.43 (dd, J = 7.1, 1.5 Hz, 1 H); 5.12 (t, J = 7.1 Hz, 1 H); 5.02 (t, J = 4.8 Hz, 1 H); 4.10 (d, J = 4.9 Hz, 1 H); 3.95-4.00 (m, 1 H); 3.71 (dd, J = 11.4, 4.2 Hz, 1 H); 3.66 (dd, J = 11.1, 2.7 Hz, 1 H); 3.62 (s, 1 H); 3.28 (s, 3 H); 3.03-3.09 (m, 1 H); 2.57 (d, J = 7.0 Hz, 1 H); 2.44-2.49 (m, 2 H): 2.28-2.35 (m, 2 H); 1.81 (s, 3 H); 1.32-1.36 (m, 1 H); 1.24 (d, J = 7.0 Hz, 3 H); 1.20 (d, J = 6.2 Hz, 3 H); 0.91 (d, J = 6.9 Hz, 3 H). |

Example 47

(3R,7S,8aS,10aR,11R,12R,13R,14R,14aS,14bS,E)-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate (S)-3-((1S,2S,4aR,5R,6R,7R,8R,8aS)-6-((1H-pyrrole-2-carbonyl)oxy)-8-hydroxy-14((R,E)-5-hydroxy-4-methylpent-2-en-2-yl)-7-methyl-1,2,4a,5,6,7,8,8a-octahydro-1,5-epoxynaphthalen-2-yl)-2-methoxypropanoic acid (S)-3-((1S,2S,4aR,5R,6R,7R,8R,8aS)-6-((1H-pyrrole-2-carbonyl)oxy)-8-hydroxy-7-methyl-1-((R,E)-4-methyl-5-oxopent-2-en-2-yl)-1,2,4a,5,6,7,8,8a-octahydro-1,5-epoxynaphthalen-2-yl)-2-methoxypropanoic acid (91.5 mg, 0.188 mmol) was dissolved in methanol (3.6 ml) to give a yellow solution that was cooled to 0° C. in an ice bath. Sodium borohydride was added to the reaction mixture in 7 portions (several mgs each) over the course of an hour, resulting in vigorous gas evolution. Additional methanol (0.5 ml) was added to the reaction mixture just prior to the final portion of sodium borohydride to improve stirring. Following the final addition of sodium borohydride, the reaction mixture was warmed to room temperature and acidified with 2N HCl to a pH of 1.5-2. The reaction mixture was stirred for about 5 minutes before neutralizing with a saturated aqueous sodium bicarbonate solution. The reaction mixture was concentrated under reduced pressure to about 0.5 ml, resulting in the formation of a white residue. Methanol (0.5 ml) was added to suspend the residue and the resulting suspension was filtered, rinsing over with methanol (3×0.5 ml). The filtrate was concentrated under reduced pressure to about 0.5 ml, diluted with methanol, and filtered (0.45 μm syringe filter) before being purified on a Waters Sunfire C18, 30×150 mm column, eluting with Acetonitrile/Water +0.1% TFA at 20 ml/min using a 17 minute 20-100% Acetonitrile/Water gradient followed by a 2 minute Acetonitrile flush. The product fractions were combined, evaporated under reduced pressure, and lyophilized from ethanol and benzene to give the desired compound as a white solid. LC-MS: calculated for $C_{26}H_{35}NO_8$ 489.24 observed m/e: 490.12 $(M+H)^+$ (Rt 1.71/4 min).

(3R,7S,8aS,10aR,11R,12R,13R,14R,14aS,14bS,E)-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate Triethylamine (5 μl, 0.036 mmol) and 2,4,6-trichlorobenzoyl chloride (4.75 μl, 0.030 mmol) were added to a stirred solution of (S)-3-((1S,2S,4aR,5R,6R,7R,8R,8aS)-6-((1H-pyrrole-2-carbonyl)oxy)-8-hydroxy-1-((R,E)-5-hydroxy-4-methylpent-2-en-2-yl)-7-methyl-1,2,4a,5,6,7,8,8a-octahydro-1,5-epoxynaphthalen-2-yl)-2-methoxypropanoic acid (2.9 mg, 5.92 μmol) in tetrahydrofuran (60 μl). After 40 minutes, the reaction mixture was diluted with toluene (1.4 ml). The reaction mixture was added dropwise (2-3 drops/min) to a stirred solution of 4-dimethylaminepyridine (9.2 mg, 0.075 mmol) in toluene (4.4 ml) over a 52 minute period. The solution became hazy and increased in haziness during the course of the addition, so that by the end of the addition the reaction mixture was almost white. After 1 hour, the reaction mixture was evaporated under reduced pressure to give a white residue, which was purified on a Waters Sunfire C18, 30x150 mm column, eluting with Acetonitrile/Water +0.1% TFA at 20 ml/min using a 17 minute 20-100% Acetonitrile/Water gradient followed by a 2 minute Acetonitrile flush. The product fractions were combined, evaporated under reduced pressure, and lyophilized from ethanol and benzene to give the title compound as a white solid. $C_{26}H_{33}NO_7$ $^1$H NMR δ (ppm) $CD_3OD$: 11.31 (s, 1 H); 6.97 (td, J=2.7, 1.5 Hz, 1 H); 6.86 (dt, J=3.7, 1.9 Hz, 1 H); 6.19 (dt, J=3.7, 2.4 Hz, 1 H); 5.92 (ddd, J=9.4, 6.9, 2.0 Hz, 1 H); 5.37 (dd, J=9.5, 2.6 Hz, 1 H); 5.32 (dd, J=10.3, 1.5 Hz, 1 H); 5.07 (t, J=4.9 Hz, 1 H); 4.52 (t, J=10.7 Hz, 1 H); 4.15 (d, J=4.8 Hz, 1 H); 4.03 (dd, J=10.3, 7.0 Hz, 1 H); 3.66 (dd, J=10.8, 2.9 Hz, 1 H); 3.60 (d, J=8.8 Hz, 1 H); 3.21 (s, 3 H); 2.91-2.97 (m, 2 H); 2.61 (d, J=6.9 Hz, 1 H); 2.51-2.57 (m, 1 H); 2.50 (d, J=3.1 Hz, 1 H); 2.44-2.48 (m, 1 H); 1.76 (s, 3 H); 1.41 (d, J=15.4 Hz, 1 H); 1.01 (d, J=6.5 Hz, 3 H); 0.90 (d, J=6.9 Hz, 3 H).

Example 48

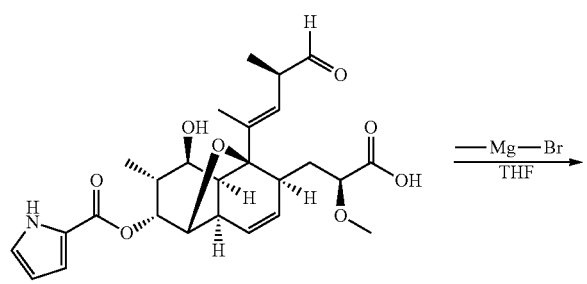

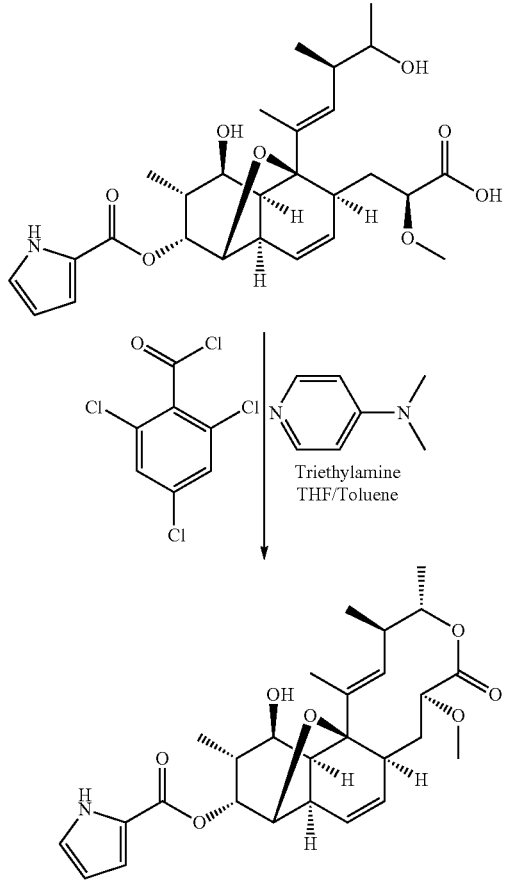

(3R,4S,7S,8aS,10aR,11R,12R,13R,14R,14aS,14bS,E)-14-hydroxy-7-methoxy-1,3,4,13-tetramethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate (2S)-3-((1S,2S,4aR,5R,6R,7R,8R,8aS)-6-((1H-pyrrole-2-carbonyl)oxy)-8-hydroxy-1-((4R,E)-5-hydroxy-4-methylhex-2-en-2-yl)-7-methyl-1,2,4a,5,6,7,8,8a-octahydro-1,5-epoxynaphthalen-2-yl)-2-methoxypropanoic acid (S)-3-((1S,2S,4aR,5R,6R,7R,8R,8aS)-6-((1H-pyrrole-2-carbonyl)oxy)-8-hydroxy-7-methyl-1-((R,E)-4-methyl-5-oxopent-2-en-2-yl)-1,2,4a,5,6,7,8,8a-octahydro-1,5-epoxynaphthalen-2-yl)-2-methoxypropanoic acid (20.3 mg, 0.042 mmol) was dissolved in tetrahydrofuran (0.15 ml) and added dropwise to a stirred solution of methylmagnesium bromide (70 μl, 0.210 mmol) in tetrahydrofuran (0.25 ml), rinsing over with tetrahydrofuran (0.1 ml). The reaction mixture was a yellow solution that was stirred at room temperature. After 1.5 hours, additional methylmagnesium bromide (70 μl, 0.210 mmol) was added to the reaction mixture, resulting in the immediate formation of a white precipitate. After another 1.5 hours, additional methylmagnesium bromide (35 μl, 0.105 mmol) was added to the reaction mixture. After another 30 minutes, additional methylmagnesium bromide (50 μl, 0.150 mmol) was added to the reaction mixture. After an additional 30 minutes, the reaction mixture was quenched with methanol (~1 ml) and evaporated under reduced pressure. The resulting residue was purified on a Waters Sunfire C18, 30×150 mm column, eluting with Acetonitrile/Water +0.1% TFA at 20 ml/min using a 17 minute 20-100% Acetonitrile/Water gradient followed by a 2 minute Acetonitrile flush. The product fractions were combined, evaporated under reduced pressure, and lyophilized from ethanol and benzene to give the desired product as a white solid. LC-MS: calculated for $C_{27}H_{37}NO_8$ 503.25 observed m/e: 526.03 (M+Na) (Rt 1.80/4 min).

(3R,4S,7S,8aS,10aR,11R,12R,13R,14R,14aS,14bS, E)-14-hydroxy-7-methoxy-1,3,4,13-tetramethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate Triethylamine (15 µl, 0.108 mmol) and 2,4,6-trichlorobenzoyl chloride (14 µl, 0.090 mmol) were added to a stirred solution of (2S)-3-((1S,2S,4aR,5R,6R,7R,8R,8aS)-6-((1H-pyrrole-2-carbonyl)oxy)-8-hydroxy-1-((4R,E)-5-hydroxy-4-methylhex-2-en-2-yl)-7-methyl-1,2,4a,5,6,7,8,8a-octahydro-1,5-epoxynaphthalen-2-yl)-2-methoxypropanoic acid (8.9 mg, 0.018 mmol) in tetrahydrofuran (175 µl). The reaction mixture was a pale yellow solution that was stirred at room temperature. After 40 minutes, the reaction mixture was diluted with toluene (4.25 ml) and added dropwise to a solution of 4-dimethylaminopyridine (27.8 mg, 0.228 mmol) in toluene (13.25 ml) using an addition funnel over a 38 minute period. The reaction mixture steadily increased in haziness during the course of the addition. After 30 minutes, the reaction mixture was diluted with methanol and evaporated under reduced pressure. The resulting residue was purified on a Waters Sunfire C18, 30×150 mm column, eluting with Acetonitrile/Water +0.1% TFA at 20 ml/min using a 17 minute 20-100% Acetonitrile/Water gradient followed by a 2 minute Acetonitrile flush. The product fractions were combined, evaporated under reduced pressure, and lyophilized from ethanol and benzene to give the title compound as a white solid. LC-MS: calculated for $C_{27}H_{35}NO_7$ 485.24 observed m/e: 508.07 (M+Na) (Rt 2.09/4 min); $^1$H NMR δ (ppm) CD$_3$OD: 11.28 (s, 1 H); 6.97 (td, J=2.7, 1.5 Hz, 1 H); 6.84-6.85 (m, 1 H); 6.19 (dt, J=3.7, 2.4 Hz, 1 H); 5.92 (ddd, J=9.5, 6.8, 2.1 Hz, 1 H); 5.42 (dd, J=10.1, 1.5 Hz, 1 H); 5.37 (dd, J=9.5, 2.6 Hz, 1 H); 5.07 (t, J=4.9 Hz, 1 H); 4.15 (d, J=4.8 Hz, 1 H); 3.65 (dd, J=10.8, 3.0 Hz, 1 H); 3.56 (d, J=8.8 Hz, 1 H); 3.22 (s, 3 H); 2.91-2.94 (m, 1 H); 2.61 (d, J=6.9 Hz, 1 H); 2.43-2.55 (m, 4 H); 1.76 (s, 3 H); 1.38-1.41 (m, 4 H); 1.05 (d, J=6.5 Hz, 3 H); 0.89 (d, J=6.9 Hz, 3 H).

Examples 49-55

Examples 49-55 were generally prepared according to the methods in Example 48.

| Examples | Structure | [M + H]+ or $^1$H NMR |
|---|---|---|
| 49 | 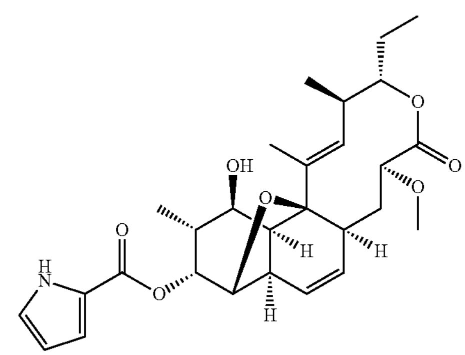 [SMILES: CC[C@@H]1OC(=O)[C@@H](OC)C[C@H]2C=C[C@H]3[C@H]4O[C@]2(/C(C)=C/[C@H]1C)[C@@H]3[C@H](O)[C@@H](C)[C@H]4OC(=O)c1ccc[nH]1] | $^1$H NMR δ (ppm) CD$_3$OD: 11.28 (s, 1 H); 6.96-6.97 (m, 1 H); 6.85 (ddd, J = 3.6, 2.4, 1.5 Hz, 1 H); 6.19 (dt, J = 3.7, 2.3 Hz, 1 H); 5.92 (ddd, J = 9.4, 6.9, 2.0 Hz, 1 H); 5.42 (dd, J = 10.0, 1.5 Hz, 1 H); 5.37 (dd, J = 9.5, 2.5 Hz, 1 H); 5.07 (t, J = 4.9 Hz, 1 H); 4.63 (td, J = 9.7, 2.3 Hz, 1 H); 4.16 (d, J = 4.8 Hz, 1 H); 3.65 (dd, J = 10.8, 2.9 Hz, 1 H); 3.59 (d, J = 8.8 Hz, 1 H); 3.22 (s, 3 H); 2.94 (dt, J = 10.2, 2.0 Hz, 1 H); 2.44-2.62 (m, 5 H); 1.89-1.95 (m, 1 H); 1.75 (s, 3 H); 1.57-1.65 (m, 1 H); 1.41 (d, J = 15.4 Hz, 1 H); 1.05 (d, J = 6.5 Hz, 3 H); 1.00 (t, J = 7.3 Hz, 3 H); 0.89 (d, J = 6.9 Hz, 3 H). |
| 50 | 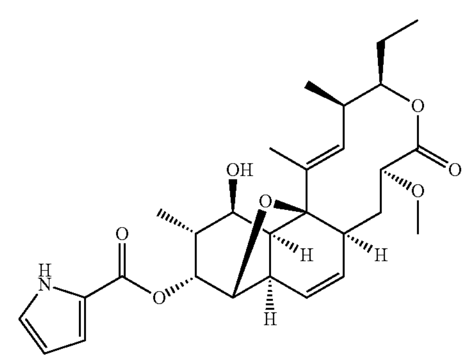 [SMILES: CC[C@H]1OC(=O)[C@@H](OC)C[C@H]2C=C[C@H]3[C@H]4O[C@]2(/C(C)=C/[C@H]1C)[C@@H]3[C@H](O)[C@@H](C)[C@H]4OC(=O)c1ccc[nH]1] | 500.15 |

-continued

| Examples | Structure | [M + H]+ or ¹H NMR |
|---|---|---|
| 51 | 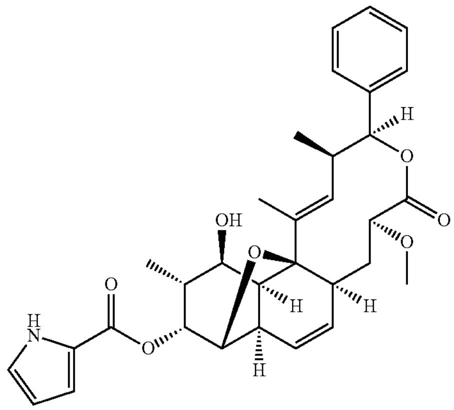 [SMILES: CO[C@H]1C[C@H]2C=C[C@H]3[C@H]4O[C@]2(/C(C)=C/[C@@H](C)[C@@H](c2ccccc2)OC1=O)[C@@H]3[C@H](O)[C@@H](C)[C@H]4OC(=O)c1ccc[nH]1] | 548.19 |
| 52 | 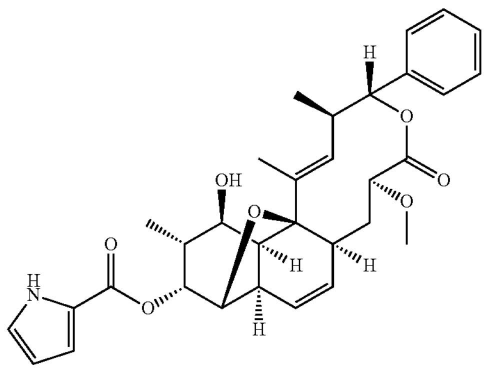 [SMILES: CO[C@H]1C[C@H]2C=C[C@H]3[C@H]4O[C@]2(/C(C)=C/[C@@H](C)[C@H](c2ccccc2)OC1=O)[C@@H]3[C@H](O)[C@@H](C)[C@H]4OC(=O)c1ccc[nH]1] | 548.16 |
| 53 | 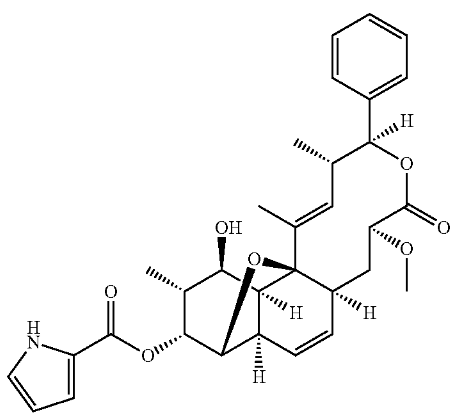 [SMILES: CO[C@H]1C[C@H]2C=C[C@H]3[C@H]4O[C@]2(/C(C)=C/[C@H](C)[C@@H](c2ccccc2)OC1=O)[C@@H]3[C@H](O)[C@@H](C)[C@H]4OC(=O)c1ccc[nH]1] | 548.18 |
| 54 | 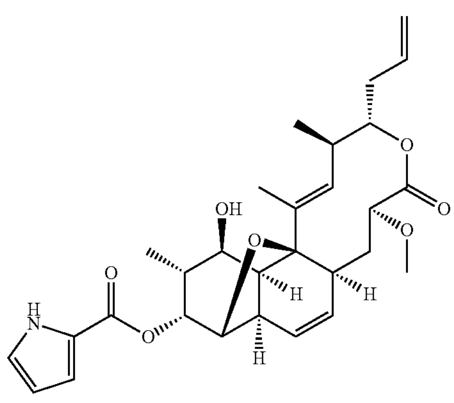 [SMILES: C=CC[C@@H]1OC(=O)[C@@H](OC)C[C@H]2C=C[C@H]3[C@H]4O[C@]2(/C(C)=C/[C@H]1C)[C@@H]3[C@H](O)[C@@H](C)[C@H]4OC(=O)c1ccc[nH]1] | 512.09 |

| Examples | Structure | [M + H]+ or ¹H NMR |
|---|---|---|
| 55 | 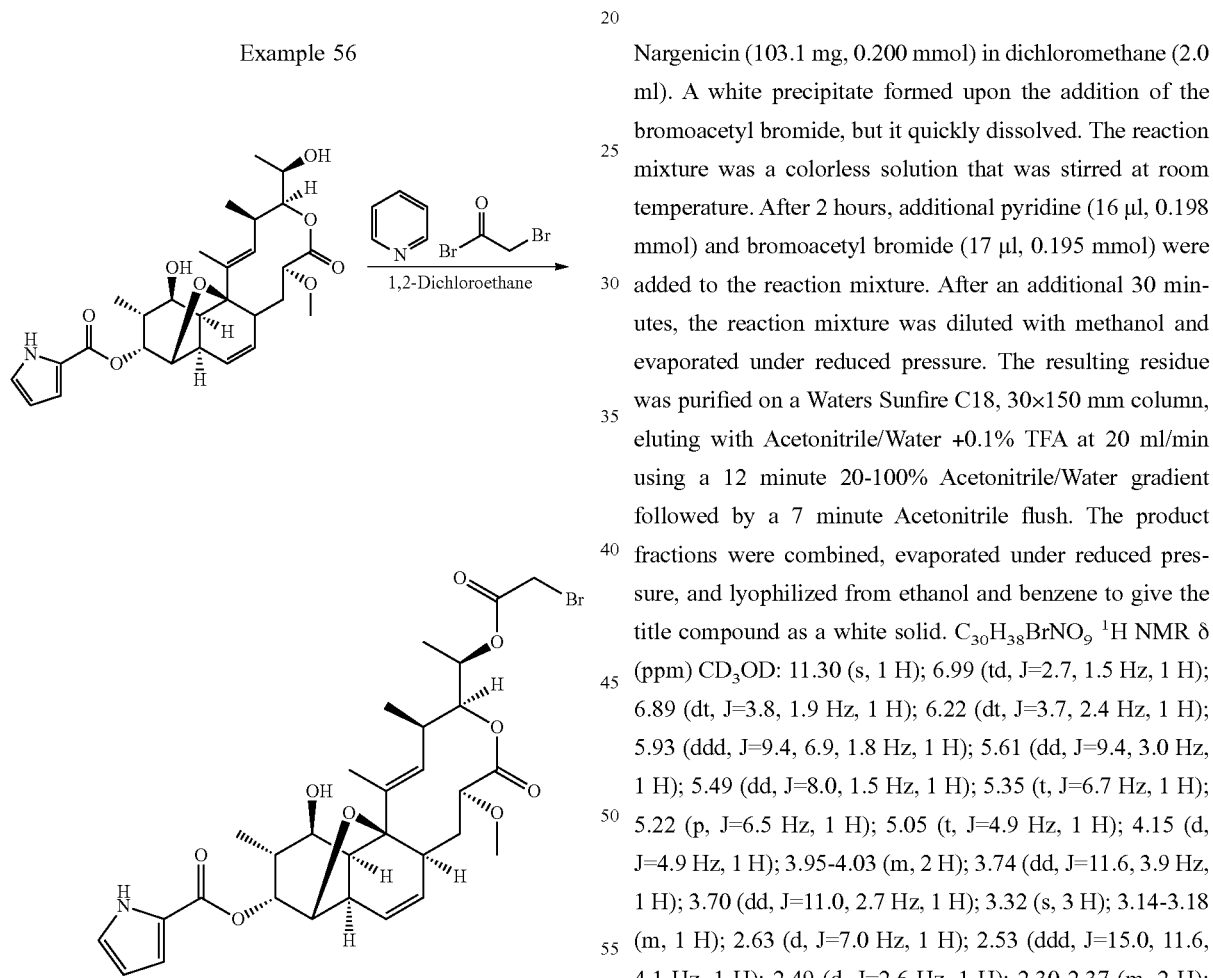 | 512.07 |

Example 56

(3R,4S,7S,8aS,10aR,11R,12R,13R,14R,14aS,14bS,E)-4-((R)-1-(2-bromoacetoxy)ethyl)-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate.

Pyridine (28 µl, 0.346 mmol) and bromoacetyl bromide (30 µl, 0.343 mmol) were added to a stirred solution of Nargenicin (103.1 mg, 0.200 mmol) in dichloromethane (2.0 ml). A white precipitate formed upon the addition of the bromoacetyl bromide, but it quickly dissolved. The reaction mixture was a colorless solution that was stirred at room temperature. After 2 hours, additional pyridine (16 µl, 0.198 mmol) and bromoacetyl bromide (17 µl, 0.195 mmol) were added to the reaction mixture. After an additional 30 minutes, the reaction mixture was diluted with methanol and evaporated under reduced pressure. The resulting residue was purified on a Waters Sunfire C18, 30×150 mm column, eluting with Acetonitrile/Water +0.1% TFA at 20 ml/min using a 12 minute 20-100% Acetonitrile/Water gradient followed by a 7 minute Acetonitrile flush. The product fractions were combined, evaporated under reduced pressure, and lyophilized from ethanol and benzene to give the title compound as a white solid. $C_{30}H_{38}BrNO_9$ ¹H NMR δ (ppm) $CD_3OD$: 11.30 (s, 1 H); 6.99 (td, J=2.7, 1.5 Hz, 1 H); 6.89 (dt, J=3.8, 1.9 Hz, 1 H); 6.22 (dt, J=3.7, 2.4 Hz, 1 H); 5.93 (ddd, J=9.4, 6.9, 1.8 Hz, 1 H); 5.61 (dd, J=9.4, 3.0 Hz, 1 H); 5.49 (dd, J=8.0, 1.5 Hz, 1 H); 5.35 (t, J=6.7 Hz, 1 H); 5.22 (p, J=6.5 Hz, 1 H); 5.05 (t, J=4.9 Hz, 1 H); 4.15 (d, J=4.9 Hz, 1 H); 3.95-4.03 (m, 2 H); 3.74 (dd, J=11.6, 3.9 Hz, 1 H); 3.70 (dd, J=11.0, 2.7 Hz, 1 H); 3.32 (s, 3 H); 3.14-3.18 (m, 1 H); 2.63 (d, J=7.0 Hz, 1 H); 2.53 (ddd, J=15.0, 11.6, 4.1 Hz, 1 H); 2.49 (d, J=2.6 Hz, 1 H); 2.30-2.37 (m, 2 H); 1.80 (s, 3 H); 1.35-1.40 (m, 4 H); 1.18 (d, J=7.1 Hz, 3 H); 0.94 (d, J=6.9 Hz, 3 H).

Examples 57-67

Examples 57 and 59-67 were generally prepared according to the methods in Example 56.

| Examples | Structure | [M + Na] or ¹H NMR |
|---|---|---|
| 57 | 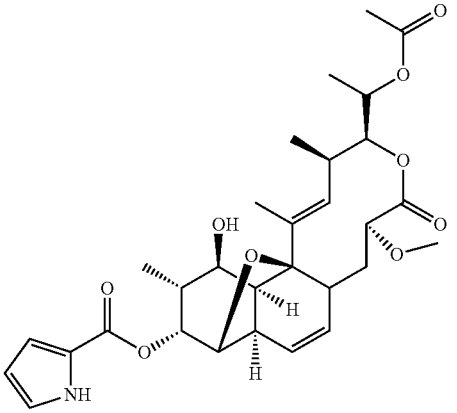 | M + 1-HOAc = 498.15 |
| 58 | 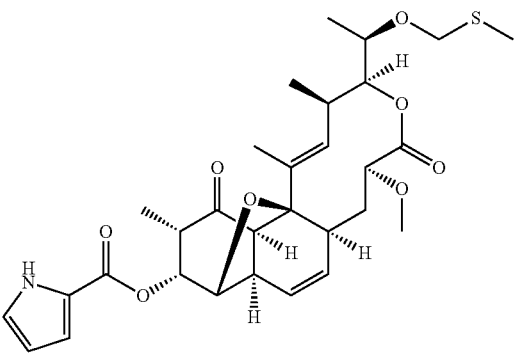 [SMILES: CO[C@H]1C[C@H]2C=C[C@H]3[C@H]4O[C@]2(/C(C)=C/[C@@H](C)[C@@H]([C@@H](C)OCSC)OC1=O)[C@@H]3C(=O)[C@@H](C)[C@H]4OC(=O)c1ccc[nH]1] | ¹H NMR δ (ppm) CD₃CN: 10.05 (s, 1 H) 6.97 (brs, 1 H) 6.90 (brs, 1 H); 6.20 (m, 1 H) 5.95-5.99 (m, 1 H) 5.68-5.72 (dd, J = 9.5, 2.8 Hz, 1 H) 5.47-5.50 (m, 1 H) 5.42 (t, J = 5.1 Hz, 1 H) 5.20 (t, J = 6.1 Hz, 1 H) 4.68-4.77 (dd, J = 11.4, 33.2 Hz, 2 H) 4.40 (d, J = 4.8 Hz, 1 H) 4.00-4.16 (m, 1 H) 3.75-3.80 (m, 1 H) 3.22 (s, 3 H) 2.90-3.10 (m, 4 H) 2.38-2.40 (m, 2 H) 2.18 (s, 3 H) 2.15 (s, 3 H) 1.95-1.98 (m, 1 H) 1.24 (d, J = 7.0 Hz, 3 H) 1.19 (d, J = 6.0 Hz, 3 H) 0.91 (d, J = 6.9 Hz, 3 H) |
| 59 | 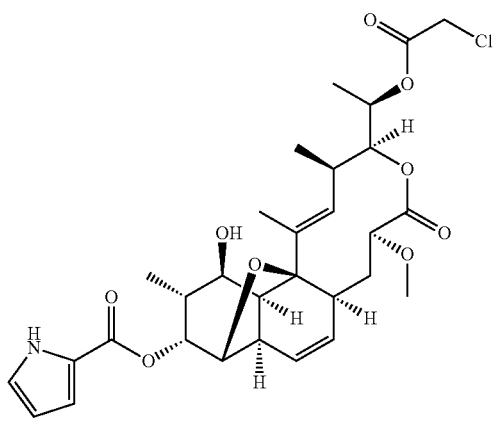 [SMILES: CO[C@H]1C[C@H]2C=C[C@H]3[C@H]4O[C@]2(/C(C)=C/[C@@H](C)[C@@H]([C@@H](C)OC(=O)CCl)OC1=O)[C@@H]3[C@H](O)[C@@H](C)[C@H]4OC(=O)c1ccc[nH]1] | ¹H NMR δ (ppm) CD₃OD: 11.27 (s, 1 H); 6.97 (td, J = 2.7, 1.5 Hz, 1 H); 6.85-6.86 (m, 1 H); 6.19 (dt, J = 3.8, 2.4 Hz, 1 H); 5.90 (ddd, J = 9.4, 6.9, 1.8 Hz, 1 H); 5.58 (dd, J = 9.3, 3.1 Hz, 1 H); 5.47 (dd, J = 8.1, 1.5 Hz, 1 H); 5.32 (t, J = 6.6 Hz, 1 H); 5.23 (p, J = 6.4 Hz, 1 H); 5.03 (t, J = 4.9 Hz, 1 H); 4.18-4.24 (m, 2 H); 4.12 (d, J = 4.9 Hz, 1 H); 3.71 (dd, J = 11.5, 3.9 Hz, 1 H); 3.68 (dd, J = 11.0, 2.8 Hz, 1 H); 3.28 (s, 3 H); 3.11-3.17 (m, 1 H); 2.60 (d, J = 7.0 Hz, 1 H); 2.50 (ddd, J = 15.0, 11.6, 4.1 Hz, 1 H); 2.46 (d, J = 2.6 Hz, 1 H); 2.28-2.33 (m, 2 H); 1.77 (s, 3 H); 1.34-1.37 (m, 4 H); 1.15 (d, J = 7.1 Hz, 3 H); 0.91 (d, J = 6.8 Hz, 3 H). |

-continued
| Examples | Structure | [M + Na] or ¹H NMR |
|---|---|---|
| 60 | 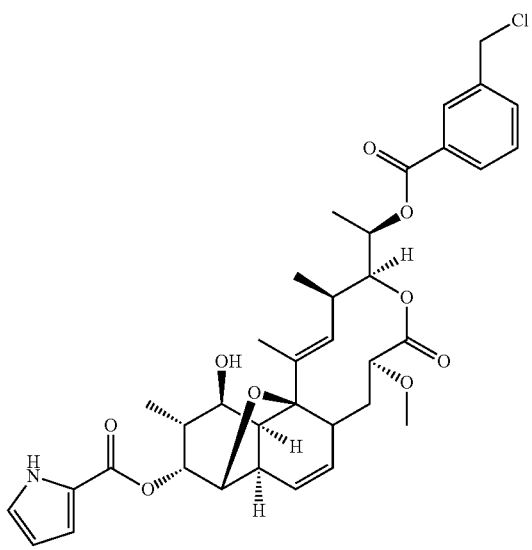 [SMILES: CO[C@H]1CC2C=C[C@H]3[C@H]4O[C@]2(/C(C)=C/[C@@H](C)[C@@H]([C@@H](C)OC(=O)c2cccc(CCl)c2)OC1=O)[C@@H]3[C@H](O)[C@@H](C)[C@H]4OC(=O)c1ccc[nH]1] | ¹H NMR δ (ppm) CD₃OD: 11.30 (s, 1 H); 8.04-8.06 (m, 2 H); 7.56-7.58 (m, 2 H); 6.99 (td, J = 2.7, 1.5 Hz, 1 H); 6.89 (dt, J = 3.7, 1.9 Hz, 1 H); 6.22 (dt, J = 3.7, 2.4 Hz, 1 H); 5.92 (ddd, J = 9.4, 6.9, 1.7 Hz, 1 H); 5.61 (dd, J = 9.4, 3.0 Hz, 1 H); 5.55 (dd, J = 8.2, 1.5 Hz, 1 H); 5.47 (t, J = 6.5 Hz, 1 H); 5.42 (p, J = 6.3 Hz, 1 H); 5.05 (t, J = 4.9 Hz, 1 H); 4.72 (s, 2 H); 4.14 (d, J = 4.9 Hz, 1 H); 3.75 (dd, J = 11.5, 3.8 Hz, 1 H); 3.71 (dd, J = 11.0, 2.7 Hz, 1 H); 3.32 (s, 3H); 3.20-3.27 (m, 1 H); 2.63 (d, J = 7.0 Hz, 1 H); 2.56 (ddd, J = 15.0, 11.6, 4.2 Hz, 1 H); 2.50 (d, J = 2.6 Hz, 1 H); 2.33-2.39 (m, 2 H); 1.84 (s, 3 H); 1.47 (d, J = 6.2 Hz, 3 H); 1.40 (dt, J = 15.1, 3.4 Hz, 1 H); 1.21 (d, J = 7.1 Hz, 3 H); 0.94 (d, J = 6.8 Hz, 3 H). |
| 61 | (structure) Dichloromethane was used as the solvent. | [M + Na] 642.13 |
| 62 | (structure) Dichloromethane was used as the solvent. | [M + Na] 690.10 |

| Examples | Structure | [M + Na] or ¹H NMR |
|---|---|---|
| 63 | 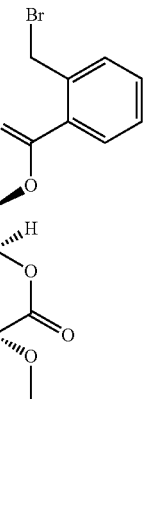 Dichloromethane was used as the solvent. | [M + Na] 734.01, 736.01 |
| 64 | 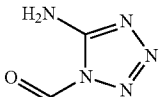<br> | M + 1 = 627.25 |
| 65 | 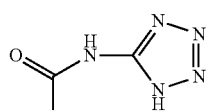<br>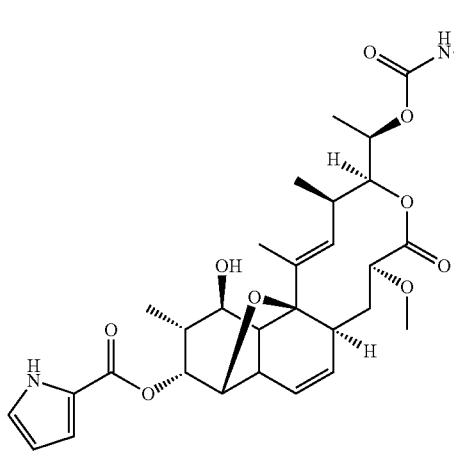 | M + 1 = 627.26 |

-continued

| Examples | Structure | [M + Na] or ¹H NMR |
|---|---|---|
| 66 | 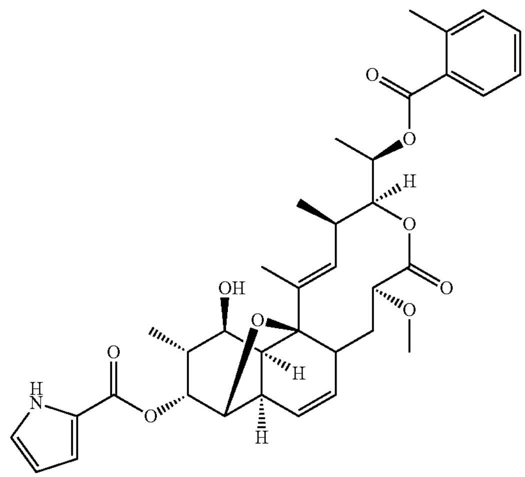 [SMILES: CO[C@H]1CC2C=C[C@H]3[C@H]4O[C@]2(/C(C)=C/[C@@H](C)[C@@H]([C@@H](C)OC(=O)c2ccccc2C)OC1=O)[C@@H]3[C@H](O)[C@@H](C)[C@H]4OC(=O)c1ccc[nH]1] | [M + H]⁺ 634.18 |

Dichloromethane was used as the solvent.

| 67 | | M + 1-H₂O = 602.22 |

Example 68

1-(2-((R)-1-((3R,4S,7S,8aS,10aR,11R,12R,13R,14R, 14aS,14bS,E)-12-(((1H-pyrrole-2-carbonyl)oxy)-14-hydroxy-7-methoxy-1,3,13-trimethyl-6-oxo-3,4,6,7, 8,8a,10a,11,12,13,14,14a-dodecahydro-11,14b-epoxynaphtho[2,1-e]oxecin-4-yl)ethoxy-2-oxoethyl)-4-methylpyridin-1-ium bromide.

4-Picoline (10 µl, 0.102 mmol) was added to a stirred solution of (3R,4S,7S,8aS,10aR,11R,12R,13R,14R,14aS, 14bS,E)-4-((R)-1-(2-bromoacetoxy)ethyl)-14-hydroxy-7-methoxy-1,3,13-trimethyl-6-oxo-3,4,6,7,8,8a,10a,11,12,13, 14,14a-dodecahydro-11,14b-epoxynaphtho[2,1-e]oxecin-12-yl 1H-pyrrole-2-carboxylate (5.2 mg, 8.17 µmol) in acetonitrile (0.2 ml). The reaction mixture was a colorless solution that was heated to 75° C. After 18 hours, the reaction mixture was cooled to room temperature and evaporated under reduced pressure to give an amber residue. The resulting residue was purified on a Waters Sunfire C18, 30×150 mm column, eluting with Acetonitrile/Water +0.1% TFA at 20 ml/min using a 17 minute 20-100% Acetonitrile/Water gradient followed by a 2 minute Acetonitrile flush.

The product fractions were combined, evaporated under reduced pressure, and lyophilized from ethanol and benzene to give the title compound as a white solid. LC-MS: calculated for $C_{36}H_{45}N_2O_9^+$ 649.31 observed m/e: 649.21 (M$^+$) (Rt 1.66/4 min); $^1$H NMR δ (ppm) CD$_3$OD: 11.29 (s, 1 H); 8.77-8.79 (m, 2 H); 7.99-8.00 (m, 2 H); 6.97 (td, J=2.7, 1.5 Hz, 1 H); 6.86 (dt, J=3.8, 1.9 Hz, 1 H); 6.20 (dt, J=3.8, 2.3 Hz, 1 H); 5.91 (ddd, J=9.4, 6.9, 1.9 Hz, 1 H); 5.58 (dd, J=9.4, 2.9 Hz, 1 H); 5.54 (s, 2 H); 5.48 (dd, J=8.6, 1.6 Hz, 1 H); 5.36 (p, J=5.9 Hz, 1 H); 5.31 (dd, J=7.0, 5.0 Hz, 1 H); 5.03 (t, J=4.8 Hz, 1 H); 4.12 (d, J=4.9 Hz, 1 H); 3.67-3.71 (m, 2 H); 3.27 (s, 3 H); 3.14-3.18 (m, 1 H); 2.72 (s, 3 H); 2.62 (d, J=7.0 Hz, 1 H); 2.50 (ddd, J=15.0, 11.7, 4.2 Hz, 1 H); 2.47 (d, J=2.6 Hz, 1 H); 2.35 (dt, J=4.2, 2.3 Hz, 1 H); 2.27-2.32 (m, 1 H); 1.74 (s, 3 H); 1.43 (d, J=6.3 Hz, 3 H); 1.37 (dt, J=15.1, 3.2 Hz, 1 H); 1.17 (d, J=7.1 Hz, 3 H); 0.91 (d, J=6.9 Hz, 3 H).

Examples 69-112

Examples 70-112 were generally prepared according to the methods in Example 68.

| Example | Structure | [M + H]$^+$ |
|---|---|---|
| 70 | 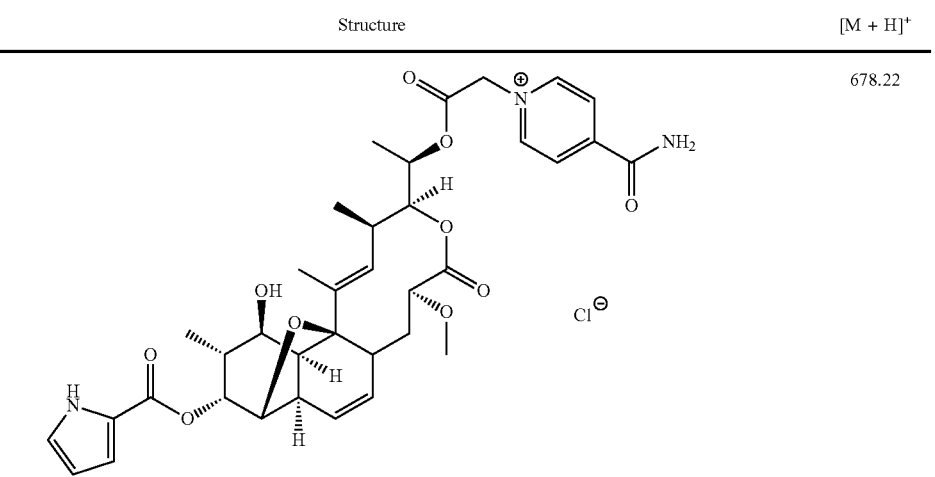 | 678.22 |
| 71 | 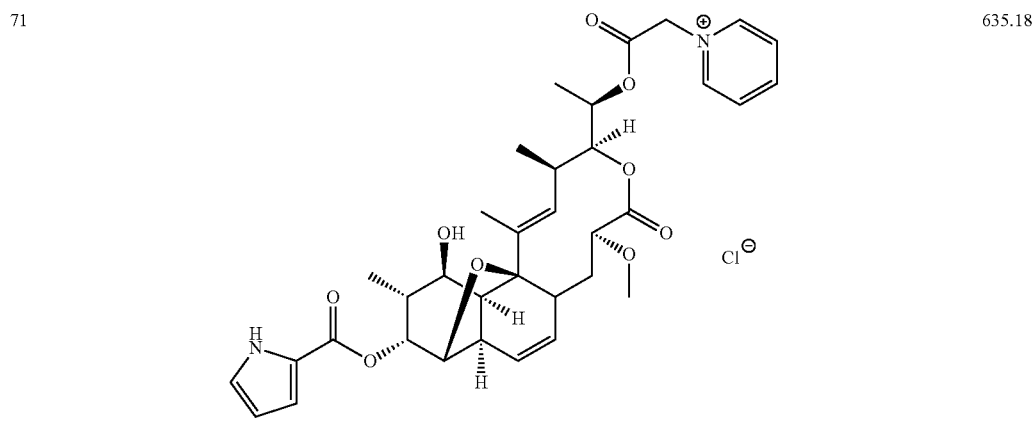 | 635.18 |

The reaction was run neat in pyridine and heated to 100° C.

-continued
| Example | Structure | [M + H]+ |
|---|---|---|
| 72 | 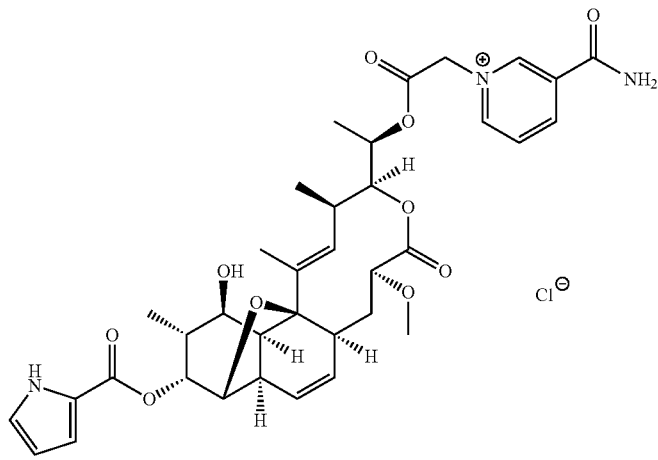 [SMILES: CO[C@H]1C[C@H]2C=C[C@H]3[C@H]4O[C@]2(/C(C)=C/[C@@H](C)[C@@H]([C@@H](C)OC(=O)C[n+]2cccc(C(N)=O)c2)OC1=O)[C@@H]3[C@H](O)[C@@H](C)[C@H]4OC(=O)c1ccc[nH]1 ; [Cl-]] | 678.20 |
| 73 | 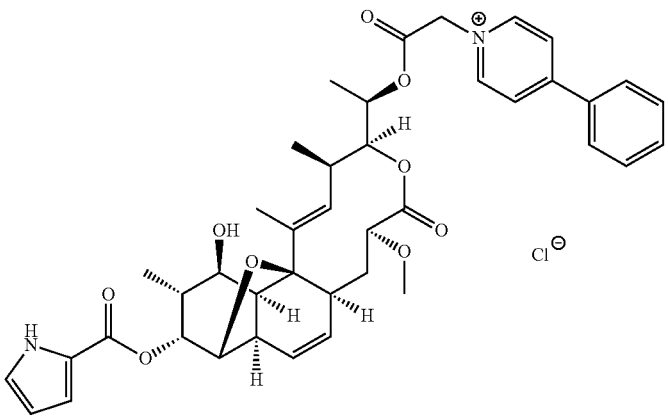 [SMILES: CO[C@H]1C[C@H]2C=C[C@H]3[C@H]4O[C@]2(/C(C)=C/[C@@H](C)[C@@H]([C@@H](C)OC(=O)C[n+]2ccc(-c5ccccc5)cc2)OC1=O)[C@@H]3[C@H](O)[C@@H](C)[C@H]4OC(=O)c1ccc[nH]1 ; [Cl-]] | 711.22 |
Examples prepared using example 56 as a starting material.
| 74 | 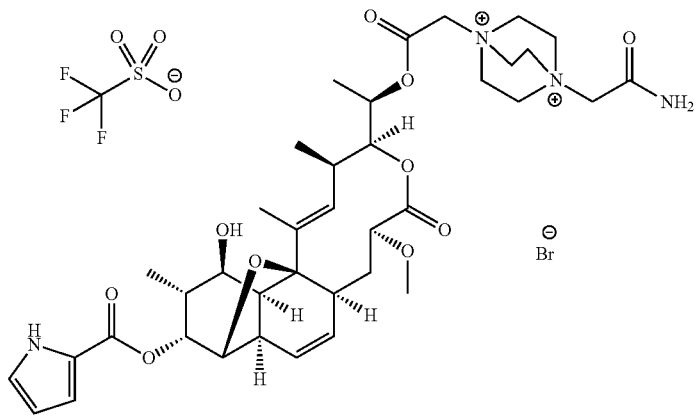 [SMILES: CO[C@H]1C[C@H]2C=C[C@H]3[C@H]4O[C@]2(/C(C)=C/[C@@H](C)[C@@H]([C@@H](C)OC(=O)C[N+]25CC[N+](CC(N)=O)(CC2)CC5)OC1=O)[C@@H]3[C@H](O)[C@@H](C)[C@H]4OC(=O)c1ccc[nH]1 ; O=S(=O)([O-])C(F)(F)F ; [Br-]] | [M − H] 725.25 [M/2] 363.21 |
The reaction was run at room temperature.

-continued
| Example | Structure | [M + H]+ |
|---|---|---|
| 75 | 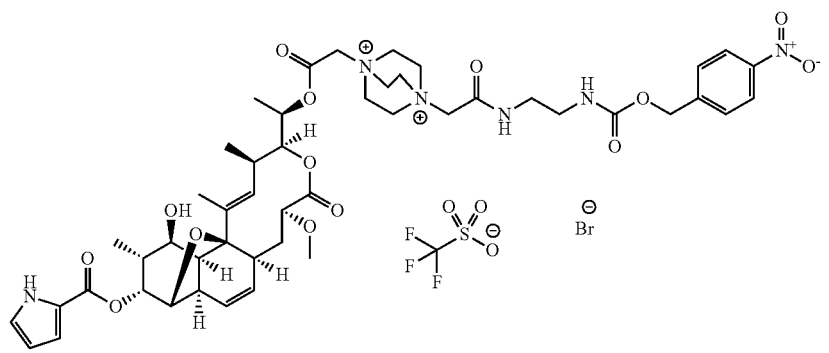 [SMILES: CO[C@H]1C[C@H]2C=C[C@H]3[C@H]4O[C@]2(/C(C)=C/[C@@H](C)[C@@H]([C@@H](C)OC(=O)C[N+]25CC[N+](CC(=O)NCCNC(=O)OCc6ccc([N+](=O)[O-])cc6)(CC2)CC5)OC1=O)[C@@H]3[C@H](O)[C@@H](C)[C@H]4OC(=O)c1ccc[nH]1 ; O=S(=O)([O-])C(F)(F)F ; [Br-]]<br>The reaction was run at 50° C. | [M − H]<br>947.47<br>[M/2]<br>474.12 |
| 76 | 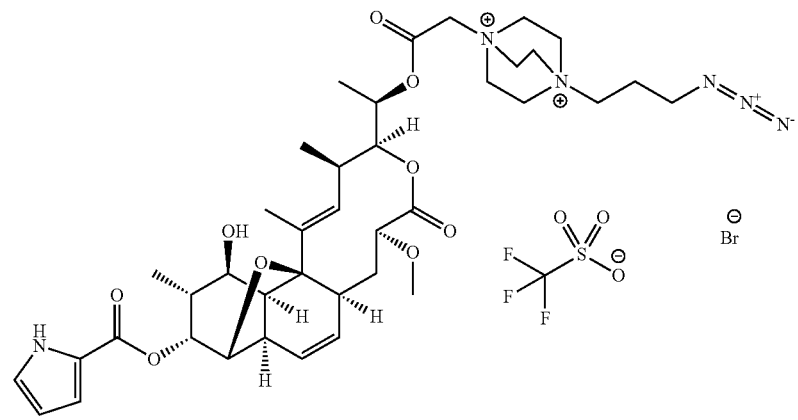 [SMILES: CO[C@H]1C[C@H]2C=C[C@H]3[C@H]4O[C@]2(/C(C)=C/[C@@H](C)[C@@H]([C@@H](C)OC(=O)C[N+]25CC[N+](CCCN=[N+]=[N-])(CC2)CC5)OC1=O)[C@@H]3[C@H](O)[C@@H](C)[C@H]4OC(=O)c1ccc[nH]1 ; O=S(=O)([O-])C(F)(F)F ; [Br-]]<br>The reaction was run at 50° C. | [M − H]<br>751.25<br>[M/2]<br>376.22 |
| 77 | 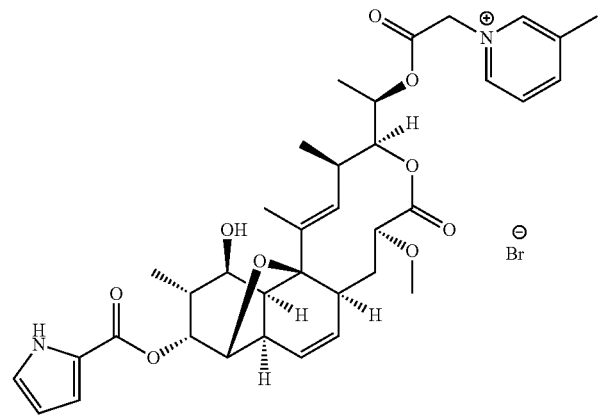 [SMILES: CO[C@H]1C[C@H]2C=C[C@H]3[C@H]4O[C@]2(/C(C)=C/[C@@H](C)[C@@H]([C@@H](C)OC(=O)C[n+]2cccc(C)c2)OC1=O)[C@@H]3[C@H](O)[C@@H](C)[C@H]4OC(=O)c1ccc[nH]1 ; [Br-]] | 649.21 |

-continued

| Example | Structure | [M + H]+ |
|---|---|---|
| 78 | 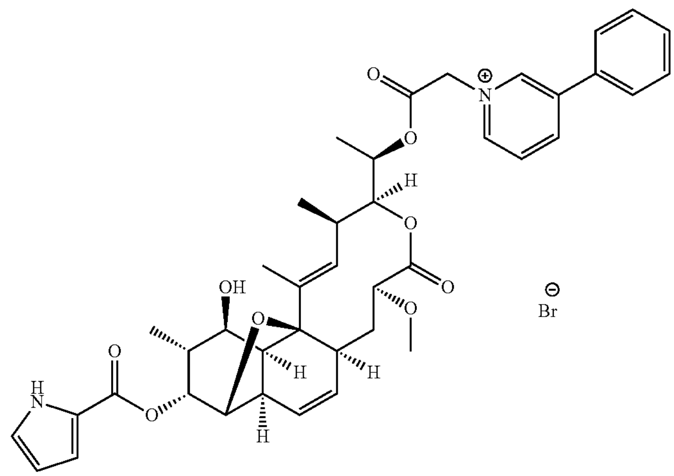 [SMILES: CO[C@H]1C[C@H]2C=C[C@H]3[C@H]4O[C@]2(/C(C)=C/[C@@H](C)[C@@H]([C@@H](C)OC(=O)C[n+]2cccc(-c5ccccc5)c2)OC1=O)[C@@H]3[C@H](O)[C@@H](C)[C@H]4OC(=O)c1ccc[nH]1 ; [Br-]] | 711.25 |
| 79 | 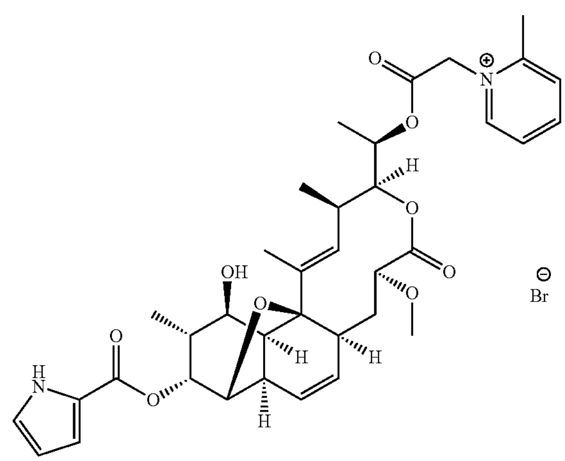 [SMILES: CO[C@H]1C[C@H]2C=C[C@H]3[C@H]4O[C@]2(/C(C)=C/[C@@H](C)[C@@H]([C@@H](C)OC(=O)C[n+]2ccccc2C)OC1=O)[C@@H]3[C@H](O)[C@@H](C)[C@H]4OC(=O)c1ccc[nH]1 ; [Br-]] | 649.19 |
| 80 | 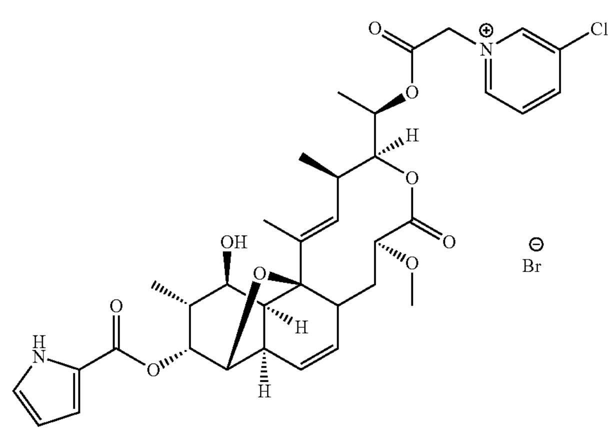 [SMILES: CO[C@H]1CC2C=C[C@H]3[C@H]4O[C@]2(/C(C)=C/[C@@H](C)[C@@H]([C@@H](C)OC(=O)C[n+]2cccc(Cl)c2)OC1=O)[C@@H]3[C@H](O)[C@@H](C)[C@H]4OC(=O)c1ccc[nH]1 ; [Br-]] | 669.16 |

| Example | Structure | [M + H]+ |
|---|---|---|
| 81 | 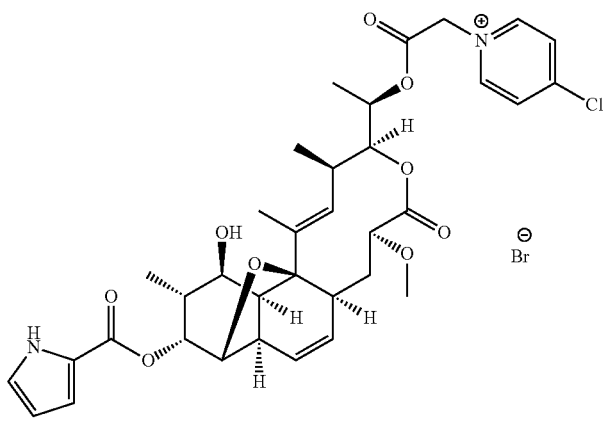 [SMILES: CO[C@H]1C[C@H]2C=C[C@H]3[C@H]4O[C@]2(/C(C)=C/[C@@H](C)[C@@H]([C@@H](C)OC(=O)C[n+]2ccc(Cl)cc2)OC1=O)[C@@H]3[C@H](O)[C@@H](C)[C@H]4OC(=O)c1ccc[nH]1 ; [Br-]] 5 equivalents of N,N-diisopropylethylamine were used in this reaction. | 669.16 |
| 82 | 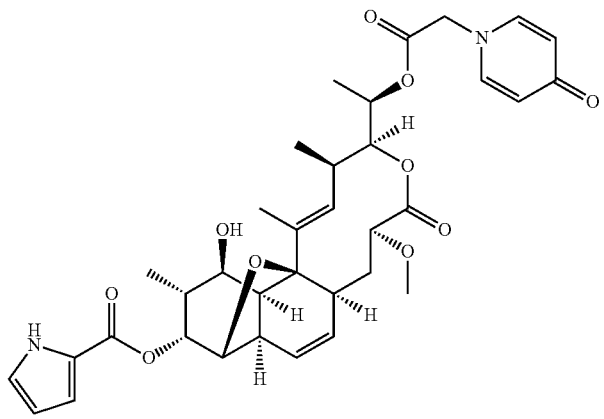 [SMILES: CO[C@H]1C[C@H]2C=C[C@H]3[C@H]4O[C@]2(/C(C)=C/[C@@H](C)[C@@H]([C@@H](C)OC(=O)Cn2ccc(=O)cc2)OC1=O)[C@@H]3[C@H](O)[C@@H](C)[C@H]4OC(=O)c1ccc[nH]1] 5 equivalents of N,N-diisopropylethylamine were used in this reaction. | [M + H]+ 651.17 |
| 83 | 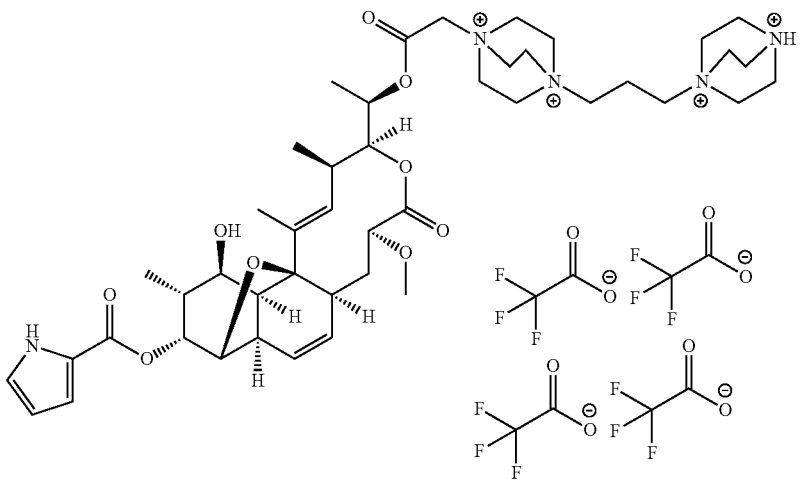 [SMILES: CO[C@H]1C[C@H]2C=C[C@H]3[C@H]4O[C@]2(/C(C)=C/[C@@H](C)[C@@H]([C@@H](C)OC(=O)C[N+]25CC[N+](CCC[N+]67CC[NH+](CC6)CC7)(CC2)CC5)OC1=O)[C@@H]3[C@H](O)[C@@H](C)[C@H]4OC(=O)c1ccc[nH]1 ; O=C([O-])C(F)(F)F ; O=C([O-])C(F)(F)F ; O=C([O-])C(F)(F)F ; O=C([O-])C(F)(F)F] | 822.55 |

| Example | Structure | [M + H]+ |
|---|---|---|
| 84 | 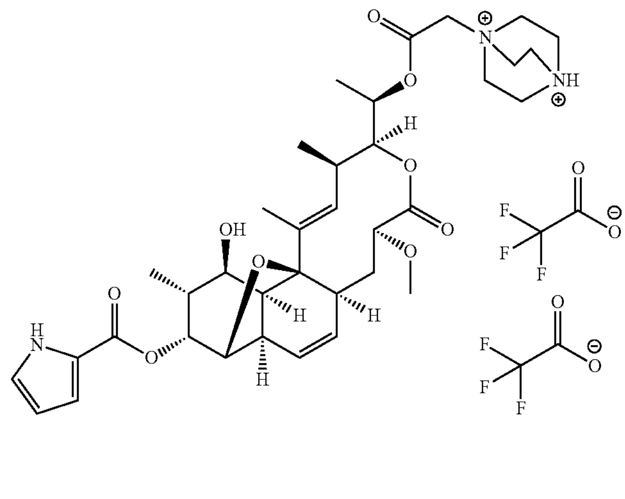 [SMILES: CO[C@H]1C[C@H]2C=C[C@H]3[C@H]4O[C@]2(/C(C)=C/[C@@H](C)[C@@H]([C@@H](C)OC(=O)C[N+]25CC[NH+](CC2)CC5)OC1=O)[C@@H]3[C@H](O)[C@@H](C)[C@H]4OC(=O)c1ccc[nH]1 ; O=C([O-])C(F)(F)F ; O=C([O-])C(F)(F)F] | 668.38 |
| 85 | 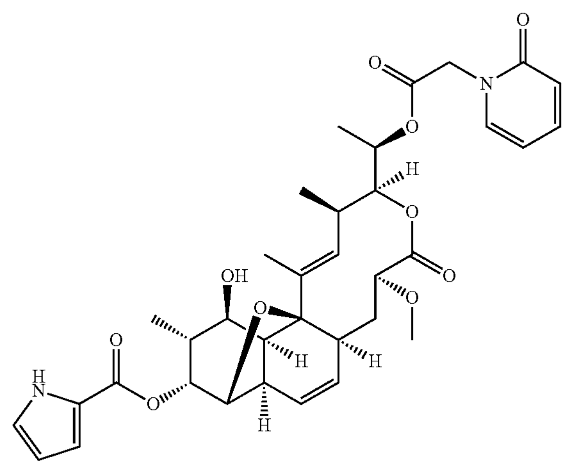 [SMILES: CO[C@H]1C[C@H]2C=C[C@H]3[C@H]4O[C@]2(/C(C)=C/[C@@H](C)[C@@H]([C@@H](C)OC(=O)Cn2ccccc2=O)OC1=O)[C@@H]3[C@H](O)[C@@H](C)[C@H]4OC(=O)c1ccc[nH]1] | 651.18 |
| 86 | 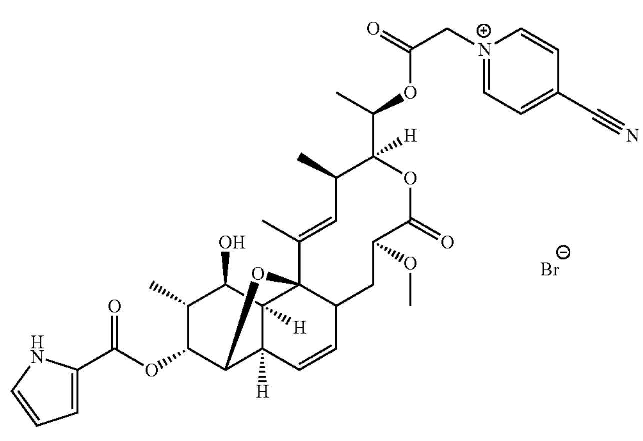 [SMILES: CO[C@H]1CC2C=C[C@H]3[C@H]4O[C@]2(/C(C)=C/[C@@H](C)[C@@H]([C@@H](C)OC(=O)C[n+]2ccc(C#N)cc2)OC1=O)[C@@H]3[C@H](O)[C@@H](C)[C@H]4OC(=O)c1ccc[nH]1 ; [Br-]] | 660.17 |

-continued

| Example | Structure | [M + H]+ |
|---|---|---|
| 87 | 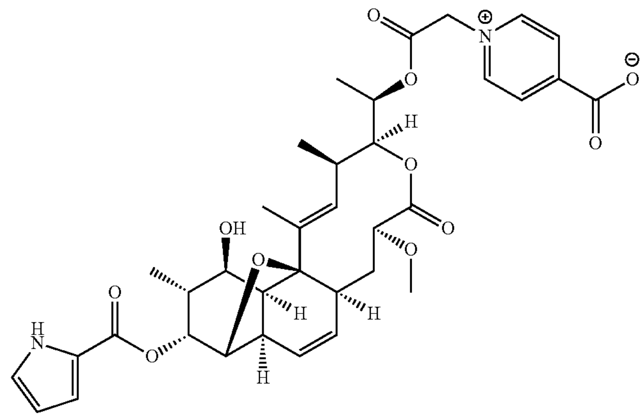 [SMILES: CO[C@H]1C[C@H]2C=C[C@H]3[C@H]4O[C@]2(/C(C)=C/[C@@H](C)[C@@H]([C@@H](C)OC(=O)C[n+]2ccc(C(=O)[O-])cc2)OC1=O)[C@@H]3[C@H](O)[C@@H](C)[C@H]4OC(=O)c1ccc[nH]1] | 697.15 |
| 88 | 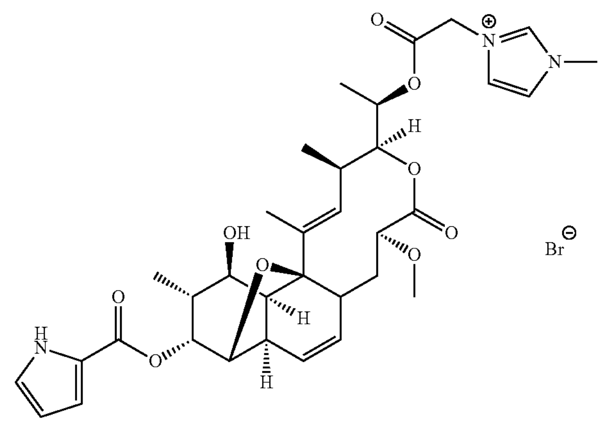 [SMILES: CO[C@H]1CC2C=C[C@H]3[C@H]4O[C@]2(/C(C)=C/[C@@H](C)[C@@H]([C@@H](C)OC(=O)C[n+]2ccn(C)c2)OC1=O)[C@@H]3[C@H](O)[C@@H](C)[C@H]4OC(=O)c1ccc[nH]1 ; [Br-]] | 638.14 |
| 89 | 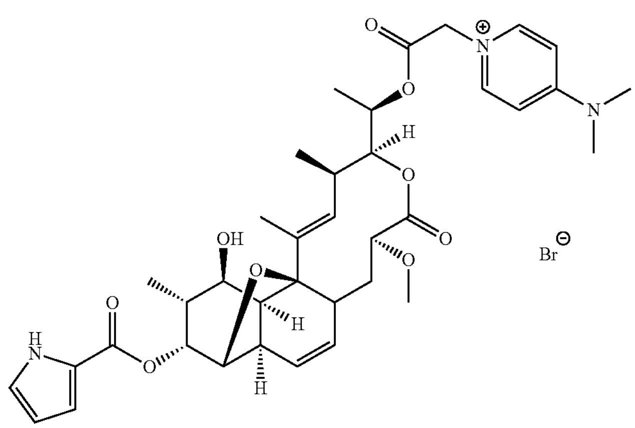 [SMILES: CO[C@H]1CC2C=C[C@H]3[C@H]4O[C@]2(/C(C)=C/[C@@H](C)[C@@H]([C@@H](C)OC(=O)C[n+]2ccc(N(C)C)cc2)OC1=O)[C@@H]3[C@H](O)[C@@H](C)[C@H]4OC(=O)c1ccc[nH]1 ; [Br-]] | 678.25 |

-continued
| Example | Structure | [M + H]⁺ |
|---|---|---|
| Examples prepared using example 60 as a starting material. | | |
| 90 | 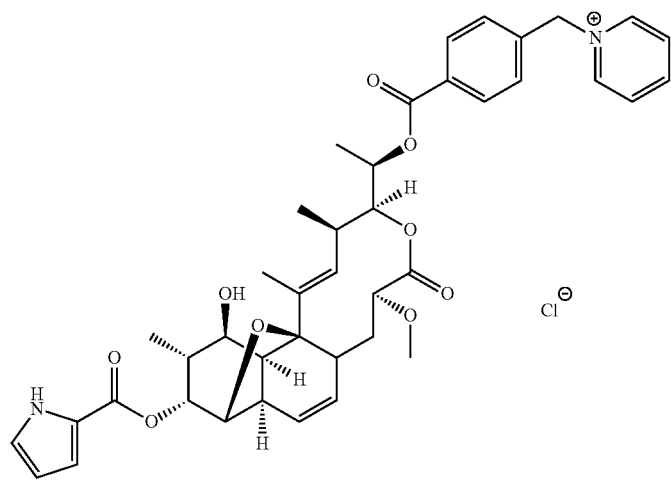 [SMILES: CO[C@H]1CC2C=C[C@H]3[C@H]4O[C@]2(/C(C)=C/[C@@H](C)[C@@H]([C@@H](C)OC(=O)c2ccc(C[n+]5ccccc5)cc2)OC1=O)[C@@H]3[C@H](O)[C@@H](C)[C@H]4OC(=O)c1ccc[nH]1 ; [Cl-]] The reaction was run neat in pyridine and heated to 100° C. | 711.29 |
| 91 | 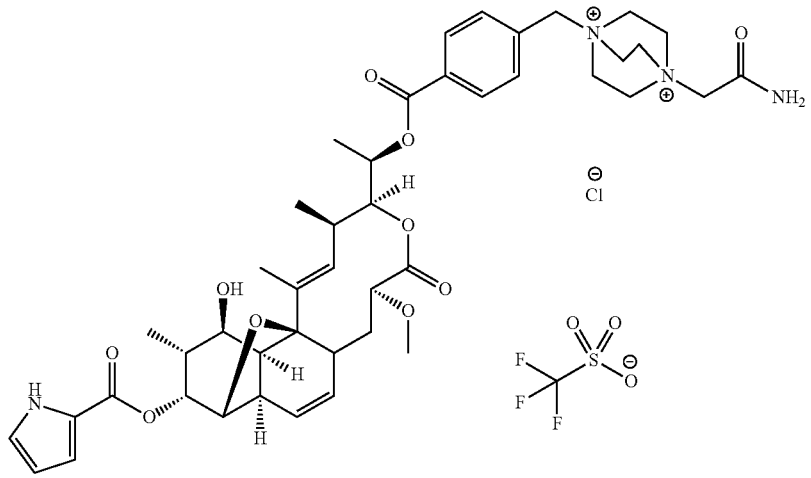 [SMILES: CO[C@H]1CC2C=C[C@H]3[C@H]4O[C@]2(/C(C)=C/[C@@H](C)[C@@H]([C@@H](C)OC(=O)c2ccc(C[N+]56CC[N+](CC(N)=O)(CC5)CC6)cc2)OC1=O)[C@@H]3[C@H](O)[C@@H](C)[C@H]4OC(=O)c1ccc[nH]1 ; O=S(=O)([O-])C(F)(F)F ; [Cl-]] | [M − H] 801.31 |
| 92 | 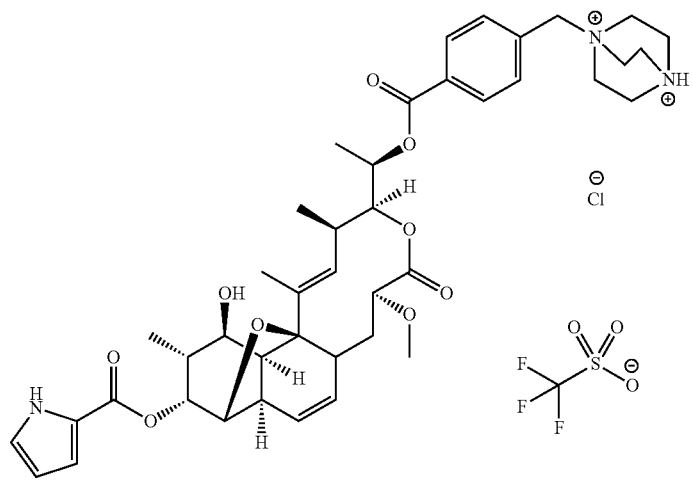 [SMILES: CO[C@H]1CC2C=C[C@H]3[C@H]4O[C@]2(/C(C)=C/[C@@H](C)[C@@H]([C@@H](C)OC(=O)c2ccc(C[N+]56CC[NH+](CC5)CC6)cc2)OC1=O)[C@@H]3[C@H](O)[C@@H](C)[C@H]4OC(=O)c1ccc[nH]1 ; O=S(=O)([O-])C(F)(F)F ; [Cl-]] | 744.31 |

-continued
| Example | Structure | [M + H]+ |
|---|---|---|
| 93 | 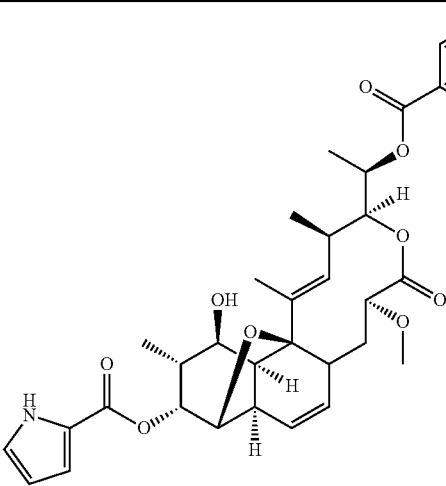 | [M − 2H] 896.55 [(M/2) − H] 448.70 |
| 94 | 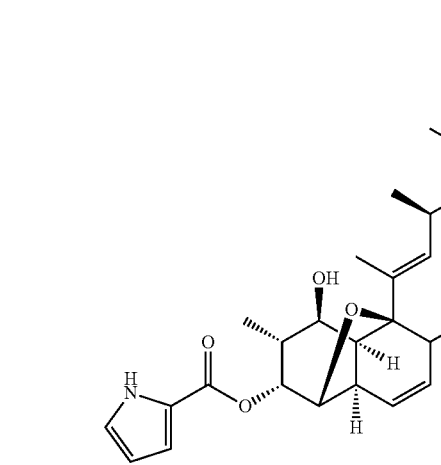 | 714.24 |
| 95 | 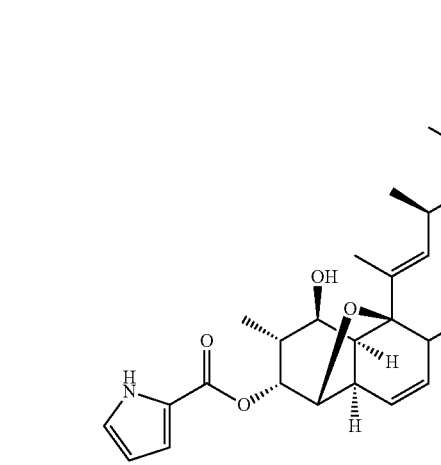 | [M − H] 758.31 |
After the first quaternization with DABCO was complete, the reaction mixture was cooled to room temperature and 19 equivalents of iodomethane were added to afford the second quaternization.

| Example | Structure | [M + H]+ |
|---|---|---|
| 96 | 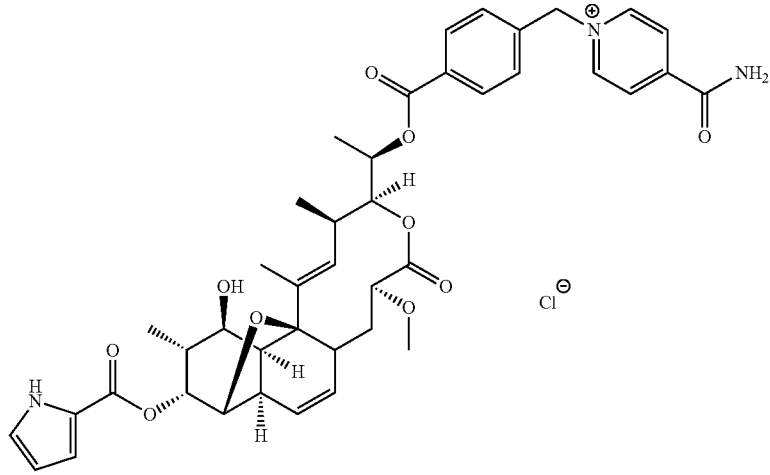 [SMILES: CO[C@H]1CC2C=C[C@H]3[C@H]4O[C@]2(/C(C)=C/[C@@H](C)[C@@H]([C@@H](C)OC(=O)c2ccc(C[n+]5ccc(C(N)=O)cc5)cc2)OC1=O)[C@@H]3[C@H](O)[C@@H](C)[C@H]4OC(=O)c1ccc[nH]1 ; [Cl-]] | 754.28 |
Examples prepared using example 61 as a starting material.
| 97 | 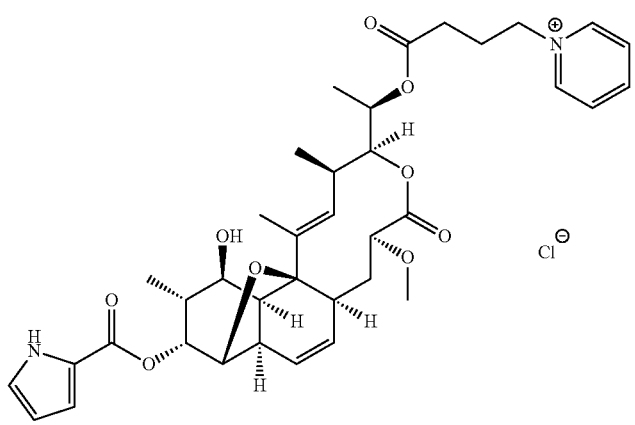 [SMILES: CO[C@H]1C[C@H]2C=C[C@H]3[C@H]4O[C@]2(/C(C)=C/[C@@H](C)[C@@H]([C@@H](C)OC(=O)CCC[n+]2ccccc2)OC1=O)[C@@H]3[C@H](O)[C@@H](C)[C@H]4OC(=O)c1ccc[nH]1 ; [Cl-]] | 663.19 |
The reaction was run neat in pyridine and heated to 100° C.
| 98 | 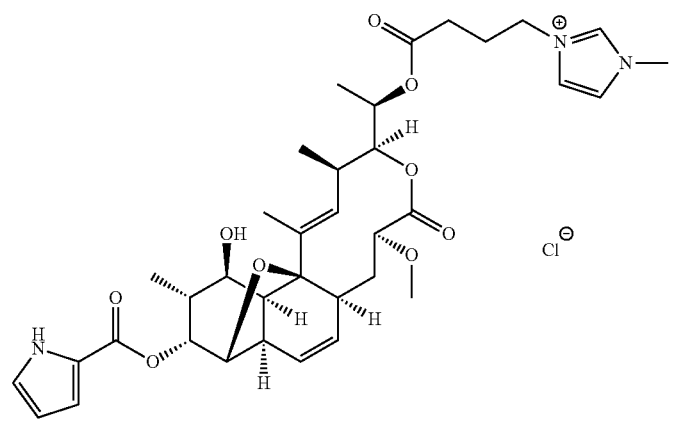 [SMILES: CO[C@H]1C[C@H]2C=C[C@H]3[C@H]4O[C@]2(/C(C)=C/[C@@H](C)[C@@H]([C@@H](C)OC(=O)CCC[n+]2ccn(C)c2)OC1=O)[C@@H]3[C@H](O)[C@@H](C)[C@H]4OC(=O)c1ccc[nH]1 ; [Cl-]] | 666.21 |
2.5 equivalents of sodium iodide were used in this reaction.

| Example | Structure | [M + H]+ |
|---|---|---|
| 99 | 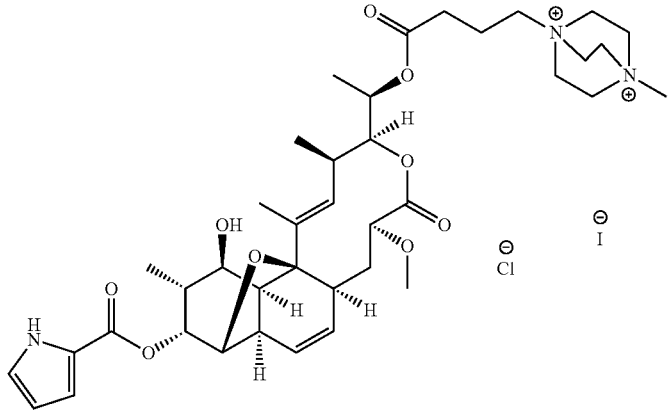 [SMILES: CO[C@H]1C[C@H]2C=C[C@H]3[C@H]4O[C@]2(/C(C)=C/[C@@H](C)[C@@H]([C@@H](C)OC(=O)CCC[N+]25CC[N+](C)(CC2)CC5)OC1=O)[C@@H]3[C@H](O)[C@@H](C)[C@H]4OC(=O)c1ccc[nH]1 ; [Cl-] ; [I-]]<br>After the first quaternization with DABCO was complete, the reaction mixture was cooled to room temperature and 17 equivalents of iodomethane were added to afford the second quaternization. | [M − H]<br>710.26<br>[M/2]<br>355.65 |
| 100 | 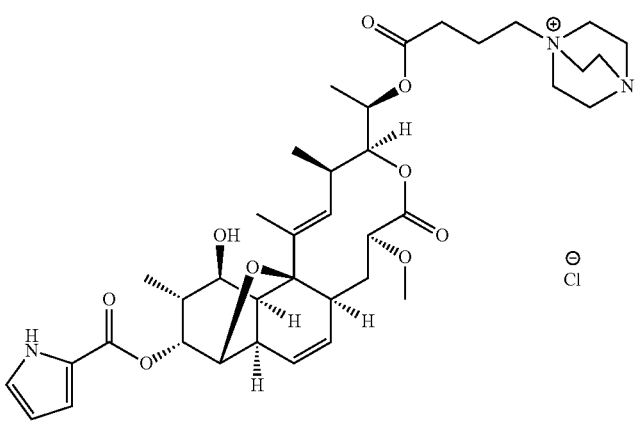 [SMILES: CO[C@H]1C[C@H]2C=C[C@H]3[C@H]4O[C@]2(/C(C)=C/[C@@H](C)[C@@H]([C@@H](C)OC(=O)CCC[N+]25CCN(CC2)CC5)OC1=O)[C@@H]3[C@H](O)[C@@H](C)[C@H]4OC(=O)c1ccc[nH]1 ; [Cl-]] | 696.31 |
| Examples prepared using example 62 as a starting material. | | |
| 101 | 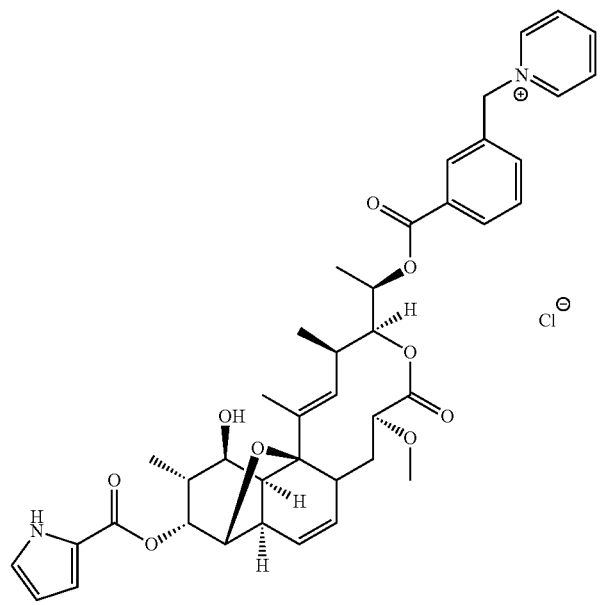 [SMILES: CO[C@H]1CC2C=C[C@H]3[C@H]4O[C@]2(/C(C)=C/[C@@H](C)[C@@H]([C@@H](C)OC(=O)c2cccc(C[n+]5ccccc5)c2)OC1=O)[C@@H]3[C@H](O)[C@@H](C)[C@H]4OC(=O)c1ccc[nH]1 ; [Cl-]]<br>The reaction was run neat in pyridine and heated to 100° C. | 711.25 |

| Example | Structure | [M + H]+ |
|---|---|---|
| 102 | 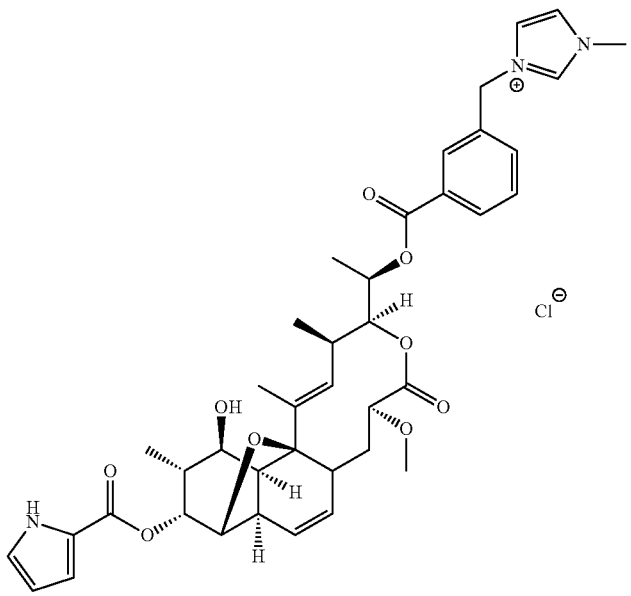 [SMILES: CO[C@H]1CC2C=C[C@H]3[C@H]4O[C@]2(/C(C)=C/[C@@H](C)[C@@H]([C@@H](C)OC(=O)c2cccc(C[n+]5ccn(C)c5)c2)OC1=O)[C@@H]3[C@H](O)[C@@H](C)[C@H]4OC(=O)c1ccc[nH]1 ; [Cl-]] | 714.25 |
| 103 | 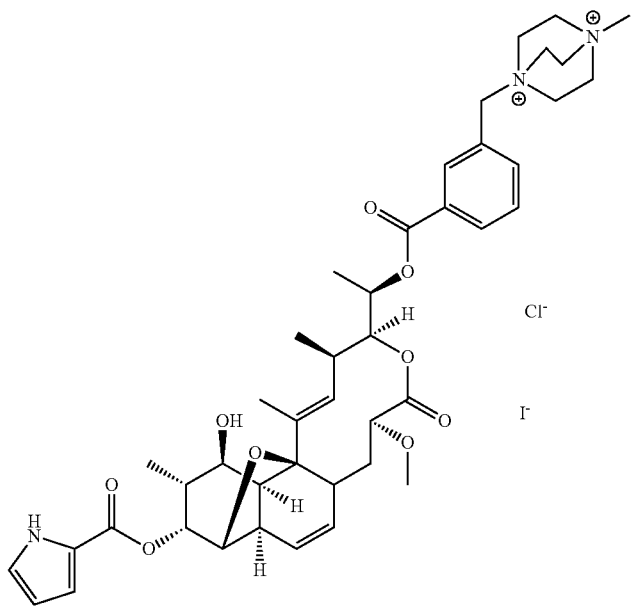 [SMILES: CO[C@H]1CC2C=C[C@H]3[C@H]4O[C@]2(/C(C)=C/[C@@H](C)[C@@H]([C@@H](C)OC(=O)c2cccc(C[N+]56CC[N+](C)(CC5)CC6)c2)OC1=O)[C@@H]3[C@H](O)[C@@H](C)[C@H]4OC(=O)c1ccc[nH]1 ; [I-] ; [Cl-]] | [M − H] 758.30 |
After the first quaternization with DABCO was complete, the reaction mixture was cooled to room temperature and 16 equivalents of iodomethane were added to afford the second quaternization.

-continued

| Example | Structure | [M + H]+ |
|---|---|---|
| 104 | 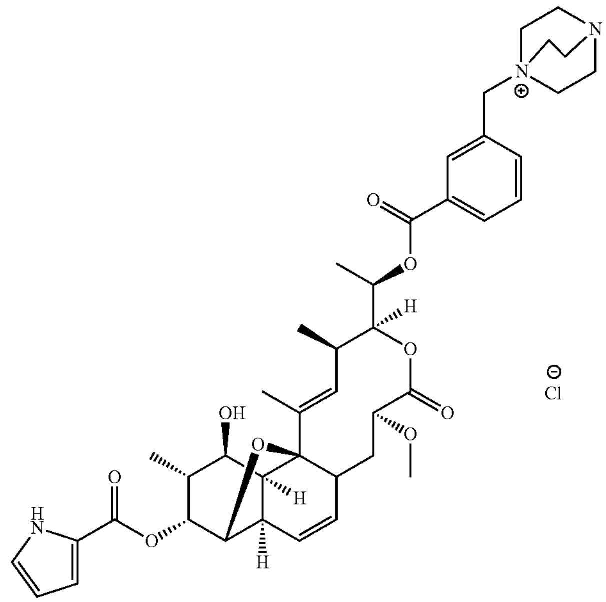 [SMILES: CO[C@H]1CC2C=C[C@H]3[C@H]4O[C@]2(/C(C)=C/[C@@H](C)[C@@H]([C@@H](C)OC(=O)c2cccc(C[N+]56CCN(CC5)CC6)c2)OC1=O)[C@@H]3[C@H](O)[C@@H](C)[C@H]4OC(=O)c1ccc[nH]1 ; [Cl-]] | 744.33 |
| 105 | 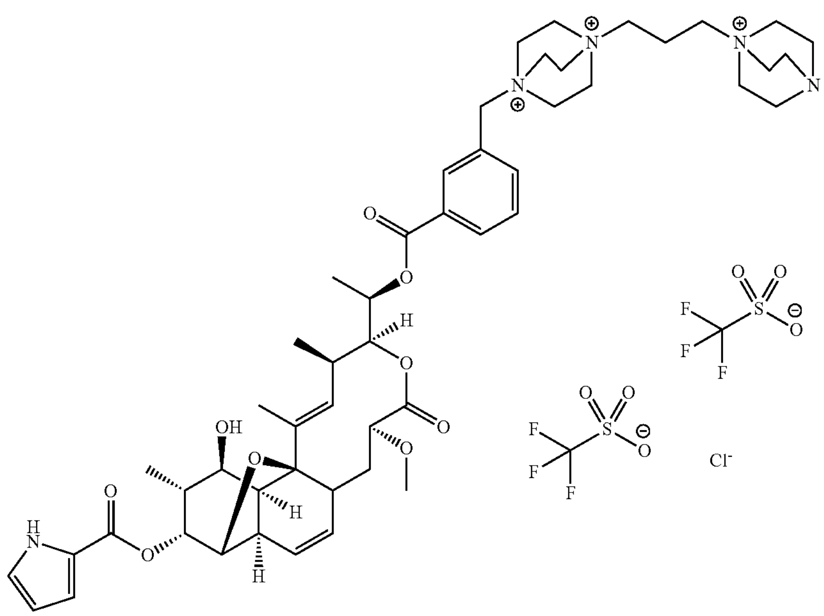 [SMILES: CO[C@H]1CC2C=C[C@H]3[C@H]4O[C@]2(/C(C)=C/[C@@H](C)[C@@H]([C@@H](C)OC(=O)c2cccc(C[N+]56CC[N+](CCC[N+]78CCN(CC7)CC8)(CC5)CC6)c2)OC1=O)[C@@H]3[C@H](O)[C@@H](C)[C@H]4OC(=O)c1ccc[nH]1 ; O=S(=O)([O-])C(F)(F)F ; O=S(=O)([O-])C(F)(F)F ; [Cl-]] | [(M/2) − H] 448.71 |

| Example | Structure | [M + H]+ |
| --- | --- | --- |
| 106 | 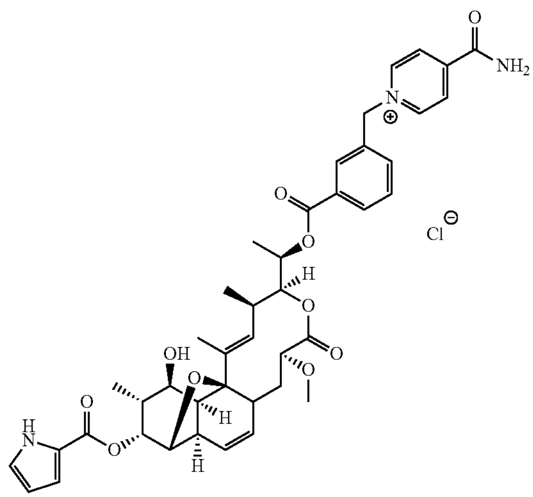 [SMILES: CO[C@H]1CC2C=C[C@H]3[C@H]4O[C@]2(/C(C)=C/[C@@H](C)[C@@H]([C@@H](C)OC(=O)c2cccc(C[n+]5ccc(C(N)=O)cc5)c2)OC1=O)[C@@H]3[C@H](O)[C@@H](C)[C@H]4OC(=O)c1ccc[nH]1 ; [Cl-]] | 754.26 |
| 107 | 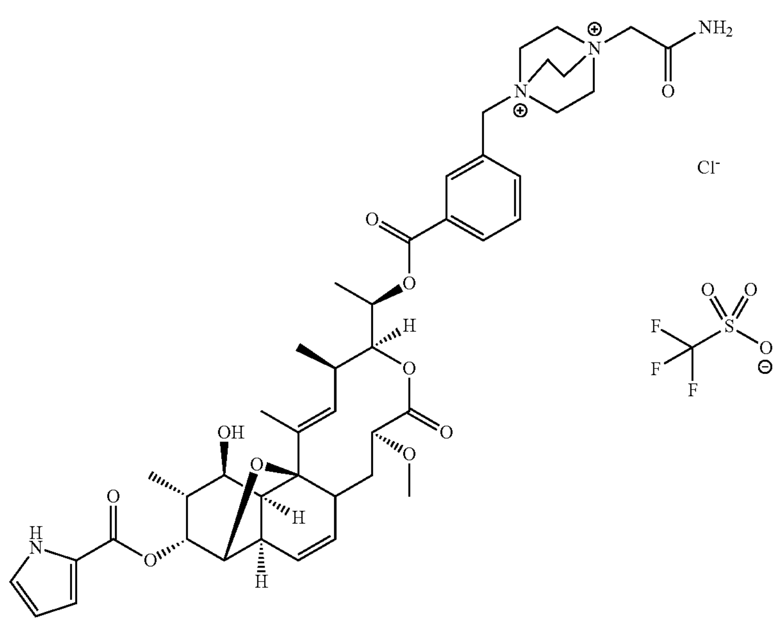 [SMILES: CO[C@H]1CC2C=C[C@H]3[C@H]4O[C@]2(/C(C)=C/[C@@H](C)[C@@H]([C@@H](C)OC(=O)c2cccc(C[N+]56CC[N+](CC(N)=O)(CC5)CC6)c2)OC1=O)[C@@H]3[C@H](O)[C@@H](C)[C@H]4OC(=O)c1ccc[nH]1 ; O=S(=O)([O-])C(F)(F)F ; [Cl-]] | [M − H] 801.38 [M/2] 401.23 |

135 136
-continued
| Example | Structure | [M + H]+ |
|---------|-----------|----------|
Examples prepared using example 63 as a starting material.
108 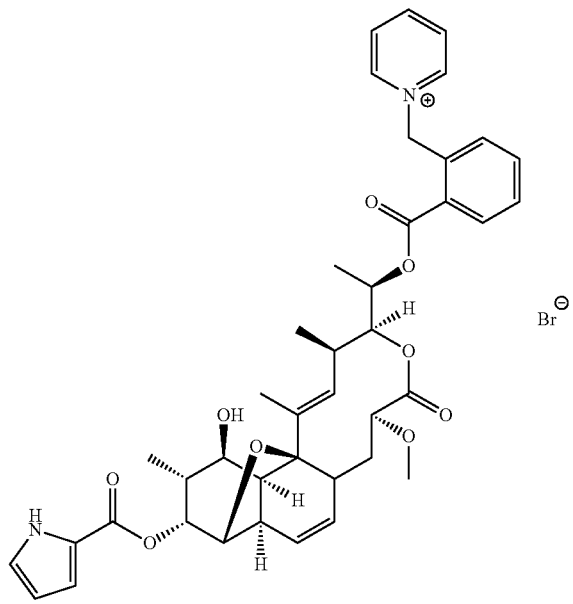 [SMILES: CO[C@H]1CC2C=C[C@H]3[C@H]4O[C@]2(/C(C)=C/[C@@H](C)[C@@H]([C@@H](C)OC(=O)c2ccccc2C[n+]2ccccc2)OC1=O)[C@@H]3[C@H](O)[C@@H](C)[C@H]4OC(=O)c1ccc[nH]1 ; [Br-]] 711.22
The reaction was run neat in pyridine and heated to 100° C.
109 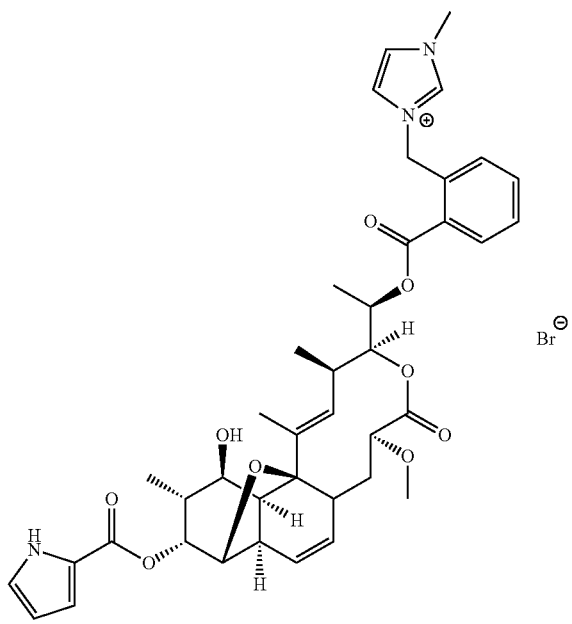 [SMILES: CO[C@H]1CC2C=C[C@H]3[C@H]4O[C@]2(/C(C)=C/[C@@H](C)[C@@H]([C@@H](C)OC(=O)c2ccccc2C[n+]2ccn(C)c2)OC1=O)[C@@H]3[C@H](O)[C@@H](C)[C@H]4OC(=O)c1ccc[nH]1 ; [Br-]] 714.24

| Example | Structure | [M + H]+ |
|---|---|---|
| 110 | 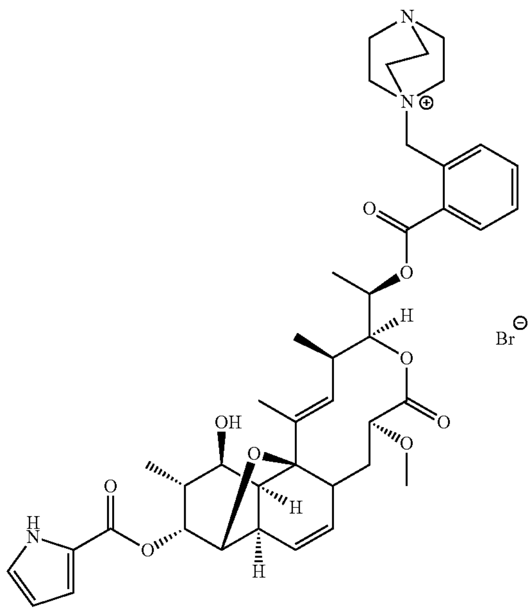 [SMILES: CO[C@H]1CC2C=C[C@H]3[C@H]4O[C@]2(/C(C)=C/[C@@H](C)[C@@H]([C@@H](C)OC(=O)c2ccccc2C[N+]25CCN(CC2)CC5)OC1=O)[C@@H]3[C@H](O)[C@@H](C)[C@H]4OC(=O)c1ccc[nH]1 ; [Br-]] | 744.33 |
| 111 | 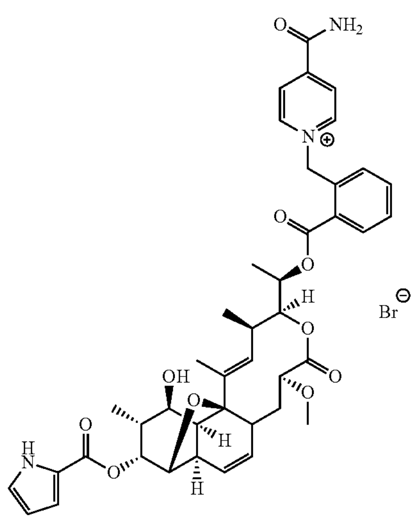 [SMILES: CO[C@H]1CC2C=C[C@H]3[C@H]4O[C@]2(/C(C)=C/[C@@H](C)[C@@H]([C@@H](C)OC(=O)c2ccccc2C[n+]2ccc(C(N)=O)cc2)OC1=O)[C@@H]3[C@H](O)[C@@H](C)[C@H]4OC(=O)c1ccc[nH]1 ; [Br-]] | 754.25 |

-continued

| Example | Structure | [M + H]+ |
|---|---|---|
| 112 | 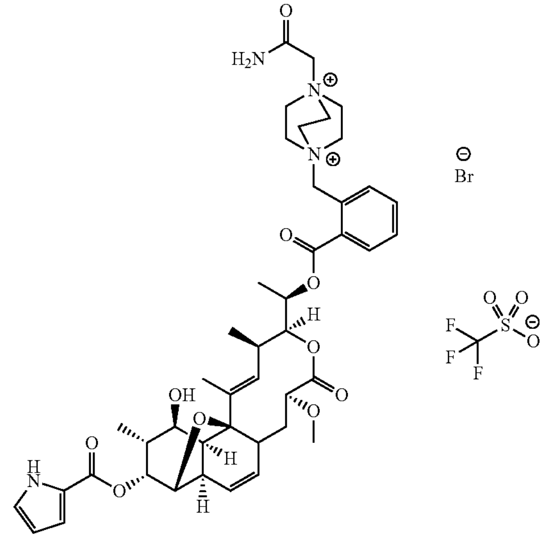 [SMILES: CO[C@H]1CC2C=C[C@H]3[C@H]4O[C@]2(/C(C)=C/[C@@H](C)[C@@H]([C@@H](C)OC(=O)c2ccccc2C[N+]25CC[N+](CC(N)=O)(CC2)CC5)OC1=O)[C@@H]3[C@H](O)[C@@H](C)[C@H]4OC(=O)c1ccc[nH]1 ; O=S(=O)([O-])C(F)(F)F ; [Br-]] | [M − H] 801.36 [M/2] 401.22 |

Example 113

1-(2-(((1R)-1-((3R,4S,7S,10aR,11R,12R,13R,14R, 14aS,14bS,E)-12-((1H-pyrrole-2-carbonyl)oxy)-14-hydroxy-7-methoxy-1,3,13-trimethyl-6-oxo-3,4,6,7, 8,8a,10a,11,12,13,14,14a-dodecahydro-11,14b-epoxynaphtho[2,1-e]oxecin-4-yl)ethoxy)carbonyl) benzyl)-4-methyl-1,4-diazabicyclo[2.2.2]octane-1,4-diium bromide iodide Iodomethane (5 μl, 0.080 mmol) was added to a stirred solution of 1-(2-(((1R)-1-((3R,4S,7S,10aR,11R,12R,13R, 14R,14aS,14bS,E)-12-((1H-pyrrole-2-carbonyl)oxy)-14-hydroxy-7-methoxy-1,3,13-trimethyl-6-oxo-3 ,4,6,7,8,8a, 10a,11,12,13,14,14a-dodecahydro-11,14b-epoxynaphtho[2, 1-e]oxecin-4-yl)ethoxy)carbonyl)benzyl)-1,4-diazabicyclo [2.2.2]octan-1-ium bromide (2.5 mg, 3.03 μmol) in Acetonitrile (0.25 ml). The reaction mixture was a colorless solution that was stirred at room temperature. After 4.5 hours, the reaction mixture was diluted with ethanol and evaporated under reduced pressure. The resulting residue was lyophilized from ethanol and benzene to give the title compound as a yellow solid. The resulting residue was purified on a Waters Sunfire C18, 30×150 mm column, eluting with Acetonitrile/Water +0.1% TFA at 20 ml/min using a 12 minute 20-100% Acetonitrile/Water gradient followed by a 7 minute Acetonitrile flush. The product fractions were combined, evaporated under reduced pressure, and lyophilized from ethanol and benzene to give the title compound as a white solid. LC-MS: calculated for $C_{43}H_{57}N_3O_9{}^{2+}$ 759.41 observed m/e: 758.33 (M−H), 379.63 (M/2) (Rt 1.60/4 min); $^1$H NMR δ (ppm) CD$_3$OD: 11.29 (s, 1 H); 8.30 (dd, J=7.8, 1.4 Hz, 1 H); 7.85 (td, J=7.5, 1.5 Hz, 1 H); 7.80 (td, J=7.6, 1.3 Hz, 1 H); 7.74 (dd, J=7.6, 1.3 Hz, 1 H); 6.98 (dt, J=2.7, 1.6 Hz, 1 H); 6.86-6.88 (m, 1 H); 6.19-6.21 (m, 1 H); 5.91 (ddd, J=9.4, 6.8, 1.9 Hz, 1 H); 5.57 (dd, J=9.4, 3.0 Hz, 1 H); 5.55 (d, J=9.1 Hz, 1 H); 5.51 (dd, J=6.7, 5.3 Hz, 1 H); 5.40 (dd, J=7.0, 5.1 Hz, 1 H); 5.30-5.37 (m, 2 H); 5.00 (t, J=4.9 Hz, 1 H); 4.07-4.11 (m, 7 H); 3.97 (t, J=7.3 Hz, 6 H); 3.68-3.72 (m, 2 H); 3.34 (s, 3 H); 3.29 (s, 3 H); 2.62 (d, J=7.0 Hz, 1 H); 2.52 (ddd, J=15.1, 11.3, 4.7 Hz, 1 H); 2.48 (d, J=2.7 Hz, 1 H); 2.40-2.42 (m, 1 H); 2.28-2.34 (m, 1 H); 1.77 (s, 3 H); 1.53 (d, J=6.4 Hz, 3 H); 1.38 (dt, J=15.1, 3.3 Hz, 1 H); 1.23 (d, J=7.2 Hz, 3 H); 0.91 (d, J=6.8 Hz, 3 H).

Example 114

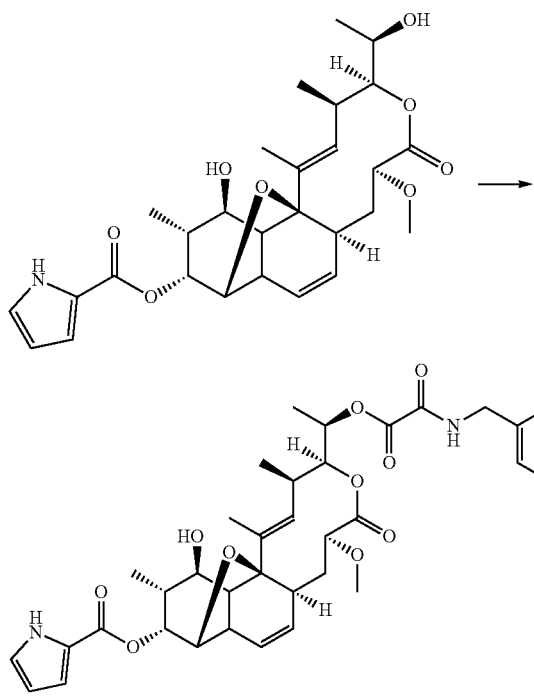

(3R,4S,7S,8aS,11R,12R,13R,14R,14bS,E)-4-((R)-1-(2-(benzylamino)-2-oxoacetoxy)ethyl)-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate A mixture of Nargenicin (24 mg, 0.047 mmol), benzyl amine (5 uL, 0.047 mmol), pyridine (15 uL, mmol) and oxalyl chloride (6 uL, 0.066 mmol) was stirred at ambient temperature in DCE (0.2 mL) for 15 minutes. The solvent was removed under vacuum, the residue was dissolved in methanol and loaded onto a 30×150 mm Sunfire column (using a gradient of MeCN/water each containing .05% TFA). The appropriate fractions were evaporated under vacuum to give the title compound as a solid after freeze-drying from benzene 5.4 mg.

LC/MS-M+1=699.17

$^1$H NMR-{0.94-0.91 (3 H, m), 1.16 (3 H, d, J=7.13 Hz), 1.44-1.40 (4 H, m), 1.60 (1 H, s), 1.81 (3 H, s), 2.49 (1 H, s), 2.63 (1 H, d, J=6.96 Hz), 3.18 (2 H, s), 3.46 (2 H, s), 3.72 (1 H, d, J=4.91 Hz), 4.14 (1 H, d, J=4.87 Hz), 4.48 (3 H, d, J=11.17 Hz), 4.59 (1 H, s), 5.05 (1 H, t, J=4.90 Hz), 5.33 (1 H, d, J=6.40 Hz), 5.43 (1 H, t, J=6.63 Hz), 5.49 (1 H, d, J=8.22 Hz), 5.61 (1 H, dd, J=9.42, 3.01 Hz), 5.93 (1 H, s), 6.22 (1 H, t, J=3.21 Hz), 6.88 (1 H, d, J=3.66 Hz), 7.00 (1 H, s), 7.34-7.32 (4 H, m).

The following examples were generally prepared according to the methods in Example 114 by substituting the amine with the appropriate alcohol to provide the described oxalate analog.

| Example @ | Structure | LC-MS |
|---|---|---|
| 69 | 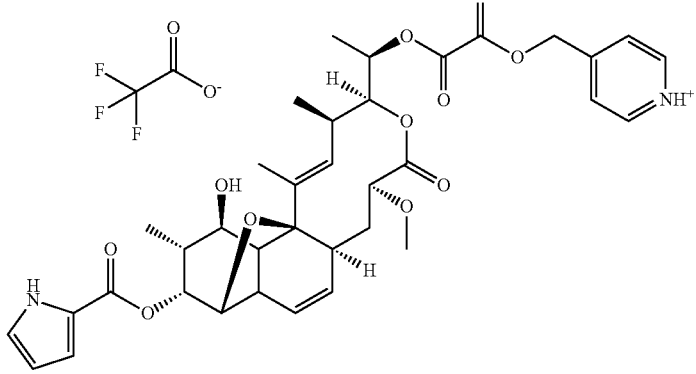 | 679.27 |
| 169 | 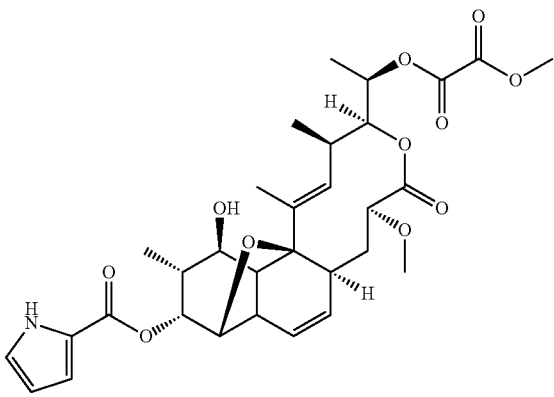 | M + 1 = 632.25 |

-continued
| Example | Structure | LC-MS |
|---|---|---|
| 205 | 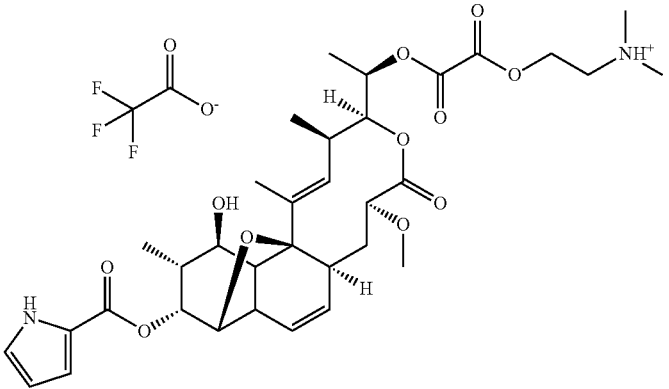 [SMILES: CO[C@H]1C[C@H]2C=CC3C4[C@H](O)[C@@H](C)[C@@H](OC(=O)c5ccc[nH]5)[C@@H]3O[C@]42/C(C)=C/[C@@H](C)[C@@H]([C@@H](C)OC(=O)C(=O)OCC[NH+](C)C)OC1=O ; O=C([O-])C(F)(F)F] | M + 1 = 659.24 |
| 206 | 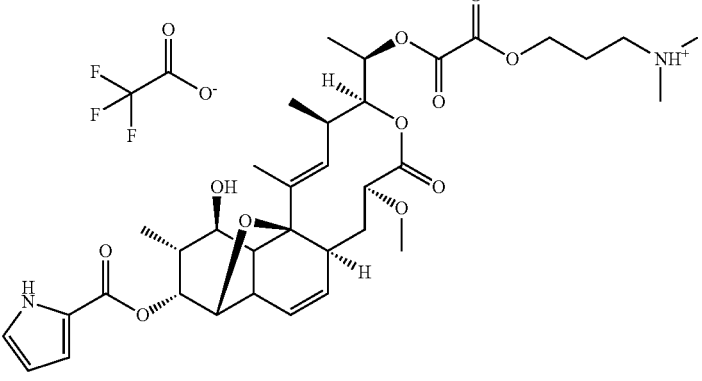 | M + 1 = 673.29 |
| 207 | 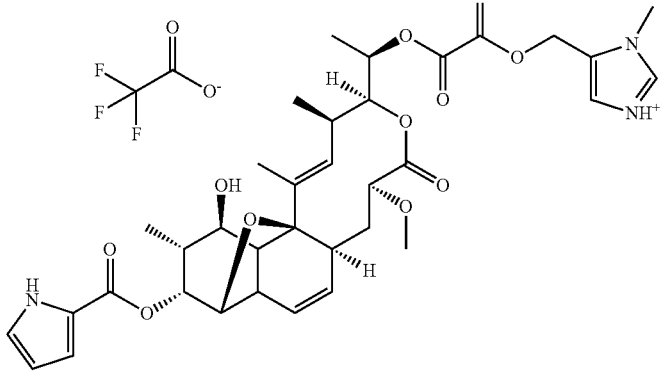 | M + 1 = 682.29 |
| 208 | 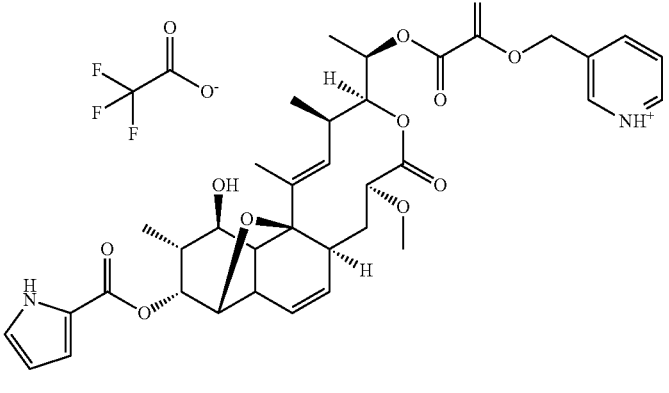 | LC/MS = 679.20 |

| Example @ | Structure | LC-MS |
|---|---|---|
| 209 | 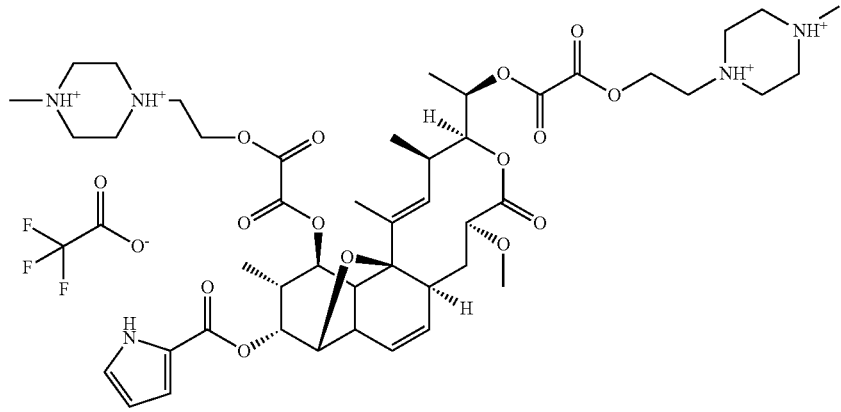 | |
| 210 | 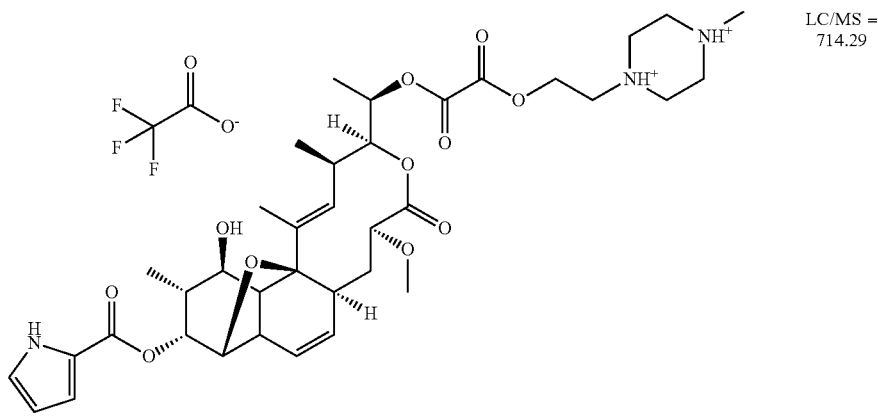 | LC/MS = 714.29 |
| 211 | 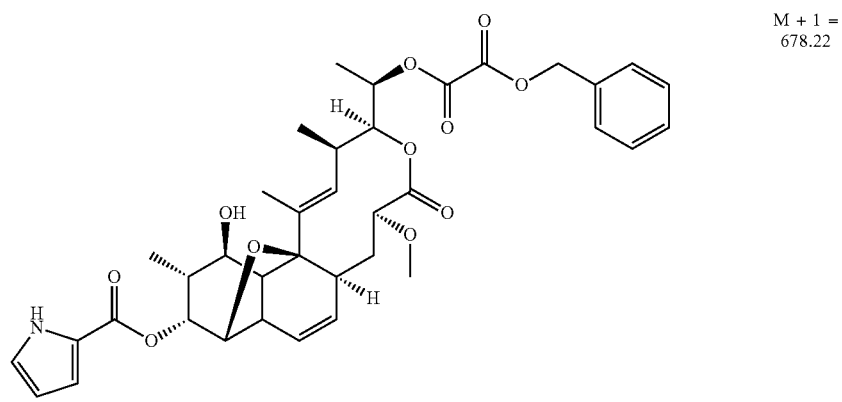 | M + 1 = 678.22 |

-continued
| Example | Structure | LC-MS |
|---|---|---|
| 212 | 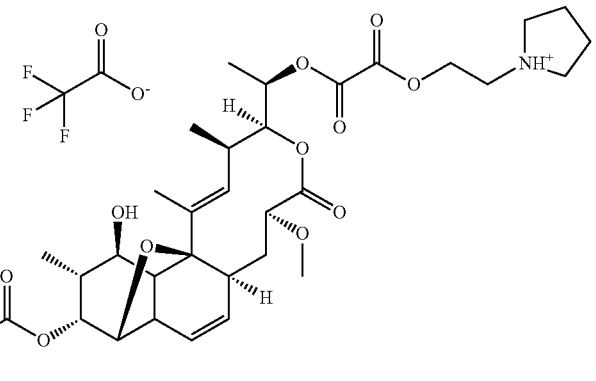 | M + 1 = 685.29 |
| 213 | 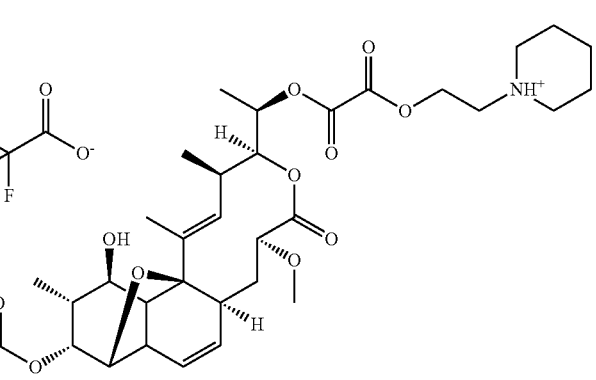 | |
Examples 115-142
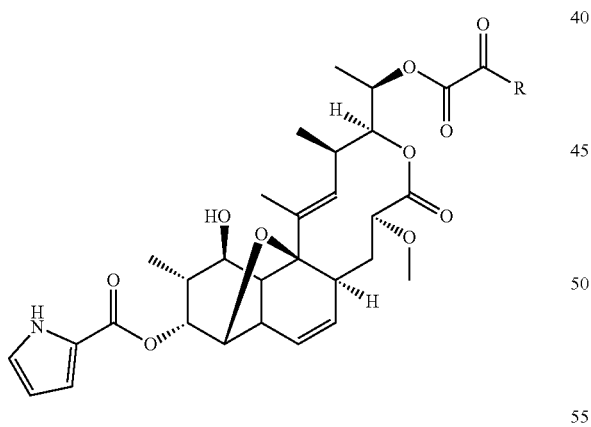
Examples 115-142 were generally prepared according to the methods in Example 114.
| EXAMPLE | R | LC/MS |
|---|---|---|
| 115 | 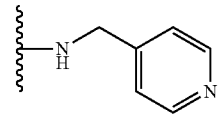 [SMILES: *NCc1ccncc1] | M + 1 = 678.19 |

-continued
| EXAMPLE | R | LC/MS |
|---|---|---|
| 116 | 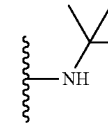 | M + Na = 665.13 |
| 117 | 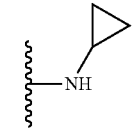 [SMILES: *NC1CC1] | M + Na = 649.12 |
| 118 | 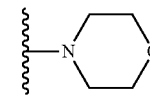 | M + Na = 679.14 |
| 119 | 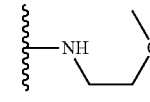 | M + Na = 667.16 |
| 120 | 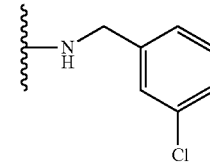 | M + Na = 733.12 |
| 121 | 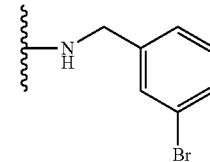 | M + Na = 777.08 and 778.95 |
| 122 | 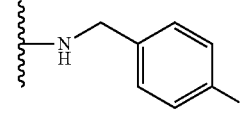 | M + Na = 777.09 and 778.96 |
| 123 | 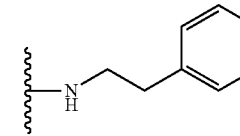 | M + Na = 713.19 |
| 124 | 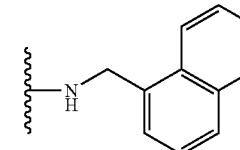 | M + Na = 749.17 |
| 125 | 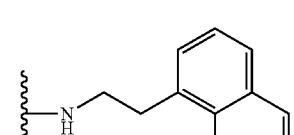 | M + Na = 763.25 |

-continued
| EXAMPLE | R | LC/MS |
|---|---|---|
| 126 |  | M + Na = 623.17 + SM |
| 127 | 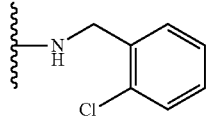 [SMILES: *NCc1ccccc1Cl] | M + Na = 733.12 |
| 128 | 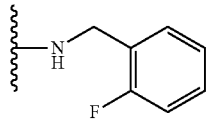 [SMILES: *NCc1ccccc1F] | M + Na = 717.18 |
| 129 | 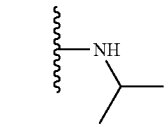 [SMILES: *NC(C)C] | M + Na = 651.16 |
| 130 | 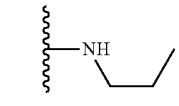 | M + Na = 651.17 |
| 131 | 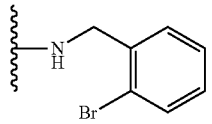 | M + Na = 777.08 and 779.00 |
| 132 | 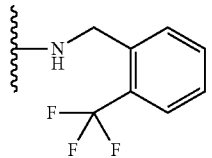 [SMILES: *NCc1ccccc1C(F)(F)F] | M + Na = 767.19 |
| 133 | 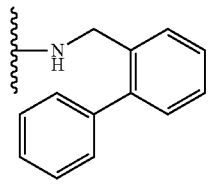 [SMILES: *NCc1ccccc1-c1ccccc1] | M + Na = 775.28 |
| 134 | 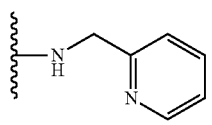 [SMILES: *NCc1ccccn1] | M = 1 = 678.22 |
| 135 | 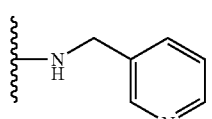 | M + 1 = 678.23 |
| 136 | 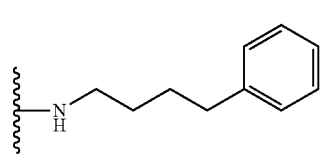 [SMILES: *NCCCCc1ccccc1] | M + Na = 741.17 |

-continued
| EXAMPLE | R | LC/MS |
|---|---|---|
| 137 | 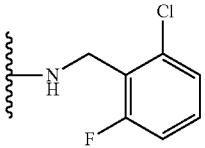 [SMILES: *NCc1c(F)cccc1Cl] | M + Na = 751.10 |
| 138 | 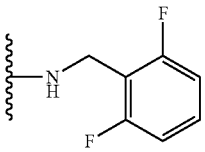 | M + Na = 735.17 |
| 139 | 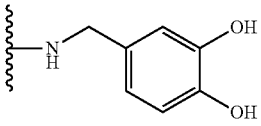 [SMILES: *NCc1ccc(O)c(O)c1] | M + Na = 731.19 |
| 140 | 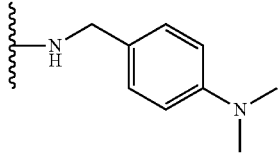 [SMILES: *NCc1ccc(N(C)C)cc1] | M + 1 = 720.27 |
| 141 | 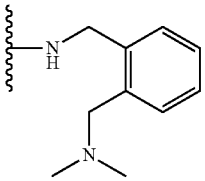 [SMILES: *NCc1ccccc1CN(C)C] | M + 1 = 734.29 |
| 142 | 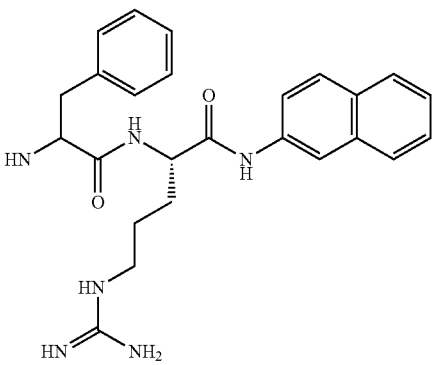 | M + 1 = 1016.71 |

Examples 143 and 144

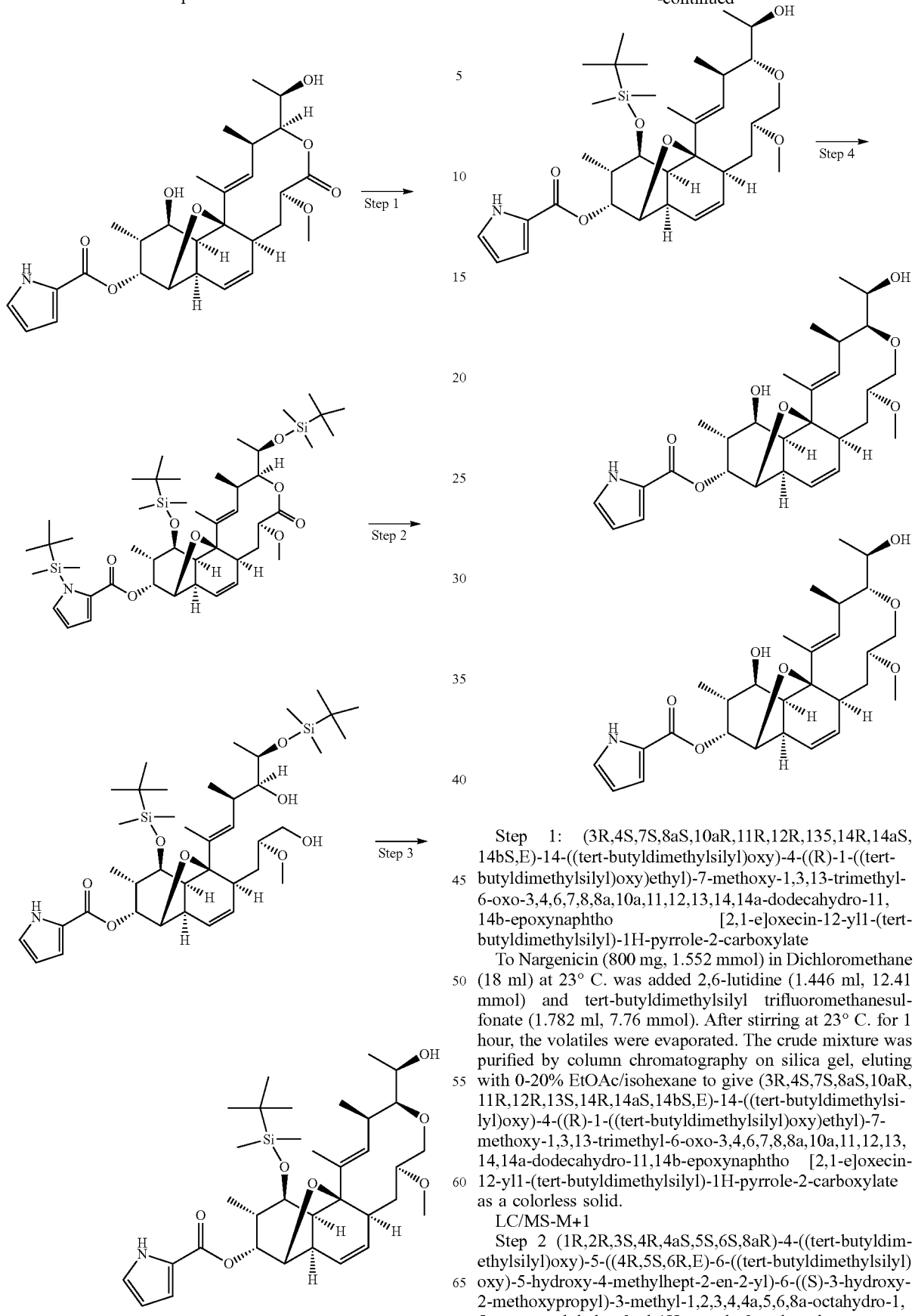

Step 1: (3R,4S,7S,8aS,10aR,11R,12R,13S,14R,14aS,14bS,E)-14-((tert-butyldimethylsilyl)oxy)-4-((R)-1-((tert-butyldimethylsilyl)oxy)ethyl)-7-methoxy-1,3,13-trimethyl-6-oxo-3,4,6,7,8,8a,10a,11,12,13,14,14a-dodecahydro-11,14b-epoxynaphtho [2,1-e]oxecin-12-yl1-(tert-butyldimethylsilyl)-1H-pyrrole-2-carboxylate To Nargenicin (800 mg, 1.552 mmol) in Dichloromethane (18 ml) at 23° C. was added 2,6-lutidine (1.446 ml, 12.41 mmol) and tert-butyldimethylsilyl trifluoromethanesulfonate (1.782 ml, 7.76 mmol). After stirring at 23° C. for 1 hour, the volatiles were evaporated. The crude mixture was purified by column chromatography on silica gel, eluting with 0-20% EtOAc/isohexane to give (3R,4S,7S,8aS,10aR,11R,12R,13S,14R,14aS,14bS,E)-14-((tert-butyldimethylsilyl)oxy)-4-((R)-1-((tert-butyldimethylsilyl)oxy)ethyl)-7-methoxy-1,3,13-trimethyl-6-oxo-3,4,6,7,8,8a,10a,11,12,13,14,14a-dodecahydro-11,14b-epoxynaphtho [2,1-e]oxecin-12-yl1-(tert-butyldimethylsilyl)-1H-pyrrole-2-carboxylate as a colorless solid.

LC/MS-M+1

Step 2 (1R,2R,3S,4R,4aS,5S,6S,8aR)-4-((tert-butyldimethylsilyl)oxy)-5-((4R,5S,6R,E)-6-((tert-butyldimethylsilyl)oxy)-5-hydroxy-4-methylhept-2-en-2-yl)-6-((S)-3-hydroxy-2-methoxypropyl)-3-methyl-1,2,3,4,4a,5,6,8a-octahydro-1,5-epoxynaphthalen-2-yl 1H-pyrrole-2-carboxylate To (3R,4S,7S,8aS,10aR,11R,12R,13S,14R,14aS,14bS,E)-14-((tert-butyldimethylsilyl)oxy)-4-((R)-1-((tert-butyldimethylsilyl)oxy)ethyl)-7-methoxy-1,3,13-trimethyl-6-oxo-3,4,6,7,8,8a,10a,11,12,13,14,14a-dodecahydro-11,14b-epoxynaphtho [2,1-e]oxecin-12-yl 1-(tert-butyldimethylsilyl)-1H-pyrrole-2-carboxylate (100 mg, 0.116 mmol) in THF(2 mL) was added LAH (8.8 mg, 0,.23 mmol). After stirring at rt for 30 mins, the reaction mixture was quenched with NH₄Cl solution, back extracted with CH₂Cl₂, and dried filtered. The reaction mixture was purified by column chromatography on silica gel, eluting with 10-100% EtOAc/hexanes to give (1R,2R,3S,4R,4aS,5S,6S,8aR)-4-((tert-butyldimethylsilyl)oxy)-5-((4R,5S,6R,E)-6-((tert-butyldimethylsilyl)oxy)-5-hydroxy-4-methylhept-2-en-2-yl)-6-((S)-3-hydroxy-2-methoxypropyl)-3-methyl-1,2,3,4,4a,5,6,8a-octahydro-1,5-epoxynaphthalen-2-yl 1H-pyrrole-2-carboxylate.

LC/MS-M+1: 748.57

Step 3, (3R,4S,7S,8aS,10aR,11R,12R,13S,14R,14aS,14bS,E)-14-((tert-butyldimethylsilyl)oxy)-4-((R)-1-hydroxyethyl)-7-methoxy-1,3,13-trimethyl-3,4,6,7,8,8a,10a,11,12,13,14,14a-dodecahydro-11,14b-epoxynaphtho [2,1-e]oxecin-12-yl 1H-pyrrole-2-carboxylate and (3R,4R,7S ,8aS ,10aR,11R,12R,13 S ,14R,14aS ,14bS,E)-14-((tert-butyldimethylsilyl)oxy)-4-((R)-1-hydroxyethyl)-7-methoxy-1,3,13-trimethyl-3,4,6,7,8,8a,10a,11,12,13,14,14a-dodecahydro-11,14b-epoxynaphtho [2,1-e]oxecin-12-yl 1H-pyrrole-2-carboxylate To (1R,2R,3S,4R,4aS,5S,6S,8aR)-4-((tert-butyldimethylsilyl)oxy)-5-((4R,5S,6R,E)-6-((tert-butyldimethylsilyl)oxy)-5-hydroxy-4-methylhept-2-en-2-yl)-6-((S)-3-hydroxy-2-methoxypropyl)-3-methyl-1,2,3,4,4a,5,6,8a-octahydro-1,5-epoxynaphthalen-2-yl 1H-pyrrole-2-carboxylate (63 mg, 0.084 mmol) in DCM (1.5 mL) was added DMAP (31 mg, 0.25 mmol) and p-toluene sulfonic anhydride (33 mg, 0.10 mmol). After stirring at room temperature overnight, the reaction was heated at 40° C. for 24 hours, diluted with dichloromethane and EtOAc, filtered through a pad of silica (All DMAP and p-toluenesulfonic anhydride (33.0 mg, 0.101 mmol) were removed) and give about 110 mg crude, which contains about 50% desired product.

To this crude product in DMF (3 mL) was added NaH (4.7 mg, 0.116 mmol). After stirring at room temperature for 30 minutes, quenched with NH₄Cl solution, back extracted with CH₂Cl₂, dried filtered. The reaction mixture was purified by column chromatography on silica gel, eluting with 10-100% EtOAc/hexanes to give a mixture of (3R,4S,7S,8aS,10aR,11R,12R,13S,14R,14aS,14bS,E)-14-((tert-butyldimethylsilyl)oxy)-4((R)-1-hydroxyethyl)-7-methoxy-1,3,13-trimethyl-3,4,6,7,8,8a,10a,11,12,13,14,14a-dodecahydro-11,14b-epoxynaphtho[2,1-e]oxecin-12-yl 1H-pyrrole-2-carboxylate and (3R,4r,7S,8aS,10aR,11R,12R,13S,14R,14aS,14bS,E)-14-((tert-butyldimethylsilyl)oxy)-4-((R)-1-hydroxyethyl)-7-methoxy-1,3,13-trimethyl-3,4,6,7,8,8a,10a,11,12,13,14,14a-dodecahydro-11,14b-epoxynaphtho[2,1-e]oxecin-12-yl 1H-pyrrole-2-carboxylate (16 mg, 0.026 mmol).

LC/MS-M+1=616.28

Step 4, (3R,4S,7S,8aS,10aR,11R,12R,13R,14R,14aS,14bS,E)-14-hydroxy-4-((R)-1-hydroxyethyl)-7-methoxy-1,3,13-trimethyl-3,4,6,7,8,8a,10a,11,12,13,14,14a-dodecahydro-11,14b-epoxynaphtho[2,1-e]oxecin-12-yl 1H-pyrrole-2-carboxylate and (3R,4R,7S,8aS,10aR,11R,12R,13R,14R,14414bS,E)-14-hydroxy-4-((R)-1-hydroxyethyl)-7-methoxy-1,3,13-trimethyl-3,4,6,7,8,8a,10a,11,12,13,14,14a-dodecahydro-11,14b-epoxynaphtho[2,1-e]oxecin-12-yl 1H-pyrrole-2-carboxylate To the mixture of (3R,4S,7S,8aS,10aR,11R,12R,13S,14R,14aS,14bS,E)-14-((tert-butyldimethylsilyl)oxy)-4-((R)-1-hydroxyethyl)-7-methoxy-1,3,13-trimethyl-3,4,6,7,8,8a,10a,11,12,13,14,14a-dodecahydro-11,14b-epoxynaphtho[2,1-e]oxecin-12-yl 1H-pyrrole-2-carboxylate and (3R,4r,7S,8aS,10aR,11R,12R,13S,14R,14aS,14bS,E)-14-((tert-butyldimethylsilyl)oxy)-4-((R)-1-hydroxyethyl)-7-methoxy-1,3,13-trimethyl-3,4,6,7,8,8a,10a,11,12,13,14,14a-dodecahydro-11,14b-epoxynaphtho[2,1-e]oxecin-12-yl 1H-pyrrole-2-carboxylate (16 mg, 0.026 mmol) in Tetrahydrofuran (1.5 ml) in a plastic vial at room temperature was added HF-Pyridine (772 mg, 7.79 mmol) dropwise (Exothermol). After stirring at room temperature for 1 hour, the mixture was diluted with dichloromethane, neutralized with aqueous sodium hydrogen carbonate, the organic layer was dried (sodium sulfate), filtered and the solvent was evaporated under reduced pressure. The crude was purified with MassLinx to give (3R,4S,7S,8aS,10aR,11R,12R,13R,14R,14aS,14bS,E)-14-hydroxy-4-((R)-1-hydroxyethyl)-7-methoxy-1,3,13-trimethyl-3,4,6,7,8,8a,10a,11,12,13,14,14a-dodecahydro-11,14b-epoxynaphtho[2,1-e]oxecin-12-yl 1H-pyrrole-2-carboxylate (0.53 mg, 0.001 mmol) and (3R,4R,7S,8aS,10aR,11R,12R,13R,14R,14aS,14bS,E)-14-hydroxy-4-((R)-1-hydroxyethyl)-7-methoxy-1,3,13-trimethyl-3,4,6,7,8,8a,10a,11,12,13,14,14a-dodecahydro-11,14b-epoxynaphtho[2,1-e]oxecin-12-yl 1H-pyrrole-2-carboxylate (0.61 mg, 0.001 mmol)

LC/MS-M+1=502.12

Example 145

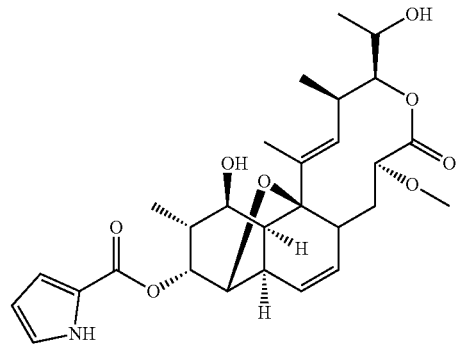 [SMILES: CO[C@H]1CC2C=C[C@H]3[C@H]4O[C@]2(/C(C)=C/[C@@H](C)[C@@H](C(C)O)OC1=O)[C@@H]3[C@H](O)[C@@H](C)[C@H]4OC(=O)c1ccc[nH]1]

The above example illustrates Nargenicin-A₁, which is known in the art and was isolated as a natural product.

Example 146

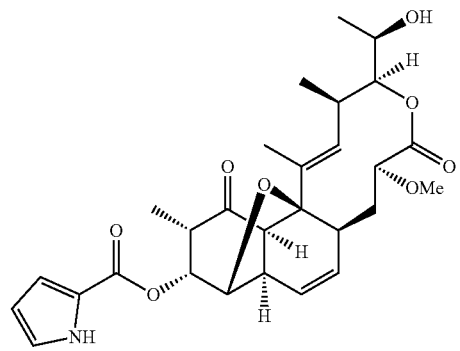 [SMILES: CO[C@H]1C[C@H]2C=C[C@H]3[C@H]4O[C@]2(/C(C)=C/[C@@H](C)[C@@H]([C@@H](C)O)OC1=O)[C@@H]3C(=O)[C@@H](C)[C@H]4OC(=O)c1ccc[nH]1]

(3R,4S,7S,8aS,10aR,11R,12R,13S,14aR,14bS,E)-4-((R)-1-hydroxyethyl)-7-methoxy-1,3,13-trimethyl-6,14-dioxo-3,4,6,7,8,8a,10a,11,12,13,14,14a-dodecahydro-11,14b-epoxynaphtho[2,1-e]oxecin-12-yl 1H-pyrrole-2-carboxylate Dichloromethane (6 mL), potassium carbonate (40 mg 0.29 mmol), and t-butyl hydroperoxide (1.2 mL, 5M, 5.8 mmol) were added to a flask containing (3R,4S,7S,8aS,10aR,11R,12R,13R,14R,14aS,14bS,E)-14-hydroxy-4-((R)-1-hydroxyethyl)-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate (300 mg, 0.58 mmol). Dirhodium tetracaprolactamate (1 mg, 0.002 mmol) was added and the resulting solution was stirred at room temperature overnight. The crude reaction mixture was purified by column chromatography on silica (10-100% ethyl acetate in hexanes) to give (3R,4S,7S,8aS,10aR,11R,12R,13S,14aR,14b S,E)-4-((R)-1-hydroxyethyl)-7-methoxy-1,3,13-trimethyl-6,14-dioxo-3,4,6,7,8,8a,10a,11,12,13,14,14 a-do decahydro-11,14b-epoxynaphtho [2,1-e]oxecin-12-yl 1H-pyrrole-2-carboxylate (185 mg, 0.36 mmol). $^1$H NMR (500 MHz, CD$_3$OD): δ 6.97 (t, J=1.9 Hz, 1H), 6.84 (dd, J=3.8, 1.5 Hz, 1H), 6.19 (dd, J=3.8, 2.5 Hz, 1H), 5.95-5.98 (m, 1H), 5.71 (dd, J=9.4, 2.7 Hz, 1H), 5.54 (d, J=6.8 Hz, 1H), 5.45 (t, J=5.4 Hz, 1H), 5.16 (dd, J=9.3, 5.6 Hz, 1H), 4.42 (d, J=4.8 Hz, 1H), 3.93-3.99 (m, 1H), 3.78 (dd, J=11.8, 5.0 Hz, 1H), 3.30 (s, 3H), 3.05 (d, J=6.9 Hz, 1H), 3.01 (s, 1H), 2.95-2.98 (m, 1H), 2.90-2.93 (m, 1H), 2.40-2.46 (m, 2H), 1.53 (s, 3H), 1.50-1.55 (m, 1H), 1.26 (d, J=7.0 Hz, 3H), 1.18 (d, J=6.1 Hz, 3H), 0.94 (d, J=6.9 Hz, 3H)

Example 147

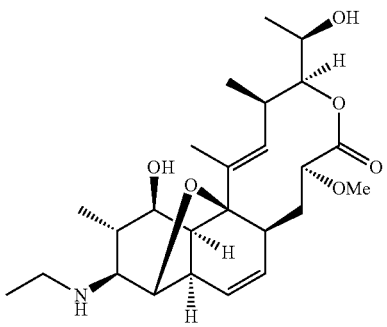 [SMILES: CCN[C@H]1[C@H](C)[C@@H](O)[C@@H]2[C@H]3C=C[C@@H]4C[C@H](OC)C(=O)O[C@H]([C@@H](C)O)[C@H](C)/C=C(\C)[C@@]24O[C@H]31]

(3R,4S,7S,8aS,10aR,11R,12S,13S,14R,14aS,14bS,E)-12-(ethylamino)-14-hydroxy-4-((R)-1-hydroxyethyl)-7-methoxy-1,3,13-trimethyl-3,4,8,8a,10a,11,12,13,14,14a-decahydro-11,14b-epoxynaphtho[2,1-e]oxecin-6(7H)-one (3R,4S,7S,8aS,10aR,11R,12R,13S,14aR,14bS,E)-4-((R)-1-hydroxyethyl)-7-methoxy-1,3,13-trimethyl-6,14-dioxo-3,4,6,7,8,8a,10a,11,12,13,14,14a-dodecahydro-11,14b-epoxynaphtho[2,1-e]oxecin-12-yl 1H-pyrrole-2-carboxylate (6 mg, 0.01 mmol) was dissolved in toluene (0.1 mL). Ethyl amine (0.05 mL, 2 M in THF, 0.5 mmol) and acetic acid (0.02 mL, 1.05 g/mL, 0.35 mmol) were added to this mixture which was then stirred at room temperature under a nitrogen atmoshphere for 2 hours. Toluene was removed under reduced pressure. Methanol (0.1 mL) and sodium borohydride (0.5 mg, 0.1 mmol) were added to the residue and the mixture was stirred at room temperature for several minutes. The crude mixture was purified by mass directed HPLC (19×100 mm Waters Sunfire 5 μm, Electrospray positve detection, gradient: Water +0.05% TFA, MeCN +0.05% TFA, 10-100% over 12 min) to give (3R,4S,7S,8aS,10aR,11R,12S,13S,14R,14aS,14bS,E)-12-(ethylamino)-14-hydroxy-4-((R)-1-hydroxyethyl)-7-methoxy-1,3,13-trimethyl-3,4,8,8a,10a,11,12,13,14,14a-decahydro-11,14b-epoxynaphtho[2,1-e]oxecin-6(7H)-one (1.4 mg 2.4 μmol) as a film. $^1$H NMR (600 MHz, CD$_3$OD) δ 7.87 (s, 1H), 5.94-5.96 (m, 1H), 5.64-5.69 (m, 1H), 5.48 (d, J=6.9 Hz, 1H), 5.14 (s, 1H), 4.25 (s, 1H), 3.97 (dq, J=9.0, 6.2 Hz, 1H), 3.72-3.77 (m, 1H), 3.39-3.45 (m, 2H), 3.28 (s, 3H), 3.03-3.20 (m, 4H), 2.85 (d, J=10.2 Hz, 1H), 2.44-2.50 (m, 3H), 2.30 (s, 1H), 2.23 (dd, J=18.5, 6.9 Hz, 1H), 1.96-2.01 (m, 1H), 1.79 (s, 3H); 1.31 (t, J=15 Hz, 3H) 1.25 (d, J=7.1 Hz, 3H) 1.19 (d, J=6.1 Hz, 3H), 1.13 (d, J=6.5 Hz, 3H).

Example 148

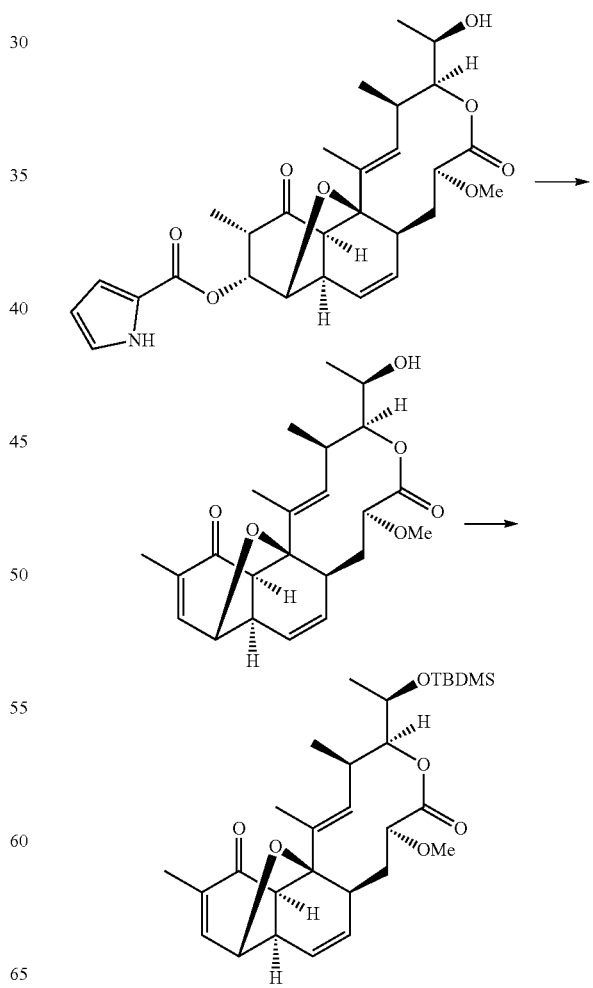

161

Step 1-(3R,4S,7S,8aS,10aR,11R,14aR,14bS,E)-4-((R)-1-hydroxyethyl)-7-methoxy-1,3,13-trimethyl-3,4,8,8a,10a,11-hexahydro-11,14b-epoxynaphtho[2,1-e]oxecine-6,14(7H,14aH)-dione 2,3,4,6,7,8,9,10-Octahydropyrimido[1,2-a]azepine (0.29 mL, 1.01 g/mL, 2.0 mmol) was added to a flask containing a solution of (3R,4S,7S,8aS,10aR,11R,12R,13S,14aR,14bS,E)-4-((R-1-hydroxyethyl)-7-methoxy-1,3,13-trimethyl-6,14-dioxo-3,4,6,7,8,8a,10a,11,12,13,14,14a-dodecahydro-11,14b-epoxynaphtho [2,1-e]oxecin-12-yl 1H-pyrrole-2-carboxylate (500 mg, 0.97 mmol) in acetonitrile (9.7 mL) under a nitrogen atmosphere. The resulting mixture was stirred at room temperature for 1 hour. The reaction mixture was partitioned between ethyl acetate (100 mL) and aqueous hydrochloric acid (100 mL, 0.5 N). The organic phase was washed with saturated aqueous sodium bicarbonate (100 mL) then brine (100 mL), then was dried over magnesium sulfate then filtered. The solvent was evaporated under reduced pressure. Dichloromethane was added to dissolve the residue, and was then evaporated under reduced pressure to give (3R,4S,7S,8aS,10aR,11R,14aR,14bS,E)-4-((R)-1-hydroxyethyl)-7-methoxy-1,3,13-trimethyl-3,4,8,8a,10a,11-hexahydro-11,14b-epoxynaphtho[2,1-e]oxecine-6,14(7H, 14aH)-dione (392 mg, 0.97 mmol) as a foam. $^1$H NMR (500 MHz, CD$_3$OD): δ 7.19 (dd, J=5.9, 1.8 Hz, 1H), 5.89-5.93 (m, 1H), 5.72 (dd, J=9.5, 2.8 Hz, 1H), 5.31 (d, J=7.1 Hz, 1H), 5.11 (dd, J=9.0, 5.9 Hz, 1 H), 3.92-3.98 (m, 1H), 3.75 (dd, J=11.7, 4.7 Hz, 1H), 3.30 (s, 3H), 3.20 (s, 1H), 2.89-2.93 (m, 1H), 2.77 (d, J=6.6 Hz, 1H), 2.52 (s, 1H), 2.39-2.45 (m, 1H), 1.67 (d, J=1.5 Hz, 3H), 1.63 (s, 3H), 1.51-1.55 (m, 1H), 1.19 (d, J=6.2 Hz, 3H), 1.17 (d, J=7.1 Hz, 3H).

Step 2: (3R,4S,7S,8aS,10aR,11R,14aR,14bS,E)-4-((R)-1-((tert-butyldimethylsilyl)oxy)ethyl)-7-methoxy-1,3,13-trimethyl-3,4,8,8a,10a,11-hexahydro-11,14b-epoxynaphtho[2,1-e]oxecine-6,14(7H, 14aH)-dione Tert-butyldimethylsilyl trifluoromethanesulfonate (0.35 mL, 1.5 mmol) followed by 2,6-lutidine (0.3 mL, 2.5 mmol) was added to a flask containing a solution of (3R,4S,7S, 8aS,10aR,11R,14aR,14bS,E)-4-((R)-1-hydroxyethyl)-7-methoxy-1,3,13-trimethyl-3,4,8,8a,10a,11-hexahydro-11,14b-epoxynaphtho [2,1-e]oxecine-6,14(7H,14aH)-dione (392 mg, 0.97 mmol) in dichloroethane (9.7 mL). The resulting mixture was stirred at room temperature for 18 hours, and was then concentrate to half volume by passing a stream of nitrogen over the reaction mixture. This mixture was purified by column chromatography on silica (10-100% ethyl acetate in hexanes) and isolated product was lyophilized from benzene to give (3R,4S,7S,8aS,10aR,11R, 14aR,14bS,E)-4-(R)-1-((tert-butyldimethylsilyl)oxy)ethyl)-7-methoxy-1,3,13-trimethyl-3,4,8,8a,10a,11-hexahydro-11, 14b-epoxynaphtho[2,1-e]oxecine-6,14(7H,14aH)-dione (0.87 mmol). $^1$H NMR (600 MHz, CD$_3$OD) δ 7.17 (d, J=5.8 Hz, 1H), 5.88 (t, J=8.0 Hz, 1H), 5.69 (dd, J=9.5, 2.8 Hz, 1H), 5.31 (d, J=7.3 Hz, 1H), 5.03 (s, 1H), 4.47 (d, J=5.9 Hz, 1H), 4.07-4.11 (m, 1H), 3.72 (dd, J=11.4, 4.5 Hz, 1H), 3.27 (s, 3H) 3.18 (s, 1H), 2.87-2.90 (m, 1H), 2.75 (d, J=6.6 Hz, 1H), 2.51 (s, 1H), 2.41 (ddd, J=15.0, 11.5, 4.5 Hz, 1H), 1.65(s, 3H); 1.59 (s, 3H); 1.49-1.53 (m, 1H), 1.18 (d, J=6.1 Hz, 3H), 1.12 (d, J=7.0 Hz, 3H), 0.90 (s, 9H), 0.12 (s, 6H).

162

Example 149

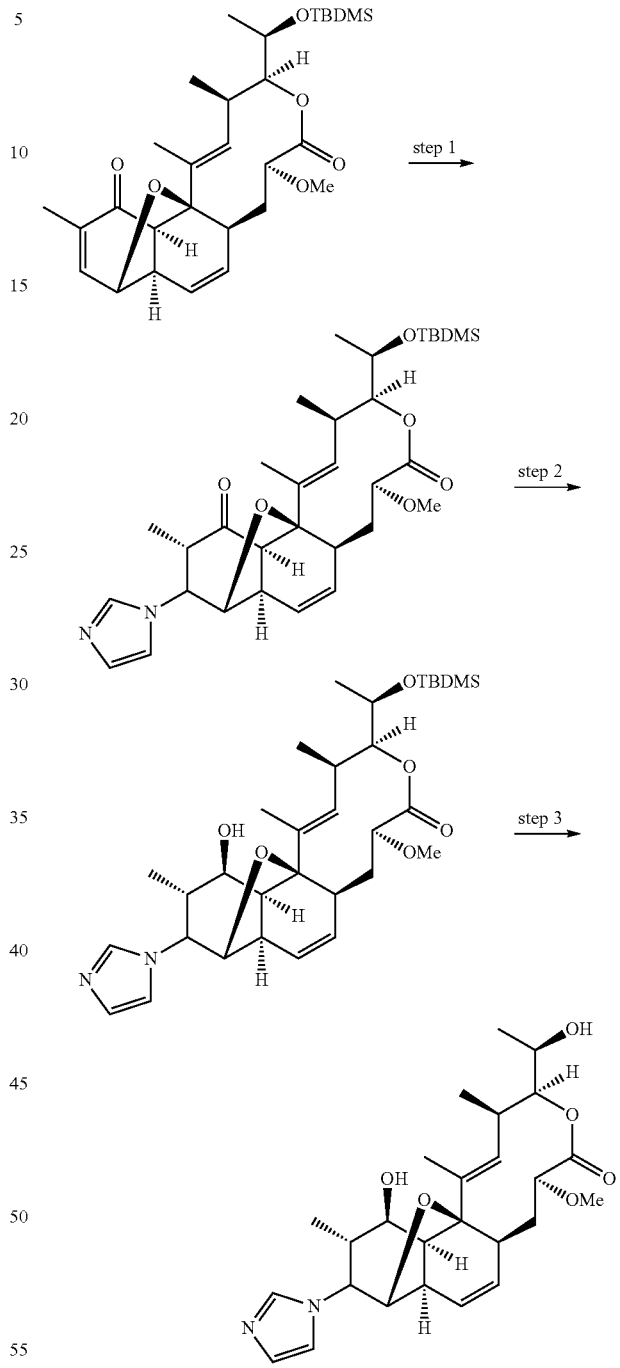

(3R,4 S,7S,8aS,10aR,11R,14R,14aS,14b S,E)-14-hydroxy-4-((R)-1-hydroxyethyl)-12-(1H-imidazol-1-yl)-7-methoxy-1,3-dimethyl-3 ,4,8,8a,10a,11,12,13,14,14a-decahydro-11,14b-epoxynaphtho[2,1-e]oxecin-6(7H)-one Step 1. (3R,4S,7S,8aS,10aR,11R,14aR,14bS,E)-4-((R)-1-((tert-butyldimethylsilyl)oxy)ethyl)-7-methoxy-1,3,13-trimethyl-3,4,8,8a,10a,11-hexahydro-11,14b-epoxynaphtho[2,1- e]oxecine-6,14(7H,14aH)-dione (36 mg, 0.07 mmol) and imidazole (14 mg, 0.2 mmol) and hafnium tetrachloride (2.2 mmg, 7 μmol) were placed into a flame-dried flask. Acetonitrile (0.35 mL) was added the resulting suspension was stirred under a nitrogen atmosphere for approximately 18 hours. The mixture was partitioned between ethyl acetate and water. The organic phase was washed with brine and then dried over magnesium sulfate, then filtered and concentrated under reduced pressure. The resulting residue containing (3R,4 S ,7S ,8aS ,10aR,11R,14aR,14b S ,E)-4-((R)-1-((tert-butyldimethylsilyl)oxy)ethyl)-12-(1H-imidazol-1-yl)-7-methoxy-1,3,13-trimethyl-3,4,8,8a,10a,11,12, 13-octahydro-11,14b-epoxynaphtho[2,1-e]oxecine-6,14 (7H,14aH)-dione (40 mg) was used without purification for the next step.

Step 2. Sodium borohydride (3 mg, 0.07 mmol) was added to a flask containing a solution of crude (3R,4S,7S, 8aS,10aR,11R,14aR,14bS,E)-4-((R)-1-((tert-butyldimethylsilyl)oxy)ethyl)-12-(1H-imidazol-1-yl)-7-methoxy-1,3,13-trimethyl-3,4,8,8a,10a,11,12,13-octahydro-11,14b-epoxynaphtho[2,1-e]oxecine-6,14(7H,14aH)-dione (40 mg) in methanol (1 mL) and the resulting mixture was stirred at room temperature for 20 minutes. The mixture was partitioned between ethyl acetate and water. The organic phase was washed with brine and then dried over magnesium sulfate, then filtered and concentrated under reduced pressure. The crude residue which contains (3R,4S,7S,8aS, 10aR,11R,14R,14aS,14bS,E)-4-((R)-1-((tert-butyldimethylsilyl)oxy)ethyl)-14-hydroxy-12-(1H-imidazol-1-yl)-7-methoxy-1,3,13-trimethyl-3,4,8,8a,10a,11,12,13,14,14a-decahydro-11,14b-epoxynaphtho[2,1-e]oxecin-6(7H)-one (24 mg, 0.04 mmol) was used without purification for the next step.

Step 3. Tetrabutylammonium fluoride (0.07 mL, 1 M in THF, 0.07 mmol) was added to a flask containing a solution of (3R,4S,7S,8aS,10aR,11R,14R,14aS,14bS,E)-4-((R)-1-((tert-butyldimethylsilyl)oxy)ethyl)-14-hydroxy-12-(1H-imidazol-1-yl)-7-methoxy-1,3,13-trimethyl-3,4,8,8a,10a,11, 12,13,14,14a-decahydro-11,14b-epoxynaphtho [2,1-e] oxecin-6(7H)-one (24 mg, 0.04 mmol) in THF (1 ml) and the mixture was stirred at room temperature for 30 minutes. Tetrabutylammonium fluoride (0.07 mL, 1 M, 0.07 mmol) was added and the mixture was stirred for 30 minutes at room temperature. The mixture was then concentrated under reduced pressure. The residue was purified by mass directed HPLC (19×100 mm Waters Sunfire 5 μm electrospray positve detection, gradient: acetonitrile +0.05% water +0.05% TFA, TFA, 10-100% over 12 min), and the product fractions were lyophilized to give (3R,4S,7S,8aS,10aR,11R, 14R,14aS,14bS,E)-14-hydroxy-4-((R)-1-hydroxyethyl)-12-(1H-imidazol-1-yl)-7-methoxy-1,3-dimethyl-3,4,8,8a,10a, 11,12,13,14,14a-decahydro-11,14b-epoxynaphtho[2,1-e] oxecin-6(7H)-one (11 mg, 0.02 mmol). ¹H NMR (600 MHz, CD₃OD): δ 8.86 (s, 1H), 7.60-7.65 (m, 2H), 5.92-5.95 (m, 1H), 5.66 (dd, J=9.2, 3.1 Hz, 1H), 5.47 (d, J=6.7 Hz, 1H), 5.19 (s, 1H), 4.16 (s, 1H), 4.11 (d, J=10.8 Hz, 1H), 3.97-4.01 (m, 1H), 3.75 (dd, J=11.6, 4.4 Hz, 1H), 3.57 (dd, J=10.2, 2.7 Hz, 1H), 3.30 (s, 3H), 3.07-3.10 (m, 1H), 2.55 (d, J=2.6 Hz, 1H), 2.44-2.50 (m, 1H), 2.34 (t, J=7.1 Hz, 2H), 2.27-2.31 (m, 1H), 1.86 (s, 3H), 1.32-1.35 (m, 1H), 1.31 (d, J=7.1 Hz, 3H), 1.23 (d, J=7.1 Hz, 1H), 1.21 (d, J=6.2 Hz, 3H), 0.91 (d, J=6.5 Hz, 3H).

Example 150

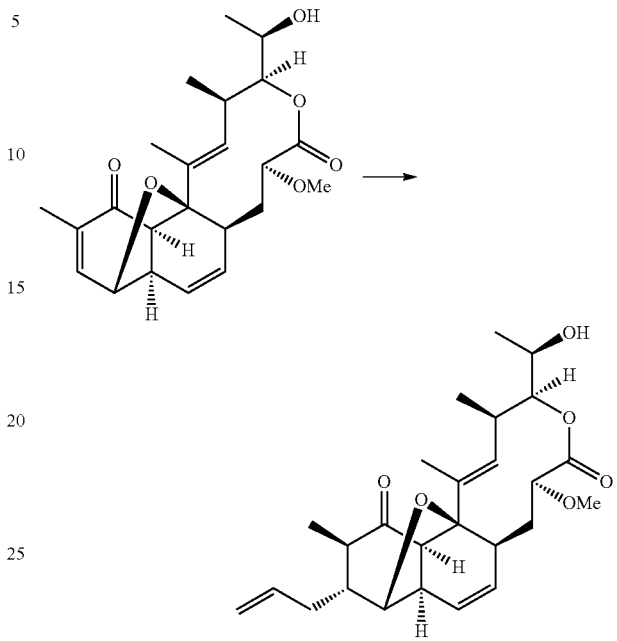

(3R,4S,7S,8aS,10aR,11S,12R,13R,14aR,14bS,E)-12-allyl-4-((R)-1-hydroxyethyl)-7-methoxy-1,3,13-trimethyl-3,4,8,8a,10a,11,12,13-octahydro-11,14b-epoxynaphtho[2,1-e]oxecine-6,14(7H,14aH)-dion (3R,4S,7S,8aS,10aR,11R,14aR,14bS,E)-4-((R)-1-hydroxyethyl)-7-methoxy-1,3,13-trimethyl-3,4,8,8a,10a,11-hexahydro-11,14b-epoxynaphtho[2,1-e]oxecine-6,14(7H, 14aH)-dione (10 mg, 0.025 mmol) was placed in a flame-dried flask which was then cooled to −78° C. Allyltrimethylsilane (14 m, 0.12 mmol) then titanium tetrachloride in dichloromethane (0.1 mL, 1M, 0.1 mmol) was added. The reaction mixture was stirred at −78° C. for 2 hours. The reaction mixture was partitioned between ethyl acetate and saturated aqueous sodium bicarbonate and this mixture was filtered through Celite washing with ethyl acetate. The organic layer was dried overs magnesium sulfate, filtered and then concentrated under reduced pressure. The crude material was purified by column chromatography on silica (10-100% ethyl acetate in hexanes) to give a 4:1 mixture (1.5 mg, 3.3 μmol) of (3R,4S,7S,8aS, 10aR,11S,12R,13R,14aR,14bS,E)-12-allyl-4-((R)-1-hydroxyethyl)-7-methoxy-1,3,13-trimethyl-3,4,8,8a,10a,11, 12,13-octahydro-11,14b-epoxynaphtho[2,1-e]oxecine-6,14 (7H,14aH)-dione and (3R,4S,5R,8S,9aS,11aR,12S,13R, 14R,15aR,15bS,E)-13-allyl-4-hydroxy-8-methoxy-1,3,5, 14-tetramethyl-4,5,9,9a,11a,12,13,14-octahydro-3H-12, 15b-epoxynaphtho[2,1-e][1]oxacycloundecine-7,15(8H, 15aH)-dione.

1H NMR δ (ppm)(CD₃OD): 5.94 (1 H, t, J=8.25 Hz), 5.77-5.86 (1 H, m), 5.64-5.67 (1 H, m), 5.34 (1 H, d, J=7.11 Hz), 5.05-5.12 (3 H, m), 4.19-4.20 (1 H, m), 3.91-3.96 (1 H, m), 3.72-3.75 (1 H, m), 3.28 (3 H, d, J=7.38 Hz), 2.89-2.92 (1 H, m), 2.83 (1 H, s), 2.75 (1 H, t, J=6.69 Hz), 2.29-2.42 (3 H, m), 2.02-2.17 (2 H, m), 1.86-1.91 (1 H, m), 1.65 (2 H, s), 1.36-1.44 (1 H, m), 1.19-1.31 (2 H, m), 1.17-1.19 (6 H, m), 0.99-1.02 (3 H, m).

Example 151

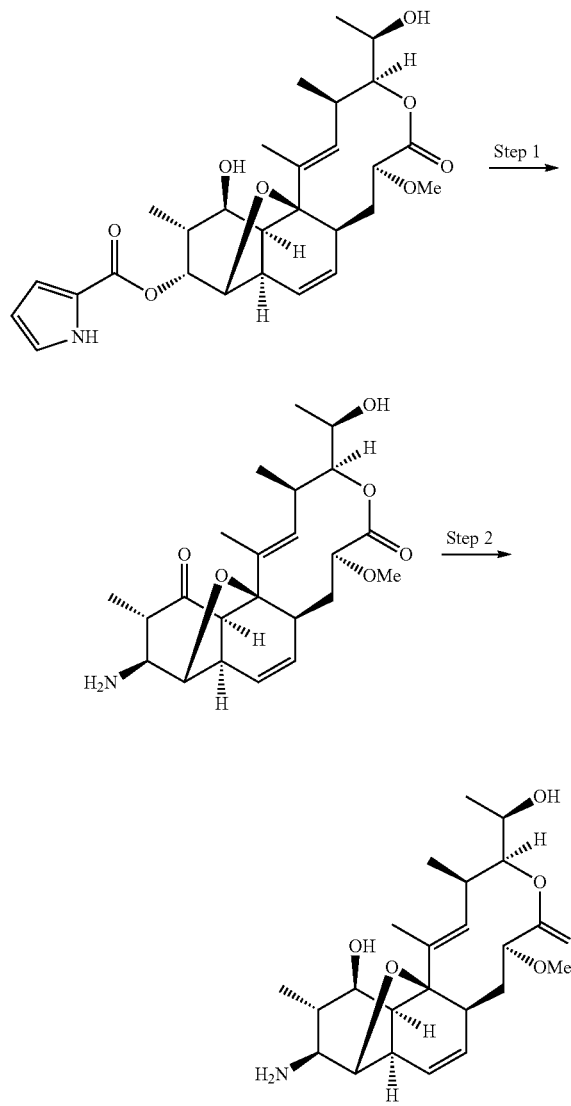

(3R,4S,7S,8aS,10aR,11R,12S,13S,14R,14aS,14bS,E)-12-amino-14-hydroxy-4-((R)-1-hydroxyethyl)-7-methoxy-1,3,13-trimethyl-3,4,8,8a,10a,11,12,13,14,14 a-decahydro-11,14b-epoxynaphtho [2,1-e] oxecin-6(7H)-one Step 1. Ammonia in methanol (0.7 mL, 7 M, 5 mmol) was added to flask containing (3R,4S,7S,8aS,10aR,11R,12R,13S,14aR,14bS,E)-4-((R)-1-hydroxyethyl)-7-methoxy-1,3,13-trimethyl-6,14-dioxo-3,4,6,7,8,8a,10a,11,12,13,14,14a-dodecahydro-11,14b-epoxynaphtho[2,1-e]oxecin-12-yl 1H-pyrrole-2-carboxylate (30 mg, 0.06 mmol) and the reaction was stirred at room temperature for 24 hours. The solvent was then evaporated under reduced pressure to give crude (3R,4S,7S,8aS,10aR,11R,12S,13S,14aR,14bS,E)-12-amino-4-((R)-1-hydroxyethyl)-7-methoxy-1,3,13-trimethyl-3,4,8,8a,10a,11,12,13-octahydro-11,14b-epoxynaphtho[2,1-e]oxecine-6,14(7H,14aH)-dione (25 mg, 0.06 mmol) which was used without purification in the next step. LCMS 420.2 (M+1).

Step 2. Methanol (0.6 mL) and then sodium borohydride (10 mg, 0.26 mmol) was added to a flask containing (3R,4S,7S,8aS,10aR,11R,12S,13S,14aR,14bS,E)-12-amino-4-((R)-1-hydroxyethyl)-7-methoxy-1,3,13-trimethyl-3,4,8,8a,10a,11,12,13-octahydro-11,14b-epoxynaphtho[2,1-e] oxecine-6,14(7H,14aH)-dione (25 mg, 0.06 mmol) and the resulting mixture was stirred at room temperature for 30 minutes. The crude material was then filtered through a 0.45 µm Acrodisc and then purified by mass directed HPLC (19×100 mm Waters Sunfire 5 µm electrospray positve detection, gradient: acetonitrile +0.05% water +0.05% TFA, TFA, 10-100% over 12 min), and the product fractions were lyophilized to give (3R,4S,7S,8aS,10aR,11R,12S,13S,14R,14aS,14bS,E)-12-amino-14-hydroxy-4-((R)-1-hydroxyethyl)-7-methoxy-1,3,13-trimethyl-3,4,8,8a,10a,11,12,13,14,14a-decahydro-11,14b-epoxynaphtho[2,1-e]oxecin-6(7H)-one (10 mg, 0.02 mmol). 1H NMR (600 MHz, CD$_3$OD): δ 5.93 (t, J=8.4 Hz, 1H); 5.66 (dd, J=9.5, 3.2 Hz, 1H); 5.51 (d, J=6.8 Hz, 1H); 5.15 (s, 1H); 4.08 (s, 1H); 3.94-3.99 (m, 1H); 3.71-3.74 (m, 1H); 3.44 (dd, J=10.3, 2.8 Hz, 1H); 3.28 (s, 3H); 3.02-3.05 (m, 1H); 2.82 (d, J=10.0 Hz, 1H); 2.46-2.50 (m, 2H); 2.29 (s, 1H); 2.21 (d, J=7.0 Hz, 1H); 1.88-1.94 (m, 1H); 1.79 (s, 3H); 1.33-1.36 (m, 1H); 1.27 (d, J=7.1 Hz, 3H); 1.20 (d, J=6.2 Hz, 3H); 1.10 (d, J=6.5 Hz, 3H).

Examples 153-157 were generally prepared according to the methods in Example 151.

| Examples | Structure | [M + Na] or ¹H NMR |
|---|---|---|
| 153 | ![structure] | M + 1 = 518.18 |

| Examples | Structure | [M + Na] or ¹H NMR |
|---|---|---|
| 154 | 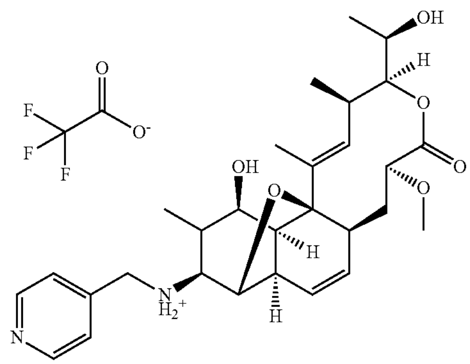 [SMILES: CO[C@H]1C[C@H]2C=C[C@H]3[C@H]4O[C@]2(/C(C)=C/[C@@H](C)[C@@H]([C@@H](C)O)OC1=O)[C@@H]3[C@H](O)C(C)[C@@H]4[NH2+]Cc1ccncc1 ; O=C([O-])C(F)(F)F] | M + 1 = 513.21 |
| 155 | 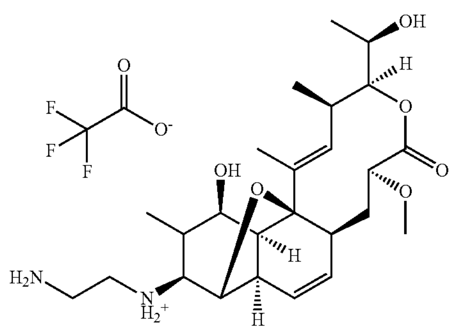 [SMILES: CO[C@H]1C[C@H]2C=C[C@H]3[C@H]4O[C@]2(/C(C)=C/[C@@H](C)[C@@H]([C@@H](C)O)OC1=O)[C@@H]3[C@H](O)C(C)[C@@H]4[NH2+]CCN ; O=C([O-])C(F)(F)F] | M + 1 = 465.18 |
| 156 | 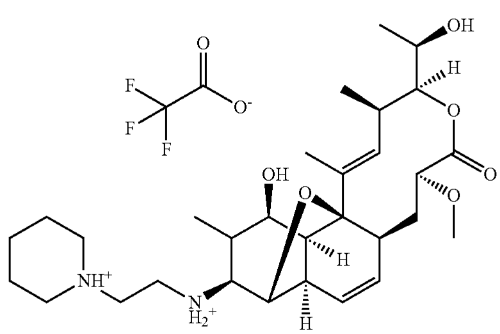 [SMILES: CO[C@H]1C[C@H]2C=C[C@H]3[C@H]4O[C@]2(/C(C)=C/[C@@H](C)[C@@H]([C@@H](C)O)OC1=O)[C@@H]3[C@H](O)C(C)[C@@H]4[NH2+]CC[NH+]1CCCCC1 ; O=C([O-])C(F)(F)F] | M + 1 = 533.27 |
| 157 | 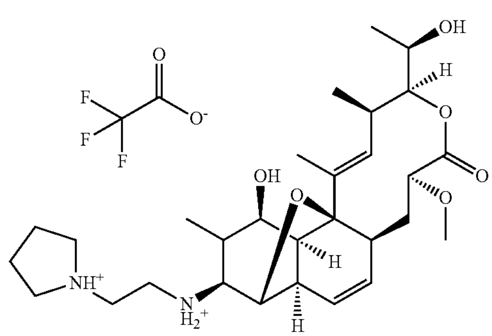 [SMILES: CO[C@H]1C[C@H]2C=C[C@H]3[C@H]4O[C@]2(/C(C)=C/[C@@H](C)[C@@H]([C@@H](C)O)OC1=O)[C@@H]3[C@H](O)C(C)[C@@H]4[NH2+]CC[NH+]1CCCC1 ; O=C([O-])C(F)(F)F] | M + 1 = 519.26 |

Example 158

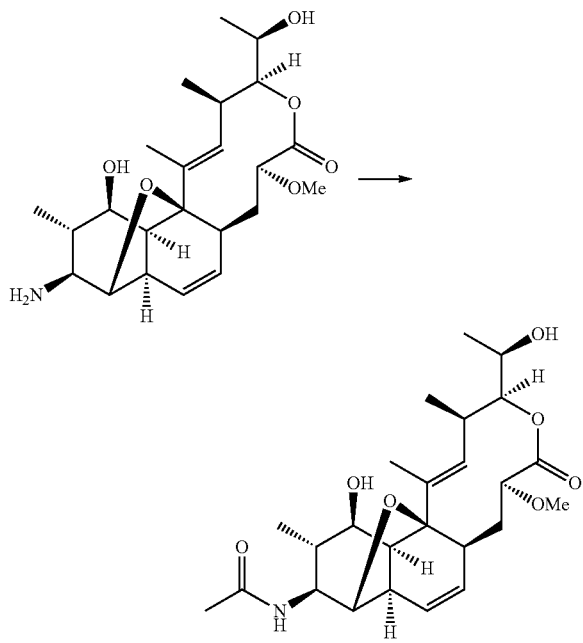

N-((3R,4S,7S,8aS,10aR,11R,12S,13S,14R,14aS,
14bS,E)-14-hydroxy-4-((R)-1-hydroxyethyl)-7-
methoxy-1,3,13-trimethyl-6-oxo-3,4,6,7,8,8a,10a,11,
12,13,14,14a-dodecahydro-11,14b-epoxynaphtho[2,
1-e]oxecin-12-yl)acetamide Acetyl chloride (2 µL, 1.10 g/mL, 0.03 mmol) was added to a flask containing (3R,4S,7S,8aS,10aR,11R,12S,13S, 14R,14aS,14bS,E)-12-amino-14-hydroxy-4-((R)-1-hydroxyethyl)-7-methoxy-1,3,13-trimethyl-3,4,8,8a,10a,11, 12,13,14,14a-decahydro-11,14b-epoxynaphtho[2,1-e] oxecin-6(7H)-one (8 mg, 0.02 mmol) in dichloromenthane (0.1 mL). The reaction mixture was stirred at room temperature for several hours and then concentrated under reduced pressure. The crude material was dissolved in methanol and then purified by mass directed HPLC (19×100 mm Waters Sunfire 5 µm electrospray positve detection, gradient: acetonitrile +0.05% water +0.05% TFA, TFA, 10-100% over 12 min), and the product fractions were lyophilized to give N-((3R,4S,7S,8aS,10aR,11R,12S,13S, 14R,14aS,14bS,E)-14-hydroxy-4-((R)-1-hydroxyethyl)-7-methoxy-1,3,13-trimethyl-6-oxo-3 ,4,6,7,8,8a,10a,11,12,13, 14,14 a-dodecahydro-11,14b-epoxynaphtho[2,1-e]oxecin-12-yl)acetamide (1 mg, 2 µmol). 1H NMR (500 MHz, CD$_3$OD): δ 8.03 (d, J=8.1 Hz, 1H), 5.92 (t, J=8.1 Hz, 1H), 5.59 (dd, J=9.3, 3.1 Hz, 1H), 5.51 (d, J=6.8 Hz, 1H), 5.15 (s, 1H), 4.00 (t, J=7.4 Hz, 1H), 3.92 (s, 1H); 3.73 (dd, J=11.4, 4.3 Hz, 1H), 3.36-3.43 (m, 2H), 3.29 (s, 3H), 3.07 (d, J=7.7 Hz, 1H), 2.48 (t, J=13.4 Hz, 1H), 2.41 (s, 1H), 2.25 (s, 1H), 2.15 (d, J=6.9 Hz, 1H), 1.99 (s, 3H), 1.89-1.91 (m, 1H), 1.79 (s, 3H), 1.34 (s, 1H), 1.30 (d, J=7.1 Hz, 3H), 1.22 (d, J=6.2 Hz, 3H), 0.98 (d, J=6.5 Hz, 3H).

Example 159

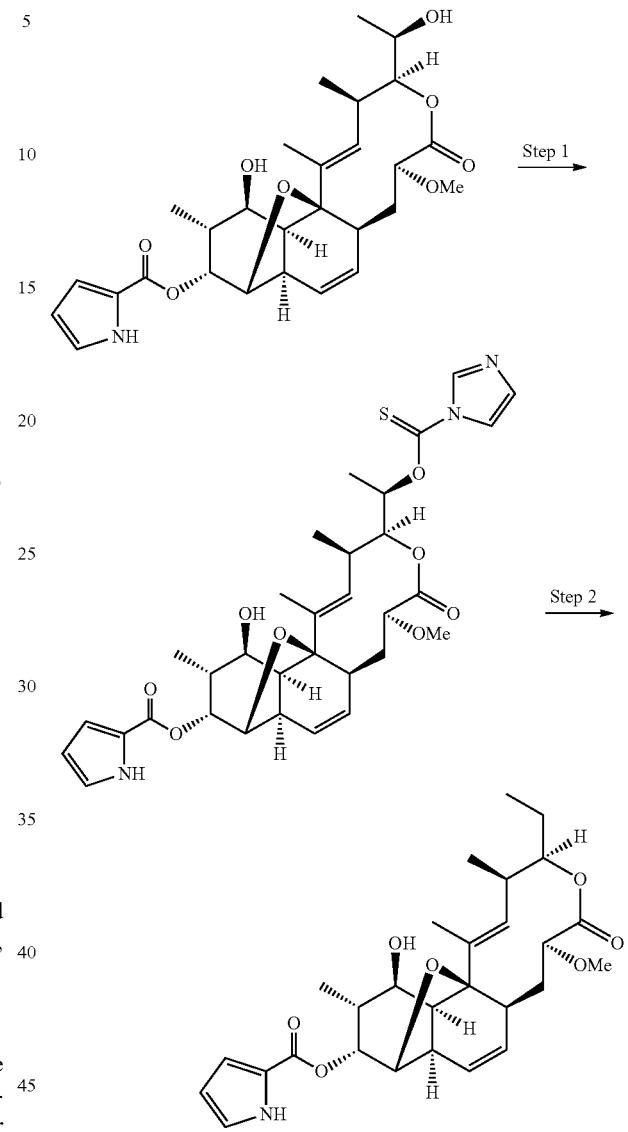

(3R,4R,7S,8aS,10aR,11R,12R,13R,14R,14aS,14bS,
E)-4-ethyl-14-hydroxy-7-methoxy-1,3,13-trimethyl-
6-oxo-3,4,6,7,8,8a,10a,11,12,13,14,14a-dodeca-
hydro-11,14b-epoxynaphtho[2,1-e]oxecin-12-yl
1H-pyrrole-2-carboxylate Step 1. Di(1H-imidazol-1-yl)methanethione (14 mg, 0.08 mmol) in dichloroethane (1 mL) was added to a tube containing (3R,4S,7S,8aS,10aR,11R,12R,13R,14R,14aS, 14bS,E)-14-hydroxy-4-((R)-1-hydroxyethyl)-7-methoxy-1, 3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate (20 mg, 0.04 mmol). The tube was then sealed and heated to 60° C. for two hours and then to 85° C. for 3.5 hours. After cooling to room temperature the crude reaction mixture was purified by preparative thin layer chromatography to give (3R,4S,7S,8aS,10aR,11R, 12R,13R,14R,14aS,14bS,E)-4-((R)-1-((1H-imidazole-1- carbonothioyl)oxy)ethyl)-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate as one component of an approximately 1:1 mixture (20 mg) with an impurity. This material was used without further purification.

Step 2. (3R,4S,7S,8aS,10aR,11R,12R,13R,14R,14aS,14bS,E)-4-((R)-1-((1H-imidazole-1-carbonothioyl)oxy)ethyl)-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate (20 mg, approximately 50% purity, 0.02 mmol) in tetrahydrofuran (0.15 mmol) was added to a vial containing a refluxing solution of tri-N-butyltin hydride (0.03 mL, 1 g/mL, 0.1 mmol) in tetrahydrofuran (0.08 mL). The vial was sealed and then heated at reflux for 20 minutes. The crude reaction mixture was purified by preparative thin layer chromatography on silica (1:1 ethyl acetate:hexanes). The product band was isolated by elution with 5% methanol in dichloromethane followed by concentration under reduced pressure. The resulting material was suspended in methanol and filter through an Acrodisc (0.45 micron) and the filtrate concentrated under reduced pressure. The resulting material was lyophilized from benzene to afford (3R,4R,7S,8aS,10aR,11R,12R,13R,14R,14aS,14bS,E)-4-ethyl-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate (3 mg, 6 μmol). See also Example 50. $^1$H NMR (600 MHz, CD$_3$OD): δ 6.98 (t, J=1.9 Hz, 1H), 6.87 (dd, J=3.7, 1.5 Hz, 1H), 6.20 (t, J=3.1 Hz, 1H), 5.88-5.91 (m, 1H), 5.57 (dd, J=9.4, 3.0 Hz, 1H), 5.48 (d, J=8.9 Hz, 1H), 5.09 (dt, J=9.1, 5.7 Hz, 1H), 5.04 (t, J=4.8 Hz, 1H), 4.12 (d, J=4.9 Hz, 1H), 3.63-3.71 (m, 2H), 3.27 (s, 3H), 3.06-3.10 (m, 1H), 2.61 (d, J=7.0 Hz, 1H), 2.52 (ddd, J=15.1, 11.3, 4.6 Hz, 1H), 2.47 (d, J=2.6 Hz, 1H), 2.40 (d, J=4.0 Hz, 1H), 2.36 (dd, J=11.9, 6.3 Hz, 1H), 1.76 (s, 3H); 1.69-1.72 (m, 2H), 1.30-1.37 (m, 2H), 1.10 (d, J=7.1 Hz, 3H), 0.97 (t, J=7.3 Hz, 3H), 0.92 (d, J=6.8 Hz, 3H).

Example 160

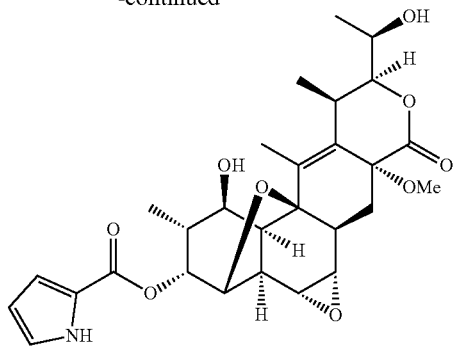

(1aS, 1bS,3S,6S,7R,9aS,9bS,10R,11R,12R,13R,13aS,13bR,E)-10-hydroxy-6-((R)-1-hydroxyethyl)-3-methoxy-7,9,11-trimethyl-4-oxo-1 a,1b,2,3,4,6,7,9b,10,11,12,13,13a,13b-tetradecahydro-9a,13-epoxyoxireno[2',3':3,4]naphtho[2,1-e]oxecin-12-yl 1H-pyrrole-2-carboxylate Meta-chloroperbenzoic acid (2.5 mg, 0.02 mmol) was added to a vial containing (3R,4S,7S,8aS,10aR,11R,12R,13R,14R,14aS,14bS,E)-14-hydroxy-4-((R)-1-hydroxyethyl)-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate (5 mg, 0.01 mmol) in ethyl acetate (0.1 mL) and the mixture was stirred at room temperature for 20 hours. The reaction mixture was then purified by preparative thin layer chromatography on silica (1:1 ethyl acetate:hexanes) to give (1aS,1bS,3S,6S,7R,9aS,9bS,10R,11R,12R,13R,13aS,13bR,E)-10-hydroxy-6-((R)-1-hydroxyethyl)-3-methoxy-7,9,11-trimethyl-4-oxo-1a,1b,2,3,4,6,7,9b,10,11,12,13,13a,13b-tetradecahydro-9a,13-epoxyoxireno[2',3':3,4]naphtho[2,1-e]oxecin-12-yl 1H-pyrrole-2-carboxylate (1 mg, 0.002 mmol) as a film. $^1$H NMR (500 MHz, CD$_3$OD): δ 6.99 (s, 1H), 6.90 (d, J=3.6 Hz, 1H), 6.21 (s, 1H), 5.36 (d, J=6.8 Hz, 1H), 5.15 (s, 2H), 5.07 (t, J=5.0 Hz, 1H), 4.30 (d, J=5.0 Hz, 1H), 3.98 (d, J=8.0 Hz, 1H), 3.75-3.77 (m, 1H), 3.56-3.60 (m, 1H), 3.30 (s, 3H), 3.02-3.03 (m, 1H), 2.95 (d, J=4.0 Hz, 1H), 2.81 (d, J=3.8 Hz, 1H), 2.63 (s, 1H), 2.32-2.36 (m, 2H), 1.86 (m, 1H), 1.75 (s, 3H), 1.48 (t, J=14.6 Hz, 1H), 1.25 (d, J=6.7 Hz, 3H), 1.20 (d, J=6.1 Hz, 3H), 0.92 (d, J=6.8 Hz, 3H).

Example 161

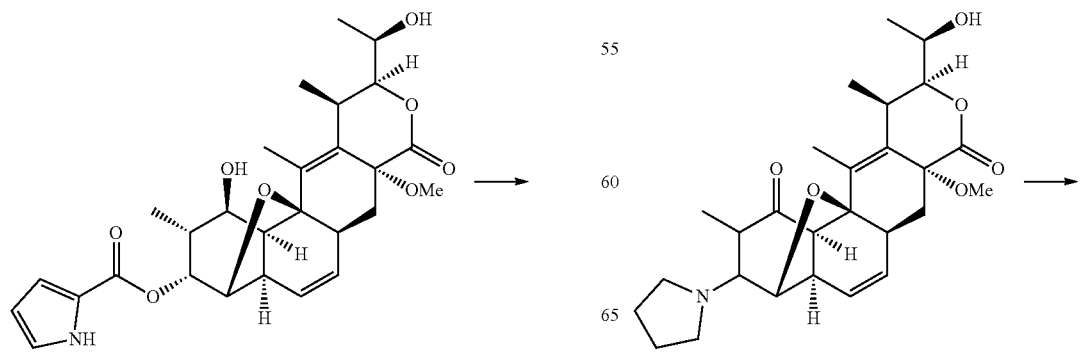

-continued

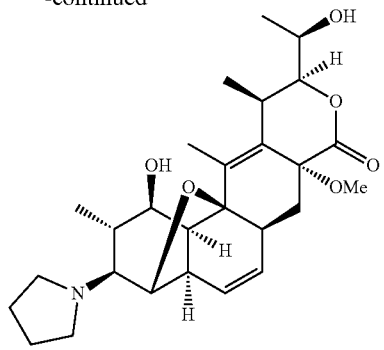

(3R,4S,7S,8aS,10aR,11R,12S,13S,14R,14aS,14bS,E)-14-hydroxy-4-((R)-1-hydroxyethyl)-7-methoxy-1,3,13-trimethyl-12-(pyrrolidin-1-yl)-3,4,8,8a,10a,11,12,13,14,14a-decahydro-11,14b-epoxynaphtho[2,1-e]oxecin-6(7H)-one Sodium borohydride (approx. 0.5 mg, 0.01 mmol) was added to a vial containing a solution of (3R,4S,7S,8aS,10aR,11R,14aR,14bS,E)-4-((R)-1-hydroxyethyl)-7-methoxy-1,3,13-trimethyl-12-(pyrrolidin-1-yl)-3,4,8,8a,10a,11,12,13-octahydro-11,14b-epoxynaphtho[2,1-e]oxecine-6,14(7H,14aH)-dione (2 mg 0.004 mmol) in methanol (0.1 mL). The crude material was dissolved in methanol and then purified by mass directed HPLC (19×100 mm Waters Sunfire 5um, electrospray positve detection, gradient: acetonitrile +0.05% water +0.05% TFA, TFA, 10-100% over 12 min), and the product fractions were lyophilized to give (3R,4S,7S,8aS,10aR,11R,12S,13S,14R,14aS,14bS,E)-14-hydroxy-4-((R)-1-hydroxyethyl)-7-methoxy-1,3,13-trimethyl-12-(pyrrolidin-1-yl)-3,4,8,8a,10a,11,12,13,14,14a-decahydro-11,14b-epoxynaphtho[2,1-e]oxecin-6(7H)-one (1 mg, 0.002 mmol). $^{1}$H NMR (500 MHz, CD3OD): δ 5.97 (t, J=8.1 Hz, 1H), 5.68 (dd, J=9.3, 3.2 Hz, 1H), 5.35 (d, J=6.9 Hz, 1H), 5.17 (s, 1H), 4.51 (s, 1H), 3.99 (dd, J=9.0, 6.0 Hz, 1H), 3.73-3.78 (m, 2H), 3.52-3.54 (m, 1H), 3.45-3.49 (m, 3H), 3.30 (s, 3H), 3.15 (d, J=10.7 Hz, 1H), 3.05-3.09 (m, 1H), 2.47-2.51 (m, 1H), 2.44 (dd, J=14.0, 3.9 Hz, 1H), 2.33 (s, 1H), 2.16-2.22 (m, 3H), 2.00-2.01 (m, 3H), 1.82 (s, 3H), 1.37-1.41 (m, 1H), 1.26 (d, J=7.0 Hz, 3H), 1.22 (d, J=6.4 Hz, 3H), 1.20 (d, J=6.4 Hz, 3H).

Example 162

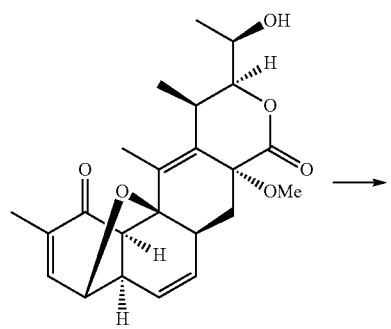

-continued

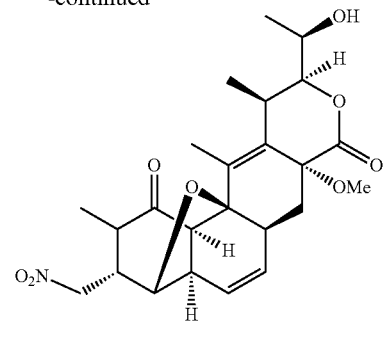

(3R,4 S ,7S ,8aS ,10aR,11R,12 S ,14aR,14b S,E)-4-((R)-1-hydroxyethyl)-7-methoxy-1,3,13-trimethyl-12-(nitromethyl)-3 ,4,8,8a,10a,11,12,13-octahydro-11,14b-epoxynaphtho [2,1-e]oxecine-6,14(7H,14aH)-dione Nitromethane (4 µL, 1.13 g/mL, 0.08 mmol) was added to a solution of 2,8,9-tri-i-propyl-2,5,8,9-tetraaza-1-phosphabicyclo[3.3.3]undecane (22 mg, 0.075 mmol) in tetrahydrofuran under an atmosphere of nitrogen. After three minutes, (3R,4S,7S ,8aS ,10aR,11R,14aR,14b S,E)-4-((R)-1-hydroxyethyl)-7-methoxy-1,3,13-trimethyl-3,4,8,8a,10a,11-hexahydro-11,14b-epoxynaphtho [2,1-e]oxecine-6,14 (7H,14aH)-dione (10 mg, 0.03 mmol) was added and the reaction mixture was stirred at room temperature for 30 minutes. The reaction mixture was then partitioned between ethyl acetate and water. The organic phase was set aside. The aqueous phase was acidified with aqueous hydrochloric acid (1 N) and then extracted with ethyl acetate. This organic extract was dried over magnesium sulfate, filtered and then concentrated under reduced pressure. The crude residue was purified by column chromatography on silica (10-100% ethyl acetate in hexanes) to give (3R,4S ,7S ,8aS ,10aR, 11R,12S ,14aR,14b S,E)-4-((R)-1-hydroxyethyl)-7-methoxy-1,3,13-trimethyl-12-(nitromethyl)-3 ,4,8,8a,10a, 11,12,13-octahydro-11,14b-epoxynaphtho [2,1-e]oxecine-6,14(7H,14aH)-dione (2 mg, 4.3 µmol) as an oil.
1H NMR (500 MHz, CD$_3$OD): δ 5.90-5.96 (m, 1 H), 5.71 (dd, 1 H), 5.54 (d, 1 H), 5.11-5.16 (m, 1 H), 4.44 (dd, 1 H), 4.30-4.34 (m, 2 H), 3.93-3.99 (m, 1 H), 3.73-3.78 (m, 1 H), 3.35 (s, 3 H), 3.34 (s, 1 H), 2.90-2.99 (m, 3 H), 2.69 (d, 1 H), 2.35-2.43 (m, 3 H), 1.49 (s, 3 H), 1.16-1.25 (m, 8 H), 0.90 (d, 3 H).

Example 163

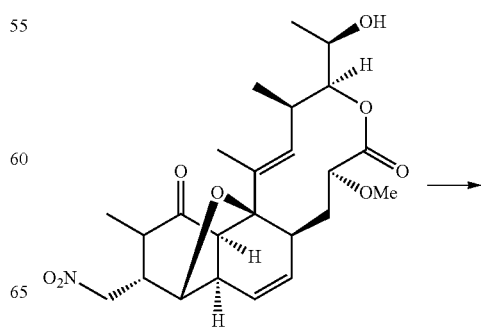

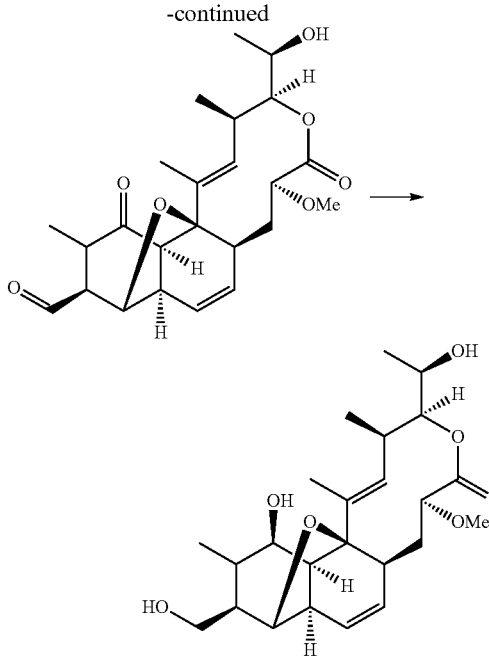

(3R,4S,7S,8aS,10aR,11R,12R,14R,14aS,14bS,E)-14-hydroxy-4-((R)-1-hydroxyethyl)-12-(hydroxymethyl)-7-methoxy-1,3,13-trimethyl-3,4,8,8a,10a,11,12,13,14,14a-decahydro-11,14b-epoxynaphtho[2,1-e]oxecin-6(7H)-one Potassium carbonate (15 mg, 0.11 mol) and then tert-butyl hydroperoxide (0.2 mL, 5 M in decane, 0.1 mmol) was added to a flask containing a solution of (50 mg, 0.11 mmol) in dichloromethane (1 mL). The resulting mixture was stirred at room temperature overnight (approximately 18 hours). The reaction mixture was partitioned between dichloromethane and aqueous sodium bicarbonate (5%). The organic phased then dried over magnesium sulfate, filtered and then concentrated under reduced pressure. The crude residue was purified by column chromatography on silica (5%-100% ethyl acetate in hexanes) and the product fractions were concentrated under reduced pressure and lyophilized from benzene to afford (3R,4S ,7S ,8aS ,10aR, 11R,12S ,14aR,14b S,E)-4-((R)-1-hydroxyethyl)-7-methoxy-1,3,13-trimethyl-6,14-dioxo-3,4,6,7,8,8a,10a,11,12,13,14,14a-dodecahydro-11,14b-epoxynaphtho [2,1-e] oxecine-12-carbaldehyde (7 mg, 0.02 mmol), with the relative stereochemistry assigned by NOEDIFF.

Step 2. Sodium borohydride (1 mg, 0.03 mnmol) was added to a vial containing a solution of (3R,4S,7S,8aS,10aR, 11R,12S,14aR,14bS,E)-4-((R)-1-hydroxyethyl)-7-methoxy-1,3,13-trimethyl-6,14-dioxo-3,4,6,7,8,8a,10a,11,12,13,14,14a-dodecahydro-11,14b-epoxynaphtho[2,1-e]oxecine-12-carbaldehyde (7 mg, 0.02 mmol) in methanol (0.5 mL). The resulting mixture was stirred at room temperature for 20 minutes. The reaction mixture was partitioned ethyl acetate and water. The organic layer was washed with brine then dried over magnesium sulfate then filtered and concentrated under reduced pressure. The crude residue was purified by preparative thin layer chromatography on silica (5% methanol in dichloromethane). The product band was isolated and then lyophilized from benzene to give (3R,4S,7S,8aS,10aR, 11R,12R,14R,14aS,14bS,E)-14-hydroxy-4-((R)-1-hydroxyethyl)-12-(hydroxymethyl)-7-methoxy-1,3,13-trimethyl-3,4,8,8a,10a,11,12,13,14,14a-decahydro-11,14b-epoxynaphtho[2,1-e]oxecin-6(7H)-one (4 mg, 6 µmole) as the major component of a 2:1 mixture with an impurity. LCMS (M +1=437.1)

Example 164

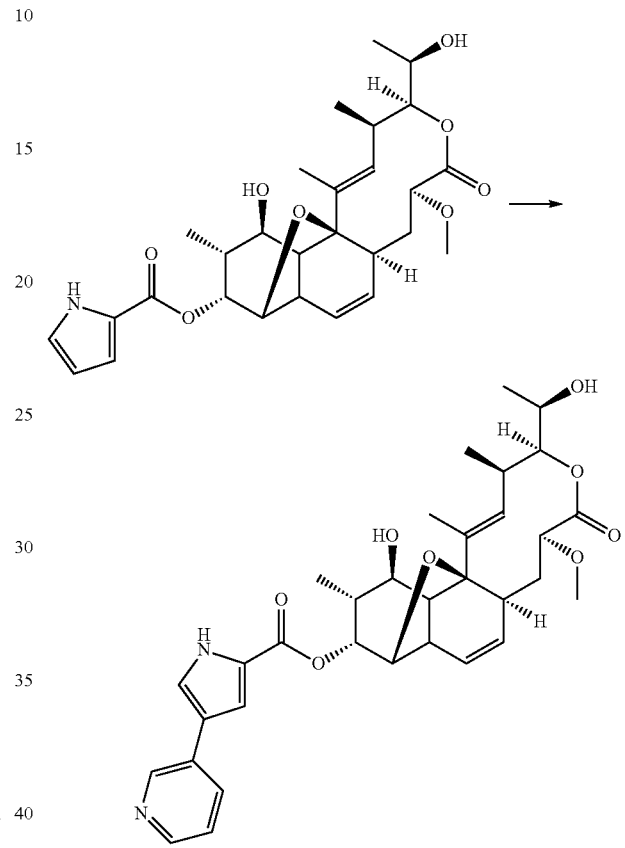

Nargenicin (104 mg, 0.202 mmol) was dissolved in acetonitrile (3 mL) and N-iodosuccinimide (45 mg, 0.202 mmol) was added. The mixture was stirred at room temperature for 18 hours. The mixture was purified by Prep HPLC using a Sunfire C18 column and 30-100% acetonitrile/water as gradient. The fractions were combined and freeze dried to afford (3R,4S,7S,8aS,11R,12R,13R,14R, 14bS,E)-14-hydroxy-4-((R)-1-hydroxyethyl)-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 4-iodo-1H-pyrrole-2-carboxylate as a white solid. LC-MS: M+1=642

(3R,4S,7S,8aS,11R,12R,13R,14R,14bS,E)-14-hydroxy-4-((R)-1-hydroxyethyl)-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 4-iodo-1H-pyrrole-2-carboxylate (39 mg, 0.061 mmol) was dissolved in dioxane/water (10:1) (1 mL) and the solution was degassed with nitrogen. Sodium carbonate (32 mg, 0.304 mmol) was added. 3-(4,4,5,5-tetramethyl-1,3,2-dioxaborolan-2-yl)pyridine (62 mg, 0.304 mmol) and Pd(dppf)Cl$_2$ (5 mg, 0.006 mmol) were added. The mixture was heated to 90° C. under nitrogen for 3 hours. The cooled mixture was concentrated and the residue was purified by Prep HPLC using a Sunfire C18 column and 30-100% acetonitrile/water as gradient to afford (3R,4S,7S,8aS,11R,12R,13R,14R,14bS,E)-14-hydroxy-4-((R)-1-hydroxyethyl)-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 4-(pyridin-3-yl)-1H-pyrrole-2-carboxylate. LC-MS: M+1=593
Examples 45 and 165-166 were generally prepared according to the methods in Example 164.
| EXAMPLE | Structure | LC-MS |
|---|---|---|
| 45 | 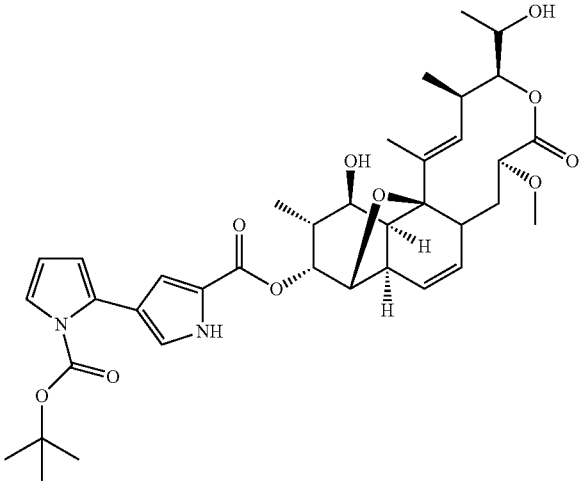 [SMILES: CO[C@H]1CC2C=C[C@H]3[C@H]4O[C@]2(/C(C)=C/[C@@H](C)[C@@H](C(C)O)OC1=O)[C@@H]3[C@H](O)[C@@H](C)[C@H]4OC(=O)c1cc(-c2cccn2C(=O)OC(C)(C)C)c[nH]1] | M + 1 = 681 |
| 165 | 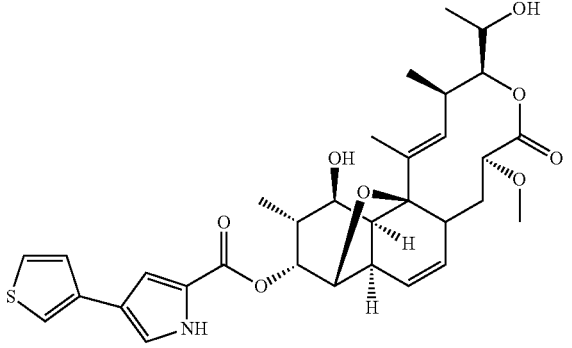 [SMILES: CO[C@H]1CC2C=C[C@H]3[C@H]4O[C@]2(/C(C)=C/[C@@H](C)[C@@H](C(C)O)OC1=O)[C@@H]3[C@H](O)[C@@H](C)[C@H]4OC(=O)c1cc(-c2ccsc2)c[nH]1] | M + 1 = 598 |
| 166 | 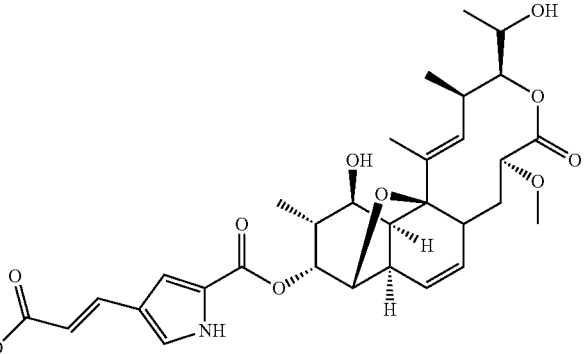 | M + 1 = 600 |

Example 167

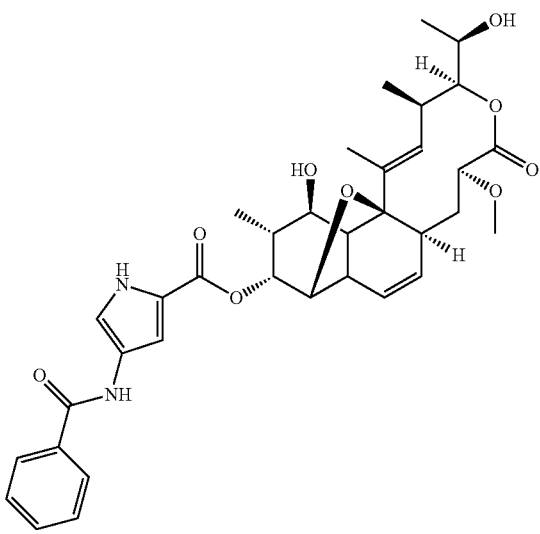 [SMILES: CO[C@H]1C[C@H]2C=CC3C4[C@H](O)[C@@H](C)[C@@H](OC(=O)c5cc(NC(=O)c6ccccc6)c[nH]5)[C@@H]3O[C@]42/C(C)=C/[C@@H](C)[C@@H]([C@@H](C)O)OC1=O]

(3R,4S,7S,8aS,11R,12R,13R,14R,14bS,E)-14-hydroxy-4-((R)-1-hydroxyethyl)-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 4-iodo-1H-pyrrole-2-carboxylate (22 mg, 0.034 mmol) was dissolved in dioxane (0.2 mL). Benzamide (20 mg, 0.171 mmol), (1S,2S)-N1,N2-dimethylcyclohexane-1,2-diamine (9.8 mg, 0.069 mmol), copper(I) iodide (6.5 mg, 0.034 mmol) and K₃PO₄ (22 mg, 0.103 mmol) were added. The mixture was heated to 100° C. in a sealed tube for 18 hours. The cooled mixture was filtered and the residue was purified by Prep HPLC using a Sunfire C18 column and 30-100% acetonitrile/water as gradient. The fractions were combined and freeze dried to afford(3R,4S,7S,8aS,11R,12R,13R,14R,14bS,E)-14-hydroxy-4-((R)-1-hydroxyethyl)-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 4-benzamido-1H-pyrrole-2-carboxylate as a white solid. LC-MS: M+1=635

Example 168

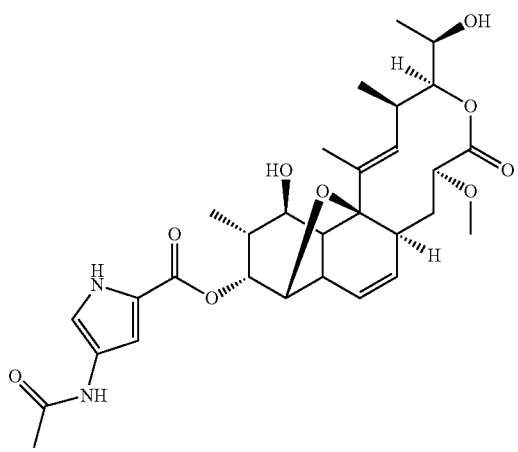 [SMILES: CO[C@H]1C[C@H]2C=CC3C4[C@H](O)[C@@H](C)[C@@H](OC(=O)c5cc(NC(C)=O)c[nH]5)[C@@H]3O[C@]42/C(C)=C/[C@@H](C)[C@@H]([C@@H](C)O)OC1=O]

(3R,4S,7S,8aS,11R,12R,13R,14R,14bS,E)-14-hydroxy-4-((R)-1-hydroxyethyl)-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 4-acetamido-1H-pyrrole-2-carboxylate was prepared from the iodo intermediate described in example 167 in a similar manner. LC-MS: M+1=573

Example 188

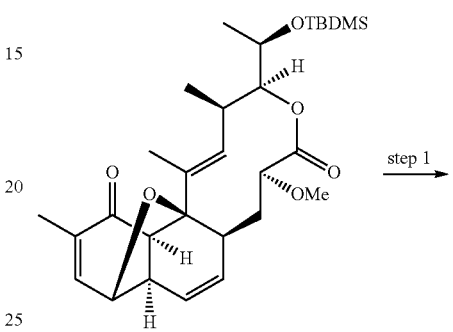
step 1

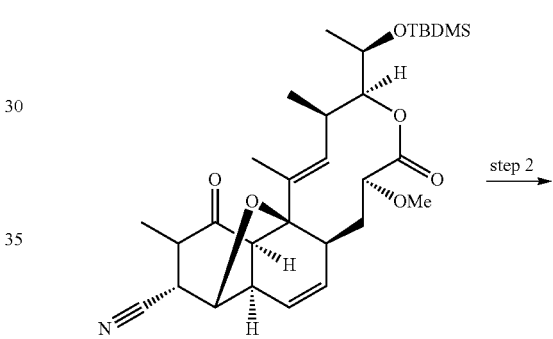
step 2

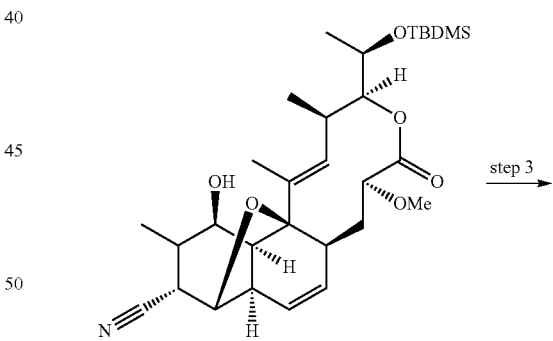
step 3

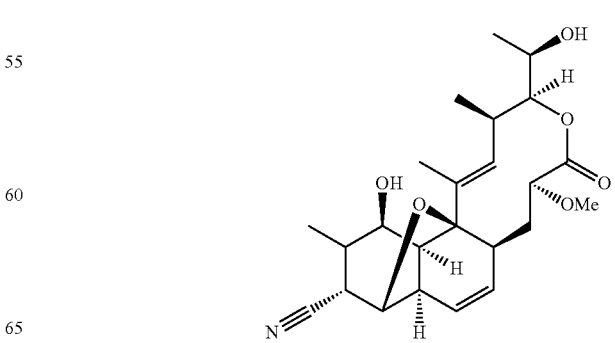

(3R,4S,7S,8aS,10aR,11R,12S,14R,14aS,14bS,E)-14-hydroxy-4-((R)-1-hydroxyethyl)-7-methoxy-1,3,13-trimethyl-6-oxo-3,4,6,7,8,8a,10a,11,12,13,14,14a-dodecahydro-11,14b-epoxynaphtho[2,1-e]oxecine-12-carbonitrile Step 1. Dimethyl formamide (1.5 mL) and water (0.4 mL) were added to a flask containing (3R,4S,7S,8aS,10aR,11R,12S,14R,14aS,14bS,E)-14-hydroxy-4-((R)-1-hydroxyethyl)-7-methoxy-1,3,13-trimethyl-6-oxo-3,4,6,7,8,8a,10a,11,12,13,14,14a-dodecahydro-11,14b-epoxynaphtho[2,1-e]oxecine-12-carbonitrile (95 mg, 0.18 mmol). Potassium cyanide (60 mg, 0.9 mmol) and ammonium chloride (50 mg, 0.9 mmol) were added ant the reaction was stirred at room temperature for 3.5 days. The reaction was quenched with excess aqueous sodium bicarbonate and then was partitioned between ethyl acetate and aqueous sodium bicarbonate. The organic phase was washed with brine, dried over magnesium sulfate, then filter and concentrated under reduced pressure. Crude (3R,4 S,7S,8aS,10aR,11R,12 S,14aR,14b S,E)-4-((R)-1-((tert-butyldimethylsilyl)oxy)ethyl)-7-methoxy-1,3,13-trimethyl-6,14-dioxo-3,4,6,7,8,8a,10a,11,12,13,14,14a-dodecahydro-11,14b-epoxynaphtho[2,1-e]oxecine-12-carbonitrile (80 mg, 0.15 mmol) was used in the next step without purification.

Step 2. (3R,4S,7S,8aS,10aR,11R,12S,14aR,14bS,E)-4-((R)-1-((tert-butyldimethylsilyl)oxy)ethyl)-7-methoxy-1,3,13-trimethyl-6,14-dioxo-3,4,6,7,8,8a,10a,11,12,13,14,14a-dodecahydro-11,14b-epoxynaphtho[2,1-e]oxecine-12-carbonitrile (80 mg, 0.15 mmol) was dissolved in methanol (3.7 mL) with gentle heating and was then allowed to cool to room temperature. Sodium borohydride (11 mg, 0.3 mmol) was added and the reaction mixture was stirred at room temperature for 30 minutes. The reaction mixture was partitioned between ethyl acetate and water. The organic phase was then washed with brine, dried over magnesium sulfate, filtered and then concentrated under reduced pressure. The resulting residue was then lyophilized from benzene to give (3R,4S,7S,8a5,10aR,11R,12S,14R,14aS,14bS,E)-4-((R)-1-((tert-butyldimethylsilyl)oxy)ethyl)-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecine-12-carbonitrile (75 mg, 0.14 mmol) as a solid. 1H NMR (500 MHz, CD3OD): δ 6.01 (t, J=8.1 Hz, 1H), 5.74 (dd, J=9.4, 2.7 Hz, 1H), 5.50 (d, J=6.8 Hz, 1H), 5.11 (t, J=6.8 Hz, 1H), 4.60 (t, J=4.4 Hz, 1H), 4.08-4.13 (m, 1H), 3.75-3.78 (m, 1H), 3.65 (dd, J=8.5, 4.4 Hz, 1H), 3.29 (s, 3H), 2.83-3.01 (m, 5H), 2.37-2.39 (m, 2H), 1.48 (s, 3H), 1.20 (d, J=7.1 Hz, 3H), 1.18 (d, J=6.1 Hz, 3H), 1.12 (d, J=6.9 Hz, 3H), 0.91 (s, 9H), 0.14 (d, J=2.6 Hz, 6H).

Step 3. Tetrabutylammonium fluoride (0.04 mL, 1 M in THF, 0.04 mmol) was added to a vial containing (3R,4S,7S,8aS,10aR,11R,12S,14R,14aS,14bS,E)-4-((R)-1-((tert-butyldimethylsilyl)oxy)ethyl)-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecine-12-carbonitrile (5 mg, 0.01 mmol) in tetrahydrofuran (0.3 mL). The resulting mixture was stirred for 20 minutes, then more tetrabutylammonium fluoride (0.04 mL, 1 M in THF, 0.04 mmol) was added. After a total reaction time of 45 minutes the reaction mixture was partitioned between ethyl acetate and water. The organic phase was then washed with brine, dried over magnesium sulfate, filtered and then concentrated under reduced pressure. The crude material was purified by preparative thin layer chromatography to give (3R,4S,7S,8aS,10aR,11R,12S,14R,14aS,14bS,E)-14-hydroxy-4-((R)-1-hydroxyethyl)-7-methoxy-1,3,13-trimethyl-6-oxo-3,4,6,7,8,8a,10a,11,12,13,14,14a-dodecahydro-11,14b-epoxynaphtho[2,1-e]oxecine-12-carbonitrile (2.8 mg, 6.5 μmol) as a film. 1H NMR (500 MHz, CD3OD) δ 7.34 (s, 1H), 5.97 (t, J=8.2 Hz, 1H), 5.66 (dd, J=9.4, 3.1 Hz, 1H), 5.40 (d, J=7.1 Hz, 1H), 5.14 (s, 1H), 4.29 (d, J=4.6 Hz, 1H), 3.95-4.00 (m, 1H), 3.73 (dd, J=11.4, 4.3 Hz, 1H), 3.47 (dd, J=11.0, 2.5 Hz, 1H), 3.29 (s, 3H), 3.13 (t, J=5.6 Hz, 1H), 3.05-3.09 (m, 1H), 2.41-2.51 (m, 3H), 2.29-2.34 (m, 2H), 1.80 (s, 3H), 1.35 (dt, J=15.0, 3.9 Hz, 1H), 1.23 (d, J=7.5 Hz, 3H), 1.21 (d, J=7.5 Hz, 3H), 1.12 (d, J=6.8 Hz, 3H).

Example 189

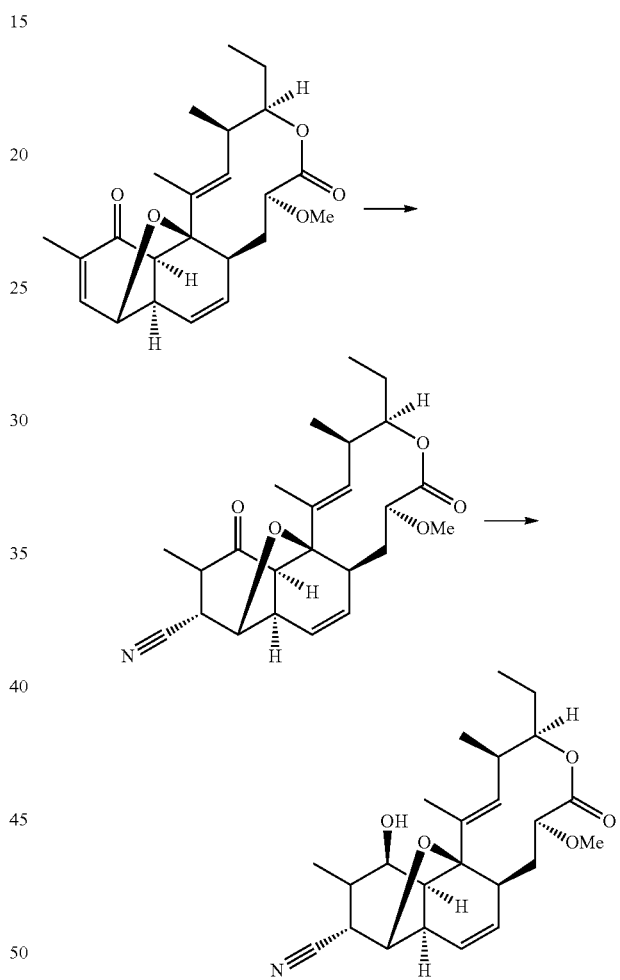

(3R,4R,7S,8aS,10aR,11R,12S,14R,14aS,14bS,E)-4-ethyl-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecine-12-carbonitrile Step 1. To a solution of (3R,4R,7S,8aS,10aR,11R,14aR,14bS,E)-4-ethyl-7-methoxy-1,3,13-trimethyl-3,4,8,8a,10a,11-hexahydro-11,14b-epoxynaphtho[2,1-e]oxecine-6,14(7H,14aH)-dione (10 mg, 0.03 mmol) in DMF (0.4 mL) was added potassium cyanide (8.4 mg, 0.13 mmol) and ammonium chloride (7 mg, 0.13 mmol) and water (0.1 mL). This mixture was stirred at room temperature for two days. Saturated aqueous sodium bicarbonate was added and the mixture was extracted with ethyl acetate. The organic layer was washed with brine, dried over magnesium sulfate, filtered and concentrate under reduced pressure to give a 12 mg of a crude reaction mixture which was used in the second step without purification.

Step 2. The crude reaction mixture from step 1 was dissolved in methanol (0.5 mL) and then sodium borohydride (4 mg, 0.1 mmol) was added. After stirring at room temperature for one hour the reaction was partitioned between ethyl acetate and water. The organic layer was washed with brine, then dried over magnesium sulfate, filtered and then concentrated under reduced pressure. The reaction was purified by preparative thin layer chromatography (2:1 Hexanes: Ethyl Acetate) and the isolated product lyophilized from a dilute solution of methanol in benzene to give (3R,4R,7S,8aS,10aR,11R,12S,14R,14aS,14bS,E)-4-ethyl-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecine-12-carbonitrile (5 mg, 0.01 mmol).

1H NMR (500 MHzCD$_3$OD): δ 5.96 (1 H, t, J=8.16 Hz), 5.62 (1 H, dd, J=9.40, 2.96 Hz), 5.43 (1 H, d, J=8.89 Hz), 5.09 (1 H, q, J=6.90 Hz), 4.30 (1 H, d, J=4.56 Hz), 3.64 (1 H, dd, J=11.30, 3.44 Hz), 3.46 (1 H, dd, J=10.86, 2.49 Hz), 3.28 (3 H, s), 3.05-3.14 (2 H, m), 2.44-2.51 (3 H, m), 2.39 (1 H, s), 2.30-2.35 (1 H, m), 1.67-1.73 (5 H, m), 1.32-1.36 (1 H, m), 1.10 (3 H, d, J=6.81 Hz), 1.07 (3 H, d, J=7.11 Hz), 0.97 (3 H, t, J=7.30 Hz).

Example 190

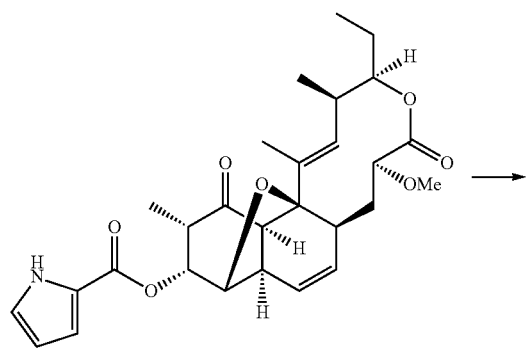

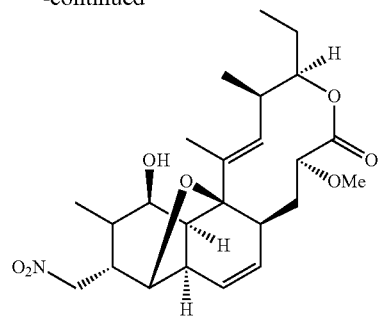

(3R,4R,7S,8aS,10aR,11R,12S,14R,14aS,14bS,E)-4-ethyl-14-hydroxy-7-methoxy-1,3,13-trimethyl-12-(nitromethyl)-3,4,8,8a,10a,11,12,13,14,14a-decahydro-11,14b-epoxynaphtho[2,1-e]oxecin-6(7H)-one Step 1) To a solution of (3R,4R,7S,8aS,10aR,11R,12R,13R,14R,14aS,14bS,E)-4-ethyl-14-hydroxy-7-methoxy-1,3,13-trimethyl-6-oxo-3,4,6,7,8,8a,10a,11,12,13,14,14a-dodecahydro-11,14b-epoxynaphtho[2,1-e]oxecin-12-yl 1H-pyrrole-2-carboxylate (25 mg, 0.05 mmol) in acetonitrile (0.5 mL) was added nitromethane (16 μL, 0.3 mmol) and DBU (23 μL, 0.15 mmol). After stirring at room temperature overnight the reaction mixture was concentrated under reduced pressure. The crude residue was purified by flash chromatography using a gradient of 10%-100% ethyl acetate in hexanes to give (3R,4R,7S,8aS,10aR,11R,12S,14aR,14bS,E)-4-ethyl-7-methoxy-1,3,13-trimethyl-12-(nitromethyl)-3,4,8,8a,10a,11,12,13-octahydro-11,14b-epoxynaphtho[2,1-e]oxecine-6,14(7H,14aH)-dione (10 mg).

Step 2) To a solution of (3R,4R,7S,8aS,10aR,11R,12S,14aR,14bS,E)-4-ethyl-7-methoxy-1,3,13-trimethyl-12-(nitromethyl)-3,4,8,8a,10a,11,12,13-octahydro-11,14b-epoxynaphtho[2,1-e]oxecine-6,14(7H,14aH)-dione (3 mg, 0.007 mmol) in methanol was added sodium borohydride (0.25 mg, 0.007 mmol). After stirring at room temperature the crude reaction mixture was purified directly by preparative thin layer chromatography to give (3R,4R,7S,8aS,10aR,11R,12S,14R,14aS,14bS,E)-4-ethyl-14-hydroxy-7-methoxy-1,3,13-trimethyl-12-(nitromethyl)-3,4,8,8a,10a,11,12,13,14,14a-decahydro-11,14b-epoxynaphtho [2,1-e]oxecin-6(7H)-one (1 mg). M +Na 472.12.

Example 179

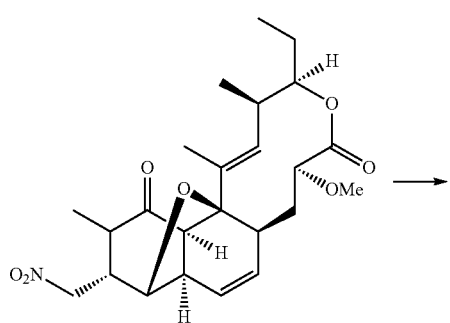

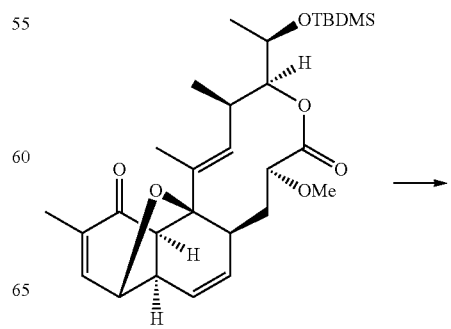

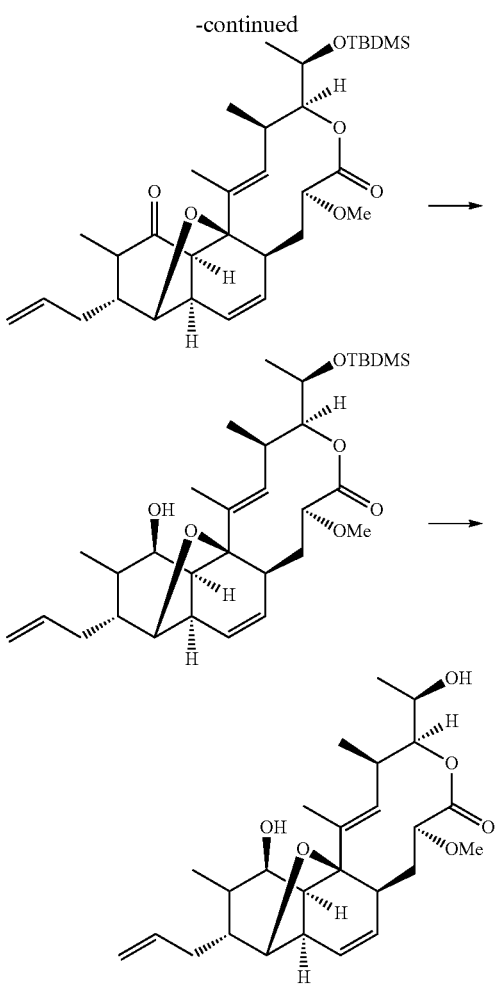

(3R,4S,7S,8aS,10aR,11S,12R,14R,14aS,14bS,E)-12-allyl-14-hydroxy-4-((R)-1-hydroxyethyl)-7-methoxy-1,3,13-trimethyl-3,4,8,8a,10a,11,12,13,14,14a-decahydro-11,14b-epoxynaphtho[2,1-e]oxecin-6(7H)-one Step 1. To (3R,4S,7S,8aS,10aR,11R,14aR,14bS,E)-4-((R)-1-((tert-butyldimethylsilyl)oxy)ethyl)-7-methoxy-1,3,13-trimethyl-3,4,8,8a,10a,11-hexahydro-11,14b-epoxynaphtho[2,1-e]oxecine-6,14(7H,14aH)-dione (18 mg, 0.04 mmol), which had been cooled to −78 C, was added a solution of titanium tetrachloride (0.18 mL, 1M in dichloromethane, 0.18 mmol). To this mixture was added dichloromethane (0.2 mL) followed by allyltrimethylsilane (0.03 mL, 0.04 mmol). After 1.25 hours the reaction was partitioned between ethyl acetate and saturated aqueous sodium bicarbonate. This mixture was filtered through celite. The organic layer was dried with magnesium sulfate and then filtered and concentrated under reduced pressure. The crude residue was purified by silica gel column chromatography using a gradient of 10-100% ethyl acetate in hexanes to give (3R,4S,7S,8aS,10aR,11S,12R,14aR,14bS,E)-12-allyl-4-((R)-1-((tert-butyldimethylsilyl)oxy)ethyl)-7-methoxy-1,3,13-trimethyl-3,4,8,8a,10a,11,12,13-octahydro-11,14b-epoxynaphtho[2,1-e]oxecine-6,14(7H,14aH)-dione (5 mg, 0.008 mmol)

Step 2. (3R,4S,7S,8aS,10aR,11S,12R,14aR,14bS,E)-12-allyl-4-((R)-1-((tert-butyldimethylsilyl)oxy)ethyl)-7-methoxy-1,3,13-trimethyl-3,4,8,8a,10a,11,12,13-octahydro-11,14b-epoxynaphtho[2,1-e]oxecine-6,14(7H,14aH)-dione (5 mg, 0.008 mmol) was dissolved in methanol (0.3 mL) and then sodium borohydride (5 mg, 0.1 mmol) was added. After stirring at room temperature for one hour the reaction was partitioned between ethyl acetate and water. The organic layer was washed with brine, then dried over magnesium sulfate, filtered and then concentrated under reduced pressure to give crude (3R,4S,7S,8aS,10aR,11S,12R,14R,14aS,14bS,E)-12-allyl-4-((R)-1-((tert-butyldimethylsilyl)oxy)ethyl)-14-hydroxy-7-methoxy-1,3,13-trimethyl-3,4,8,8a,10a,11,12,13,14,14a-decahydro-11,14b-epoxynaphtho[2,1-e]oxecin-6(7H)-one (4 mg, 0.006 mmol).

Step 3. Tetrabutylammonium fluoride (0.02 mL, 1 M in THF, 0.02 mmol) was added to a vial containing (3R,4S,7S,8aS,10aR,11S,12R,14R,14a5,14bS,E)-12-allyl-4-((R)-1-((tert-butyldimethylsilyl)oxy)ethyl)-14-hydroxy-7-methoxy-1,3,13-trimethyl-3,4,8,8a,10a,11,12,13,14,14a-decahydro-11,14b-epoxynaphtho[2,1-e]oxecin-6(7H)-one (4 mg, 0.006 mmol) in tetrahydrofuran (0.2 mL). The resulting mixture was stirred for 45 minutes, then more tetrabutylammonium fluoride (0.02 mL, 1 M in THF, 0.02 mmol) was added. After a total reaction time of 90 minutes the reaction mixture was purified by preparative thin layer chromatography to give (3R,4S,7S,8aS,10aR,11S,12R,14R,14aS,14bS,E)-12-allyl-14-hydroxy-4-((R)-1-hydroxyethyl)-7-methoxy-1,3,13-trimethyl-3,4,8,8a,10a,11,12,13,14,14a-decahydro-11,14b-epoxynaphtho[2,1-e]oxecin-6(7H)-one (1 mg, 2.2 µmol) as a film.

$^1$H NMR δ (500 MHz, CD$_3$OD): 5.86 (1 H, t, J=8.16 Hz), 5.71-5.77 (1 H, m), 5.60 (1 H, dd, J=9.29, 3.14 Hz), 5.25 (1 H, d, J=6.81 Hz), 5.12 (1 H, s), 4.94-5.03 (2 H, m), 4.57 (1 H, s), 4.07 (1 H, dd, J=7.62, 4.34 Hz), 3.95-3.97 (2 H, m), 3.70 (1 H, dd, J=11.80, 4.59 Hz), 3.28 (3 H, s), 2.95-2.98 (1 H, m), 2.43-2.48 (2 H, m), 2.27 (1 H, d, J=7.06 Hz), 2.15 (1 H, s), 1.96-2.00 (1 H, m), 1.91-1.94 (1 H, m), 1.76 (3 H, s), 1.6-1.73 (1 H, m), 1.27-1.32 (3 H, m), 1.20 (3 H, d, J=7.01 Hz), 1.18 (3 H, d, J=6.19 Hz), 1.04 (3 H, d, J=7.54 Hz).

Example 176

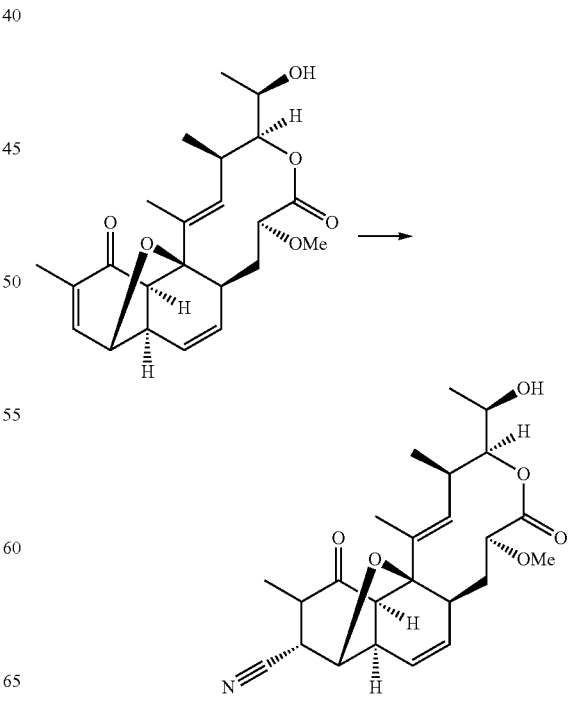

(3R,4S,7S,8aS,10aR,11R,12S,14aR,14bS,E)-4-((R)-1-hydroxyethyl)-7-methoxy-1,3,13-trimethyl-6,14-dioxo-3,4,6,7,8,8a,10a,11,12,13,14,14a-dodecahydro-11,14b-epoxynaphtho[2,1-e]oxecine-12-carbonitrile To a solution of (3R,4S,7S,8aS,10aR,11R,14aR,14bS,E)-4-((R)-1-hydroxyethyl)-7-methoxy-1,3,13-trimethyl-3,4,8,8a,10a,11-hexahydro-11,14b-epoxynaphtho[2,1-e]oxecine-6,14(7H,14aH)-dione (7 mg, 0.02 mmol) in DMF (0.13 mL) was added potassium cyanide (8 mg, 0.1 mmol) and ammonium chloride (7 mg, 0.1 mmol) and water (0.03 mL). This mixture was stirred at room temperature for one hour. The reaction mixture partitioned between ethyl acetate and water. The organic layer was washed with brine, then dried over magnesium sulfate, filtered and then concentrated under reduced pressure. The crude reaction mixture was then purified by preparative thin layer chromatography to give (3R,4S,7S,8aS,10aR,11R,12S,14aR,14bS,E)-4-((R)-1-hydroxyethyl)-7-methoxy-1,3,13-trimethyl-6,14-dioxo-3,4,6,7,8,8a,10a,11,12,13,14,14a-dodecahydro-11,14b-epoxynaphtho [2,1-e]oxecine-12-carbonitrile (6 mg, 0.1 mmol). LCMS (M+1=430.15)

The following compounds of Formula I were also made.

| EXAMPLES | Structure | [M + Na] or $^1$H NMR |
|---|---|---|
| 152 | 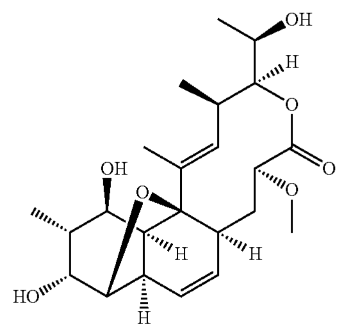 [SMILES: CO[C@H]1C[C@H]2C=C[C@H]3[C@H]4O[C@]2(/C(C)=C/[C@@H](C)[C@@H]([C@@H](C)O)OC1=O)[C@@H]3[C@H](O)[C@@H](C)[C@H]4O] | M + 1 = 423.74 |
| 170 | 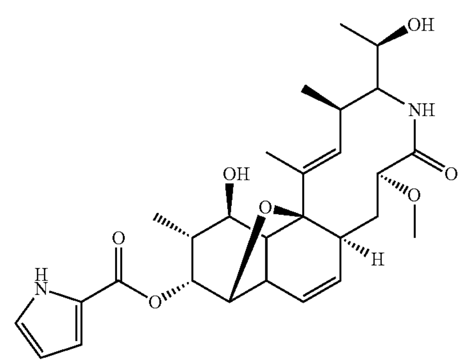 [SMILES: CO[C@H]1C[C@H]2C=CC3C4[C@H](O)[C@@H](C)[C@@H](OC(=O)c5ccc[nH]5)[C@@H]3O[C@]42/C(C)=C/[C@@H](C)C([C@@H](C)O)NC1=O] | 515.30 |
| 171 | 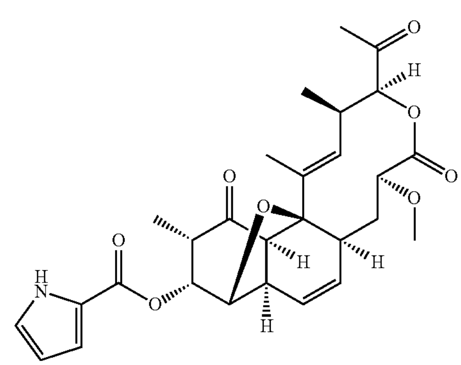 [SMILES: CO[C@H]1C[C@H]2C=C[C@H]3[C@H]4O[C@]2(/C(C)=C/[C@@H](C)[C@@H](C(C)=O)OC1=O)[C@@H]3C(=O)[C@@H](C)[C@H]4OC(=O)c1ccc[nH]1] | M + Na = 534.10 |

-continued

| EXAMPLES | Structure | [M + Na] or ¹H NMR |
|---|---|---|
| 172 | 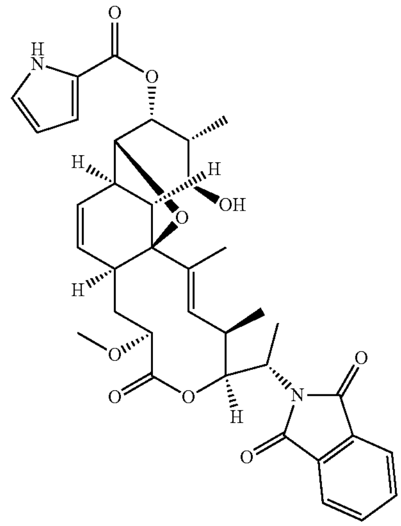 | M + 1 = 646 |
| 173 | 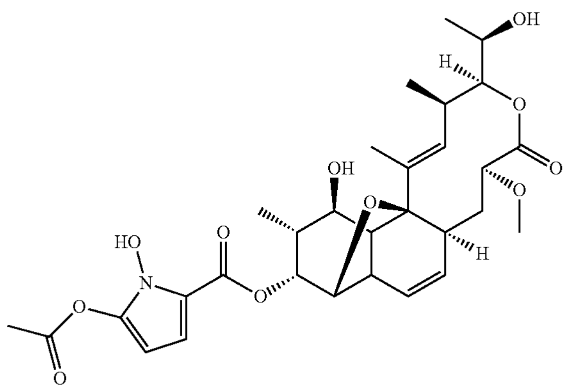 [SMILES: CO[C@H]1C[C@H]2C=CC3C4[C@H](O)[C@@H](C)[C@@H](OC(=O)c5ccc(OC(C)=O)n5O)[C@@H]3O[C@]42/C(C)=C/[C@@H](C)[C@@H]([C@@H](C)O)OC1=O] | M + Na = 612.13 |
| 174 | 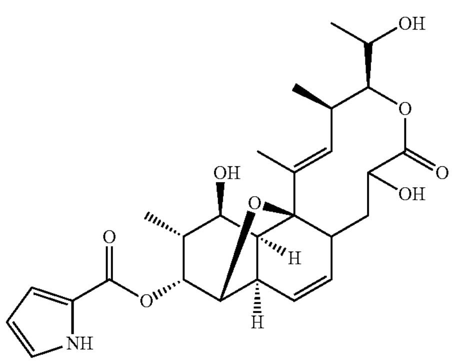 [SMILES: C/C1=C\[C@@H](C)[C@@H](C(C)O)OC(=O)C(O)CC2C=C[C@H]3[C@H]4O[C@@]12[C@@H]3[C@H](O)[C@@H](C)[C@H]4OC(=O)c1ccc[nH]1] | M + 1 = 502.20 |
| 175 | 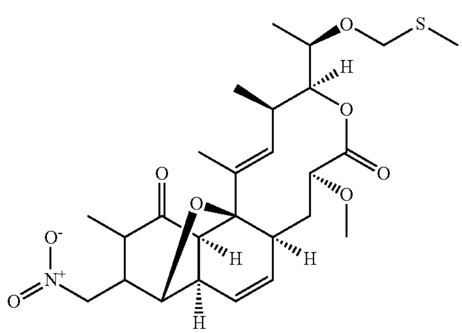 [SMILES: CO[C@H]1C[C@H]2C=C[C@@H]3[C@H]4C(=O)C(C)C(C[N+](=O)[O-])[C@@H]3O[C@@]24/C(C)=C/[C@@H](C)[C@@H]([C@@H](C)OCSC)OC1=O] | M + Na = 546.38 |

| EXAMPLES | Structure | [M + Na] or ¹H NMR |
|---|---|---|
| 177 | 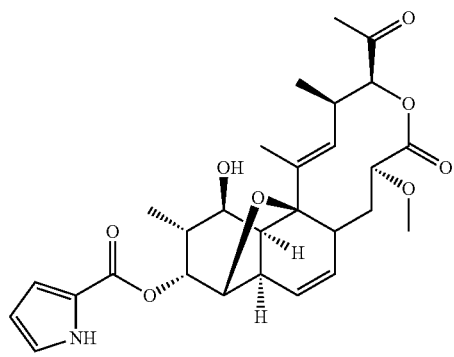 [SMILES: CO[C@H]1CC2C=C[C@H]3[C@H]4O[C@]2(/C(C)=C/[C@@H](C)[C@@H](C(C)=O)OC1=O)[C@@H]3[C@H](O)[C@@H](C)[C@H]4OC(=O)c1ccc[nH]1] | M + 1 = 514.00 |
| 178 | 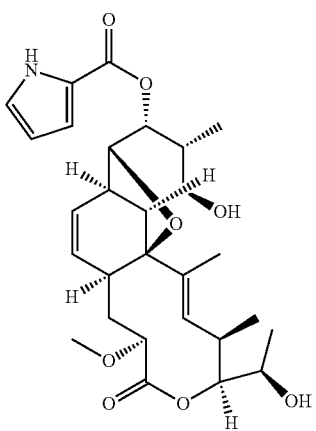 | M + Na = 538.46 |
| 180 | 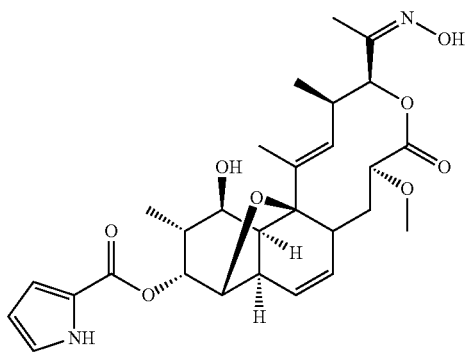 [SMILES: CO[C@H]1CC2C=C[C@H]3[C@H]4O[C@]2(/C(C)=C/[C@@H](C)[C@@H](/C(C)=N\O)OC1=O)[C@@H]3[C@H](O)[C@@H](C)[C@H]4OC(=O)c1ccc[nH]1] | M + 1 = 529.00 |
| 181 | 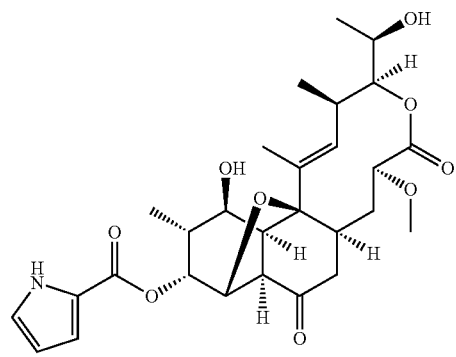 [SMILES: CO[C@H]1C[C@H]2CC(=O)[C@H]3[C@H]4O[C@]2(/C(C)=C/[C@@H](C)[C@@H]([C@@H](C)O)OC1=O)[C@@H]3[C@H](O)[C@@H](C)[C@H]4OC(=O)c1ccc[nH]1] | M + 1 = 532.17 |

| EXAMPLES | Structure | [M + Na] or ¹H NMR |
|---|---|---|
| 182 | 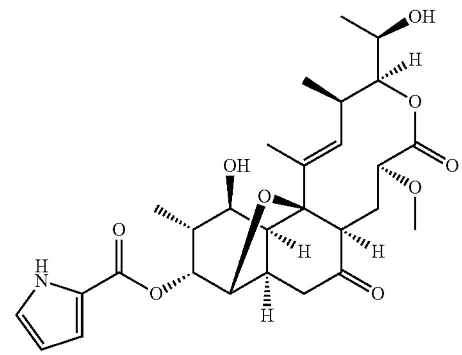 [SMILES: CO[C@H]1C[C@H]2C(=O)C[C@H]3[C@H]4O[C@]2(/C(C)=C/[C@@H](C)[C@@H]([C@@H](C)O)OC1=O)[C@@H]3[C@H](O)[C@@H](C)[C@H]4OC(=O)c1ccc[nH]1] | M + 1 = 532.19 |
| 183 | 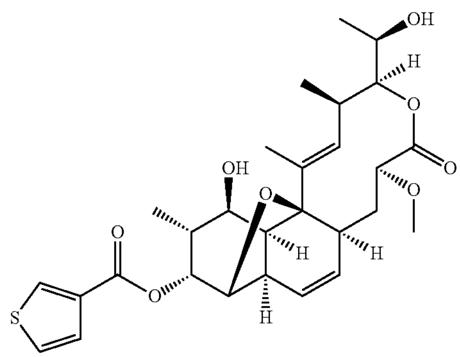 [SMILES: CO[C@H]1C[C@H]2C=C[C@H]3[C@H]4O[C@]2(/C(C)=C/[C@@H](C)[C@@H]([C@@H](C)O)OC1=O)[C@@H]3[C@H](O)[C@@H](C)[C@H]4OC(=O)c1ccsc1] | M + Na = 555.00 |
| 184 | 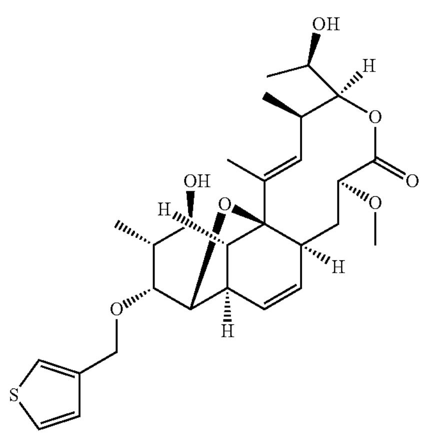 | ¹H NMR δ (ppm)(CDCl₃): 7.36 (1 H, s), 7.30 (1 H, dd, J = 4.99, 2.97 Hz), 7.17 (1 H, s), 7.04 (1 H, d, J = 5.00 Hz), 5.89 (1 H, t, J = 8.16 Hz), 5.55 (1 H, dd, J = 9.36, 3.08 Hz), 5.46 (1 H, d, J = 7.96 Hz), 5.12 (1 H, t, J = 6.98 Hz), 4.53 (1 H, d, J = 12.19 Hz), 4.48 (1 H, d, J = 12.17 Hz), 4.07-4.12 (2 H, m), 3.68 (1 H, dd, J = 11.72, 3.82 Hz), 3.56 (1 H, d, J = 10.58 Hz), 3.51 (1 H, t, J = 4.81 Hz), 3.31 (3 H, s), 3.13-3.15 (1 H, m), 2.56 (1 H, d, J = 6.98 Hz), 2.49 (1 H, ddd, J = 15.11, 11.68, 3.91 Hz), 2.44 (1 H, d, J = 2.73 Hz), 2.30 (1 H, s), 2.07-2.13 (1 H, m), 1.77 (3 H, s), 1.37-1.40 (1 H, m), 1.31 (3 H, d, J = 6.23 Hz), 1.24 (3 H, d, J = 7.14 Hz), 0.99 (3 H, d, J = 6.86 Hz). |
| 185 | 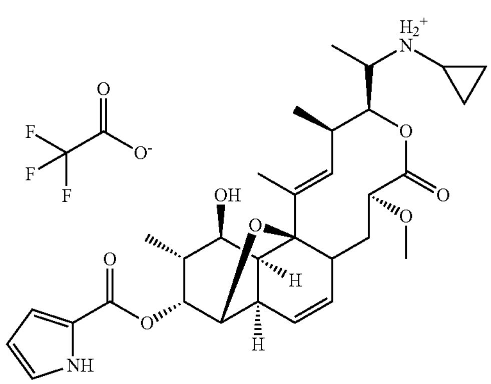 | M + 1 = 555.00 |

| EXAMPLES | Structure | [M + Na] or ¹H NMR |
|---|---|---|
| 186 | 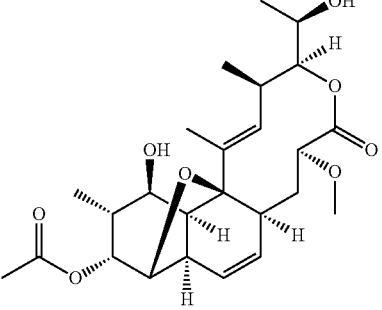 | 2M + Na = 951.63 |
| 187 | 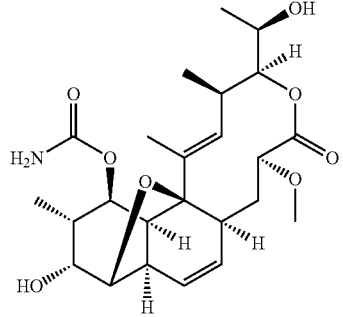 [SMILES: CO[C@H]1C[C@H]2C=C[C@H]3[C@H]4O[C@]2(/C(C)=C/[C@@H](C)[C@@H]([C@@H](C)O)OC1=O)[C@@H]3[C@H](OC(N)=O)[C@@H](C)[C@H]4O] | M + Na = 488.37 |
| 191 | 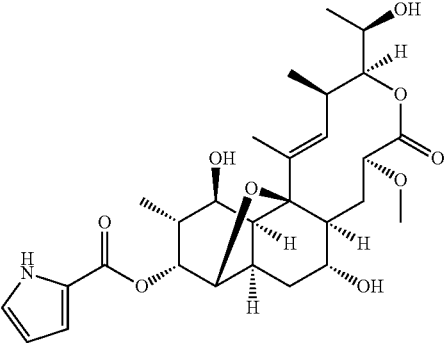 [SMILES: CO[C@H]1C[C@H]2[C@H](O)C[C@H]3[C@H]4O[C@]2(/C(C)=C/[C@@H](C)[C@@H]([C@@H](C)O)OC1=O)[C@@H]3[C@H](O)[C@@H](C)[C@H]4OC(=O)c1ccc[nH]1] | M + 1 = 534.21 |
| 192 | 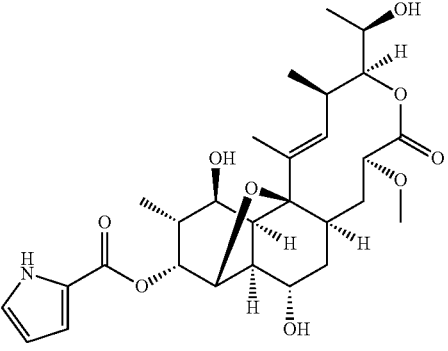 [SMILES: CO[C@H]1C[C@H]2C[C@H](O)[C@H]3[C@H]4O[C@]2(/C(C)=C/[C@@H](C)[C@@H]([C@@H](C)O)OC1=O)[C@@H]3[C@H](O)[C@@H](C)[C@H]4OC(=O)c1ccc[nH]1] | M + 1 = 534.17 |

-continued

| EXAMPLES | Structure | [M + Na] or ¹H NMR |
|---|---|---|
| 193 | 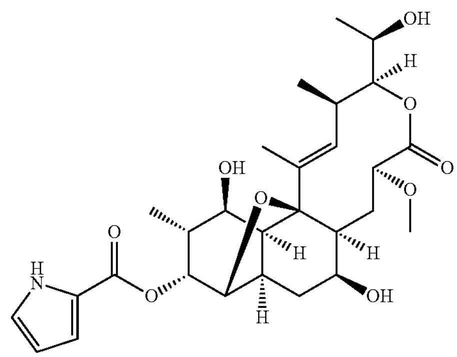 [SMILES: CO[C@H]1C[C@H]2[C@@H](O)C[C@H]3[C@H]4O[C@]2(/C(C)=C/[C@@H](C)[C@@H]([C@@H](C)O)OC1=O)[C@@H]3[C@H](O)[C@@H](C)[C@H]4OC(=O)c1ccc[nH]1] | ¹H NMR δ (ppm)(CD₃OD): 10.00 (1H, s) 6.98 (1H, s), 6.88 (1H, s) 6.20 (1H, s) 5.35-5.40 (1H, m) 5.06-5.10 (1H, m) 4.88-4.90 (1H, m) 3.85-4.02 (2H, m) 3.80-3.82 (1H, m) 3.50-3.60 (2H, m) 3.40-3.49 (2H, m) 3.23 (3H, s) 3.15-3.20 (1H, m) 2.90-2.98 (2H, m) 2.30-40 (2H, m) 2.00-2.20 (2H, m) 1.75 (3H, s) 1.70-1.80 (1H, m) 1.20 (3H, d, J = 6.8 Hz), 1.05-1.15 (2H, m) 1.13 (3H, d, J = 6.2 Hz) 0.83 (3H, d, J = 6.89 Hz) |
| 194 | 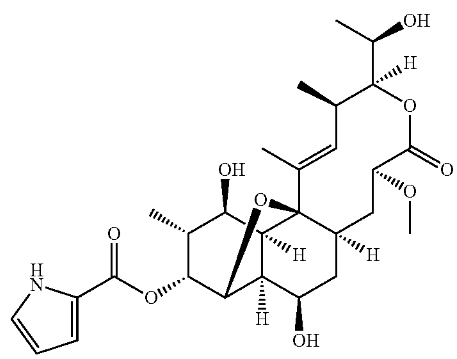 [SMILES: CO[C@H]1C[C@H]2C[C@@H](O)[C@H]3[C@H]4O[C@]2(/C(C)=C/[C@@H](C)[C@@H]([C@@H](C)O)OC1=O)[C@@H]3[C@H](O)[C@@H](C)[C@H]4OC(=O)c1ccc[nH]1] | M + 1 = 534.17 |
| 195 | 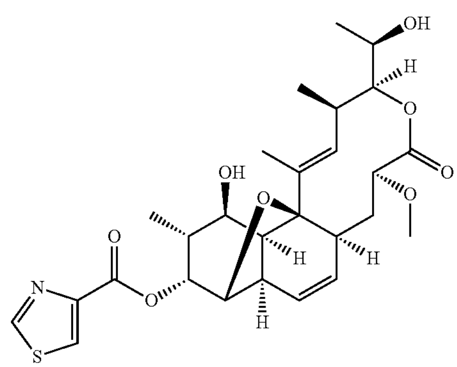 [SMILES: CO[C@H]1C[C@H]2C=C[C@H]3[C@H]4O[C@]2(/C(C)=C/[C@@H](C)[C@@H]([C@@H](C)O)OC1=O)[C@@H]3[C@H](O)[C@@H](C)[C@H]4OC(=O)c1cscn1] | M + Na = 557.32 |
| 196 | 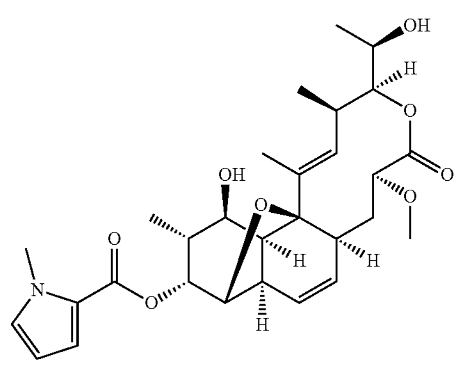 [SMILES: CO[C@H]1C[C@H]2C=C[C@H]3[C@H]4O[C@]2(/C(C)=C/[C@@H](C)[C@@H]([C@@H](C)O)OC1=O)[C@@H]3[C@H](O)[C@@H](C)[C@H]4OC(=O)c1cccn1C] | M + Na = 552.10 |

-continued

| EXAMPLES | Structure | [M + Na] or ¹H NMR |
|---|---|---|
| 197 | 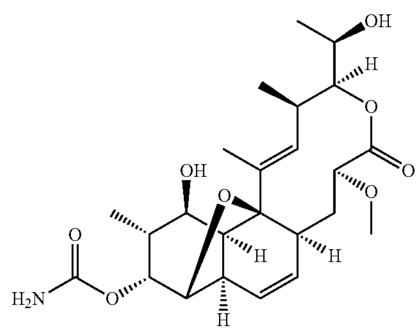 [SMILES: CO[C@H]1C[C@H]2C=C[C@H]3[C@H]4O[C@]2(/C(C)=C/[C@@H](C)[C@@H]([C@@H](C)O)OC1=O)[C@@H]3[C@H](O)[C@@H](C)[C@H]4OC(N)=O] | M + Na = 488.06 |
| 198 | 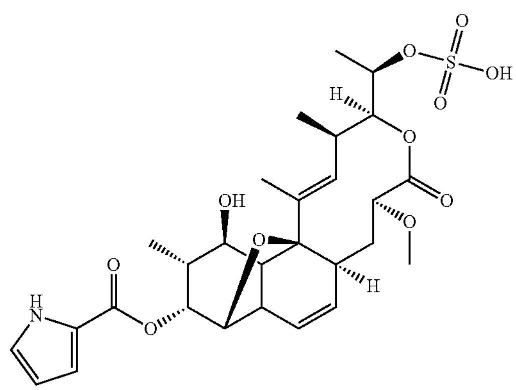 [SMILES: CO[C@H]1C[C@H]2C=CC3C4[C@H](O)[C@@H](C)[C@@H](OC(=O)c5ccc[nH]5)[C@@H]3O[C@]42/C(C)=C/[C@@H](C)[C@@H]([C@@H](C)OS(=O)(=O)O)OC1=O] | M + 1 = 596.10 |
| 199 | 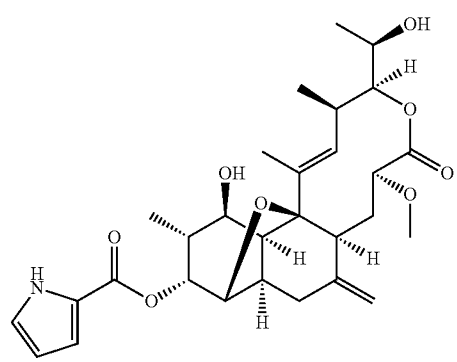 | M + 1 = 530.15 |
| 200 | 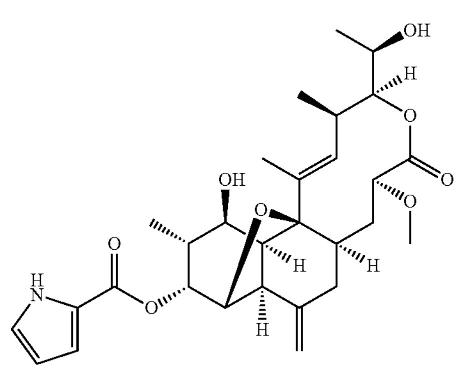 [SMILES: C=C1C[C@@H]2C[C@H](OC)C(=O)O[C@H]([C@@H](C)O)[C@H](C)/C=C(\C)[C@]23O[C@H]2[C@H](OC(=O)c4ccc[nH]4)[C@H](C)[C@@H](O)[C@@H]3[C@@H]12] | M + 1 − H₂O = 512.14 |

| EXAMPLES | Structure | [M + Na] or ¹H NMR |
|---|---|---|
| 201 | 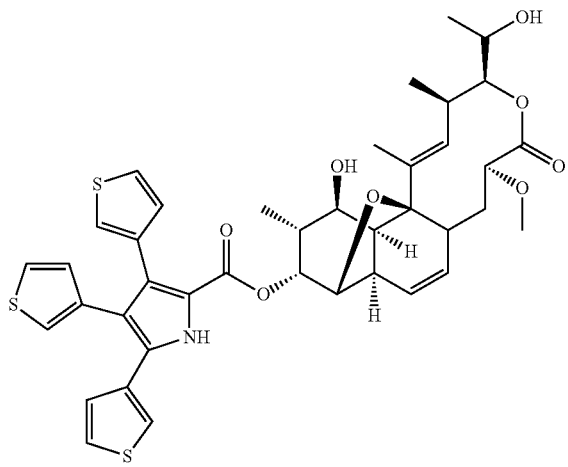 [SMILES: CO[C@H]1CC2C=C[C@H]3[C@H]4O[C@]2(/C(C)=C/[C@@H](C)[C@@H](C(C)O)OC1=O)[C@@H]3[C@H](O)[C@@H](C)[C@H]4OC(=O)c1[nH]c(-c2ccsc2)c(-c2ccsc2)c1-c1ccsc1] | |
| 202 | 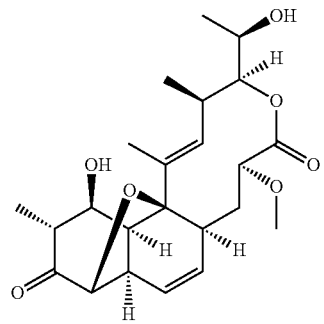 [SMILES: CO[C@H]1C[C@H]2C=C[C@@H]3[C@H]4[C@H](O)[C@@H](C)C(=O)[C@@H]3O[C@]42/C(C)=C/[C@@H](C)[C@@H]([C@@H](C)O)OC1=O] | M + Na = 443.22 |
| 203 | 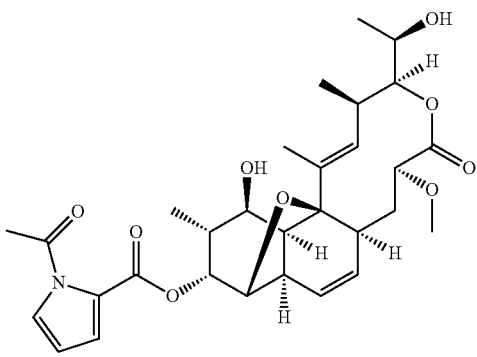 [SMILES: CO[C@H]1C[C@H]2C=C[C@H]3[C@H]4O[C@]2(/C(C)=C/[C@@H](C)[C@@H]([C@@H](C)O)OC1=O)[C@@H]3[C@H](O)[C@@H](C)[C@H]4OC(=O)c1cccn1C(C)=O] | M + 1 = 558.31 |
| 204 | 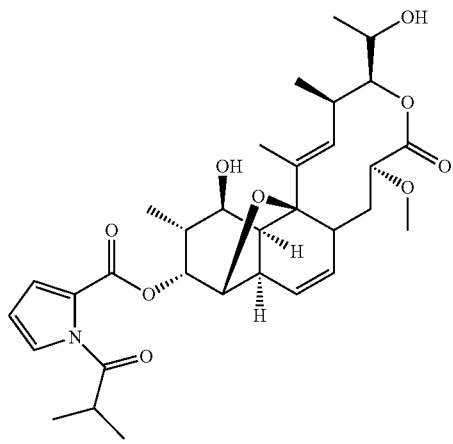 [SMILES: CO[C@H]1CC2C=C[C@H]3[C@H]4O[C@]2(/C(C)=C/[C@@H](C)[C@@H](C(C)O)OC1=O)[C@@H]3[C@H](O)[C@@H](C)[C@H]4OC(=O)c1cccn1C(=O)C(C)C] | M + 1 = 586.00 |

Biological Assays

DnaE Purification:

Plasmids encoding EcDnaE (*E. coli* DnaE residues 1-1160) and SaDnaE (*S. aureus* DnaE residues 1-1065) with 6×His N-terminal tags, were overexpressed in BL21(DE3) and BL21-AI cells (Invitrogen), respectively. Cells were grown in LB media to an OD ~0.45 pelleted and then resuspended in Minimal Media, as described in Pryor et al. (1997, Protein Expr Purif. 10:309-19), and inducer (0.4 mM IPTG or 0.2% arabinose) for 21 hours at 18° C. at 220 rpm. Cells were then harvested, frozen for 20 minutes at −80° C. and thawed. Pellets were resuspended in 1× Talon buffer (50 mM Sodium Phosphate, 300 mM Sodium Chloride, pH 7.4) +10% glycerol +Roche PI's (-EDTA). Cells were lysed with two passes through a French press, then centrifuged for 45 minutes at 40,000 rpm (70Ti, Beckman). Supernatant was bound to 5 mL TALON resin (CLONTECH) for 1 hour at room temperature on Nutator. TALON resin was washed with 10 mM imidizole, and DnaE was eluted with 250 mM imidizole. Eluate was concentrated and run on a size exclusion column (SEC200, GE Healthcare) in the following buffer; 25 mM HEPES, 30 mM NaCl, 1 mM $CaCl_2$, 5% glycerol, pH 7.9. Pool SEC fractions based on SDS-PAGE run, aliquot, freeze, and store at -80° C.

DnaE was diluted in 50 mM potassium phosphate pH 7.5, 5 mM BME, 10% glycerol and 200 mM NaCl prior to use.

In Vitro DnaE Single Enzyme Assay:

The purpose of the DnaE single enzyme assay is to determine the ability of compounds to inhibit the DNA polymerase III α-subunit homolog from *Staphylococcus aureus* or the α-subunit from *Escherichia coli* without the other components of the replication machinery. The DnaE single enzyme assay was a modified version of the method, Standard Pol III Assay Using Activated DNA and Four dNTPs, described by Butler et al., 2008, Methods in Molecular Medicine: New Antibiotic Targets 142:25-36. Briefly, in 96-well plates, enzyme was added to a mixture containing 30 mM Tris-HCl pH 7.5, 20% glycerol, 4 mM DTT, 10 mM Mg acetate, 0.025 mM dATP, 0.025 mM dGTP, 0.025 mM dc:TP, 0.011 mM $^3$H-dTTP 1 mCi/ml (Perkin-Elmer), and 0.298 mg/mL Dnase I (Sigma) treated "activated" Calf Thymus DNA (Worthington Biochemical). The assay was set up so that 5 μl of compound was distributed to the plates, 90 μl of reaction mix was added to the compound, and 5 μl of enzyme was added to start the reaction. Assays were initiated by the addition of 0.8 μg/ml *E. coli* or 0.05 μg/ml *S. aureus* DnaE, incubated for 30 min at 30° C., and terminated by the addition of a 20% trichloroacetic acid and 0.2% sodium pyrophosphate solution. Precipitated labeled DNA was collected on Glass-fiber Filtermat A using Micro96 Harvester, and the filters were washed, dried, and counted in a Microbeta Trilux (Perkin Elmer). Serial dilutions of compounds (in DMSO) were added to the plates before enzyme addition.

Microbiological Characterization in Non-Mycobacterium Isolates:

The purpose of the Nargenicin antibacterial assay is to determine the minimal inhibitory concentration (MIC) of nargenicin analogs against a panel of organisms, indicating their in vitro antibacterial activity/spectrum. MICs and kill curves were by CLSI methods (CLSI, 2005).

TABLE 1

Cell lines

| MB number | Other identifier | Organism | Description |
|---|---|---|---|
| MB5747 | LS 883 | Escherichia coli | K12 C600 leu thr lac (thi) galK tolC:tn10 |
| MB5890 | CB1101 | Pseudomonas aeruginosa | Δ(mexAB-oprM) Δ(mexCD-oprJ) Δ(mexXY) Δ(mexJKL) Δ(mexHI-opmD) Δ(opmH) |
| MB6266 | COL | Staphylococcus aureus | MRSA COL-Painter* |
| MB6357 | CL 2883 | Streptococcus pneumoniae | BACMIC strain |

Cell lines shown in Table 1 were prepared from appropriate slants prepared from a single colony by inoculation of slant into 3 ml Trypticase Soy Broth (TSB)(for MB5890 and MB6266), TSB with 10 μg/ml tetracycline (for MB5747), or Trypticase Soy Agar +5% Sheep's Blood (TSA+SB)(for MB6357), and incubated overnight at 37° C.

Drug dilutions were prepared at 20× the desired final drug concentration. Stock solutions of test compounds are typically made at 5.12 mg/ml in 100% DMSO and when diluted 1:2 in sterile water and then 1:20 into the final micro assay give a final highest starting concentration of 128 μg/ml. Samples and controls were prepared in 50% DMSO and serially diluted 1:2 in 50% DMSO. Drug was serially diluted across assay plates filled with 95 μl of Mueller Hinton Broth II (MHII, Becton Dickinson) (for MB5890 and MB5747), 95 μl of MHII broth +50% Human serum (for MB 6266), or 95 μl of Isosensitest broth (Oxoid, for MB6357).

The overnight inoculum was diluted as follows: 0.4 ml of ON to 39.6 ml of sterile 0.85% saline (for MB5890 and MB6266), 0.8 ml of ON to 39.2 ml saline (for MB6355) or by preparing a 1 MacFarland in 5 ml saline by swabbing from the TSA blood agar plate so that its density was equivalent to a 1 McFarland standard, reading tubes using the Dade Behring Turbidity reader (~$10^8$ CFU/mL) and diluted by transferring the 1 MacFarland in 5 ml saline to 35 ml saline (for MB6357). 40 ml of the diluted inoculum was transferred into an inoculating tray and then using the 96-pin Inoculator, ~1.5 μl was transferred from the inoculating tray to the assay plate. The assay plates were incubated overnight at 37° C. for 18-22 hours.

A microtiter plate viewer was used to score wells for the minimal inhibitory concentration (MIC) for each compound.

Representative compounds of the present invention exhibit inhibition of DnaE in this assay and/or have antibacterial activity against one or more of the tested strains. For example, representative compounds of EXAMPLES 1-213 were tested in this assay and were found to have the $IC_{50}$ values and $MIC_{50}$ values shown in Table 2. Nargenicin (Nar) was used as a control. Data for nargenicin represents a range of values resulting from multiple trials in each assay.

Expression and Purification of DnaE for *Mycobacterium tuberculosis* "Mtb" Enzyme Assay A high titer viral stock (2.5×$10^8$ pfu/ml) containing the mycobacterium tuberculosis DnaE1 gene was prepared. This was done by cloning the cDNA for *mycobacterium tuberculosis* DnaE1 into a pFBHT-MAL plasmid which has an additional coding sequence for N-terminal 6×-His maltose binding protein tag. Sf9 insect cells were grown in serum-free medium up to a density of 2.5×$10^6$ cells/ml and viability of ≥95%. A liter of cell culture was transfected with the MAL-DnaE1 viral stock to get an MOI of 1. At 72 hours post infection, the cells were harvested by centrifugation and the pellet was resuspended in binding buffer (50 mM Tris-HCl, pH 8, 100 mM NaCl, 10 mM MgCl$_2$, 1 mM DTT and 10% glycerol). After sonication, cell debris was pelleted out using centrifugation. After removal of the cell debris by centrifugation, the MBP-tagged DnaE1 was purified with a linear gradient of 0-10 mM maltose in 50 mM Tris-HCl, pH 8.0, 200 mM NaCl, 1 mM DTT, 10% glycerol using Amylose column (New England Biolabs). The MBP tag was cleaved by dialysis (50 mM Tris, pH 8.0, 100 mM NaCl, 10% (v/v) glycerol) with the protease Factor Xa at 4° C. overnight. The untagged DnaE1 was further purified over three chromatography steps: heparin-Sepharose, Amylose column, and a size exclusion column.

Polymerase Assay

The *M. tuberculosis* polymerase enzymatic activity was measured using the EvaEZ™ Fluorometric Polymerase Activity Assay kit (Biotium, Hayward, Calif.) according to the manufacturer's instructions. The recombinant DnaE1 were incubated with water or inhibitor samples. The enzymatic activity was quantified by fluorescence using 7500 Real-Time PCR System (Applied Biosystems). The fluorescence was read every 1 min for 12 min at 37° C. The rate of fluorescence change (fluorescence unit/minute) resulting from the polymerase activity was taken to calculate IC$_{50}$.

*Mycobacterium tuberculosis* MIC Determination:

Isolated *Mycobacteria tuberculosis* (Mtb) cells (ATCC 27294) were grown to an OD 0.2-0.3 in 7H9 medium (4.7 g Middlebrook 7H9 broth, 900 mL water (double distilled), 2 mL glycerol, and 0.5 mL Tween 80 to which was added 100 mL ADC (5 g BSA fraction V, 2 g glucose, and 0.81 g NaCl in 100 ml water). In a 96 well plate, the compounds were serially diluted. Positive control was isoniazid. Negative control was DMSO only. 50 µl of the 1:1000 culture dilution was added to each well, approximating 1×10$^4$ bacteria per well. The plates were incubated for total of 2 weeks at 37° C. inside a zip-lock bag.

At weeks 1 and 2, the plates were read with inverted enlarging mirror plate reader and graded as either growth or no growth. The MIC is the concentration that completely inhibits growth. Photos are taken of the plates at both time points.

At week 2, 1/10$^{th}$ volume Alamar Blue was added to plates with 7H9-regular medium and those with cholesterol medium. The plates were incubated at 37° C. and read after 24 hr using visual scoring (blue=growth inhibition, pink=growth). Alamar Blue addition to cholesterol medium was necessary to distinguish cholesterol precipitation from growth which occurs if the media cooled down during MIC set-up. Alamar Blue can be read by fluorescence or absorbance but this was not done for the cross-screening.

TABLE 2

Summary of DnaE activity and antibacterial activity

| Ex. | E. coli DnaE IC50 ug/ml | S. aureus LS883 ug/ml | E. coli tolC | P. aeruginosa MB5890 efflux-del | S. aureus COL | S. pneumoniae MB2883 | Mtb 2-week MIC in GAST/Fe | Mtb 2-week MIC in 7H9/ADC/Tw | Mtb DnaE IC50 |
|---|---|---|---|---|---|---|---|---|---|
| 1 | 60 | 31 | >8 | >128 | >8 | >128 | | | |
| 2 | 31 | 0.021 | 8 | >128 | 4 | >128* | | | |
| 3 | 21 | >100 | >8 | >128 | >8 | >128 | >50 | >50 | |
| 4 | >100 | 0.7 | >128* | >128 | >128 | >128 | >50 | >50 | |
| 5 | >100 | 0.009 | 16 | >128* | 32 | >128 | | | |
| 6 | 45 | 0.011 | 4 | >128* | 8 | 128 | | | |
| 7 | 30 | <0.006 | 2 | 32 | 4 | >128 | | | |
| 8 | 30 | 0.045 | >128 | >128 | >128* | >128 | 37 | >=50 | 60 ± 30 |
| 9 | 30 | 0.02 | 8 | >128 | 8 | 32 | | | |
| 10 | >100 | 0.02 | >128* | >128 | 8 | >128 | >50 | >50 | |
| 11 | 80 | 0.019 | 16 | >128 | 32 | >128 | 37 | 37 | |
| 12 | 70 | <0.006 | 32 | >128 | >128 | >128 | | | |
| 13 | >100 | <0.006 | 8 | >128* | 32 | >128 | 25 | 25 | 0 ± 30 |
| 14 | 11 | 0.08 | >128* | >128 | >128* | 32 | >50 | >50 | |
| 15 | ~110 | <0.006 | 4 | 128 | 8 | >128 | | | |
| 16 | 60 | <0.006 | 4 | 128 | 32 | >128 | | | |
| 17 | 15 | <0.006 | 8 | >128* | 8 | >128* | | | |
| 18 | 60 | <0.006 | 4 | >128* | 8 | 128 | 25 | 50 | 60 ± 20 |
| 19 | 25 | <0.006 | 4 | 128 | 2 | 128 | 25 | 25 | |
| 20 | >100 | <0.006 | 8 | >128* | 8 | 32 | 50 | 50 | |
| 21 | >100 | <0.006 | 8 | 128 | 16 | 128 | | | |
| 22 | >100 | <0.006 | 4 | 64 | 4 | 64 | | | |
| 23 | 30 | <0.006 | 4 | 64 | 8 | >128* | 25 | 25 | |
| 24 | >100 | 0.006 | 32 | >128 | 32 | >128 | 50 | 37 | |
| 25 | >100 | 0.021 | 32 | >128 | 32 | >128 | 50 | 50 | 80 ± 20 |
| 26 | 80 | <0.006 | 4 | 128 | 4 | 128 | 25 | 25 | |
| 27 | 35 | <0.006 | 4 | >128* | 2 | 64 | >50 | 50 | 30 ± 10 |
| 28 | >100 | ~0.005 | 2 | 32 | 2 | 128 | >50 | 50 | |
| 29 | 45 | <0.006 | 8 | >128 | 2 | 16 | | | |
| 30 | 70 | <0.006 | 1 | 16 | 0.5 | 64 | | | |
| 31 | 100 | <0.006 | 2 | 32 | 2 | >128 | 9.4 | 19 | |
| 32 | >100 | ~0.0045 | 2 | 64 | 2 | >128 | | | |
| 33 | 35 | 0.021 | >64 | >128 | 32 | 8 | | | |
| 34 | 70 | 0.007 | 32 | >128 | 32 | 64 | | | |
| 35 | >50 | 0.007 | 32 | >128 | 32 | 64 | | | |
| 36 | 11 | <0.006 | 2 | 64 | 2 | >128 | 25 | 25 | 90 ± 30 |
| 37 | >100 | <0.05 | >8* | 128 | >8 | >128 | | | |
| 38 | ~110 | 0.022 | 16 | >128* | 32 | 128 | >=50 | >50 | |
| 39 | >100 | 9 | >128 | >128 | >128 | >128* | >50 | >50 | |
| 40 | >100 | 1.1 | >128* | >128 | >128 | >128* | >50 | >50 | |
| 41 | 60 | 3.1 | >128 | >128 | >128* | 8 | | | |

TABLE 2-continued

Summary of DnaE activity and antibacterial activity

| Ex. | E. coli DnaE IC50 ug/ml | S. aureus ug/ml | E. coli LS883 tolC | P. aeruginosa MB5890 efflux-del | S. aureus COL | S. pneumoniae MB2883 | Mtb 2-week MIC in GAST/Fe | Mtb 2-week MIC in 7H9/ADC/Tw | Mtb DnaE IC50 |
|---|---|---|---|---|---|---|---|---|---|
| 42 | 40 | 4 | >128 | >128 | 32 | 1 | | | |
| 43 | 45 | 0.12 | 8 | >128* | 64 | 128 | | | |
| 44 | 27 | <0.006 | 8 | 128 | 16 | 64 | | | |
| 45 | 100 | 1.5 | >128 | >128 | >128* | 4 | | | |
| 46 | 10 | 0.009 | 2 | 128 | 8 | 64 | | | |
| 47 | >100 | 0.042 | 16 | >128* | 64 | >128* | | | 210 ± 140 |
| 48 | >100 | 0.08 | 64 | >128* | >128* | 128 | >50 | >50 | 0 ± 5 |
| 49 | >100 | 0.28 | 64 | >128 | >128 | >128* | 50 | >50 | 0 ± 10 |
| 51 | 8 | <0.006 | >128 | >128 | 0.25 | >128* | | | |
| 52 | 40 | 0.6 | >128 | >128 | >128 | >128* | >=50 | >50 | 11 ± 2 |
| 53 | 40 | 0.1 | >128 | >128 | >128 | >128* | | | |
| 54 | 31 | 0.045 | 64 | >128 | 64 | >128* | 50 | >50 | |
| 55 | 6 | <0.006 | 2 | 32 | 2 | >64* | | | |
| 56 | 31 | <0.006 | 0.25 | 16 | <0.125 | 8 | 12.5 | 19 | 60 ± 40 |
| 57 | 45 | <0.006 | 4 | >128* | 8 | 64 | | | |
| 58 | 21 | >100 | >8 | >128 | >8 | >128 | >50 | >50 | |
| 59 | 10 | <0.006 | 0.25 | 16 | 0.25 | 64 | | | |
| 61 | | | | | | | 19 | 19 | |
| 62 | | | | | | | 6.25 | 6.25 | |
| 64 | 29 | <0.006 | 4 | 128 | 4 | >128 | 50 | >50 | |
| 65 | 10 | <0.006 | 2 | 64 | 2 | >128 | 25 | 50 | |
| 67 | 8 | 0.007 | >128 | >128 | >128 | >128 (2) | >50 | >50 | 50 ± 20 |
| 69 | 5 | <0.006 | 1 | 32 | 2 | >128 | | | |
| 70 | 9 | <0.006 | 0.5 | 16 | 0.5 | >128 | | | |
| 71 | 12 | <0.006 | 0.25 | 8 | 0.25 | >128 | | | |
| 73 | | | | | | | 9.4 | 9.4 | |
| 74 | 20 | <0.006 | 0.5 | 32 | 0.5 | >128 | | | |
| 78 | | | | | | | 12.5 | 25 | |
| 87 | | | | | | | 50 | >50 | |
| 90 | | | | | | | 2.3 | 0.78 | 70 ± 20 |
| 94 | | | | | | | 3.13 | 0.78 | 8 ± 3 |
| 96 | | | | | | | 3.13 | 1.56 | |
| 100 | | | | | | | 6.25 | 2.3 | 20 ± 6 |
| 101 | | | | | | | 12.5 | 4.7 | |
| 102 | | | | | | | 9.4 | 4.7 | |
| 103 | | | | | | | 19 | 12.5 | |
| 107 | | | | | | | 9.4 | 9.4 | |
| 108 | | | | | | | 2.3 | 1.2 | 15 ± 5 |
| 109 | | | | | | | 1.2 | 0.39 | |
| 111 | | | | | | | 2.3 | 3.13 | |
| 114 | 11 | <0.006 | 0.25 | 8 | <0.125 | >128 | 12.5 | 25 | |
| 115 | 9 | <0.006 | 0.5 | 8 | 0.5 | >64 | | | |
| 116 | 15 | 0.006 | 0.25 | 8 | ≤0.125 | >128* | | | |
| 117 | 11 | 0.0007 | ≤0.125 | 4 | ≤0.125 | 128 | | | |
| 118 | >100 | 0.004 | 1 | 32 | 0.5 | 128 | 12.5 | 12.5 | |
| 119 | 11 | 0.0012 | 0.25 | 8 | ≤0.125 | >128* | 6.25 | 25 | |
| 122 | | | | | | | 9.4 | 25 | |
| 127 | | | | | | | 6.25 | 25 | |
| 128 | | | | | | | 9.4 | 25 | |
| 129 | | | | | | | 9.4 | 19 | |
| 131 | | | | | | | 19 | >=50 | |
| 132 | | | | | | | 19 | 37 | |
| 137 | | | | | | | 19 | 37 | |
| 141 | 1 | <0.006 | 0.25 | 4 | 0.25 | >128* | 6.25 | 25 | |
| 145 | 0.9 | <0.006 | 0.25 | 4 | 0.25 | >128* | 6.25 | 12.5 | 22 ± 8 |
| 146 | >100 | 0.6 | 128 | >128 | >128 | 128 | | | |
| 147 | >100 | 0.3 | >128* | >128* | >128 | >128* | | | |
| 149 | >100 | 11 | 32 | 128 | >128 | >128 | >50 | >50 | 10 ± 4 |
| 150 | >50 | 2.5 | >64* | >64 | >64 | 64 | | | |
| 151 | >100 | 2.1 | >128* | >128* | >128 | >128 | | | |
| 152 | 100 | 100 | 16 | 16 | >128 | >128 | | | |
| 153 | >100 | 30 | >128* | >128 | >128 | >128 | | | |
| 154 | >100 | 70 | >128* | >128 | >128 | >128 | | | |
| 155 | >100 | 1.5 | >128 | 128 | >128 | >128 | | | |
| 156 | >100 | 21 | >128 | >128 | >128 | >128 | | | |
| 157 | >100 | 2.1 | >128 | >128 | >128 | >128 | | | |
| 159 | 18 | <0.006 | 4 | 32 | 2 | 2 | 12.5 | 37 | 60 ± 30 |
| 159 | 11 | <0.003 | 2 | 32 | 2 | >64* | | | |
| 159 | 15 | <0.006 | 2 | 32 | 4 | 32 | | | |
| 159 | 10 | <0.006 | 2 | 16 | 2 | 2 | | | |
| 160 | >100 | 2.2 | >8 | >128 | >8 | >128 | | | |
| 161 | >50 | 22 | >64 | >64 | >64 | >64 | | | |
| 162 | >100 | 8 | >128 | >128 | >128 | >128 | | | |

TABLE 2-continued

Summary of DnaE activity and antibacterial activity

| Ex. | E. coli DnaE IC50 ug/ml | S. aureus ug/ml | E. coli LS883 tolC | P. aeruginosa MB5890 efflux-del | S. aureus COL | S. pneumoniae MB2883 | Mtb 2-week MIC in GAST/Fe | Mtb 2-week MIC in 7H9/ADC/Tw | Mtb DnaE IC50 |
|---|---|---|---|---|---|---|---|---|---|
| 163 | >100 | 0.3 | 8 | 8 | >128 | >128 | | | |
| 164 | >100 | 6 | 16 | >128* | >128* | 32 | | | |
| 165 | 50 | 2.9 | 16 | >128 | >128* | 8 | | | |
| 166 | >50 | 0.18 | 64 | >64 | >64 | >64 | | | |
| 167 | >100 | 2 | >128* | >128 | >128* | >128* | | | |
| 168 | >50 | 18 | >128 | >64 | >128 | >64 | | | |
| 169 | 1 | <0.006 | 0.5 | 8 | 0.5 | >128 | 12.5 | 50 | |
| 170 | >100 | 1.3 | 128 | >128* | >128 | >128 | >50 | >50 | |
| 171 | 90 | 3.5 | >8 | >128 | >8 | >128 | >50 | >50 | 5 ± 2 |
| 172 | 41 | ~0.005 | 16 | >128 | 16 | >128 | | | |
| 173 | >100 | 0.32 | 8 | 16 | >128* | 128 | 25 | 50 | |
| 174 | 11 | 0.01 | 8 | >128* | 8 | >128 | | | |
| 175 | 50 | >100 | >128 | >128 | >128 | >128 | | | |
| 176 | >100 | 11 | >128 | >128 | >128 | >128 | | | |
| 177 | 4.5 | <0.006 | 0.5 | 8 | 1 | >128 | | | |
| 178 | >50 | 0.008 | 8 | >64* | 16 | >64* | | | |
| 179 | >50 | 13 | 64 | >64 | >64 | 64 | | | |
| 180 | 6 | <0.006 | 4 | 64 | 4 | 32 | | | |
| 181 | >100 | 0.05 | 8 | 32 | 64 | >128 | | | |
| 182 | >100 | 0.02 | 8 | 32 | 32 | >128 | | | |
| 183 | 5.2 | <0.006 | 1 | 16 | 1 | 64 | | | |
| 184 | 39 | 0.04 | 8 | 64 | 16 | 64 | | | |
| 185 | >100 | <0.006 (~0.004) | >128* | >128 | >128 | >128 | | | |
| 186 | 30 | ~0.0045 | 4 | 16 | 8 | >128 | | | |
| 187 | >100 | 0.18 | 16 | 32 | >128 | >128 | | | |
| 188 | >100 | 0.1 | 32 | 64 | 128 | 128 | | | |
| 189 | >100 | 60 | >128* | >128* | >128 | >128* | | | |
| 190 | 30 | 3 | 64 | >64 | >64 | >64 | | | |
| 191 | >100 | 4 | 128 | >128 | >128 | >128 | | | |
| 192 | >100 | 10 | >128* | >128 | >128 | >128 | | | |
| 193 | >100 | 1 | 64 | >128* | >128 | >128 | | | |
| 194 | >100 | 5 | 128 | >128* | >128 | >128 | | | |
| 195 | >100 | 0.09 | 64 | >128* | >128* | >128 | | | |
| 196 | >100 | 5.2 | 64 | >128* | >128 | 128 | | | |
| 197 | 38 | 0.011 | 2 | 2 | 128 | >128 | | | |
| 198 | 12 | <0.006 | 4 | 64 | 4 | >128 | | | |
| 199 | 75 | 0.015 | 16 | >128* | 32 | >128* | | | |
| 200 | >100 | 0.006 | 2 | 64 | 8 | 128 | | | |
| 201 | 0.4 | 0.3 | >128 | >128 | >128 | 128 | | | |
| 202 | >100 | 33 | 128 | >128* | >128 | >128* | | | |
| 203 | 6.5 | <0.006 | <0.125 | 16 | <0.125 | 128 | | | |
| 204 | | | | | | | 6.25 | 25 | 90 ± 20 |
| 205 | 6 | <0.006 | 2 | 64 | 2 | >128 | | | |
| 206 | 1.5 | <0.006 | 4 | 64 | 4 | >128 | | | |
| 207 | 2.6 | <0.006 | 4 | 64 | 4 | >64 | | | |
| 208 | 2.7 | <0.006 | 1 | 32 | 1 | >128 | | | |
| 209 | 17 | <0.006 | 4 | >128* | 4 | >128 | | | |
| 210 | 4.1 | <0.006 | 1 | 32 | 1 | >128 | | | |
| 211 | 2 | <0.006 | <0.125 | 16 | 0.5 | >128 | | | |
| 212 | 3 | <0.006 | 4 | 128 | 4 | >128 | | | |
| 213 | 3.6 | <0.006 | 4 | 128 | 4 | >128 | | | |
| Nar | 0.4-2.6 | 0.0002-<0.006 | 0.25-0.5 | 8 | 0.25-0.5 | >64 | 6.25 | 12.5 | 22 ± 8 |

*some reduction of growth versus control at 128 µg/mL

Validation of the Inhibitory Activity (MIC Profiling) of Anti-Tuberculosis Compounds in Clinical Isolates MIC Testing:

Clinical isolates were selected from a batch of 21 well characterized *M tuberculosis* strains (see Table 3) for MIC testing of new compounds. All these strains are susceptible to the conventional anti-tuberculosis drugs. For control purposes, the *M. tuberculosis* H37Rv strain was used and rifampin or isoniazid was included as the positive drug control. Normally all strains in Batch 1 were grown and then the ones that grew satisfactorily regarding OD, purity etc. were used.

TABLE 3

Drug Susceptible *M. tuberculosis* Isolates selected for MIC Testing

| Isolate SAWC No | Lineage | Cluster | Fam |
|---|---|---|---|
| Batch 1 | | | |
| 1125 | Typical Beijing - sublineage 6 | 205 | 29 |
| 2371 | Haarlem-like T4/Ceu1 | 778 | 6 |
| 3200 | LCC 3 bander/X | 326 | 130 |
| 3385 | Cas1 | 133 | 25 |
| 3388 | T1, T1-Tuscany, T5/Rus | 456 | 14 |
| 3906 | Atypical Beijing - sublineage 2 | 660 | 27 |

TABLE 3-continued

Drug Susceptible *M. tuberculosis* Isolates selected for MIC Testing

| Isolate SAWC No | Lineage | Cluster | Fam |
|---|---|---|---|
| 3933 | LCC 1 bander/T1 | 324 | 110 |
| 4046 | Haarlem-like T4/Ceu1 | 505 | 6 |
| Control | *M tuberculosis* H37RV (ATCC 27294) | | |

A pure culture of a single *M. tuberculosis* colony in 7H9 media was grown to $OD_{600nm}$ of ~0.5 equivalent to $10^8$ colony forming units/ml. 1 ml aliquots were frozen at −0° C. and one sample was used each time to start a 10 ml culture for MIC testing. The culture was grown for 3 days to $OD_{600nm}$ of ~0.3 and diluted 1:500 for the MIC assay The tested compounds were dissolved in sterile DMSO to a 20× stock (12.8 mM) amd left at room temperature for about 30 min (sometimes longer with intermittent vortexing to ensure that the compound is dissolved completely). The 12.8 mM stock was diluted in 7H9 to make a 640 µM working stock for the MIC assay In a 96 well round-bottom plate using a multichannel pipette, 100 µl of the 640 µM working stock of tested compound was added with serial dilutions in 50 µl of 7H9 media along with the appropriate controls. 50 µl of the 1:500 diluted Mtb culture was added to the wells bringing the microbial concentration to approximately $10^5$ colony forming units/ml and the drug concentration to half. The plates were placed into the original plastic bag or a Ziplock bag (purchased from Sigma). The plates were incubated in a $CO_2$ incubator and read by eye after 7 days and again after 14 days by simply looking at the plate and scoring the pellets as either growth (+++), no growth (−) or partial growth (+/−) if <50%, on the record sheet. An inverted plate reader which is basically an enlarging mirror that is placed below the plate to look at the cell pellets can also be used.

The last row in the dilution series that does not demonstrate growth represents the Minimum Inhibitory Concentration ($MIC_{99}$) of the compound.

Representative compounds of the present invention display antimycobacterial activity. For example, compounds of EXAMPLES 90, 94, 100, 108, 109, 118, and 204 were determined to have MICs equal to or better than nargenicin.

TABLE 4

Activity of Nargenicin Compounds Against MTB Panel

| EX | H37Rv Control MIC | SAWC 1125 Typical Beijing - sub 6 MIC | SAWC 3385 Cas1 MIC | SAWC 2371 Haarlem-like T4/Ceu1 MIC | SAWC 3200 LCC 3 bander/X MIC | SAWC 3388 T1, T1-Tuscany, T5/Rus MIC | SAWC 3933 LCC 1 bander/T1 MIC | SAWC 4046 Haarlem-like T4/Ceu1 MIC | SAWC 3906 Atypical Beijing - sub 2 MIC |
|---|---|---|---|---|---|---|---|---|---|
| Nar | 1.56 | 3.125 | 3.125 | 3.125 | 1.56/3.125 | 3.125 | 12.5 | 1.56/3.125 | 3.125 |
| 90 | 0.39/0.78 | 0.78 | 3.125 | 0.78 | 0.39/0.78 | 0.78 | 3.125 | 0.78/1.56 | 0.78 |
| 94 | 0.39/0.78 | 0.78 | 0.78/1.56 | 0.78 | 0.39/0.78 | 0.78 | 1.56/3.125 | 0.78 | 0.39 |
| 100 | 1.56 | 3.125 | 1.56/3.125 | 1.56 | 1.56 | 1.56 | 3.125/6.25 | 1.56 | 0.39 |
| 108 | 0.78 | 0.78 | 1.56 | 0.78/1.56 | 1.56 | 1.56 | 0.78/3.125 | 0.78/1.56 | 0.39 |
| 109 | 0.19 | 0.39 | 0.39 | 0.39 | 0.78/1.56 | 0.39/0.78 | 0.156 | 0.39/0.78 | 0.19 |
| 118 | 1.56 | 3.125 | 3.125/6.25 | 3.125 | 3.125 | 3.125 | 12.5 | 1.56/3.125 | 1.56 |
| 204 | 1.56 | 3.125 | 3.125/6.25 | 1.56 | 1.56/3.125 | 3.125 | 12.5 | 1.56/3.125 | 1.56 |

What is claimed is:

1. A compound of formula I

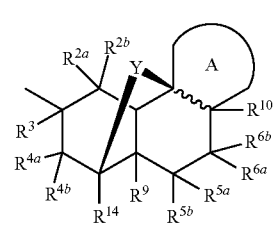

(I)

or a pharmaceutically acceptable salt thereof, wherein

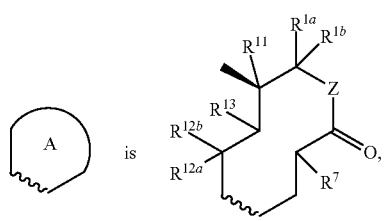

Y is O, —$NR^B$, S or —$SO_2$;
Z is O or —$NR^O$;
$R^O$ is H, $C_{1-6}$alkyl, $C_{3-6}$cycloalkyl, AryA, or HetA;

$R^{1a}$ is H; $C_{1-6}$alkyl, $C_{2-6}$alkenyl, $C_{3-6}$cycloalkyl, —C(=O)$C_{1-6}$alkyl, AryA, or HetA;
  wherein the alkyl is optionally substituted with halogen, —NR$^B$R$^C$,=NOH, —OR$^A$, -isoindoline-1,3-dione or -1H-indene-1,3(2H)-dione;
$R^{1b}$ is H, $C_{1-6}$alkyl, or $C_{2-6}$alkenyl;
$R^A$ is H, $C_{1-6}$alkyl, $C_{2-6}$alkenyl, $C_{3-6}$cycloalkyl, —C(=O)$C_{1-6}$alkyl, —C(=O)$C_{2-6}$alkenyl, —C(=O)NHR$^g$, —C(=O)OR$^g$, —C(=O)C(=O)NHR$^g$, —C(=O)C(=O)OR$^g$, AryA, HetA, —C(=O)-AryA, —C(=O)-HetA, —C(=O)C(=O)-HetA, —SO$_2$OH, or tert-butyl dimethylsilyl (TBDMS);
wherein
  any alkyl is optionally substituted with 1 or 2 substituents independently selected from halogen, —NR$^x$R$^y$, —N$^+$R$^x$R$^y$R$^z$, —SCH$_3$, AryA, and HetA; and
  any alkenyl is optionally substituted with AryA;
$R^g$ is H, $C_{1-8}$alkyl, $C_{3-6}$cycloalkyl, —C(=O)CCl$_3$, —NR$^x$R$^y$, —NHC(=O)NR$^x$R$^y$, —NHC(=O)OCH$_3$, AryA or —CH(CH$_2$-AryA)C(=O)NHCH(CH$_2$CH$_2$CH$_2$NHC(=NH)NH$_2$)C(=O)NH-AryA,
  wherein the alkyl or cycloalkyl is optionally substituted by 1 to 3 —NR$^x$R$^y$, —N$^+$R$^x$R$^y$R$^z$, —N$^+$R$^x$R$^v$R$^w$ or —OH substituents or 1 substituent selected from $C_{1-6}$alkoxy, —COOH, —C(=O)NR$^x$R$^y$, —NR$^v$R$^w$, —S(O)$_2$NR$^x$R$^y$, AryA, and HetA;
$R^x$, $R^y$ and $R^z$ are independently H or $C_{1-6}$alkyl,
$R^v$ and $R^w$ are $C_{1-6}$alkyl substituted with 1 to 3 —OH substituents;
$R^B$ is H, $C_{1-6}$alkyl, $C_{2-6}$alkenyl, —(CH$_2$)$_{0-3}$C$_{3-6}$cycloalkyl, —C(=O)R$^b$, —C(=O)NHR$^b$, —C(=O)OR$^b$,
$C_{1-6}$alkoxy, —S(=O)$_2$R$^b$, —(CH$_2$)$_{0-3}$AryA, or —(CH$_2$)$_{0-3}$HetA;
  wherein the alkyl is optionally substituted with —NR$^x$R$^y$ or —OH;
$R^C$ is H, $C_{1-6}$alkyl, or $C_{3-6}$cycloalkyl;
$R^b$ is $C_{1-6}$alkyl, $C_{3-6}$cycloalkyl, AryA, or HetA;
$R^{2a}$ is halogen, —NR$^B$R$^C$, or —OR$^{2'}$;
$R^{2b}$ is H; or
$R^{2a}$ and $R^{2b}$ together form =O, or a 3- to 6-membered ring with 0, 1, or 2 heteroatom ring atoms selected from N, O and S;
$R^{2'}$ is H, —C(=O)CH$_3$, —C(=O)NR$^x$R$^y$, —C(=O)NHCH$_2$CH$_2$N(CH$_3$)$_2$, —C(=O)NHC(=O)CCl$_3$, —C(=O)NH—$C_{3-6}$cycloalkyl, —C(=O)C(=O)OCH$_2$CH$_2$-HetA, or —C(=O)NHS(O)$_2$-AryA;
$R^3$ is H;
$R^{4a}$ is H, $C_{1-6}$hydroxyalkyl, $C_{2-6}$alkenyl, —CH$_2$NO$_2$, cyano, —NR$^x$R$^y$, —NR$^x$(CH$_2$)$_{1-3}$AryA, —NR$^x$(CH$_2$)$_{1-3}$HetA, —NR$^x$(CH$_2$)$_{1-3}$NR$^x$R$^y$, —NR$^x$(CH$_2$)$_{1-3}$NR$^y$HetA, —NHC$_{1-6}$alkyl, —NH-AryA, —NH-HetA, —NHC$_{1-6}$ alkyl-R$^z$, —NHC(=O)$C_{1-6}$alkyl, —OH, —O—$C_{1-6}$ alkyl, —O-AryA, —O-HetA, —OCH$_2$-HetA, —OCH$_2$-AryA, —OC(=O)CH$_3$, —OC(=O)NH$_2$, —OC(=O)-AryA, —SO$_2$OH, AryA, or HetA;
$R^{4b}$ is H; or
$R^3$ and $R^{4a}$ together form a bond; or
$R^{4a}$ and $R^{4b}$ together form =O;
$R^z$ is —NR$^x$R$^y$, disulfanylC$_{1-6}$alkylamine, AryA, or HetA; or
$R^{5a}$ is H, $C_{1-6}$alkyl, —OH, or AryA;
$R^{5b}$ is H; or
$R^{5a}$ and $R^{5b}$ together form =O or =C;
$R^{6a}$ is H, $C_{1-6}$alkyl, —OH, or AryA;
$R^{6b}$ is H; or $R^{6a}$ and $R^{6b}$ together form =O or =C; or
$R^{5a}$ and $R^{6a}$ together form a bond or together with the atoms to which they are attached form an oxirane; a cyclopropyl ring optionally substituted with one or two substituents independently selected from F, Cl, and —C(=O)OC$_{1-6}$alkyl; a cyclopentyl ring optionally substituted with —OR$^D$; an oxetanyl ring; a pyrrolidinyl ring, wherein the pyrrolidinyl ring is substituted with R$^B$; or an isoxazolidinyl ring, wherein the isoxazolidinyl ring is substituted with R$^b$;
$R^D$ is H, $C_{1-6}$alkyl, —C(=O)R$^b$, or —C(=O)NHR$^b$;
$R^7$ is —OR$^8$ or —NR$^B$R$^C$;
$R^8$ is H or $C_{1-6}$alkyl;
$R^9$, $R^{10}$ and $R^{11}$ are independently H, —CH$_3$, or —OH;
$R^{12a}$ is CH$_3$ or CH$_2$OH;
$R^{12b}$ and $R^{13}$ are H, or together form a bond, or together with the atoms to which they are connected form a cyclopropyl ring;
$R^{14}$ is H or $C_{1-6}$alkyl;
AryA is
1) a 4- to 6-membered monocyclic aromatic ring with 0, 1, 2, 3 or 4 ring atoms independently selected from N, N as a quaternary salt, O and S, optionally substituted with 1 to 3 substituents independently selected from halogen, $C_1$-$C_6$ alkyl, $C_1$-$C_6$haloalkyl, $C_1$-$C_6$ hydroxyalkyl, $C_1$-$C_6$ aminoalkyl, $C_1$-$C_6$ alkoxy, cyano, —(CH$_2$)$_{0-3}$NR$^x$R$^y$, —(CH$_2$)$_{0-3}$N$^+$R$^x$R$^y$R$^z$, —OH, —CH=CHC(=O)OC$_{1-6}$alkyl, —C(=O)R$^b$, —(CH$_2$)$_{0-1}$C(=O)NH$_2$, C(=O)NHR$^b$, —C(=O)OH, —C(=O)OR$^b$, —NHC(=O)$C_{1-6}$alkyl, —NHC(=O)AryB, —NO$_2$, —OC(=O)$C_{1-6}$alkyl,=O, —S(=O)$_2$R$^b$, —(CH$_2$)$_{0-3}$AryB, and (CH$_2$)$_{0-3}$HetB; or
2) a 7- to 11-membered bicyclic aromatic ring with 0, 1, 2 or 3 N, or N as a quaternary salt, ring atoms optionally substituted with 1 to 3 substituents independently selected from halogen, $C_1$-$C_6$ alkyl, $C_1$-$C_6$haloalkyl, $C_1$-$C_6$ hydroxyalkyl,
$C_1$-$C_6$ aminoalkyl, $C_1$-$C_6$ alkoxy, cyano, —(CH$_2$)$_{0-3}$NR$^x$R$^y$, —(CH$_2$)$_{0-3}$N$^+$R$^x$R$^y$R$^z$, —OH, CH=CHC(=O)OC$_{1-6}$alkyl, —C(=O)R$^b$, —(CH$_2$)$_{0-1}$C(=O)NH$_2$, —C(=O)NHR$^b$, —C(=O)OH, C(=O)OR$^b$, —NHC(=O)$C_{1-6}$alkyl, —NHC(=O)-AryB, —NO$_2$, —OC(=O)$C_{1-6}$alkyl, =O, —S(=O)$_2$R$^b$, —(CH$_2$)$_{0-3}$AryB, and —(CH$_2$)$_{0-3}$HetB;
HetA is
1) a 4- to 6-membered saturated or monounsaturated monocyclic ring with 1 or 2 heteroatom ring atoms independently selected from N, N as a quaternary salt, O and S, optionally substituted with 1 or 2 substituents independently selected from halogen, $C_1$-$C_6$ alkyl, $C_1$-$C_6$ hydroxyalkyl, $C_1$-$C_6$ aminoalkyl, $C_1$-$C_6$ alkoxy, cyano, —(CH$_2$)$_{0-3}$NR$^x$R$^y$, —(CH$_2$)$_{0-3}$N$^+$R$^x$R$^y$R$^z$, —OH, —(CH$_2$)$_{0-1}$C(=O)NH$_2$, —(CH$_2$)$_{0-1}$C(=O)NHR$^b$, —(CH$_2$)$_{0-1}$C(=O)NH(CH$_2$)$_2$NHC(=O)OCH$_2$-AryB, —(CH$_2$)$_3$N$_3$, —C(=O)R$^b$, —C(=O)OR$^b$, —S(=O)$_2$R$^b$, —(CH$_2$)$_{0-3}$AryB, and —(CH$_2$)$_{0-3}$HetB; or
2) a 7- to 11-membered saturated or monounsaturated bicyclic ring with 1, 2, or 3 heteroatom ring atoms independently selected from N, N as a quaternary salt, O and S, optionally substituted with 1 or 2 substituents independently selected from halogen, $C_1$-$C_6$ alkyl, $C_1$-$C_6$ hydroxyalkyl, $C_1$-$C_6$ aminoalkyl, $C_1$-$C_6$ alkoxy, cyano, —(CH$_2$)$_{0-3}$NR$^x$R$^y$, —(CH$_2$)$_{0-3}$N$^+$R$^x$R$^y$R$^z$, —OH, —(CH$_2$)$_{0-1}$C(=O)NH$_2$, —(CH$_2$)$_{0-1}$C(=O)NHR$^b$, —(CH$_2$)$_{0-1}$C(=O)NH (CH$_2$)$_2$NHC(=O)OCH$_2$-AryB, —(CH$_2$)$_3$N$_3$, —C(=O)R$^b$, —C(=O)OR$^b$, —S(=O)$_2$R$^b$, —(CH$_2$)$_{0-3}$AryB, and —(CH$_2$)$_{0-3}$HetB;

AryB is
1) a 4- to 6-membered monocyclic aromatic ring with 0, 1, 2, or 3 ring atoms independently selected from N, N as a quaternary salt, O and S, optionally substituted with 1 to 3 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, cyano, —NH$_2$, —OH, —(CH$_2$)$_{0-3}$C(=O)NR$^x$R$^y$, —(CH$_2$)$_{1-3}$SO$_2$NR$^x$R$^y$, —CH=CHC(=O)OC$_{1-6}$alkyl, —NHC(=O)C$_{1-6}$alkyl, —NO$_2$, —N$^+$(O)OH, —OC(=O)C$_{1-6}$alkyl, or —C(=O)OC$_{1-6}$alkyl; or
2) a 7- to 11-membered bicyclic aromatic ring with 1, 2 or 3 N, or N as a quaternary salt, ring atoms optionally substituted with 1 to 3 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, cyano, —NH$_2$, —OH, —(CH$_2$)$_{0-3}$C(=O)NR$^x$R$^y$, —(CH$_2$)$_{1-3}$ SO$_2$NR$^x$R$^y$, —CH=CHC(=O)OC$_{1-6}$alkyl, —NHC(=O)C$_{1-6}$alkyl, —NO$_2$, —OC(=O)C$_{1-6}$alkyl, and —C(=O)OC$_{1-6}$alkyl;

HetB is
1) a 4- to 6-membered saturated or monounsaturated monocyclic ring with 1 or 2 heteroatom ring atoms independently selected from N, N as a quaternary salt, O and S, optionally substituted with 1 or 2 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, —(CH$_2$)$_{0-3}$C(=O)NR$^x$R$^y$, cyano, —NH$_2$, —OH, and —(CH$_2$)$_{0-3}$HetC; or
2) a 7- to 11-membered saturated or monounsaturated bicyclic ring with 1, 2, or 3 heteroatom ring atoms independently selected from N, N as a quaternary salt, O and S, optionally substituted with 1 or 2 substituents independently selected from halogen, C$_1$-C$_6$ alkyl, C$_1$-C$_6$ hydroxyalkyl, C$_1$-C$_6$ aminoalkyl, C$_1$-C$_6$ alkoxy, —(CH$_2$)$_{0-3}$C(=O)NR$^x$R$^y$, cyano, —NH$_2$, —OH, and —(CH$_2$)$_{0-3}$HetC; and HetC is
1) a 4- to 6-membered saturated or monounsaturated monocyclic ring with 1 or 2 heteroatom ring atoms independently selected from N, N as a quaternary salt, O and S; or
2) a 7- to 11-membered saturated or monounsaturated bicyclic ring with 1, 2, or 3 heteroatom ring atoms independently selected from N, N as a quaternary salt, O and S;

with the proviso
that the compound is not nodusmicin, and
that when

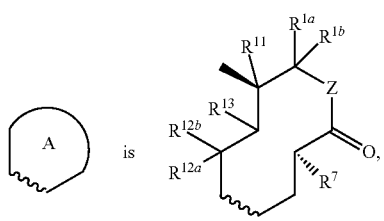

Y and Z are O;
R$^{1b}$, R$^{2b}$, R$^9$, R$^{10}$, R$^{11}$ and R$^{14}$ are H;

R$^{2a}$ is —OH;
R$^{4a}$ is —OC(=O)-pyrrolyl;
R$^{5a}$ and R$^{6a}$ together form a bond;
R$^{12b}$ and R$^{13}$ together form a bond;
R$^7$ is —OH or —OCH$_3$;
R$^{12a}$ is —CH$_3$;

then R$^{1a}$ is not ethyl optionally substituted with: —OH; C$_{1-6}$alkoxy; hydroxyl and methoxy; amine or amine substituted with C$_{1-3}$ alkyl; or =NOH.

2. The compound of claim 1, or a pharmaceutically acceptable salt thereof, wherein Y is O.

3. The compound of claim 1, which has the formula

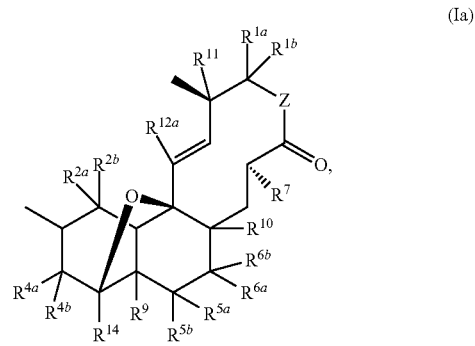

(Ia)

or a pharmaceutically acceptable salt thereof, wherein Z is O is —NH.

4. The compound of claim 1, or a pharmaceutically acceptable salt thereof, wherein R$^{1a}$ is H, C$_{1-6}$alkyl, C$_{2-6}$alkenyl, —CH(CH$_3$)NH-cyclopropyl, —CH(CH$_3$)=NOH, —CH(CH$_3$)OR$^A$, —CH(CH$_3$)-1H-indene-1,3(2H)-dione, —CH(CH$_3$)-isoindoline-1,3-dione, —C(=O)C$_{1-6}$alkyl, or AryA;

R$^{1b}$ is H;

R$^A$ is H, C$_{1-6}$alkyl, —C(=O)C$_{1-6}$alkyl, C(=O)NHR$^g$, —C(=O)OR$^g$, —C(=O)C(=O)NHR$^g$, —C(=O)C(=O)OR$^g$, —C(=O)-AryA, —C(=O)-HetA, —C(=O)C(=O)-HetA, —SO$_2$OH, or tert-butyl dimethylsilyl;

wherein the alkyl is optionally substituted with one or two substituents independently selected from halogen, —SCH$_3$, AryA, and HetA; and R$^g$ is H, C$_{1-8}$alkyl, C$_{3-6}$cycloalkyl, —C(=O)CCl$_3$, —NR$^x$R$^y$, —NHC(=O)NR$^x$R$^y$, —NHC(=O)OCH$_3$; and AryA or —CH(CH$_2$-AryA)C(=O)NHCH(CH$_2$CH$_2$CH$_2$NHC(=NH)NH$_2$)C(=O)NH-AryA, wherein the alkyl is optionally substituted by 1 to 3 —NR$^x$R$^y$ or —OH substituents or 1 substituent selected from C$_{1-6}$alkoxy, —COOH, —C(=O)NR$^x$R$^y$, AryA, and HetA.

5. The compound of claim 4, which has the formula

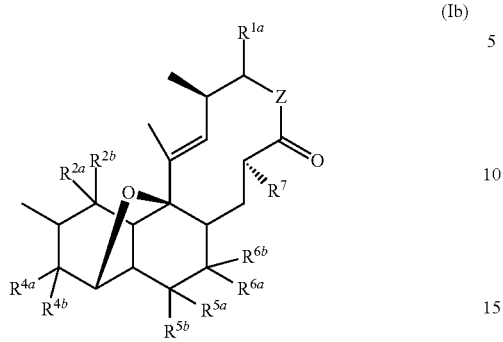

(Ib)

or a pharmaceutically acceptable salt thereof, wherein
$R^{2a}$ is halogen or —$OR^{2'}$;
$R^{2b}$ is H; or
$R^{2a}$ and $R^{2b}$ together form =O;
$R^{2'}$ is H, —C(=O)CH$_3$, —C(=O)NR$^x$R$^y$, —C(=O)NHCH$_2$CH$_2$N(CH$_3$)$_2$, —C(=O)NHC(=O)CCl$_3$, —C(=O)NHC$_{3-6}$cycloalkyl, —C(=O)C(=O)OCH$_2$CH$_2$-HetA, or —C(=O)NHS(O)$_2$-AryA;
$R^{5a}$ is H or —OH;
$R^{5b}$ is H; or
$R^{5a}$ and $R^{5b}$ together form =O or =C;
$R^{6a}$ is H or —OH;
$R^{6b}$ is H; or
$R^{6a}$ and $R^{6b}$ together form =O or =C; or
$R^{5a}$ and $R^{6a}$ together form a bond or together with the atoms to which they are attached form an oxirane;
$R^7$ is —$OR^8$;
$R^8$ is H or C$_{1-6}$alkyl;
AryA is
1) a 5- to 6-membered monocyclic aromatic ring with 0, 1, or 2 ring atoms independently selected from N, N as a quaternary salt, O and S, or 4 N ring atoms, optionally substituted with 1 to 3 substituents independently selected from halogen, C$_1$-C$_6$ alkyl, C$_1$-C$_6$haloalkyl, cyano, —(CH$_2$)$_{0-1}$NR$^x$R$^y$, —OH, —CH=CHC(=O)OC$_{1-6}$alkyl, —C(=O)C$_{1-6}$alkyl, —C(=O)NH$_2$, —C(=O)OH, —NHC(=O)C$_{1-6}$alkyl, —NHC(=O)-AryB, —OC(=O)C$_{1-6}$alkyl, =O, —(CH$_2$)$_{0-1}$AryB, and —CH$_2$HetB; or
2) a 10-membered bicyclic aromatic ring with 0 N ring atoms;
HetA is
1) a 5- to 6-membered saturated or monounsaturated monocyclic ring with 1 or 2 heteroatom ring atoms independently selected from N, N as a quaternary salt, and O, optionally substituted with 1 substituent selected from C$_1$-C$_6$ alkyl, —OH, and =O; or
2) a 8-membered saturated bicyclic ring with 2 N, or N as a quaternary salt, ring atoms, optionally substituted with 1 substituent selected from C$_1$-C$_6$ alkyl, —CH$_2$C(=O)NH$_2$, —(CH$_2$)C(=O)NH(CH$_2$)$_2$NHC(=O)OCH$_2$-AryB, —(CH$_2$)$_3$N$_3$, and —(CH$_2$)$_3$HetB;
AryB is
a 5- to 6-membered monocyclic aromatic ring with 0 or 1 ring atoms selected from N, N as a quaternary salt, and S, optionally substituted with 1 substituent selected from C$_1$-C$_6$ alkyl, —C(=O)NH$_2$,—NO$_2$, —N$^+$(O)OH, —OC(=O)C$_{1-6}$alkyl, and —C(=O)OC$_{1-6}$alkyl;

HetB is
a 8-membered saturated bicyclic ring with 2 N, or N as quaternary salt, ring atoms, optionally substituted with 1 substituent selected from C$_1$-C$_6$ alkyl, —CH$_2$C(=O)NH$_2$, and —(CH$_2$)$_3$HetC; and
HetC is
a 8-membered saturated bicyclic ring with 2 N, or N as quaternary salt, ring atoms.

6. The compound of claim 5, wherein
AryA is
1) a monocyclic ring selected from furanyl, imidazolyl, pyrazolyl, pyrrolyl, phenyl, pyridinyl, tetrazolyl, thiazolyl, or thiophenyl, wherein any N ring atom in the monocyclic ring is optionally in the form of a quaternary salt, and wherein the monocyclic ring is optionally substituted with 1 to 3 substituents independently selected from halogen, C$_1$-C$_6$ alkyl, C$_1$-C$_6$haloalkyl, cyano, —(CH$_2$)$_{0-1}$NR$^x$R$^y$, —OH, —CH=CHC(=O)OC$_{1-6}$alkyl, —C(=O)C$_{1-6}$alkyl, —C(=O)NH$_2$, —C(=O)OH, —NHC(=O)C$_{1-6}$alkyl, —NHC(=O)-AryB, —OC(=O)C$_{1-6}$alkyl, =O, —(CH$_2$)$_{0-1}$AryB, and —CH$_2$HetB, or
2) naphthalenyl,
HetA is
1) a monocyclic ring selected from morpholinyl, piperazinyl, piperidinyl, pyrrolidinyl, wherein any N ring atom in the monocyclic ring is optionally in the form of a quaternary salt, and wherein the monocyclic ring is optionally substituted with 1 substituent selected from C$_1$-C$_6$ alkyl, —OH, and =O; or
2) 1,4-diazabicyclo[2.2.2]octane, optionally substituted with 1 substituent selected from C$_1$-C$_6$ alkyl, —CH$_2$C(=O)NH$_2$, —(CH$_2$)C(=O)NH(CH$_2$)$_2$NHC(=O)OCH$_2$-AryB, —(CH$_2$)$_3$N$_3$, and —(CH$_2$)$_3$HetB;
AryB is a monocyclic ring selected from imidazolyl, phenyl, pyridinyl, pyrrolyl, thiophenyl, wherein any N ring atom in the monocyclic ring is optionally in the form of a quaternary salt, and wherein the monocyclic ring is optionally substituted with 1 substituent selected from C$_1$-C$_6$ alkyl, C(=O)NH$_2$,—NO$_2$, —N$^+$(O)OH, or —C(=O)OC$_{1-6}$alkyl;
HetB is 1,4-diazabicyclo[2.2.2]octane, optionally substituted with 1 substituent selected from C$_1$-C$_6$ alkyl, —CH$_2$C(=O)NH$_2$, and —(CH$_2$)$_3$HetC; and
HetC is 1,4-diazabicyclo[2.2.2]octane.

7. The compound of claim 1, or a pharmaceutically acceptable salt thereof, wherein
$R^{4a}$ is H, —NH$_2$, —OH, cyano,

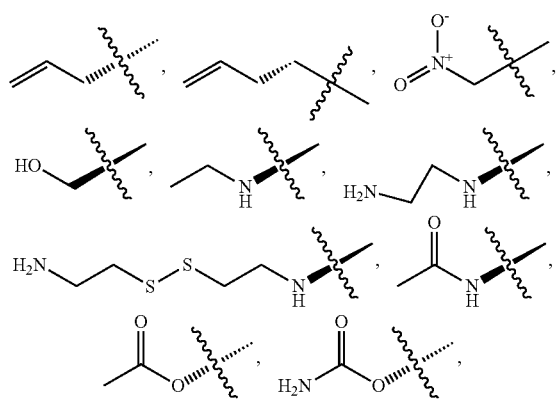

219
-continued
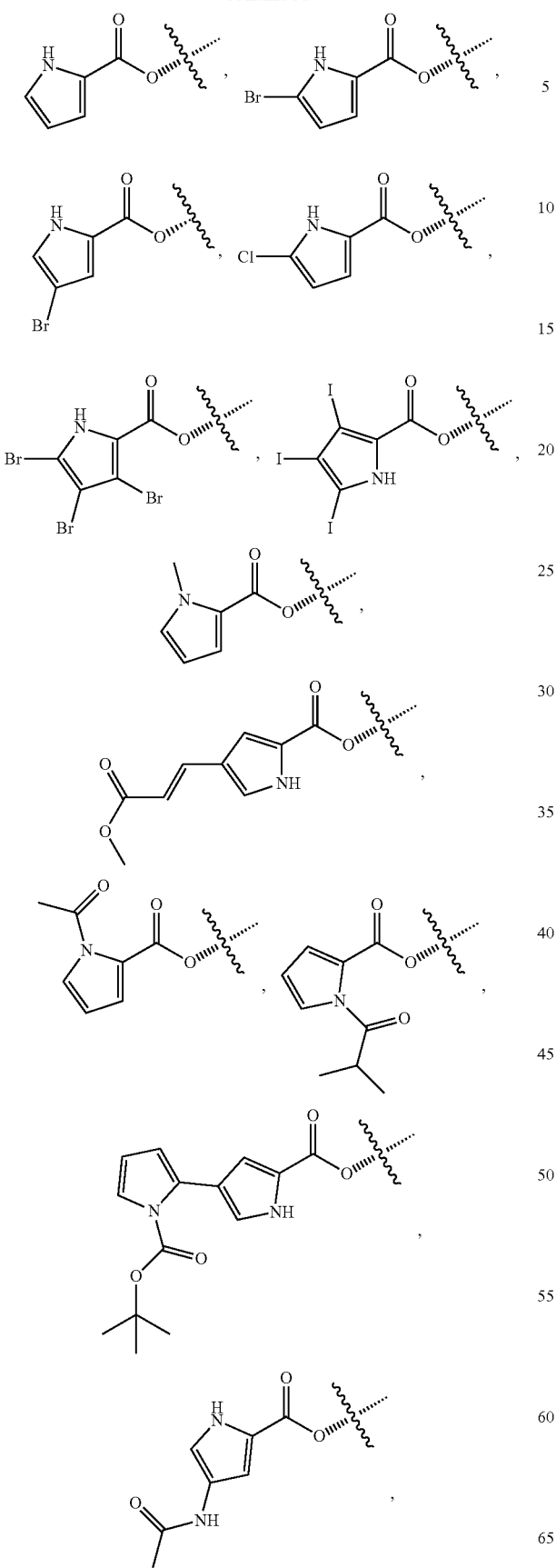
220
-continued
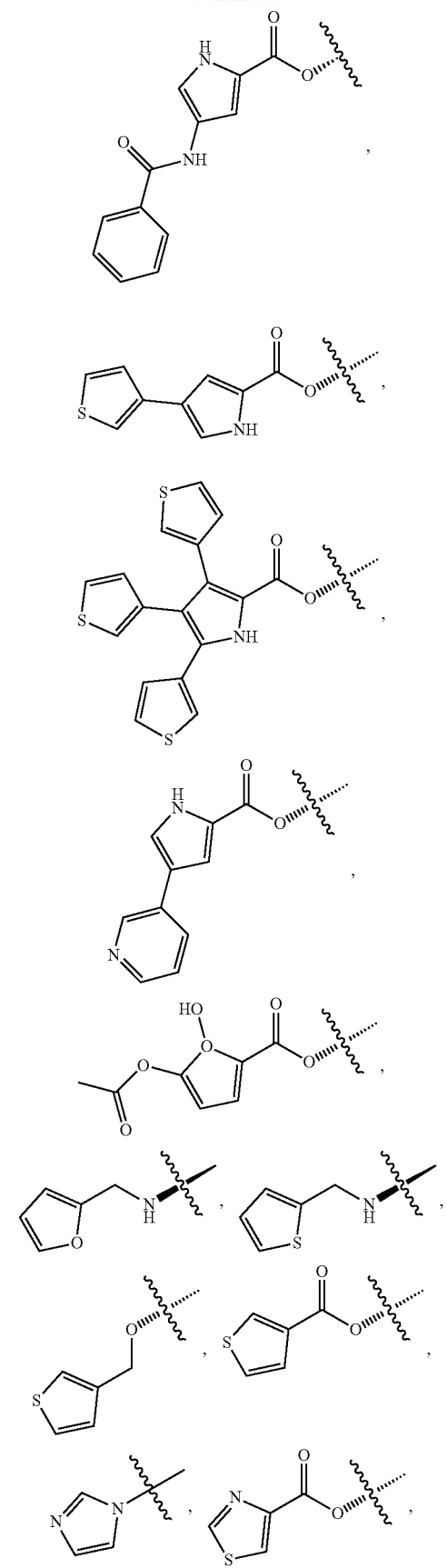

-continued
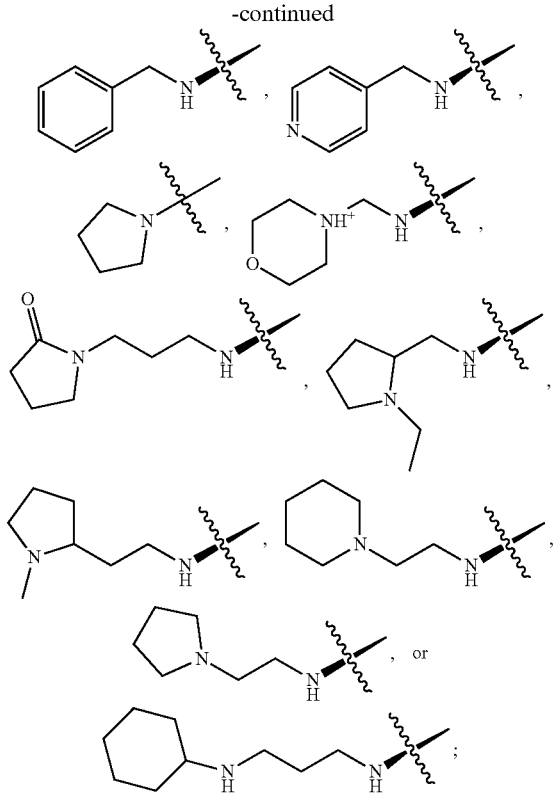
$R^{4b}$ is H; or
$R^{4a}$ and $R^{4b}$ together form =O.
8. The compound of claim 1, or a pharmaceutically acceptable salt thereof, wherein
$R^{2a}$ is —OH, F,
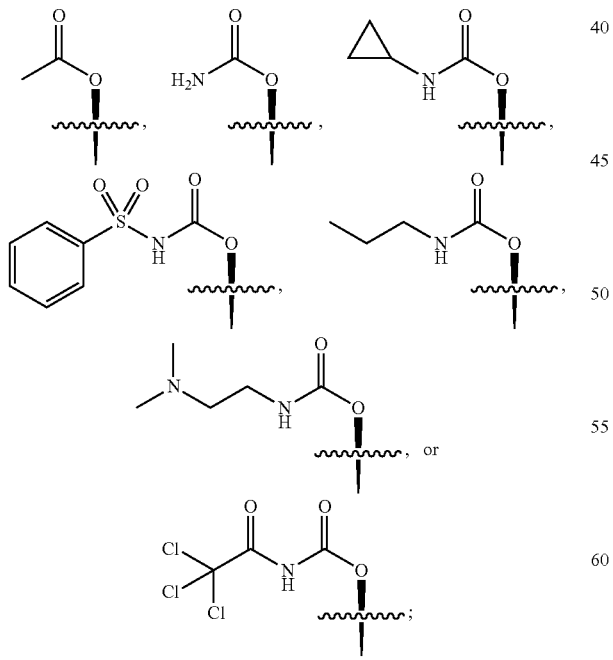
$R^{2b}$ is H; or
$R^{2a}$ and $R^{2b}$ together form =O.
9. The compound of claim 1, or a pharmaceutically acceptable salt thereof, wherein
$R^{1a}$ is H, methyl, ethyl, phenyl,
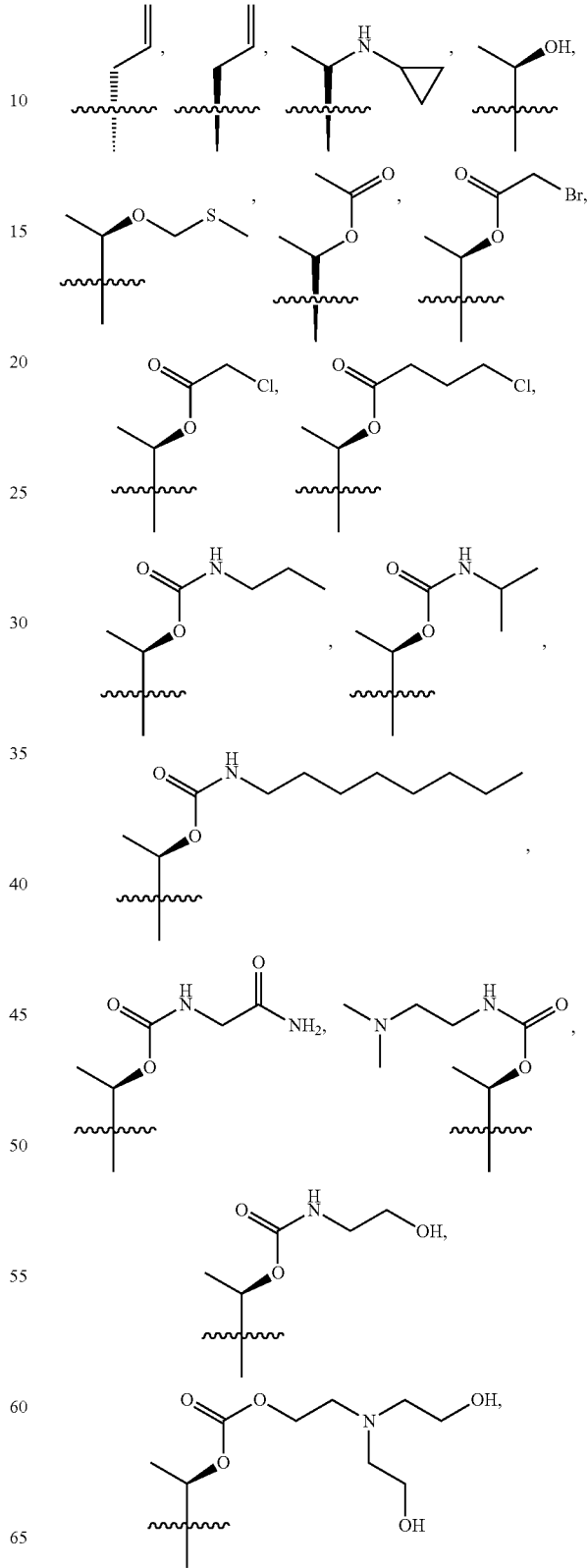

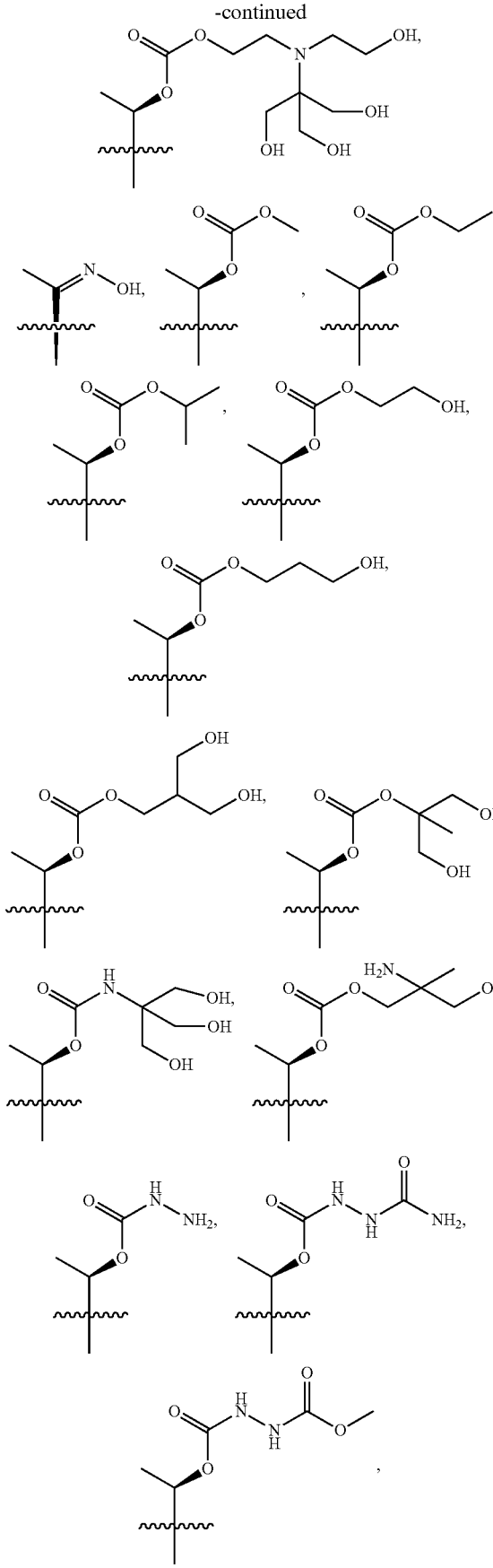

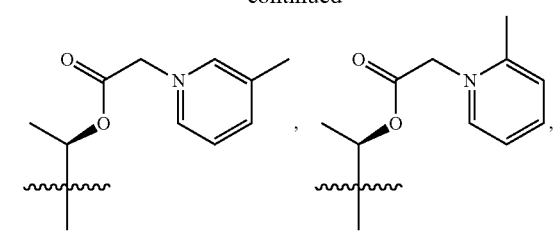
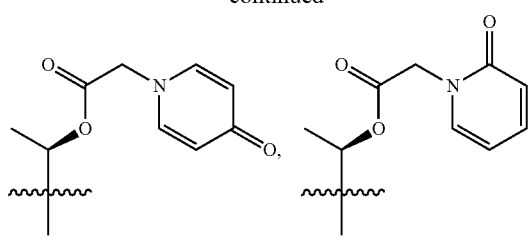
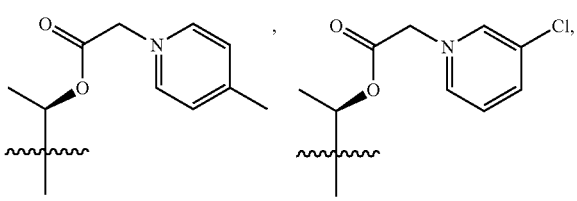
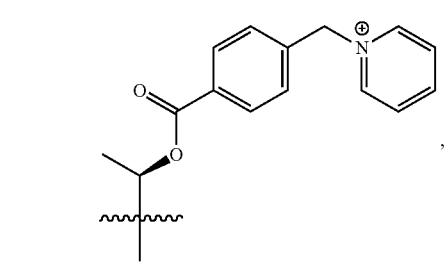
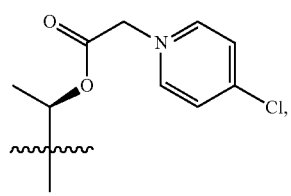
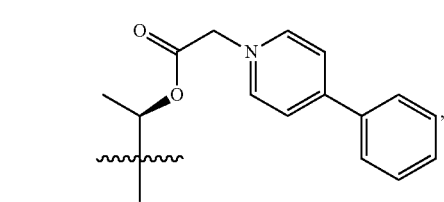
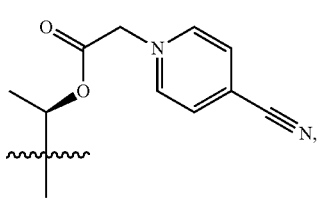
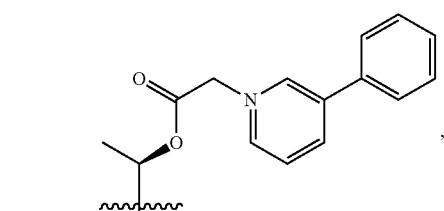
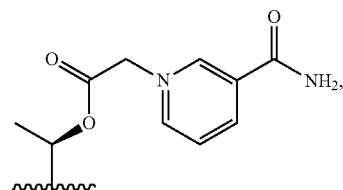
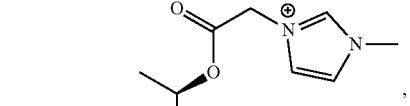
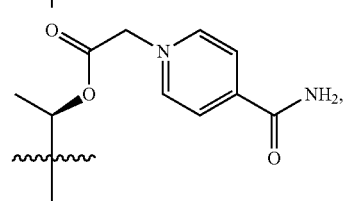
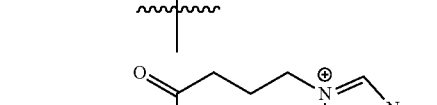
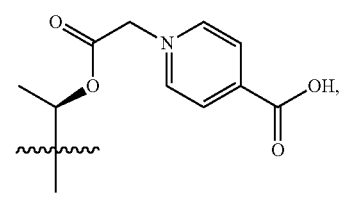
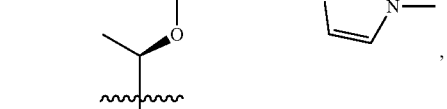
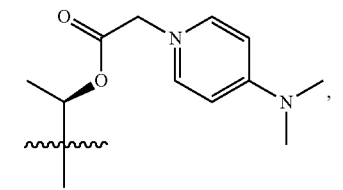
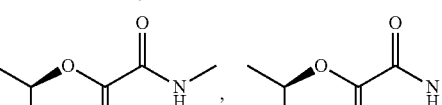
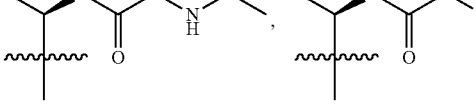

227
-continued
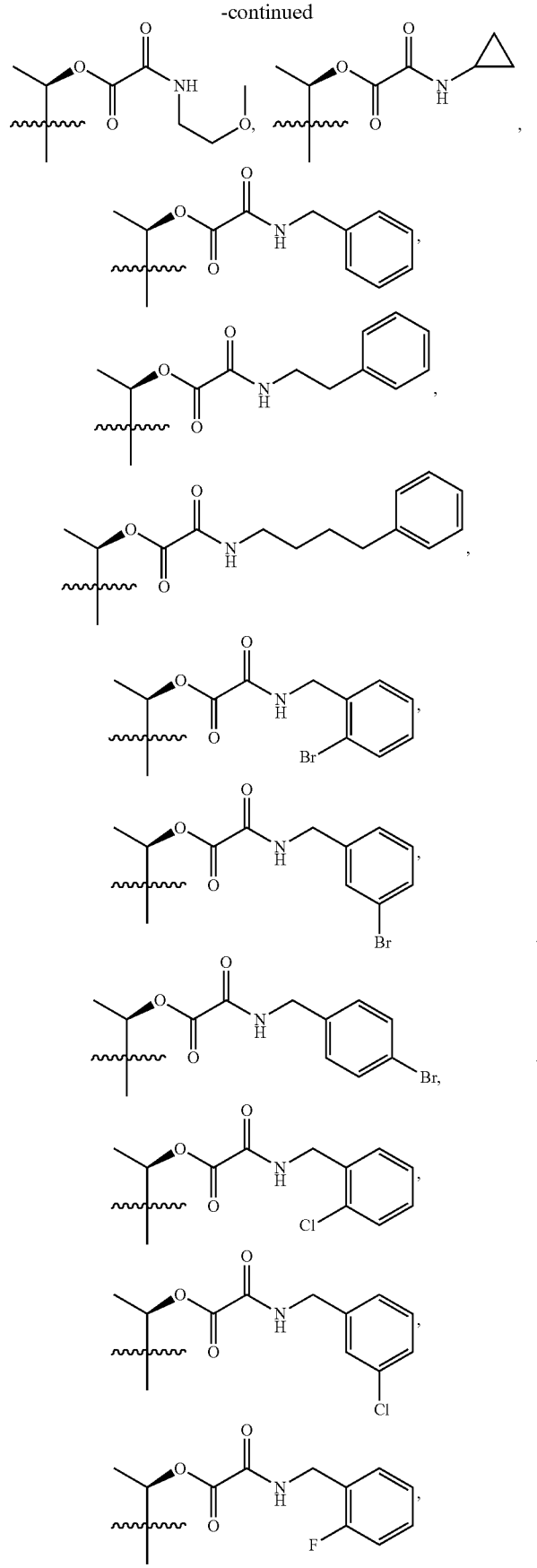
228
-continued
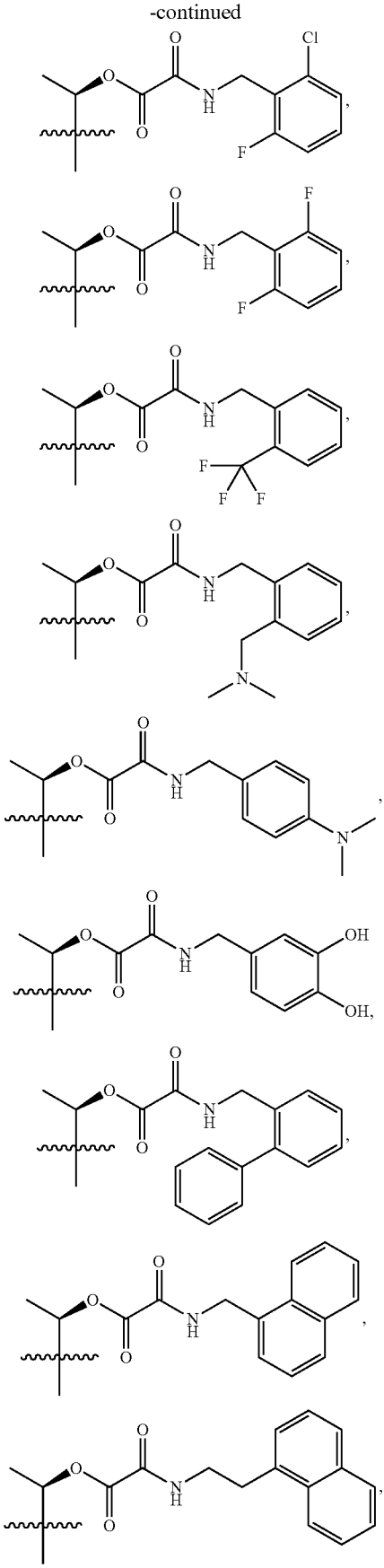

229
-continued
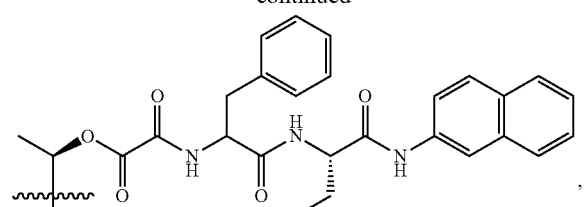
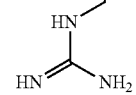,
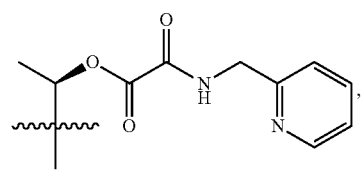,
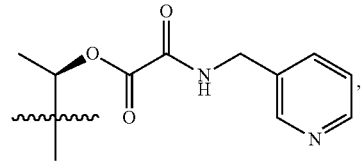,
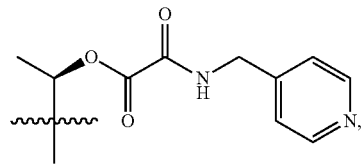,
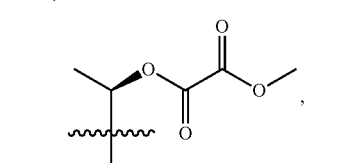,
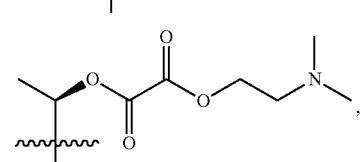,
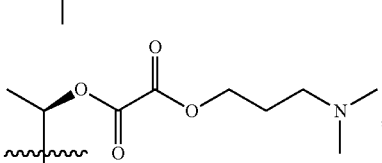,
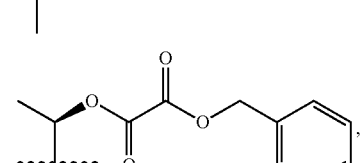,
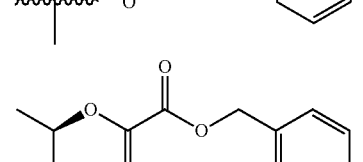,
,
230
-continued
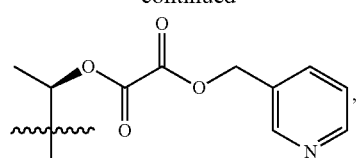,
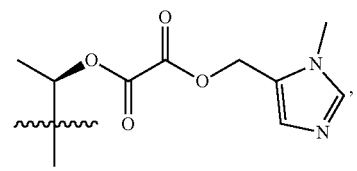,
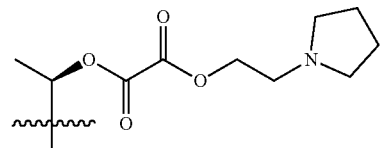,
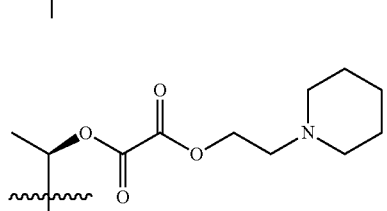,
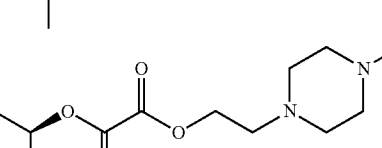,
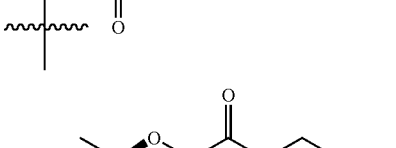,
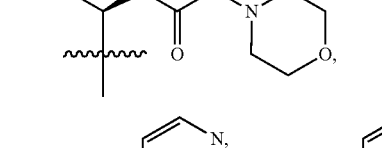,
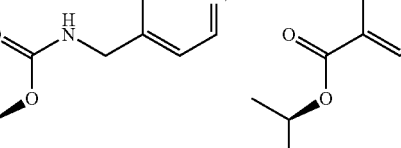,
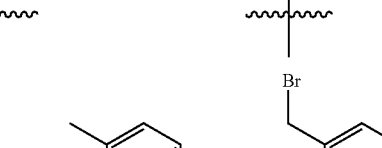,
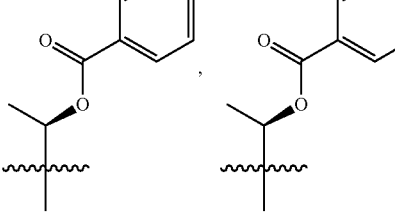,
, 231
-continued
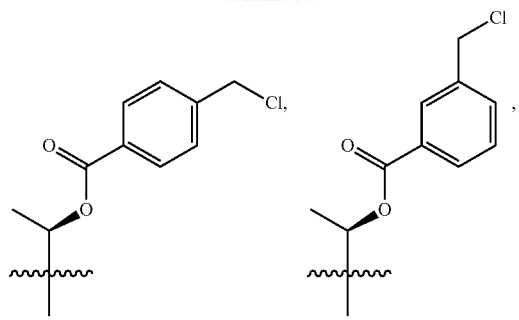
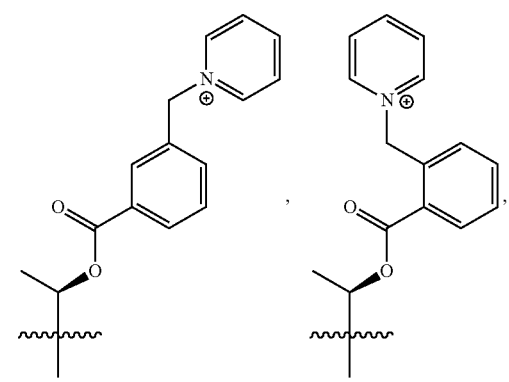
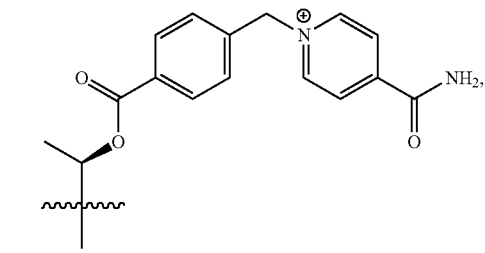
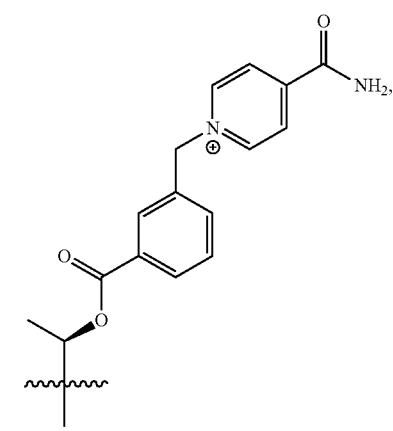
232
-continued
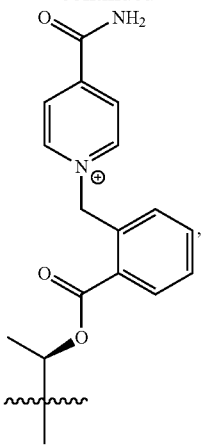
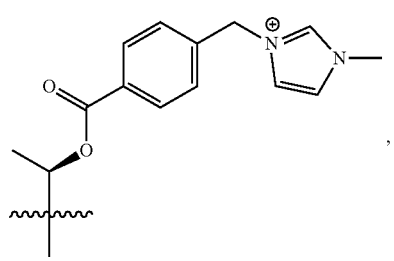
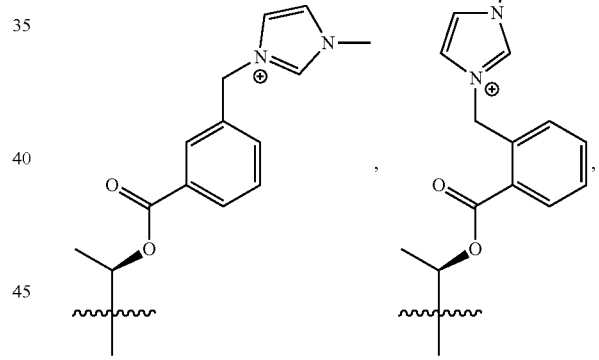
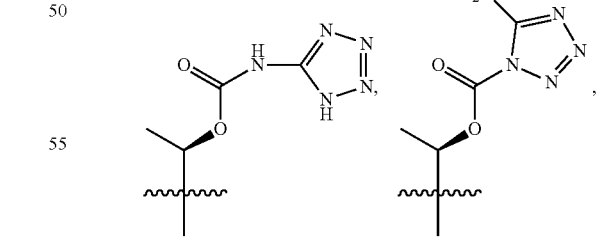
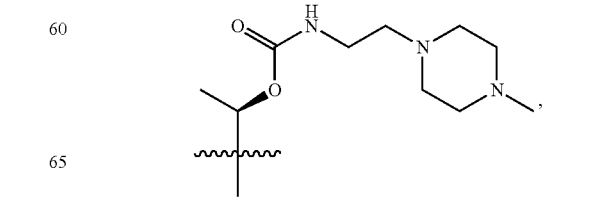

233
-continued
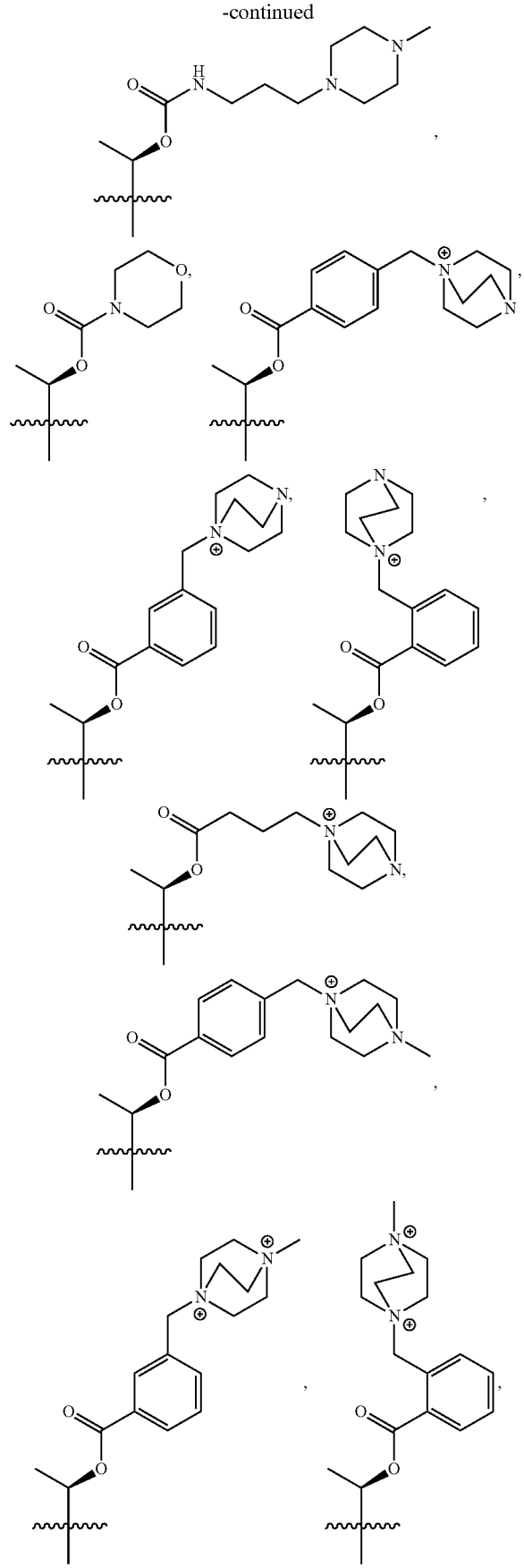
234
-continued
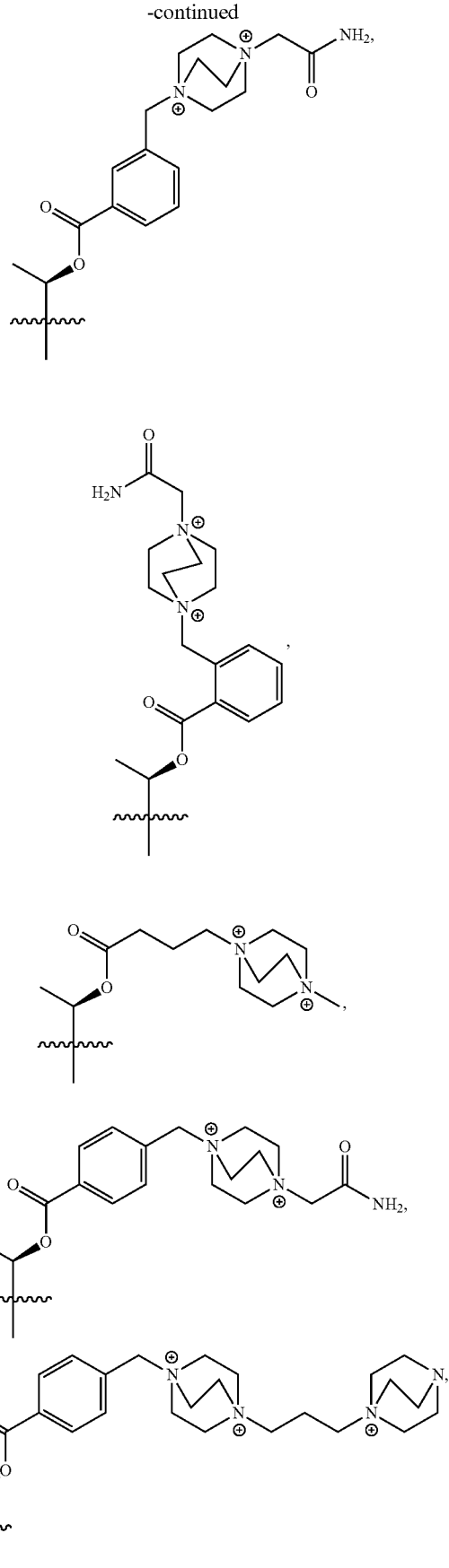

235
-continued
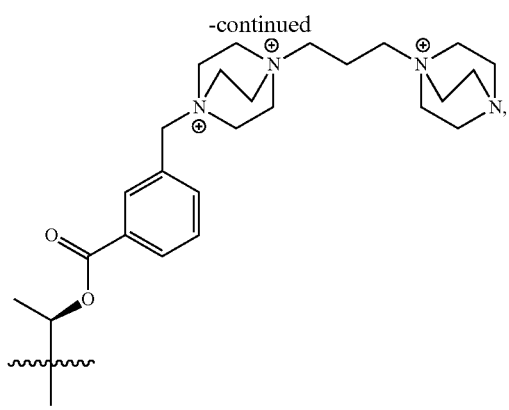
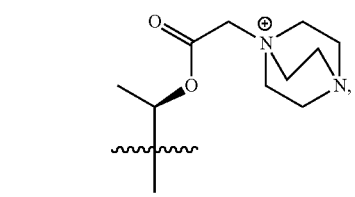
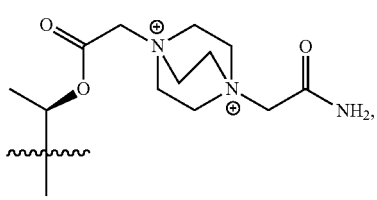
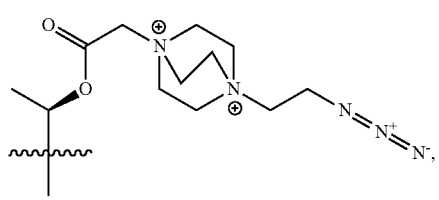
236
-continued
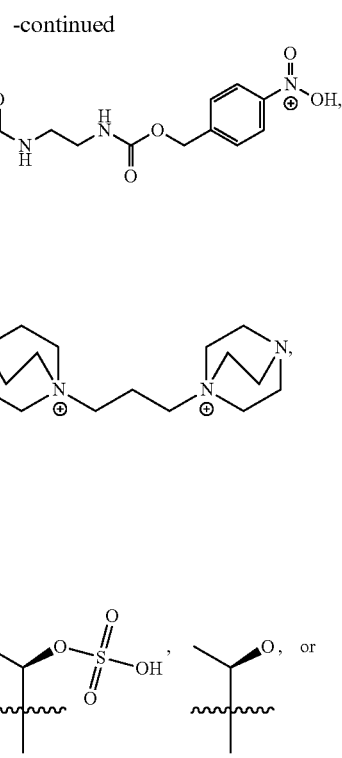
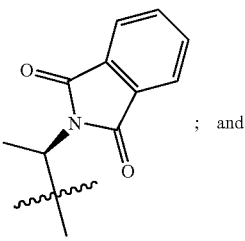 [SMILES: *[C@@H](C)N1C(=O)c2ccccc2C1=O]
; and
$R^{1b}$ is H.
10. The compound of claim 1, which is
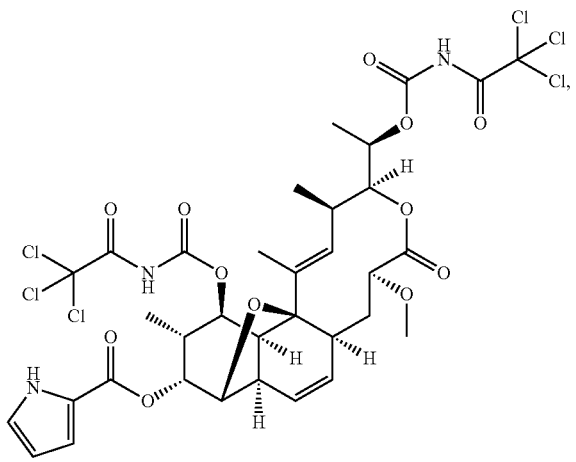
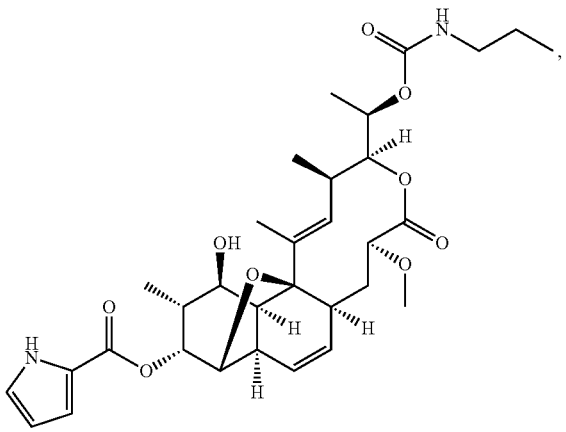

-continued
237
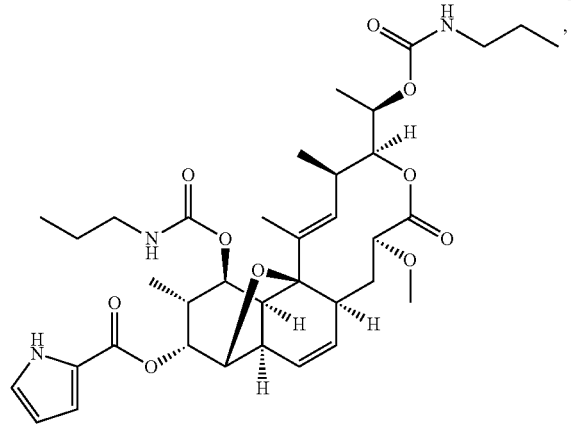
238
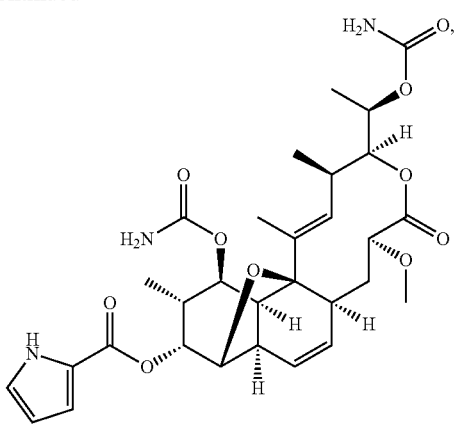
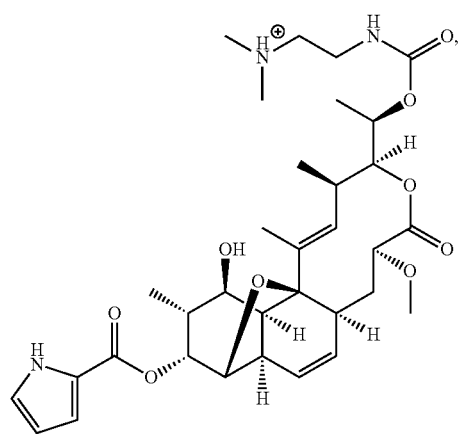
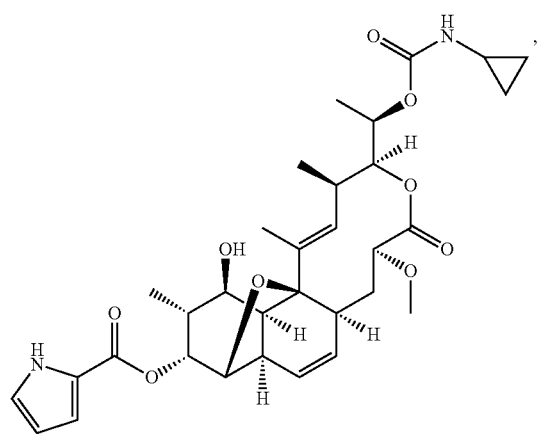
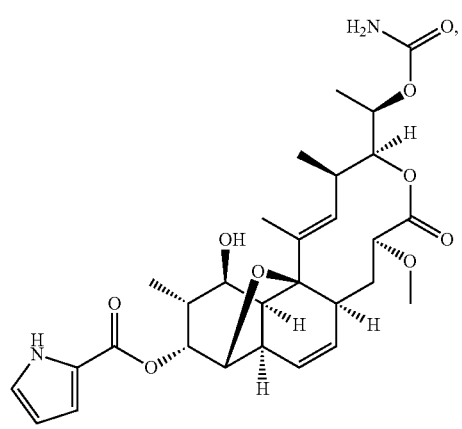
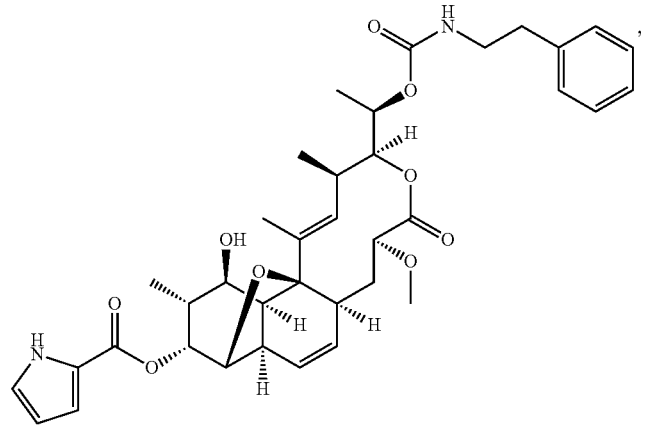

239
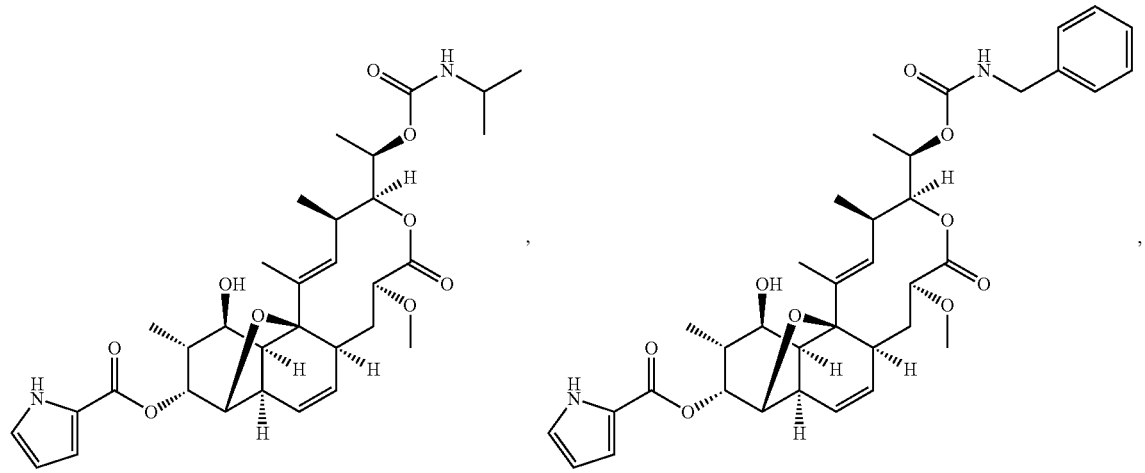
240
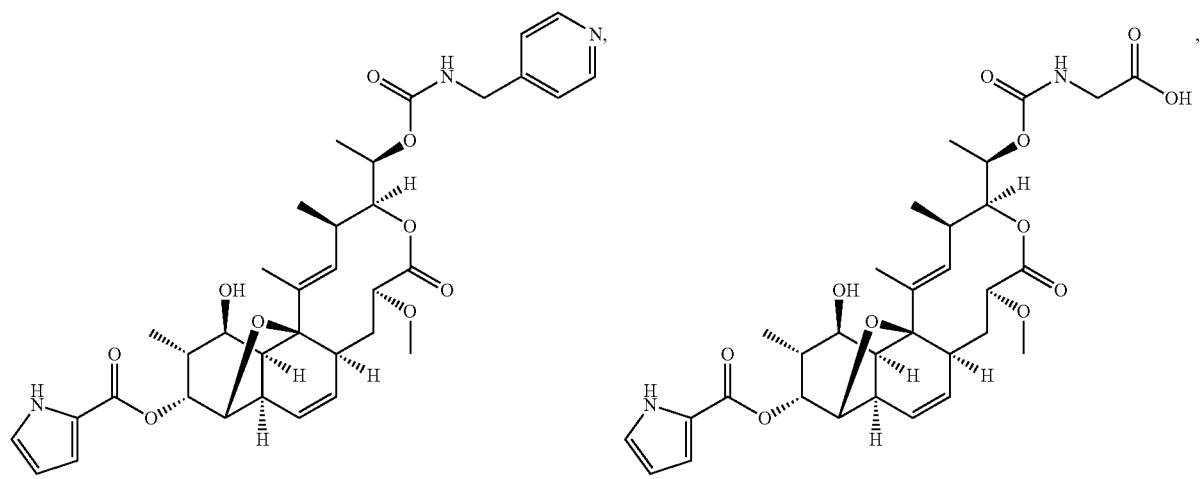
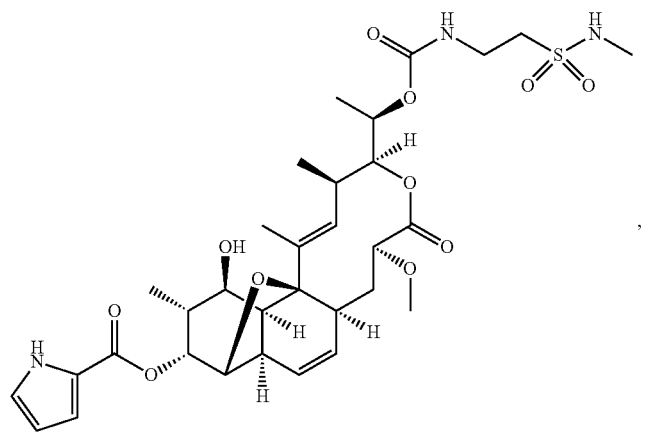

241
-continued
242
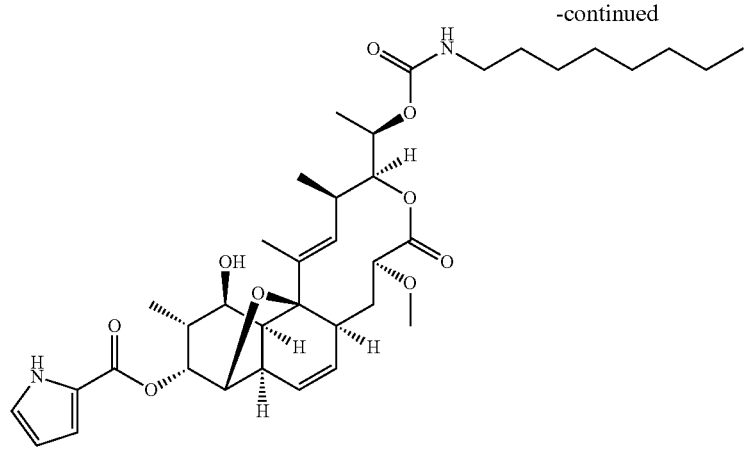
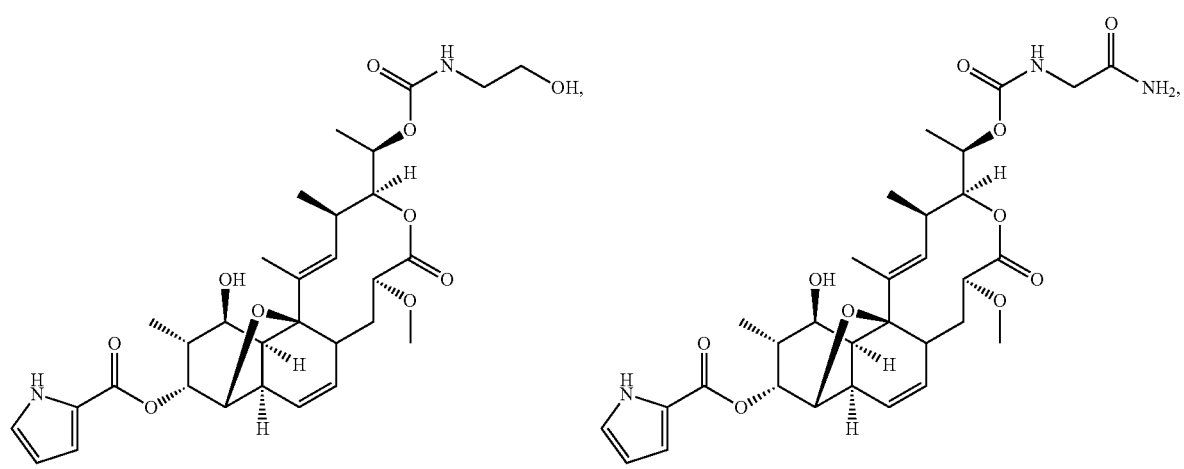
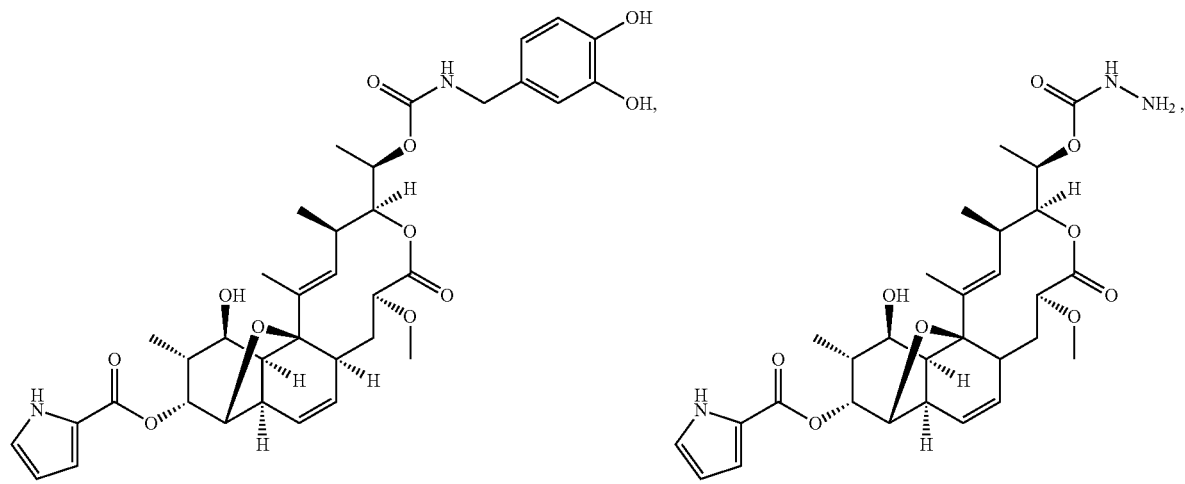

-continued
243
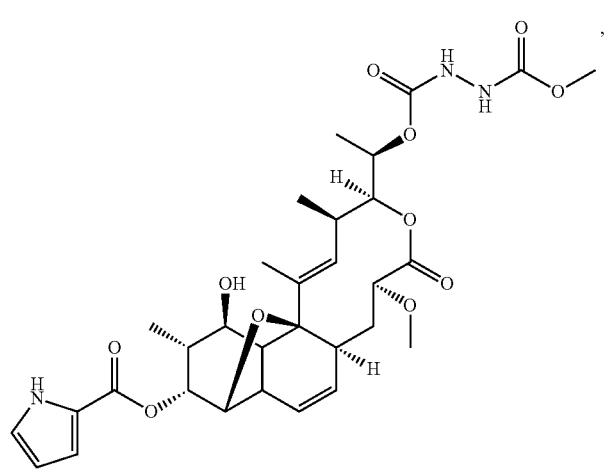
244
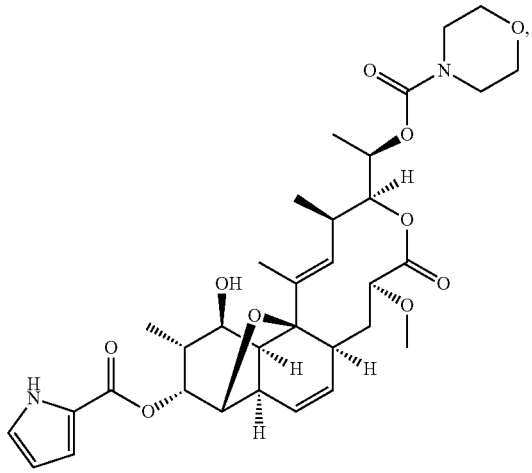
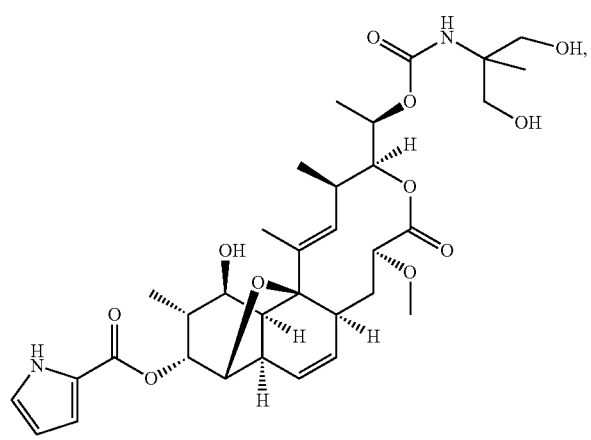
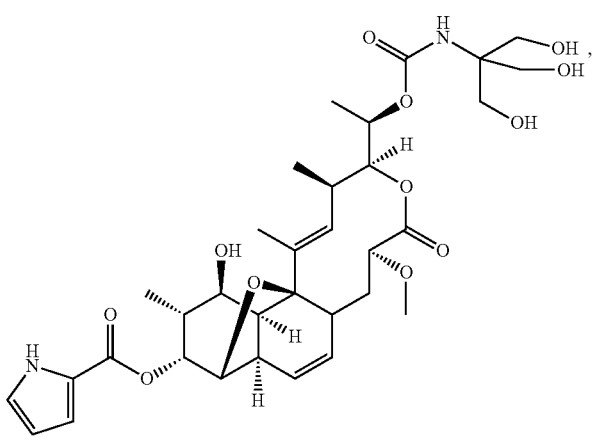
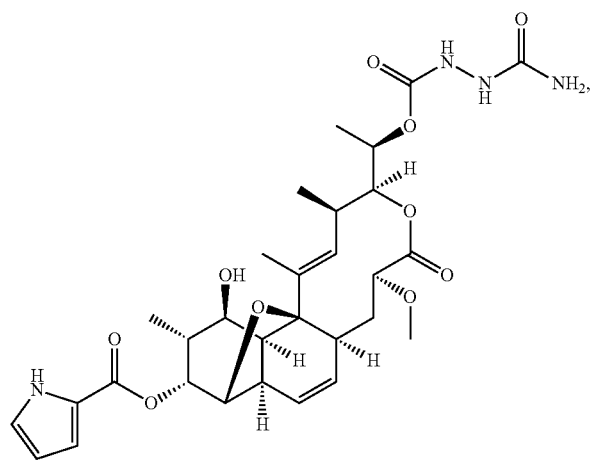

245
-continued
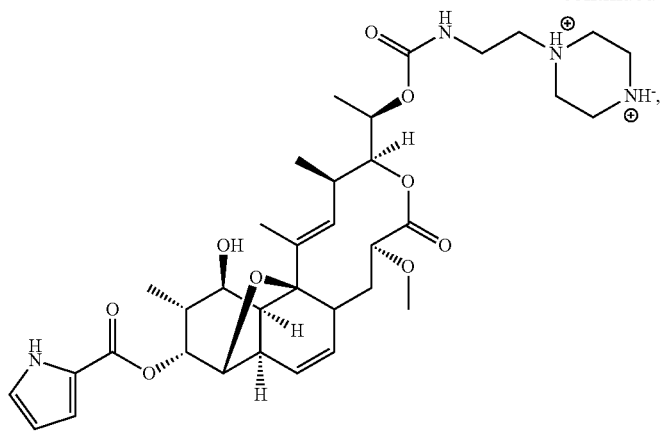
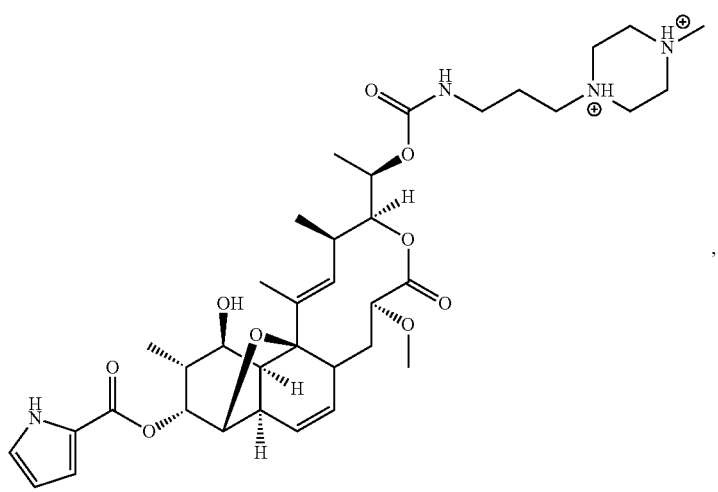
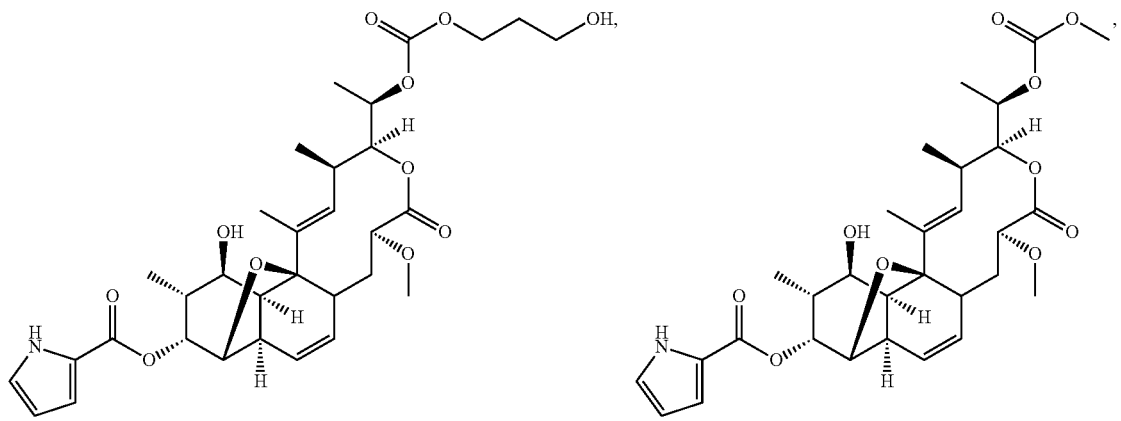

247 248
-continued
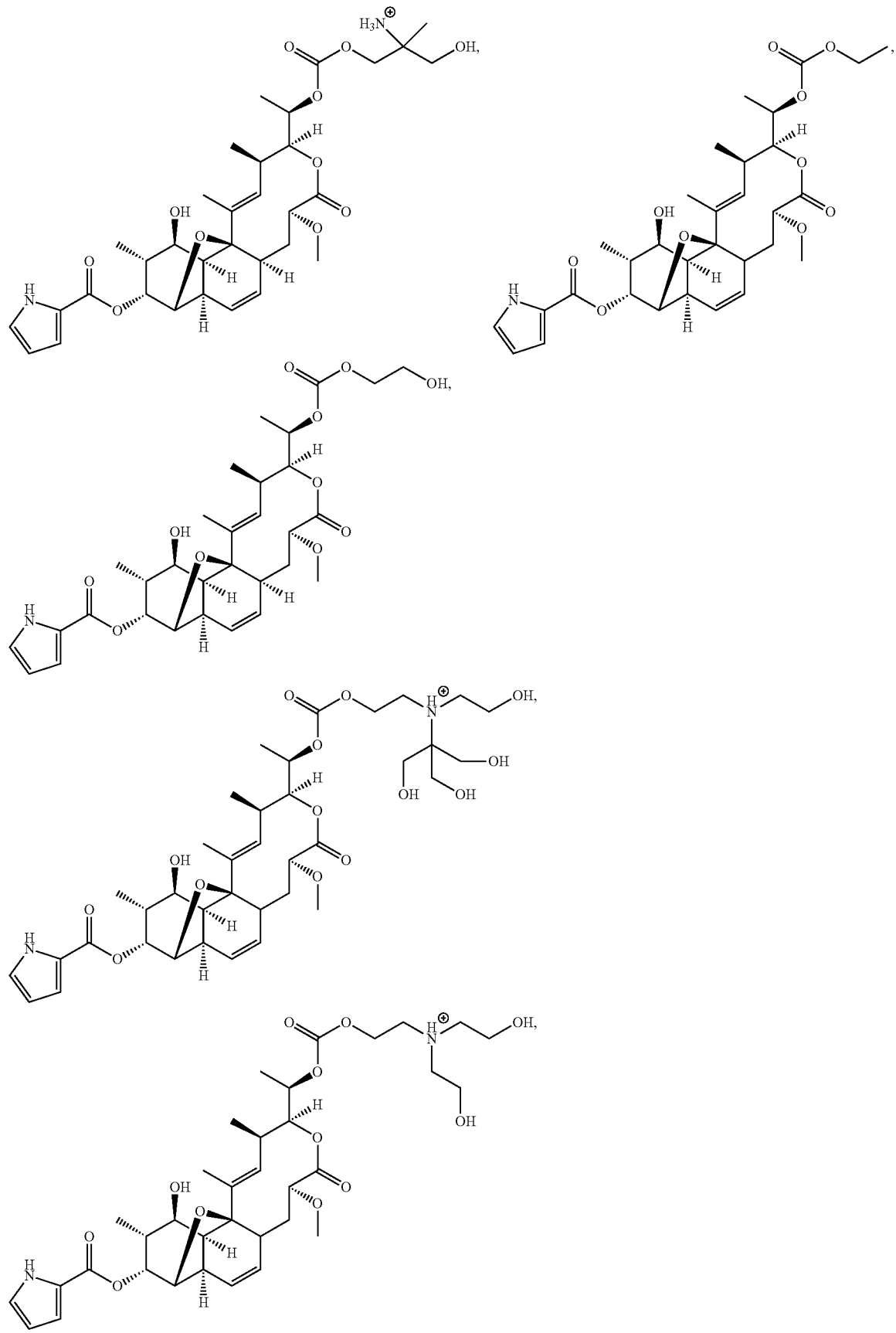

249 250
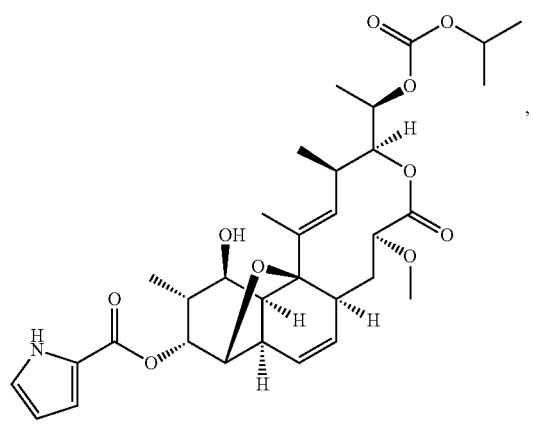
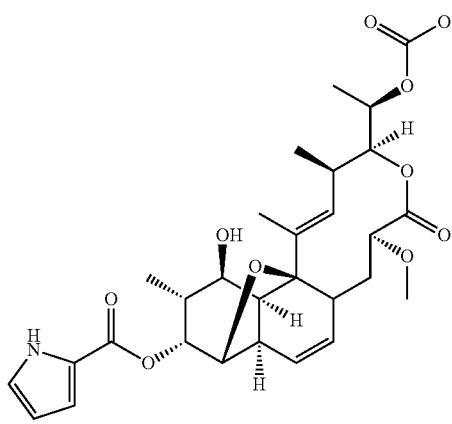
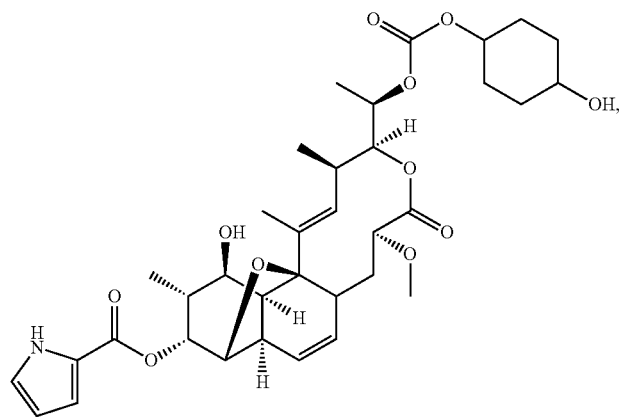
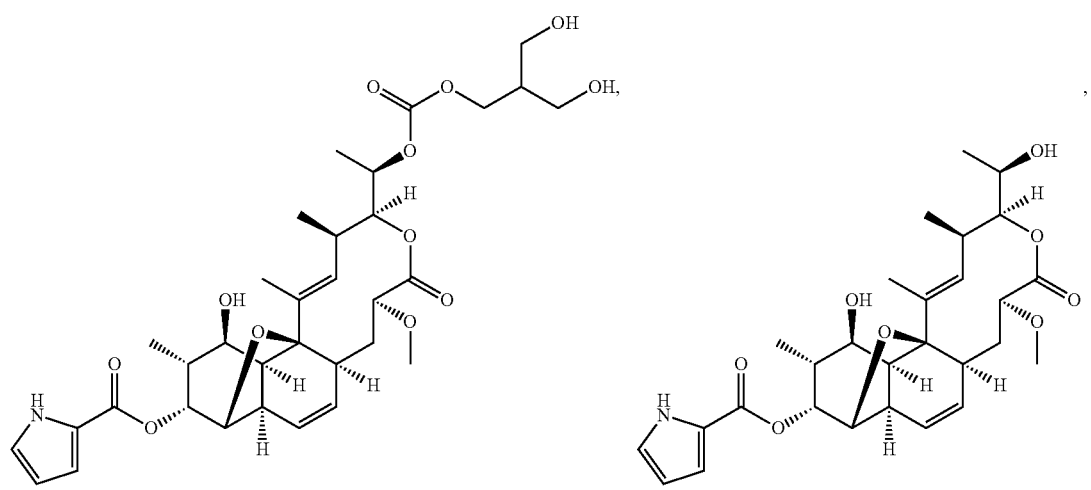
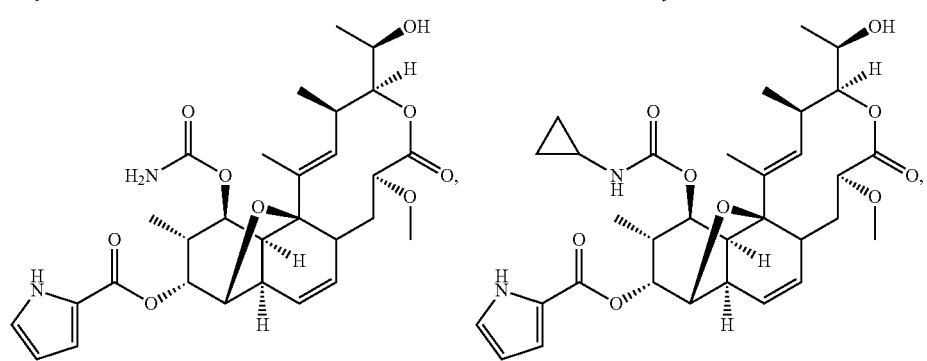

-continued
251
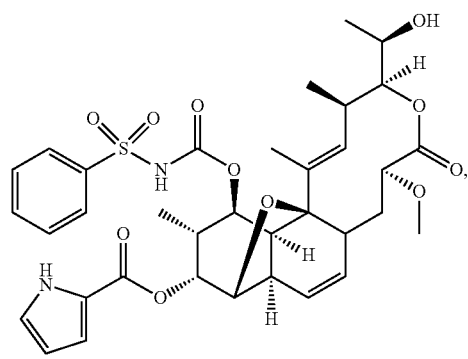
252
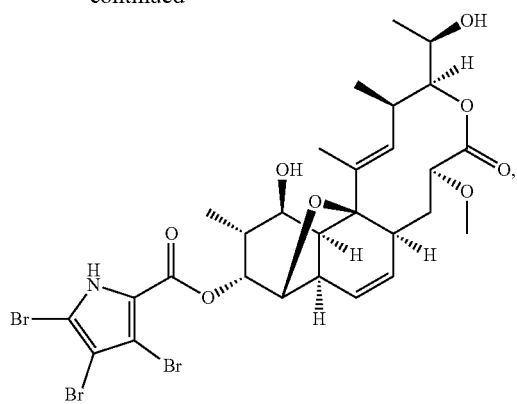
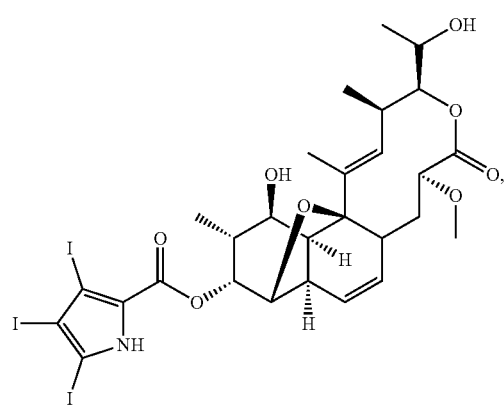
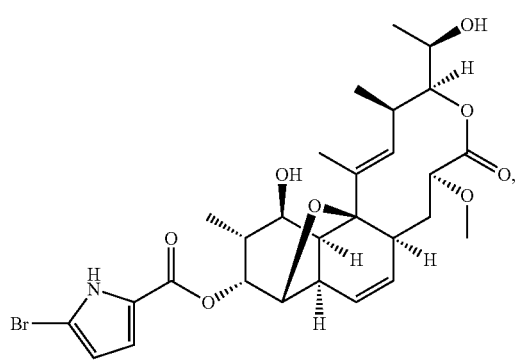
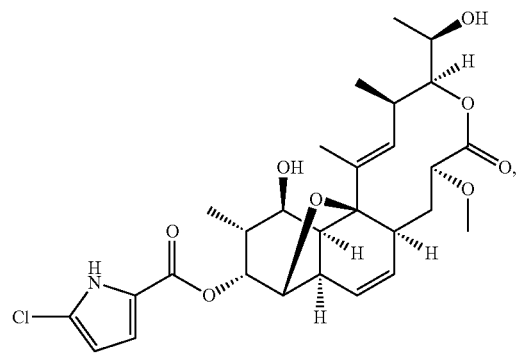
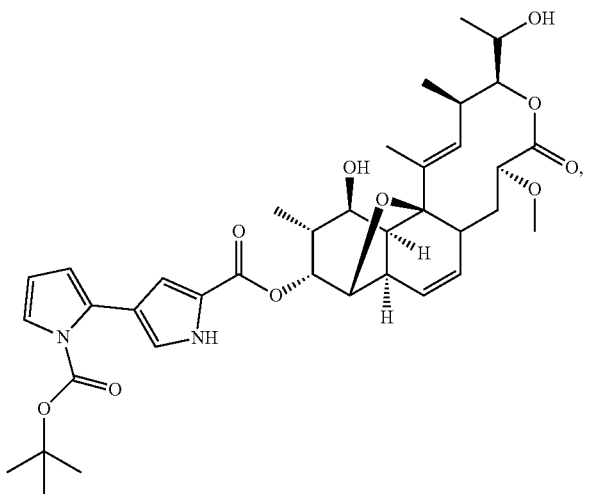
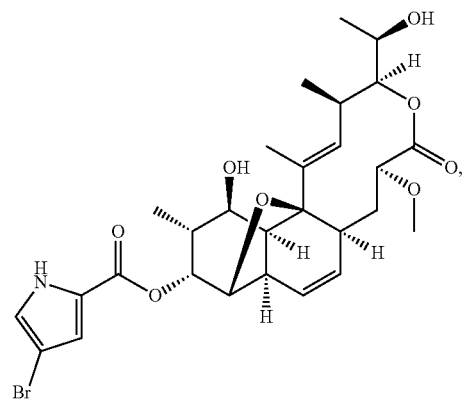
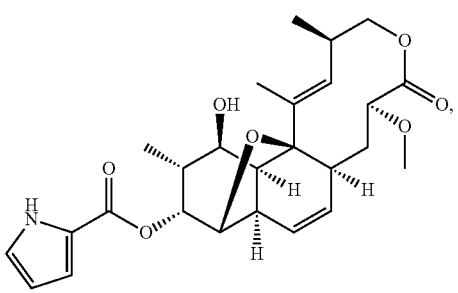

253 254
-continued
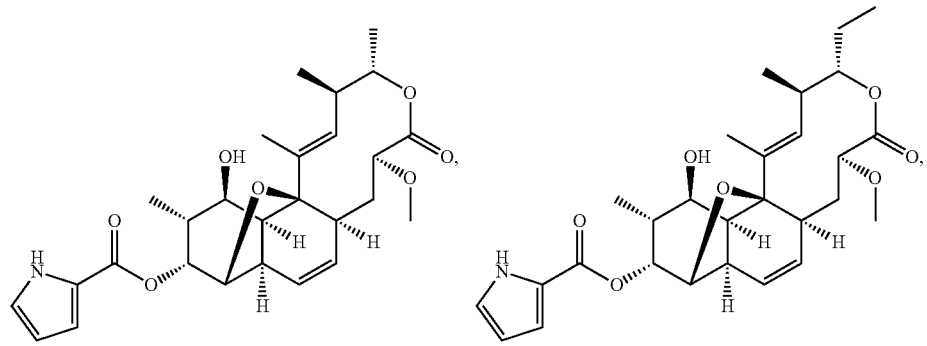
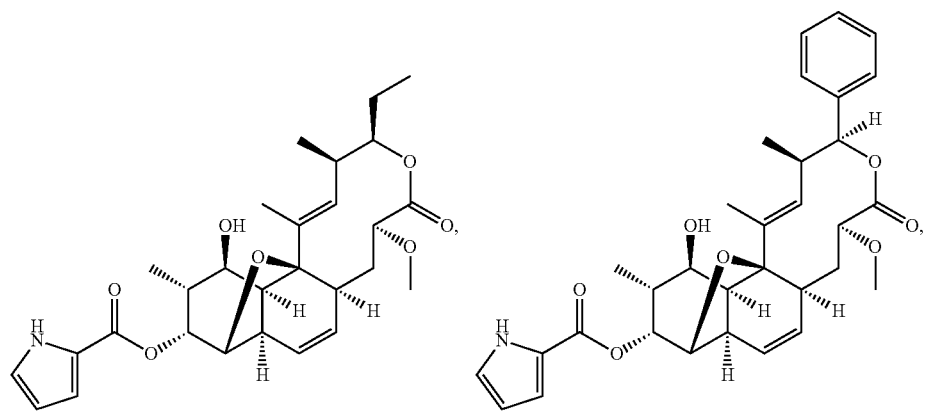
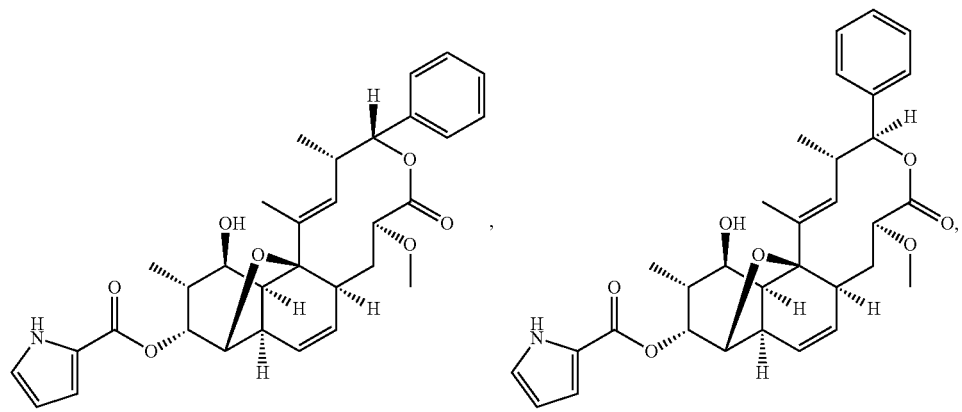
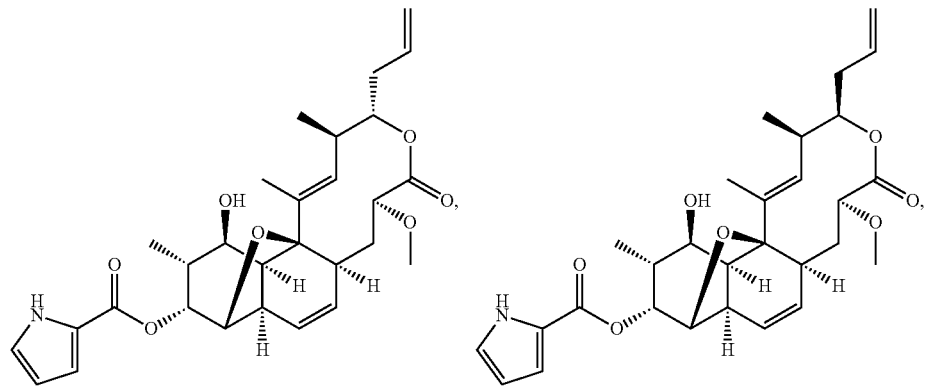

-continued
255
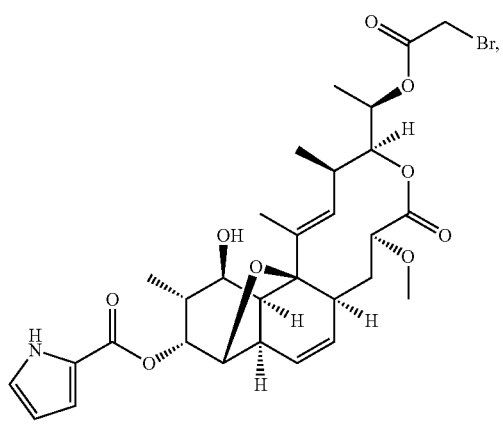
256
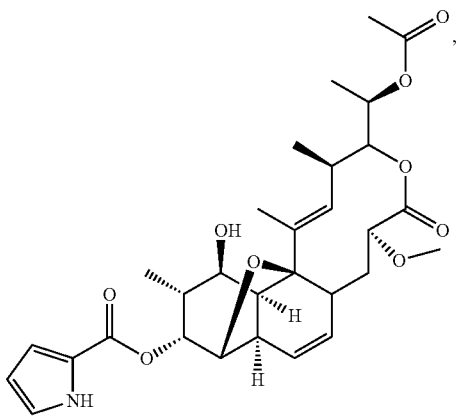
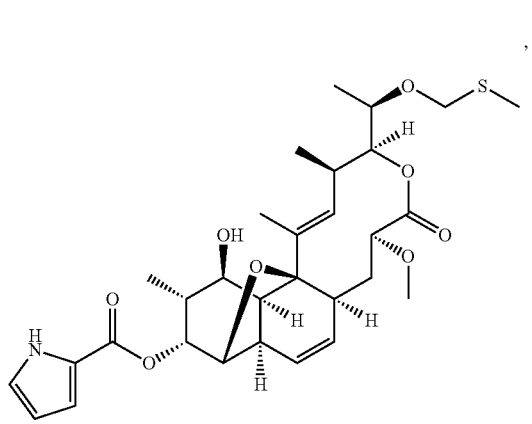
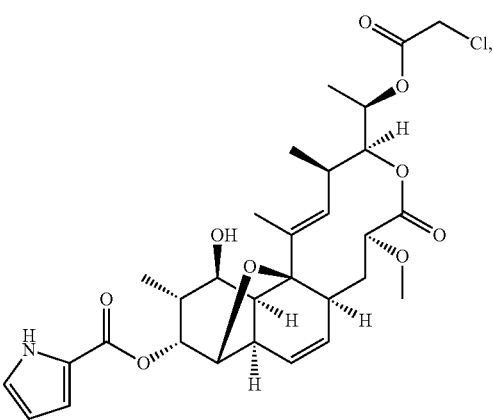
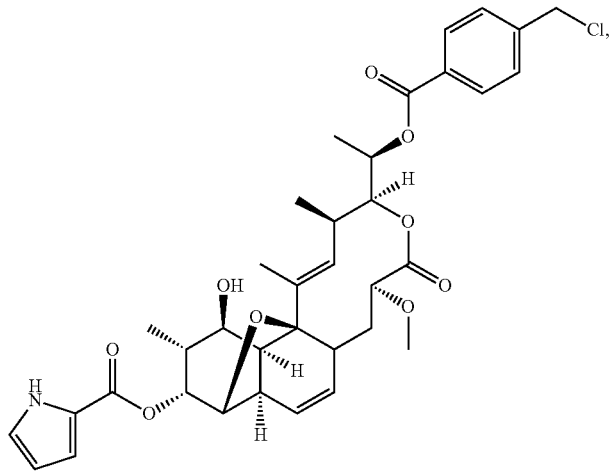
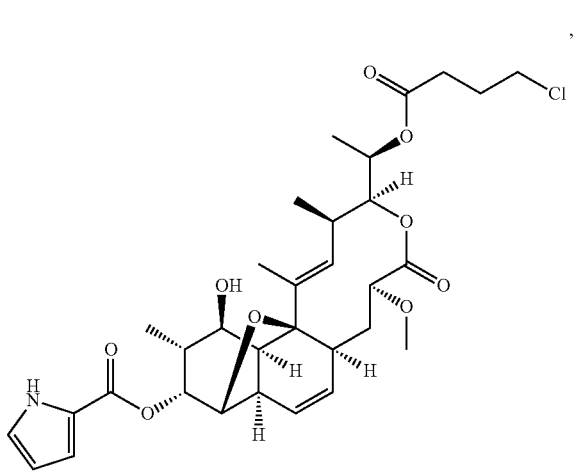

-continued
| 257 | 258 |
|---|---|
| 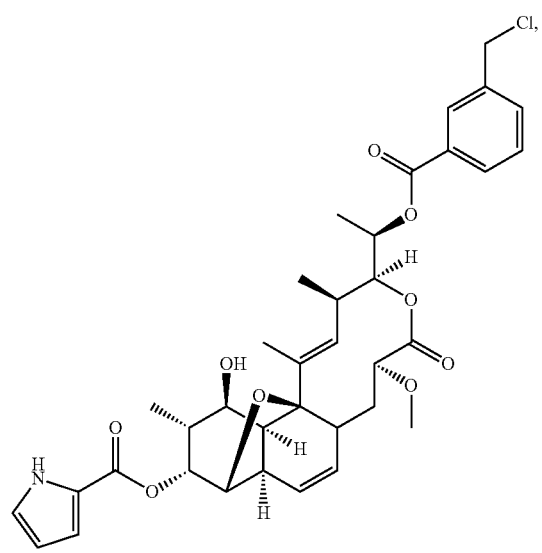 | 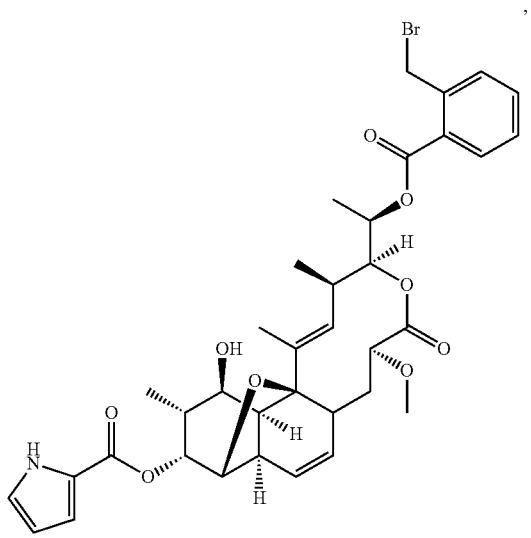 |
| 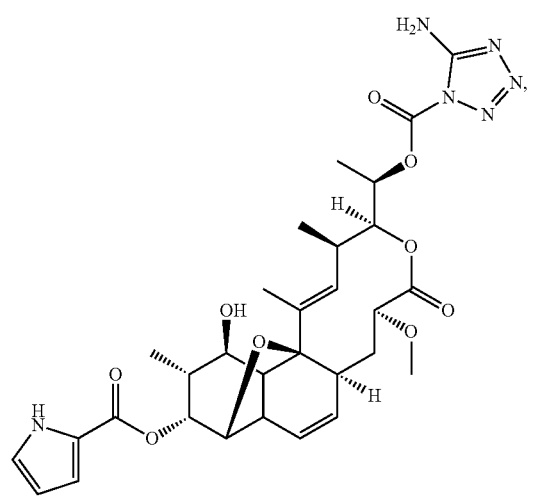 | 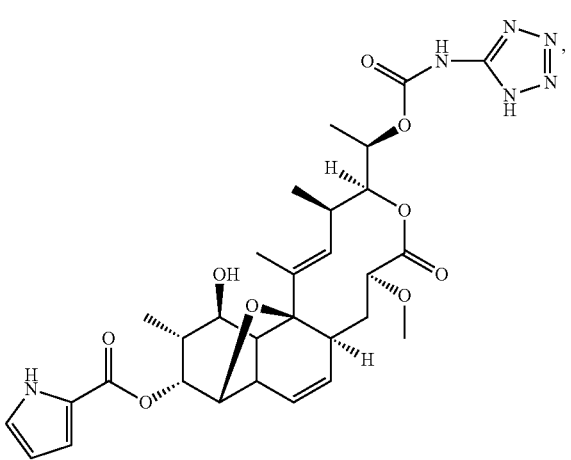 |
| 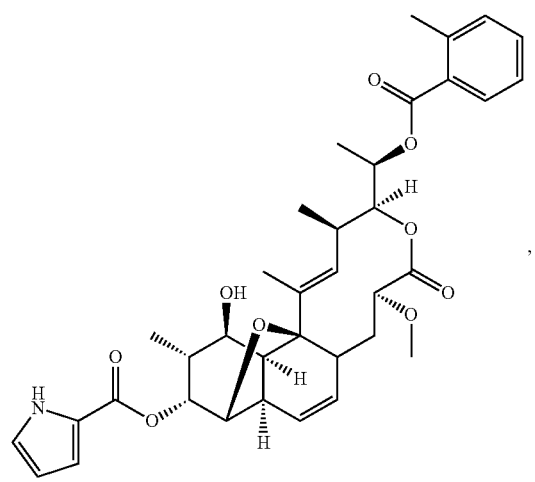 | 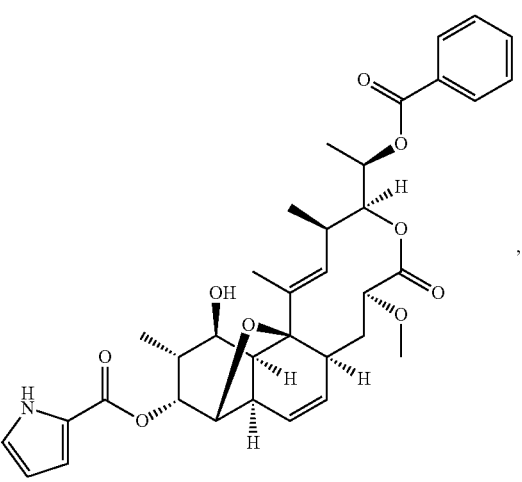 |

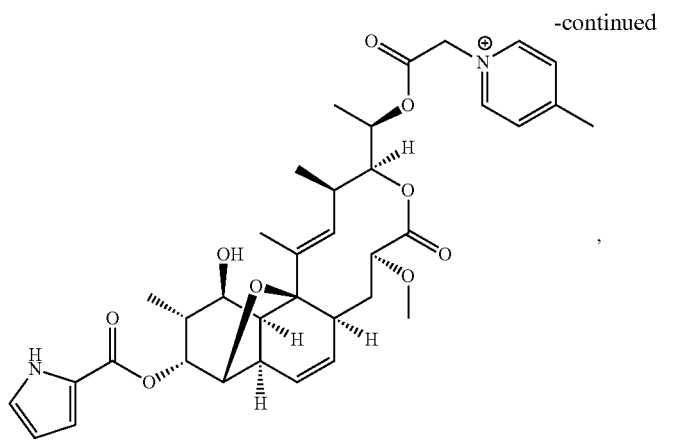
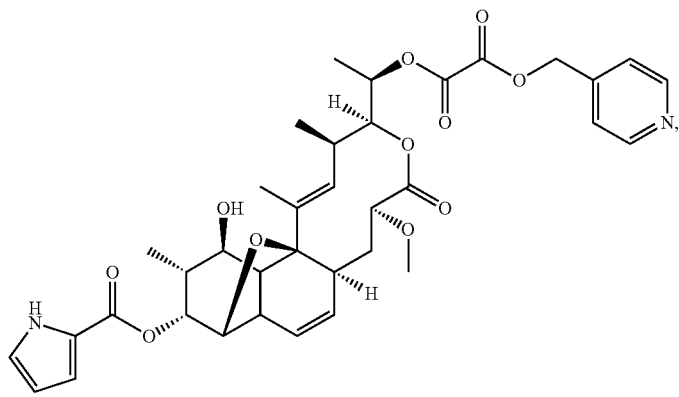
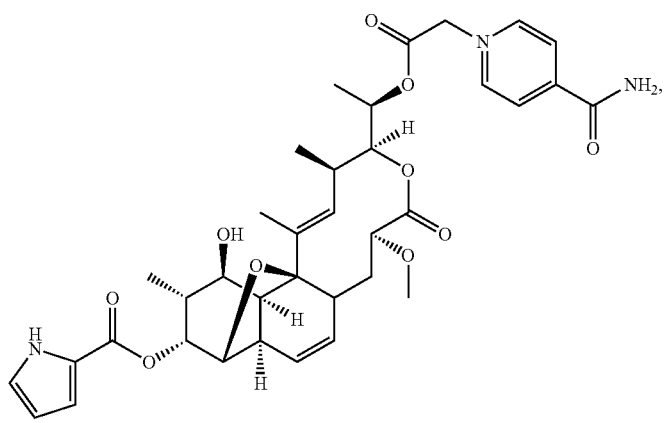
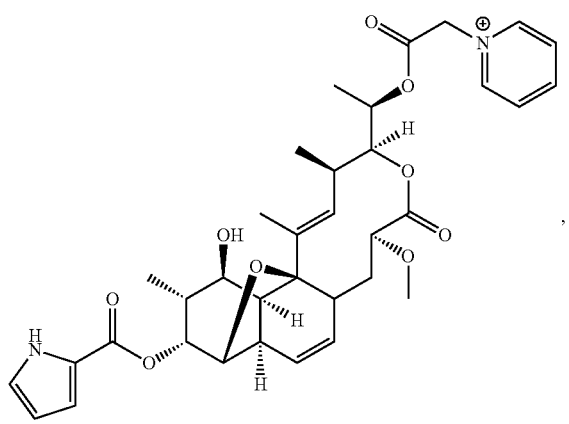

-continued
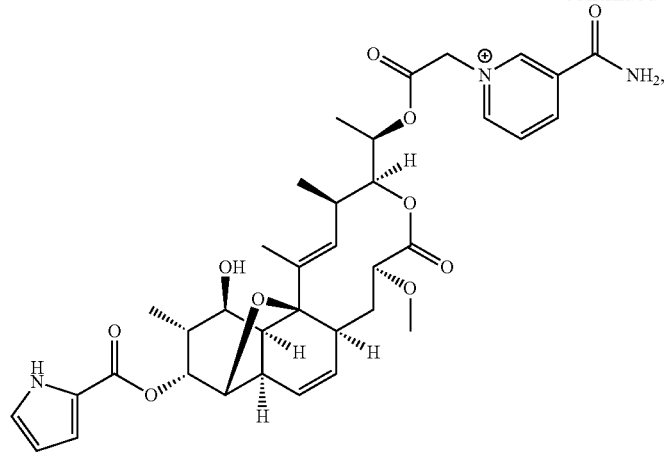
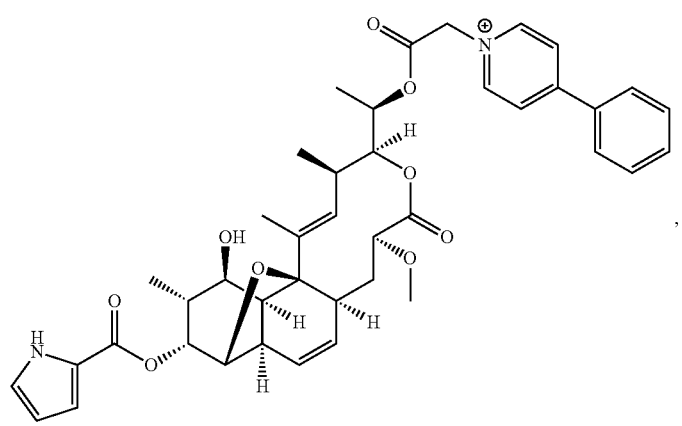
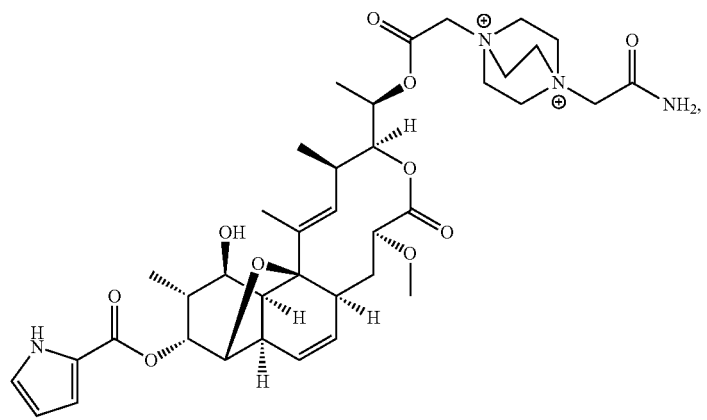

263
264
-continued
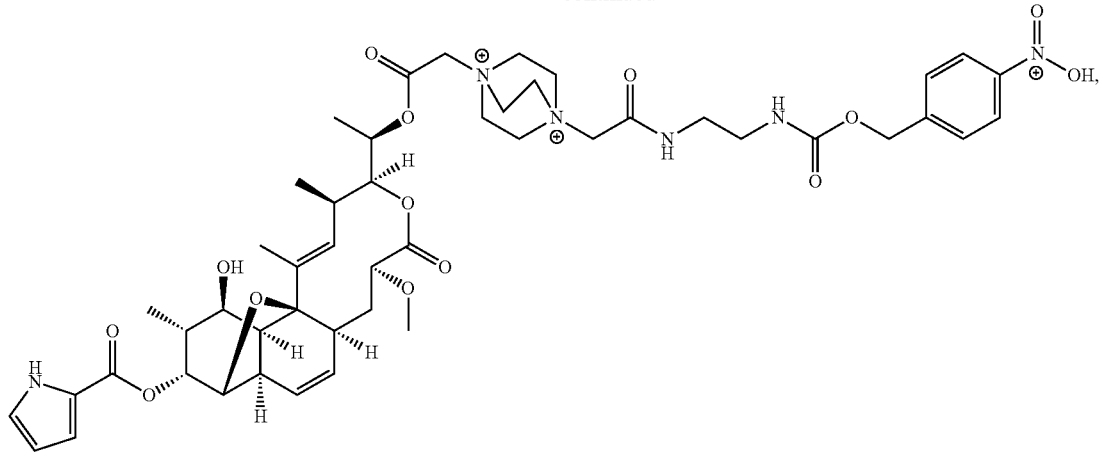
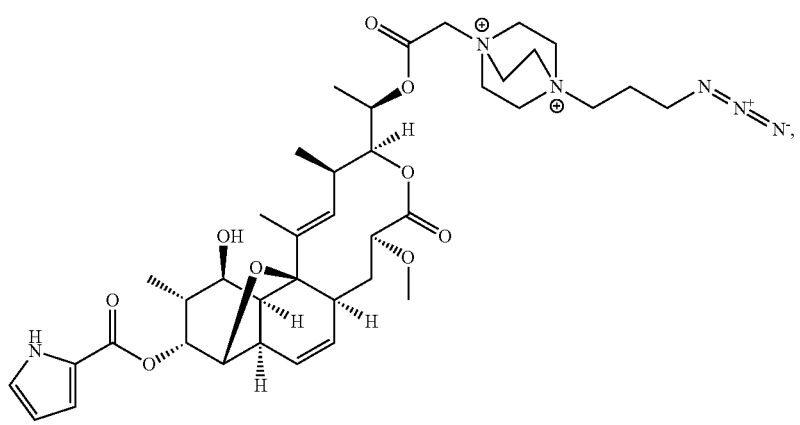
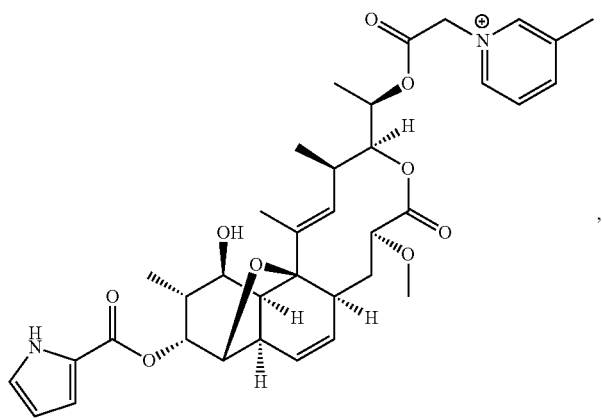

-continued
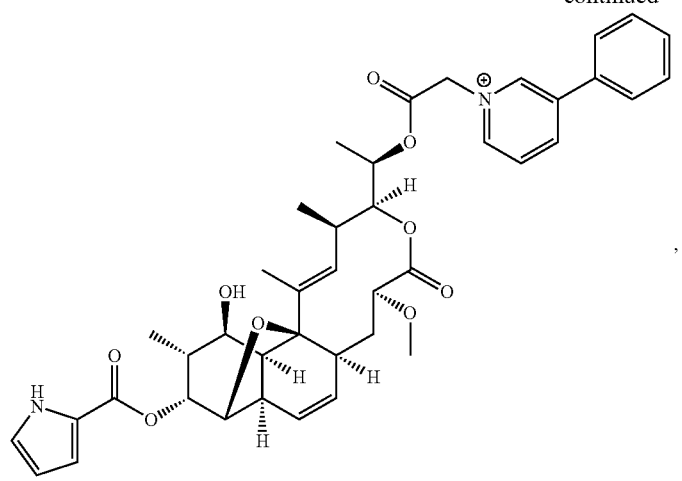
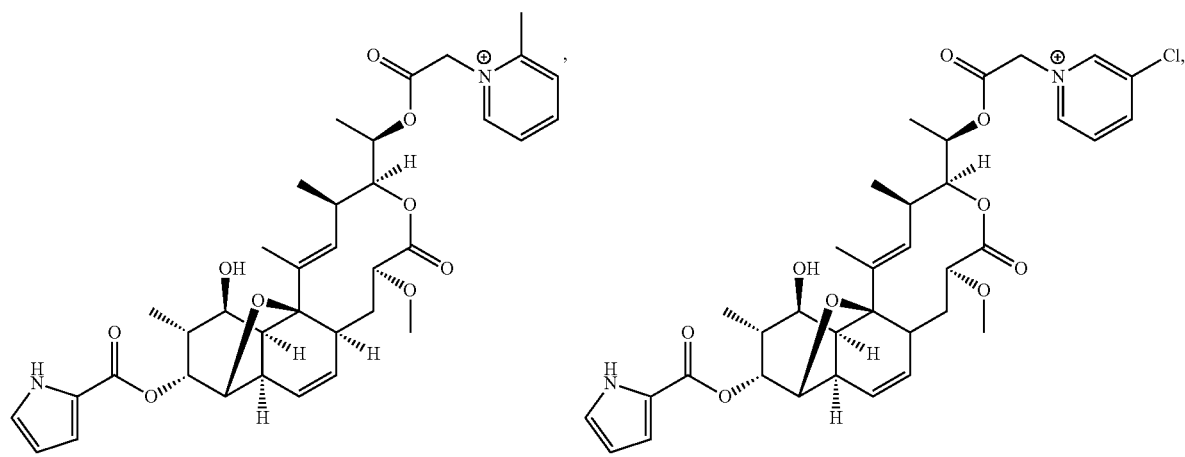
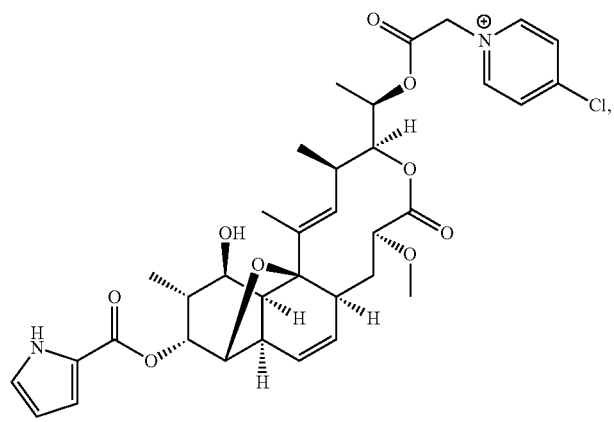

267 268
-continued
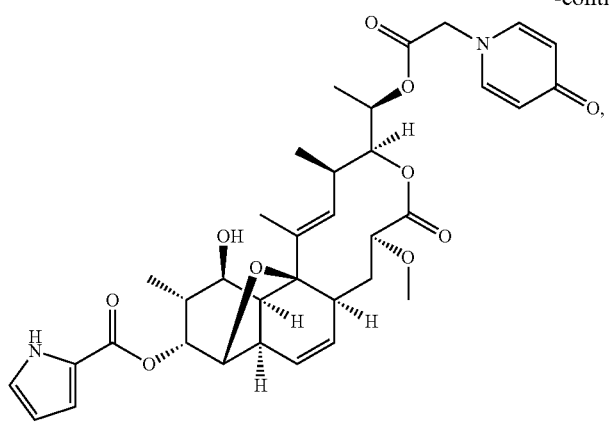
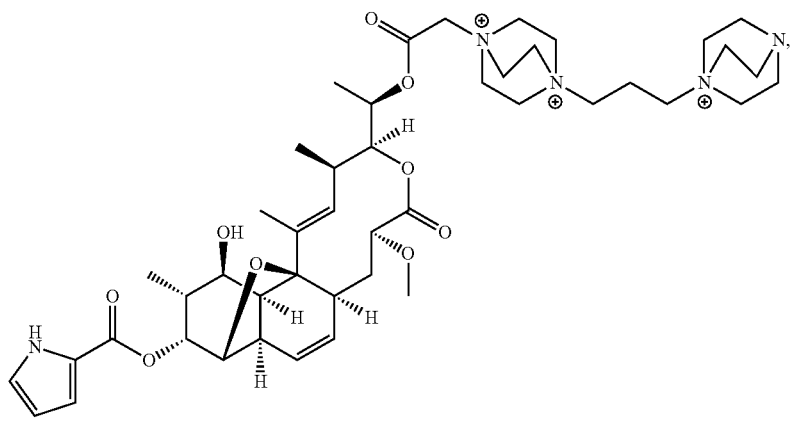
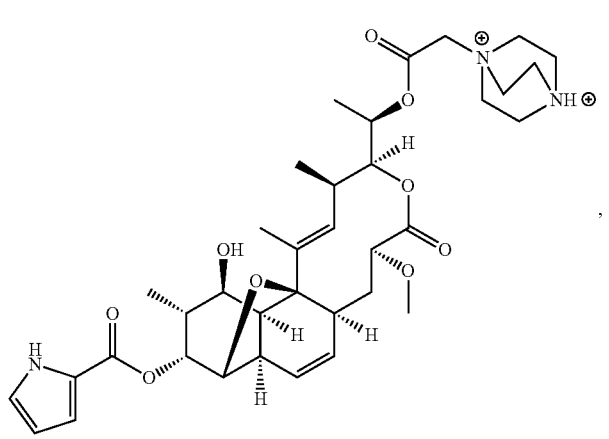
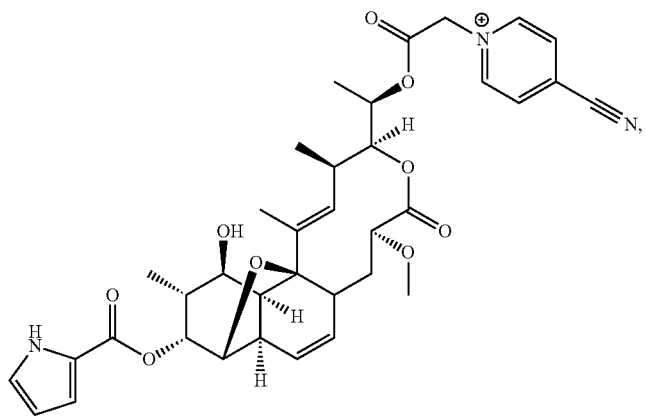

-continued
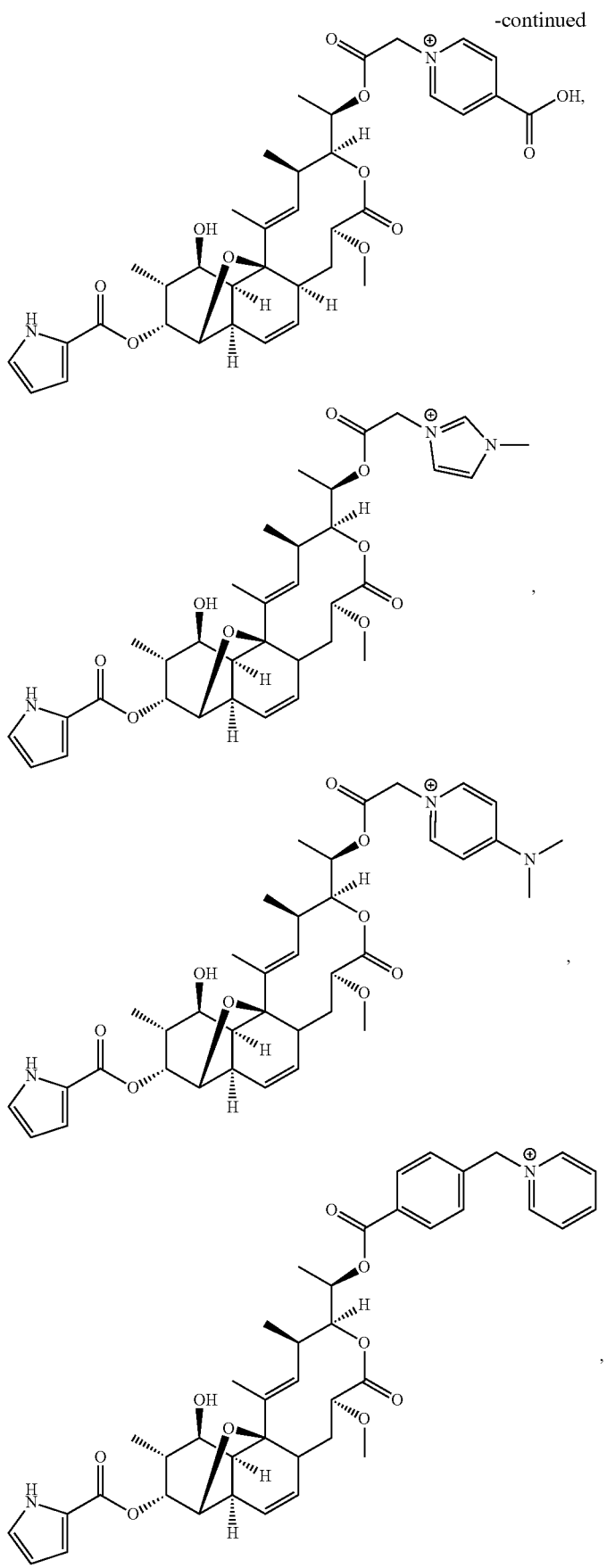

-continued
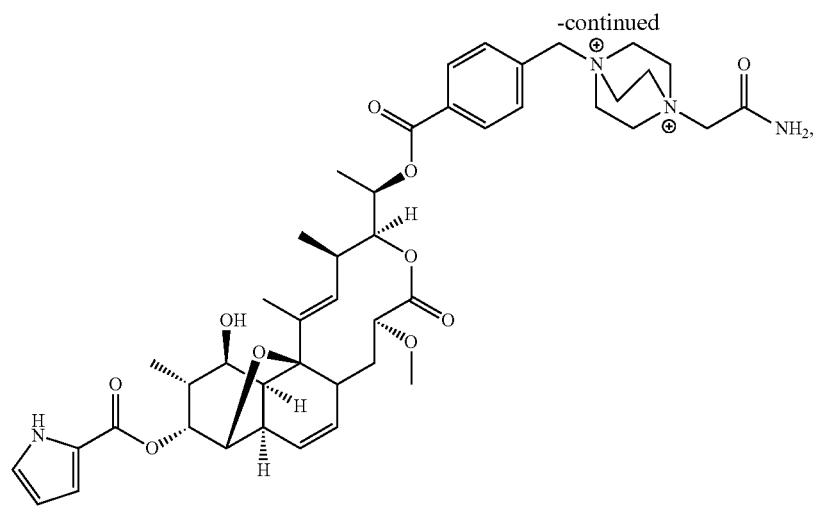
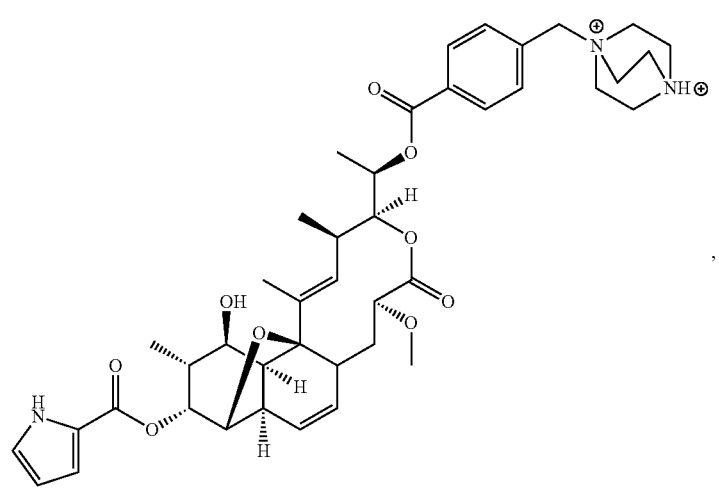
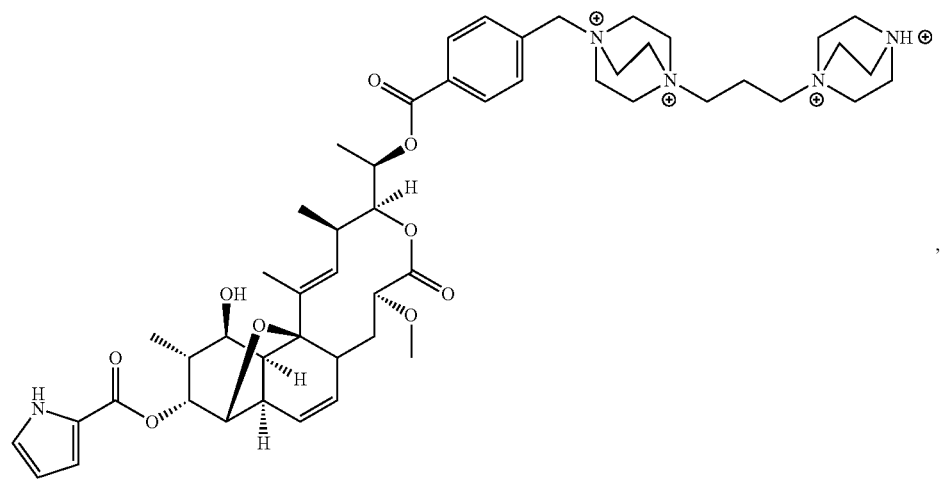

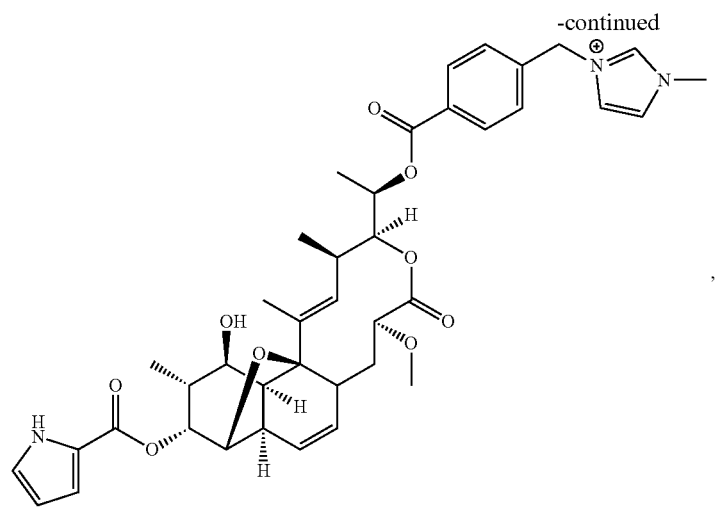
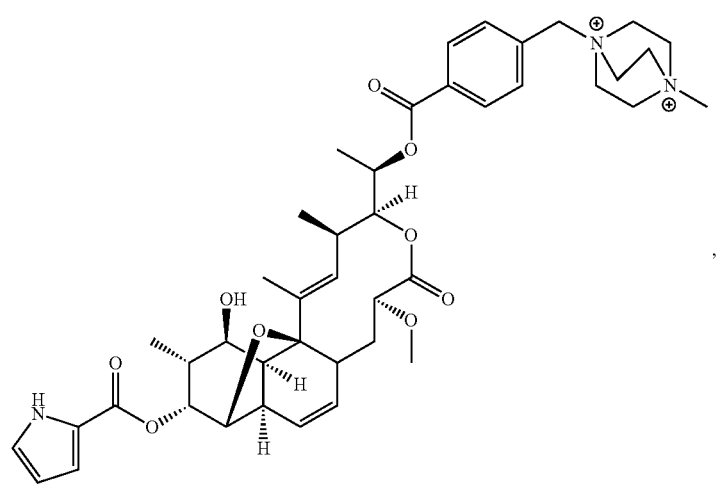
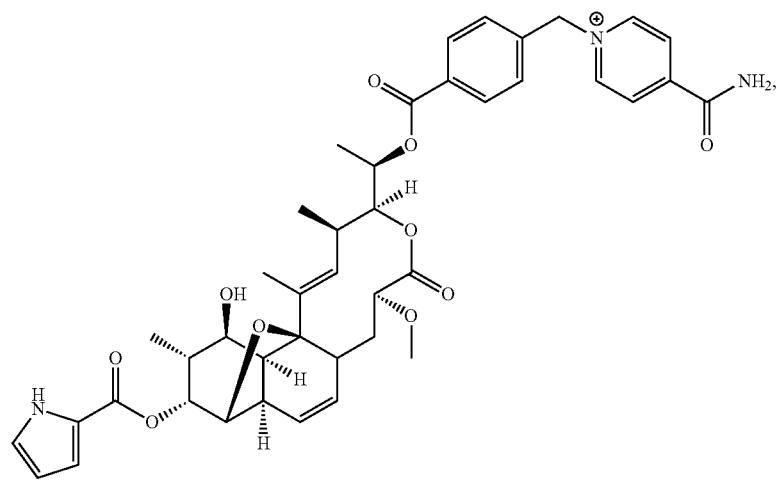

-continued
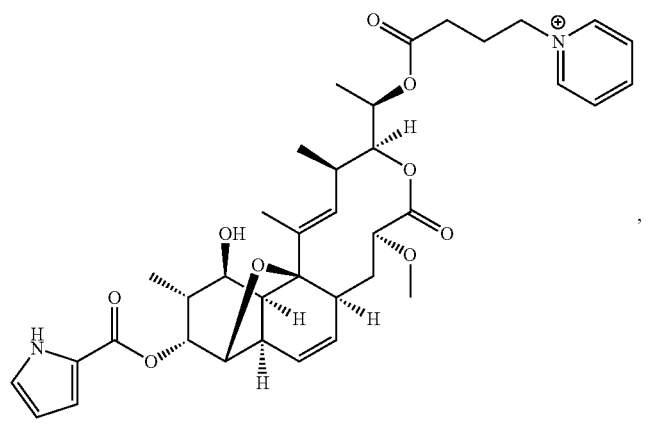
,
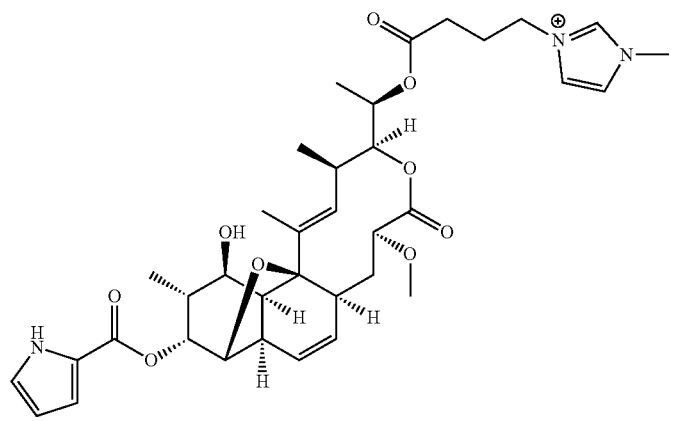
,
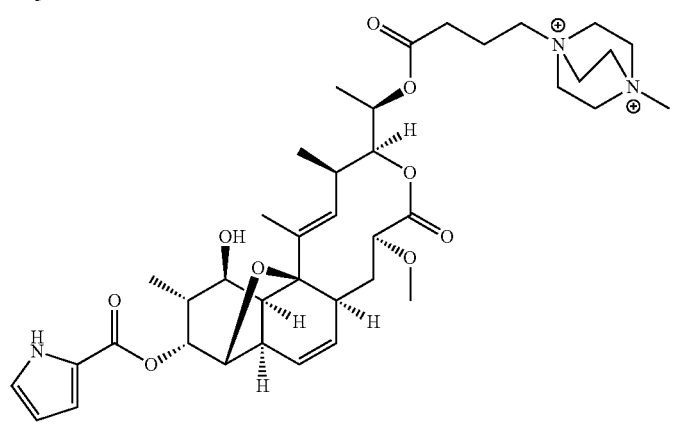
,
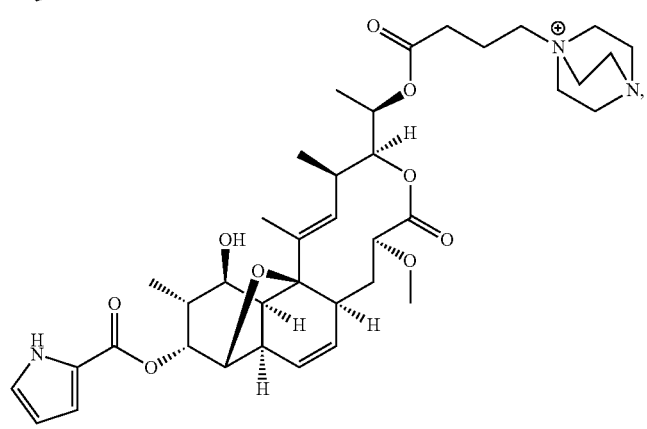
;

-continued
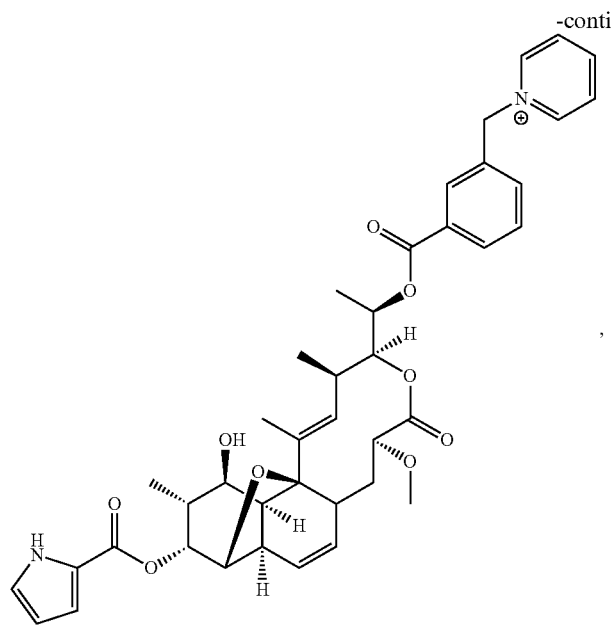
,
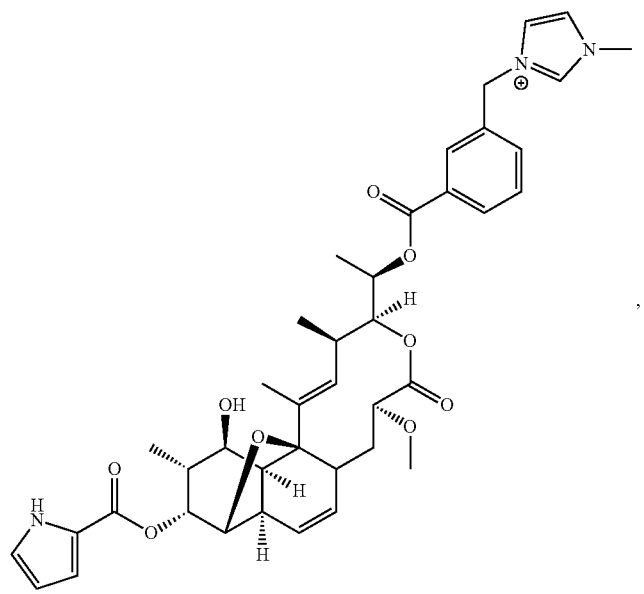
,

-continued
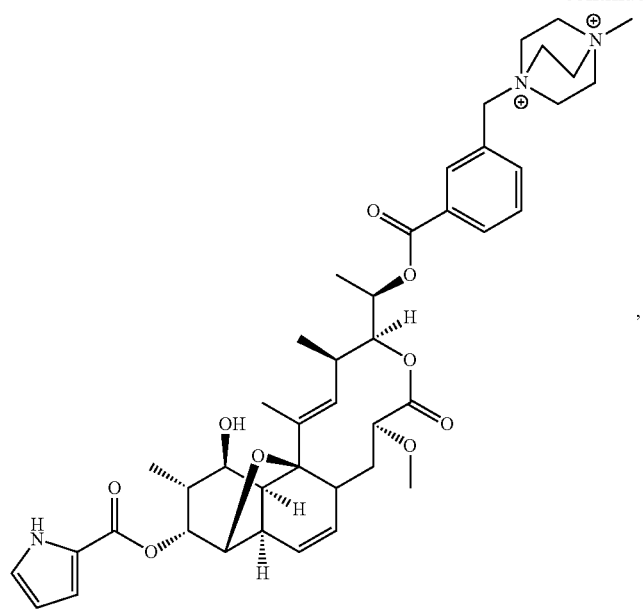
,
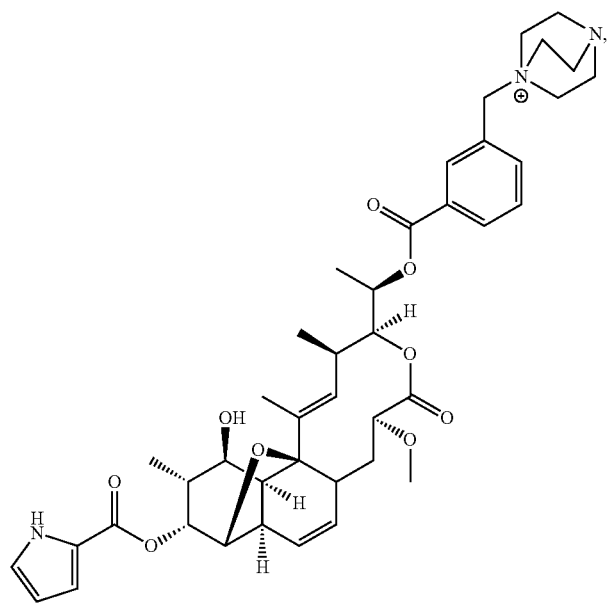

-continued
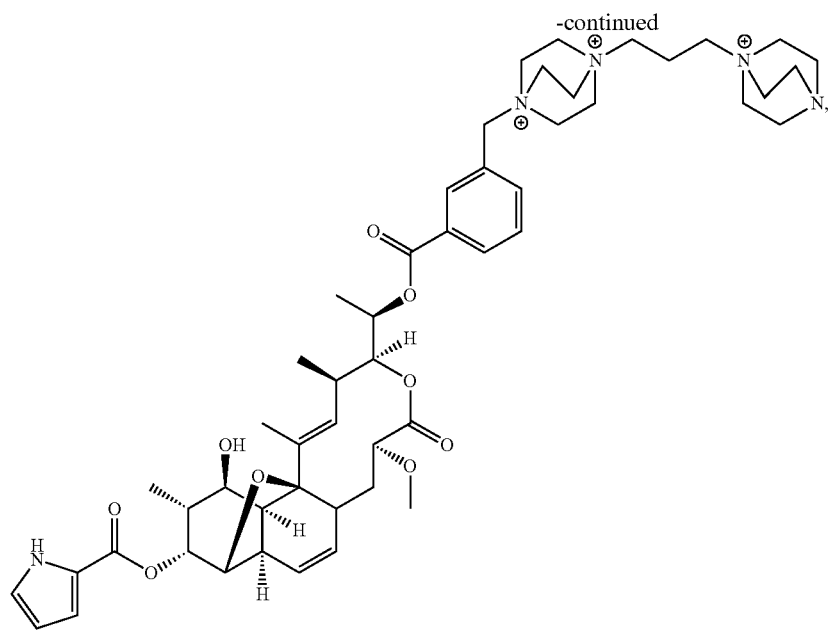
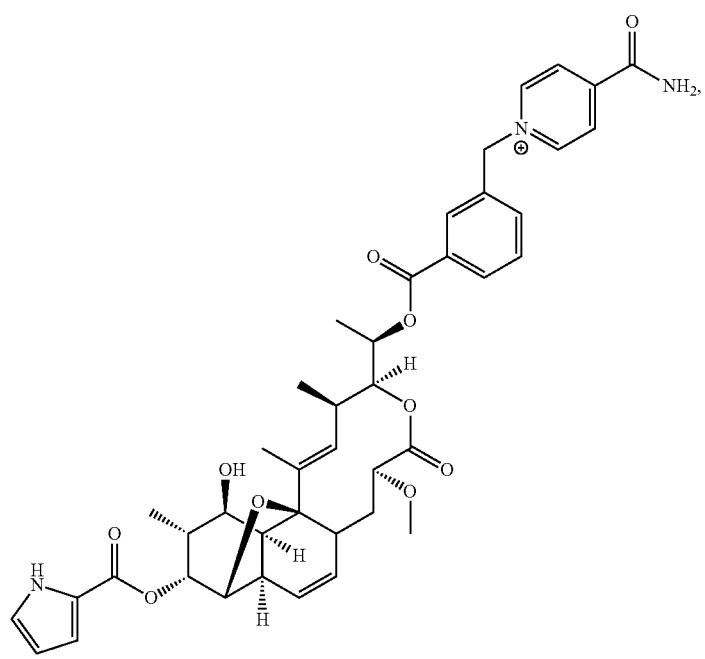

-continued
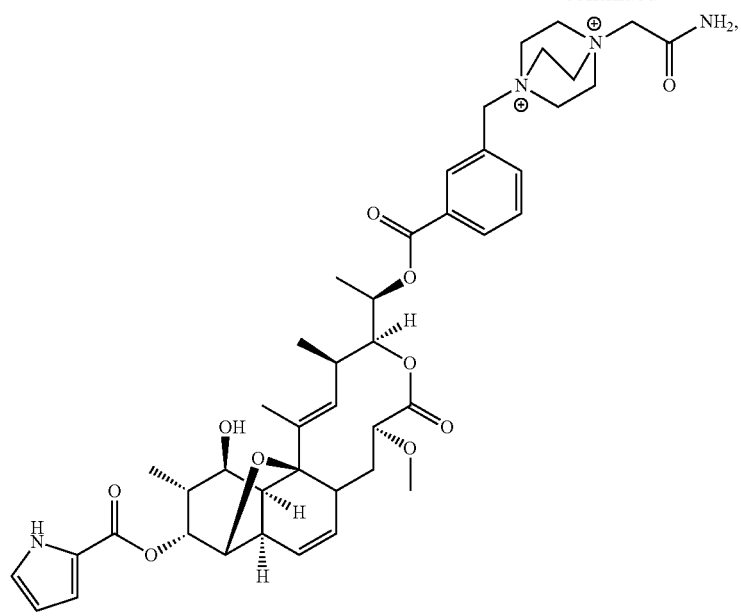
283
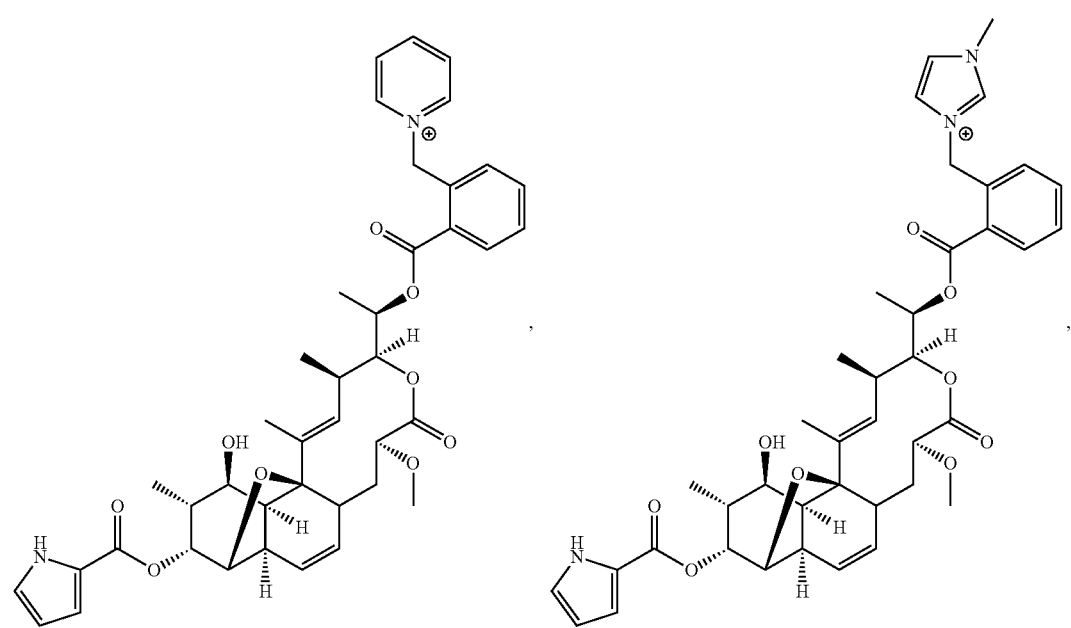
284

285
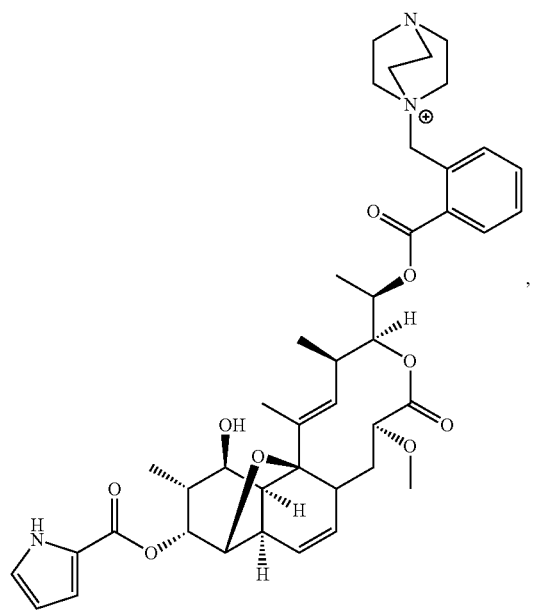
286
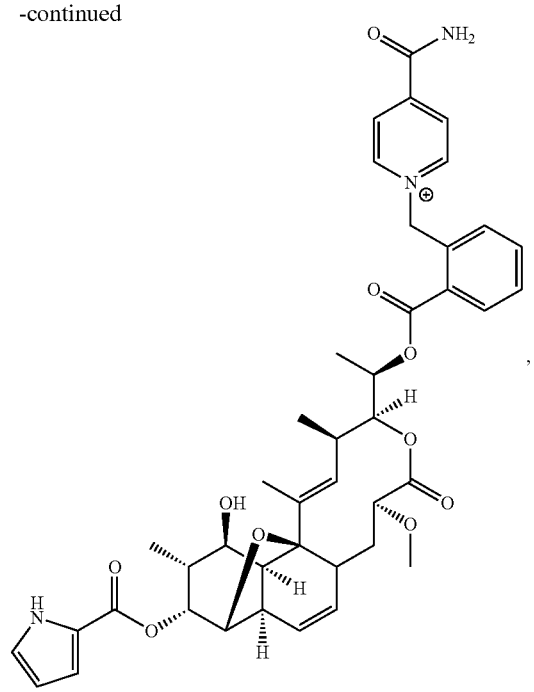
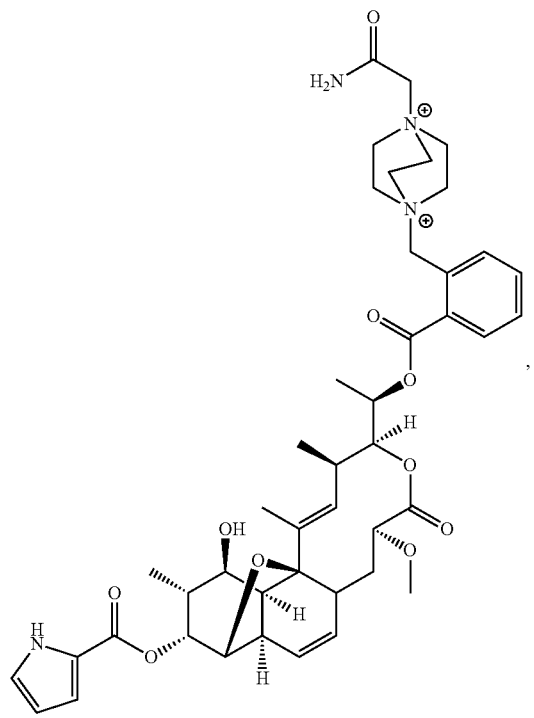
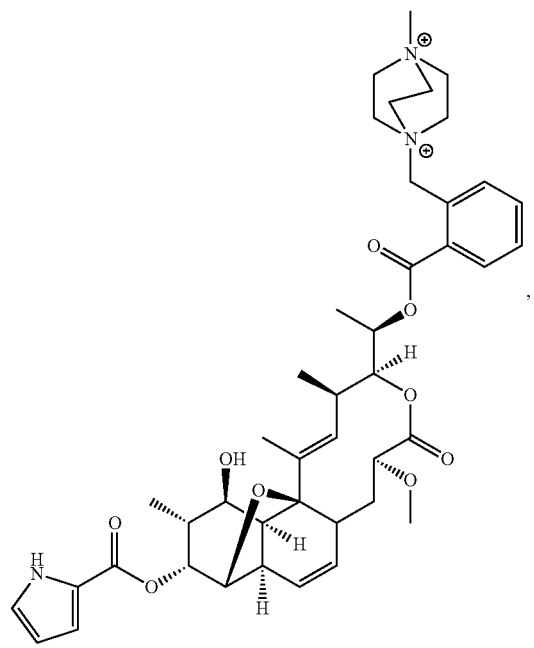

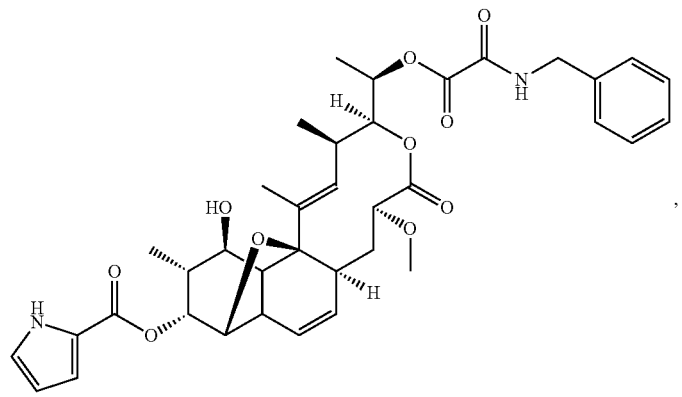
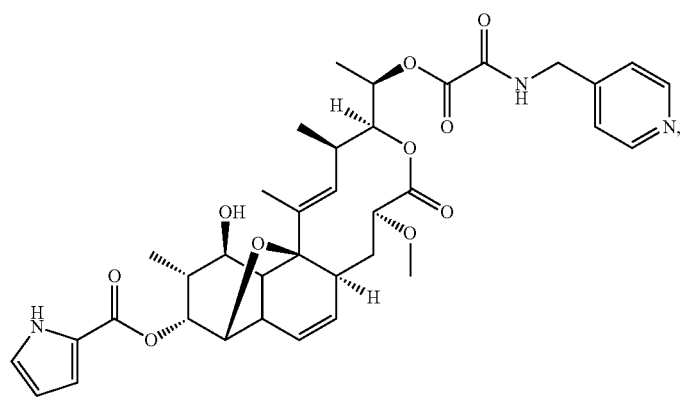
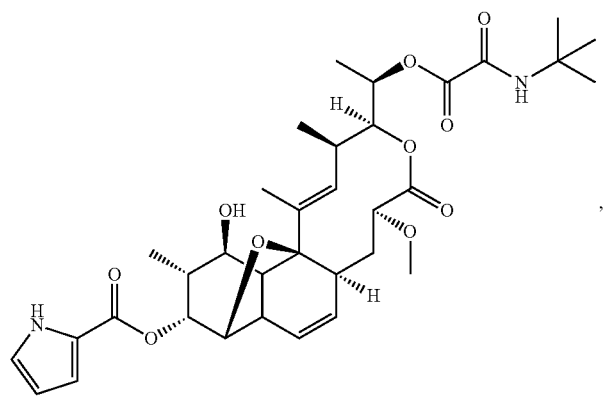
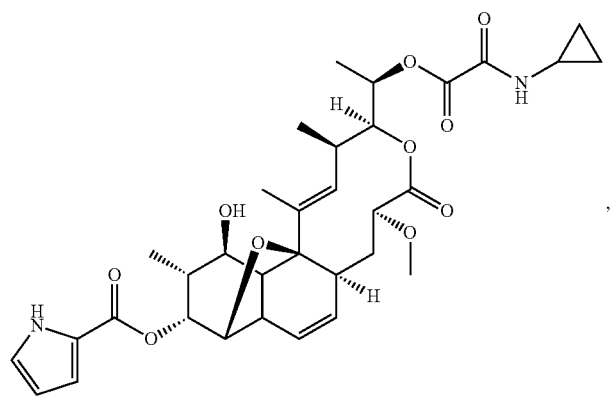

-continued
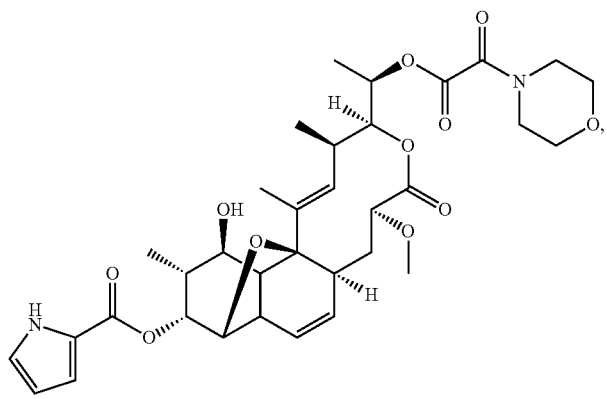
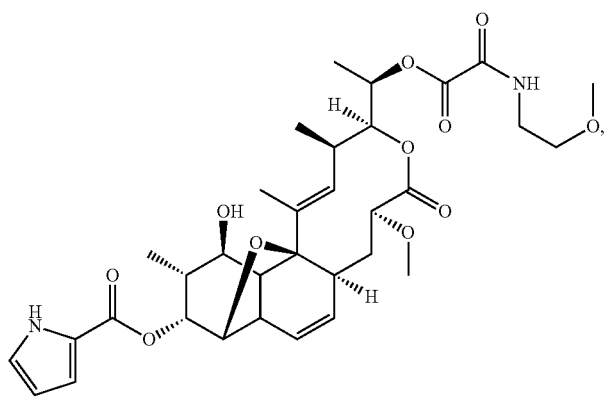
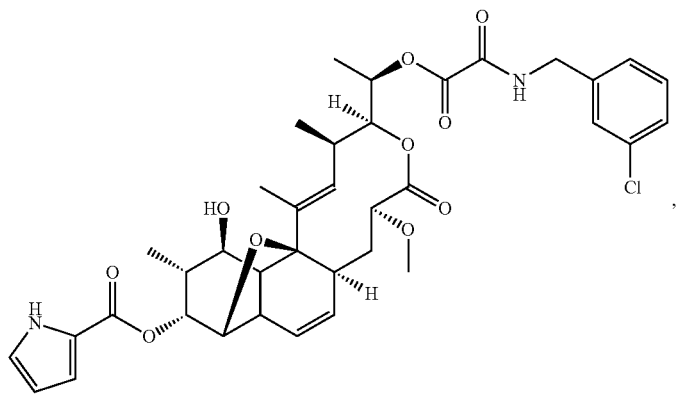
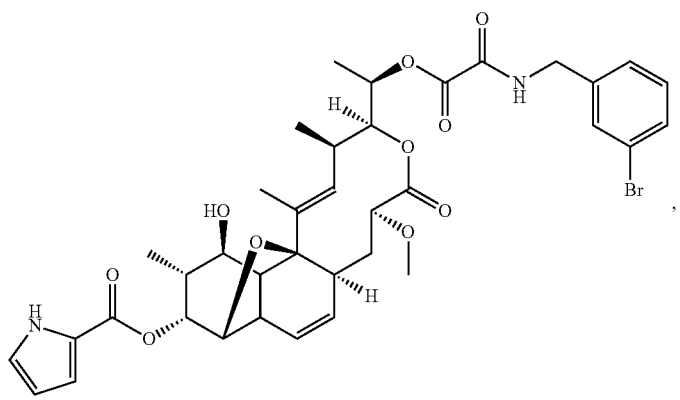

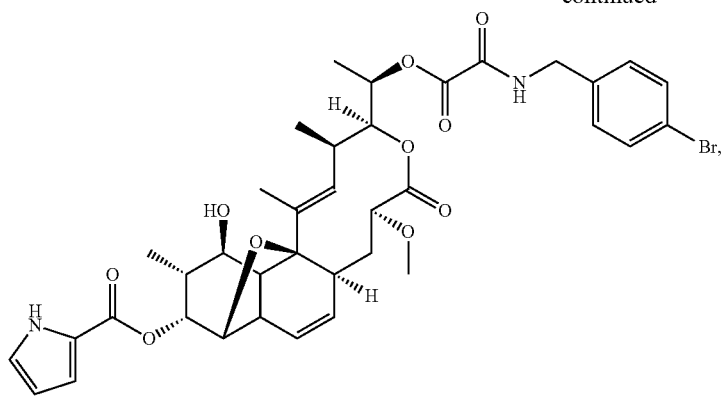
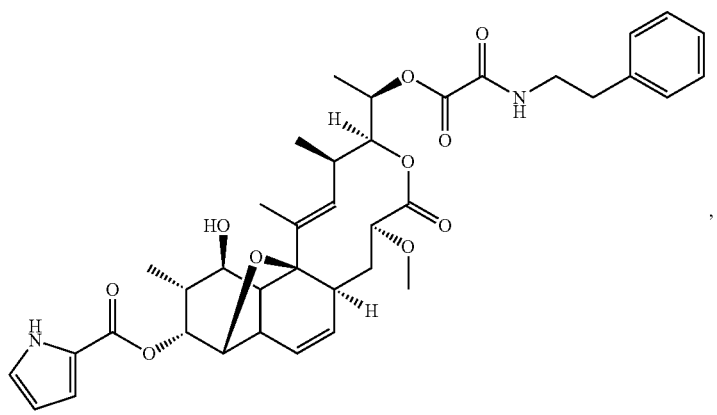
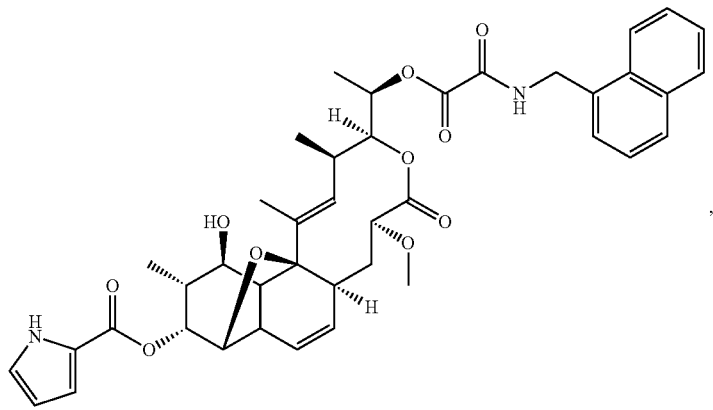
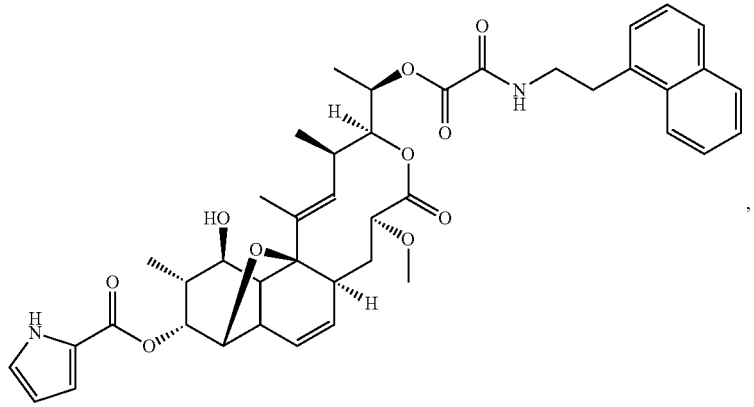

-continued
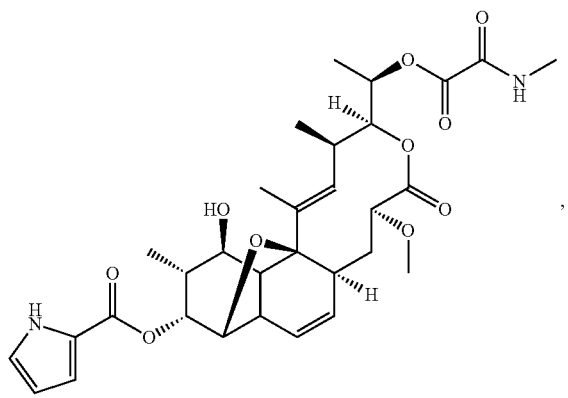
,
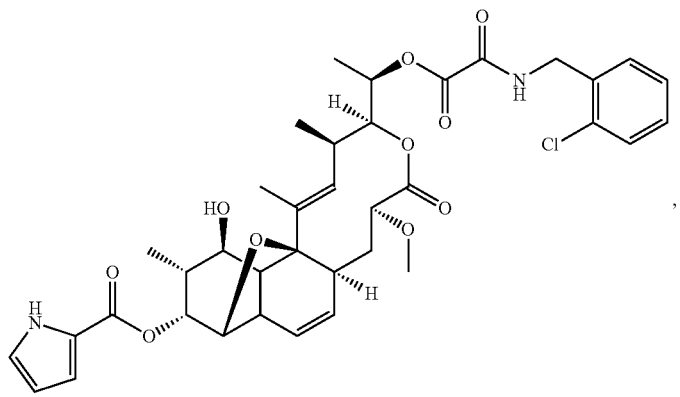
,
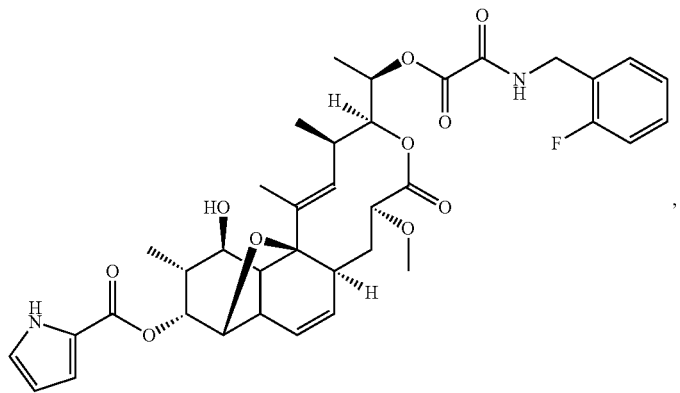
,
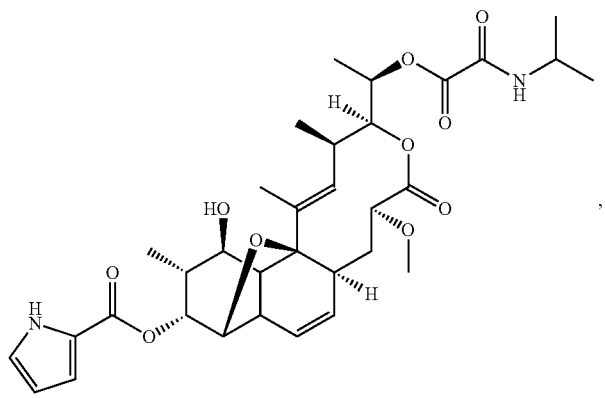
,

-continued
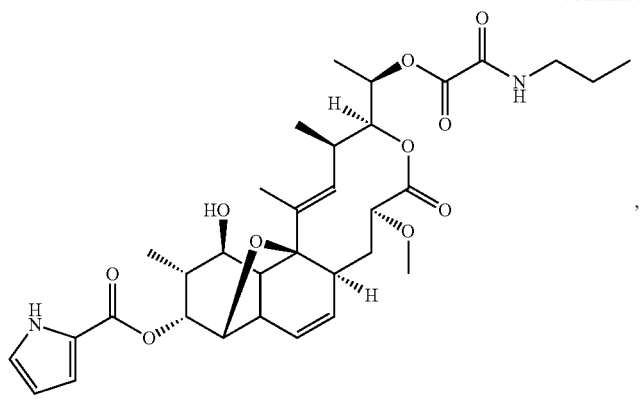
,
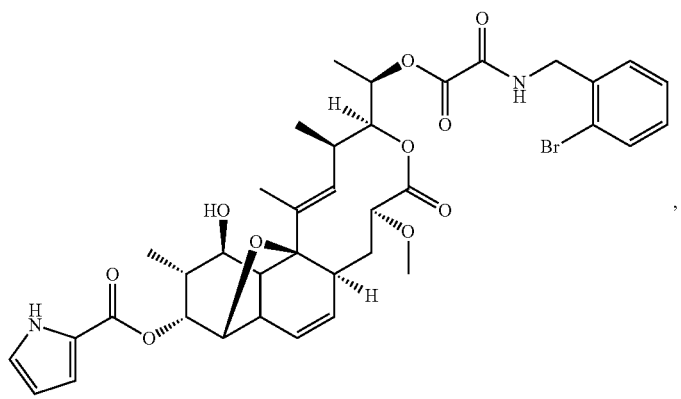
,
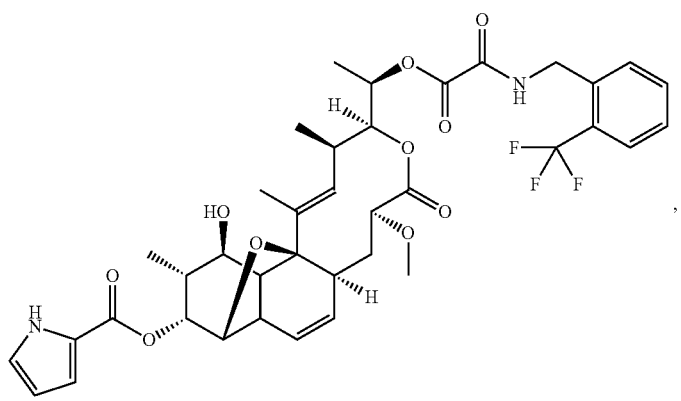
,
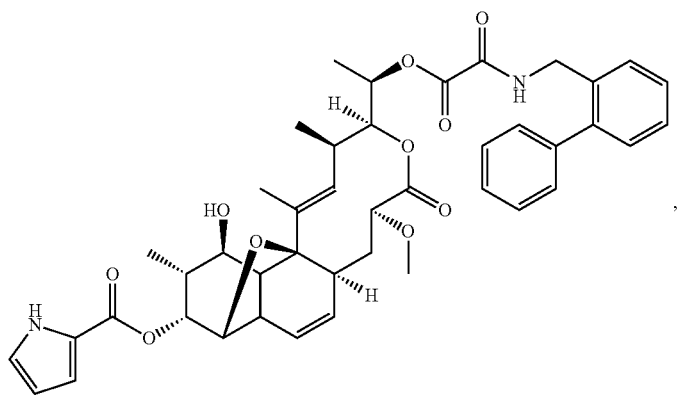
,

-continued
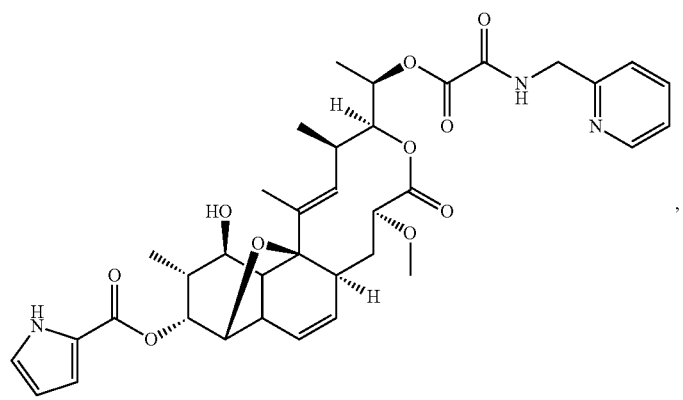
,
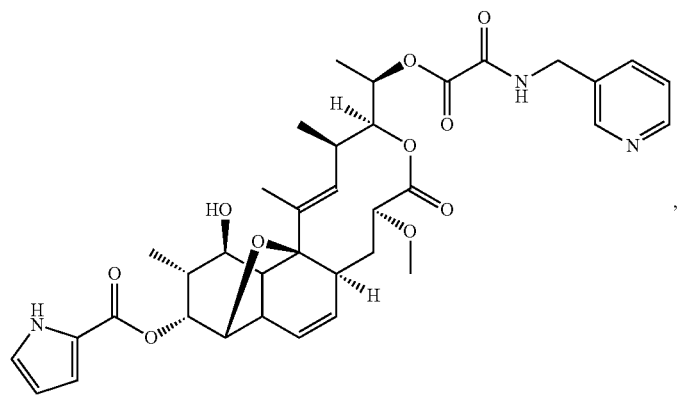
,
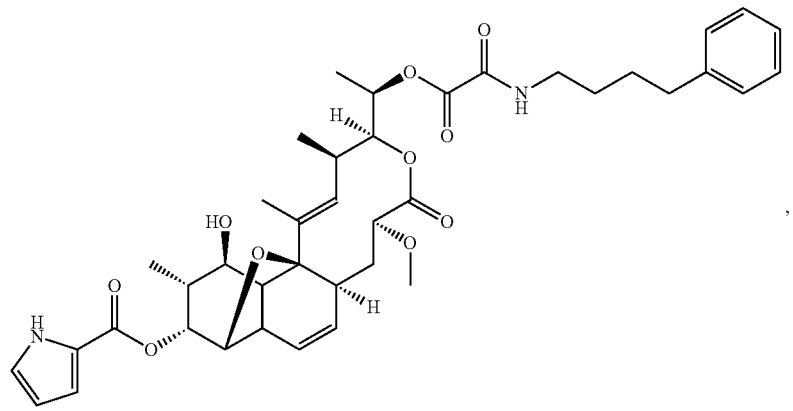
,
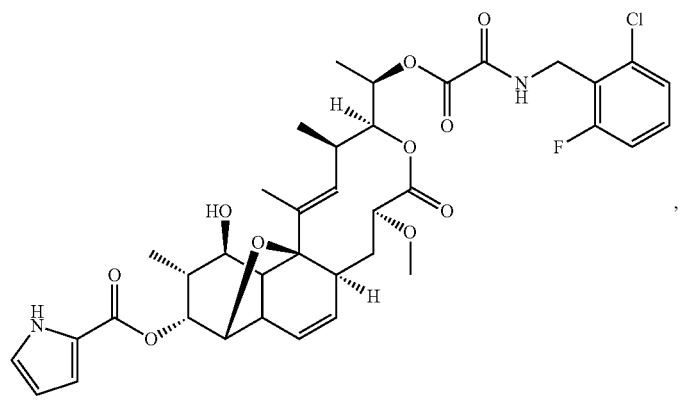
,

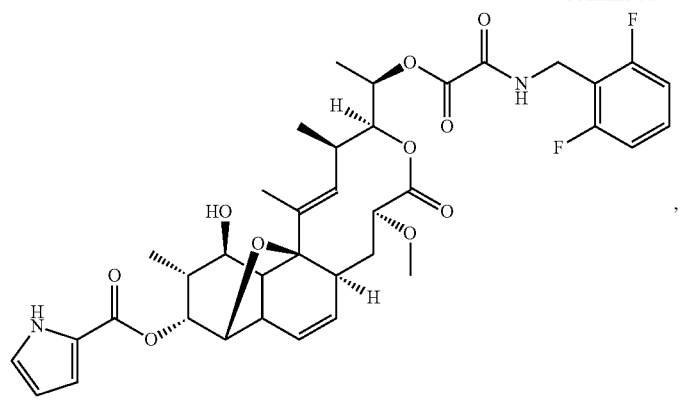
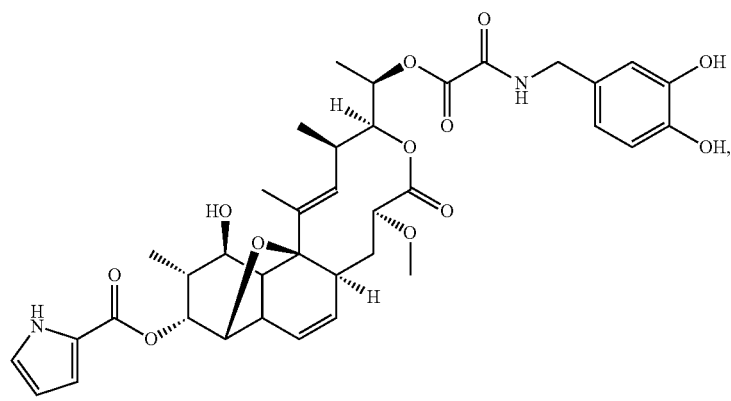
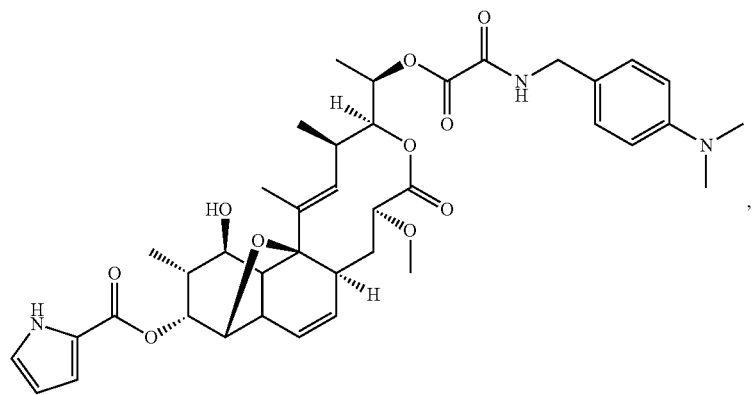
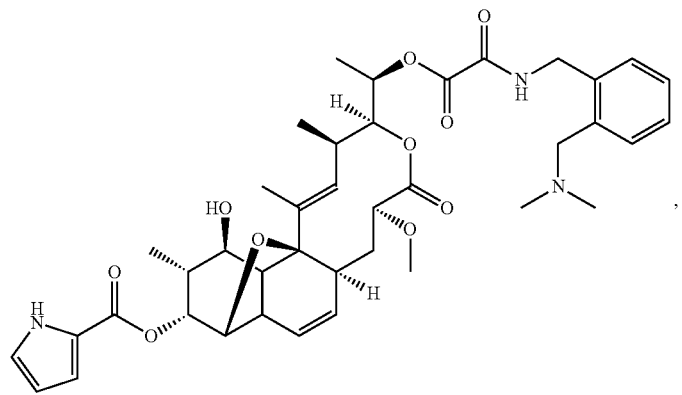

301
302
-continued
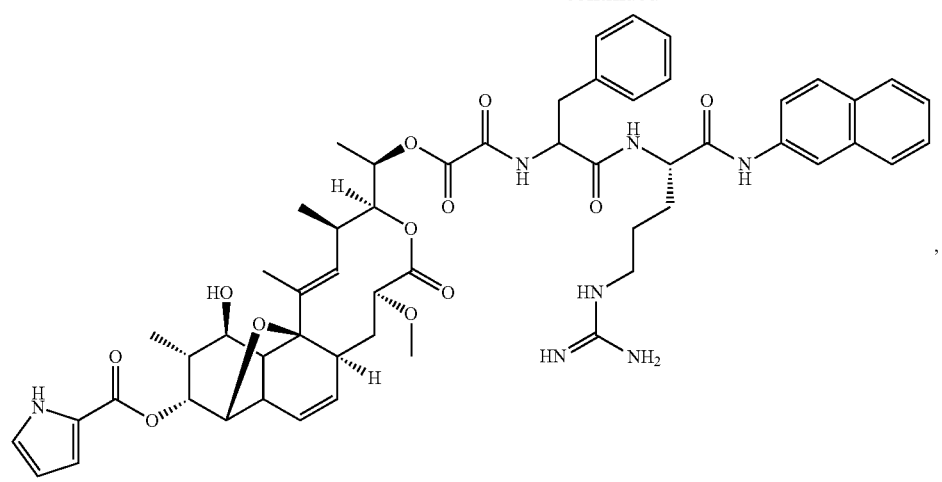
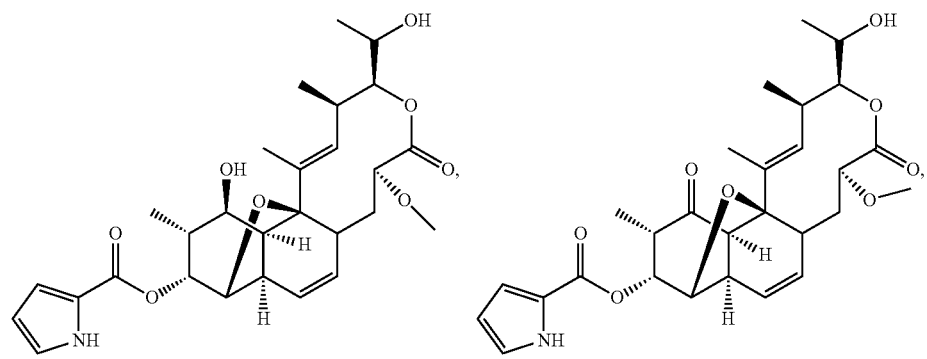
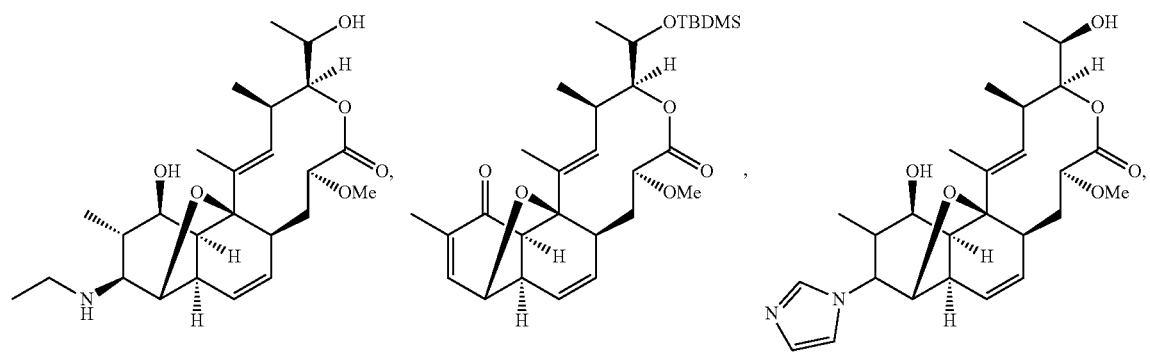
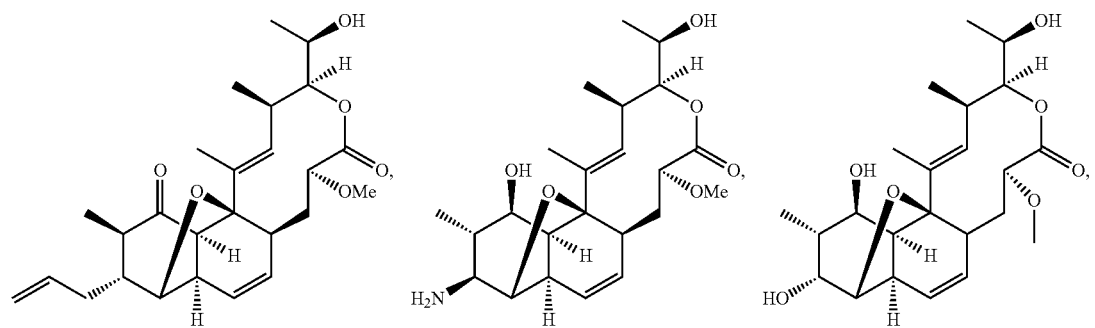

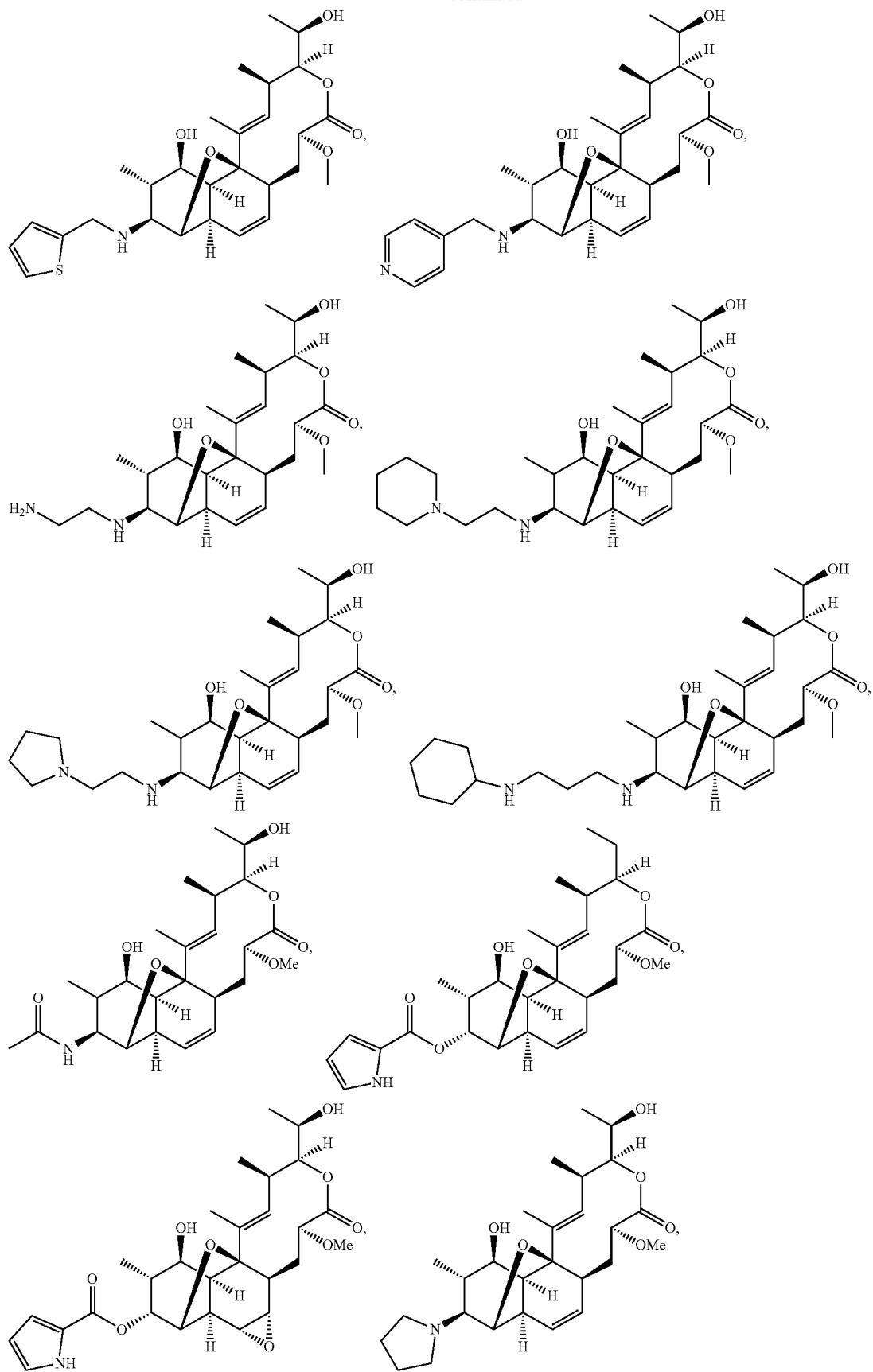

305
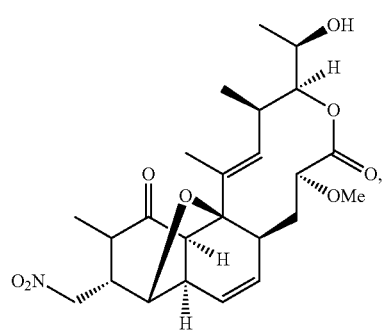
306
-continued
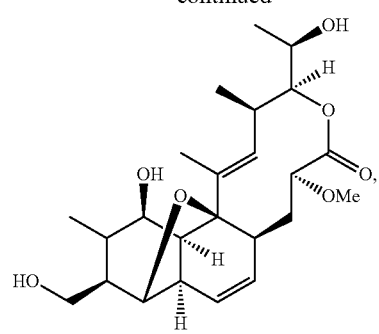
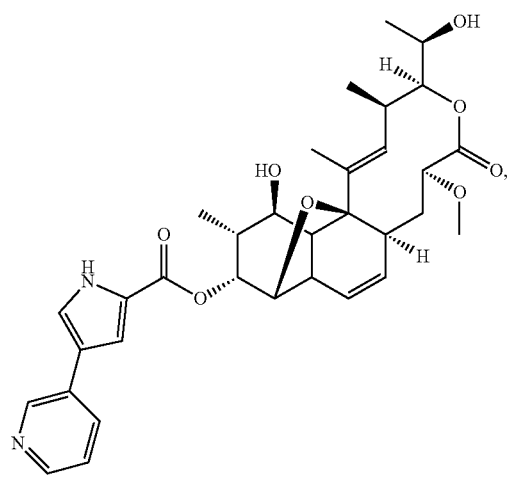
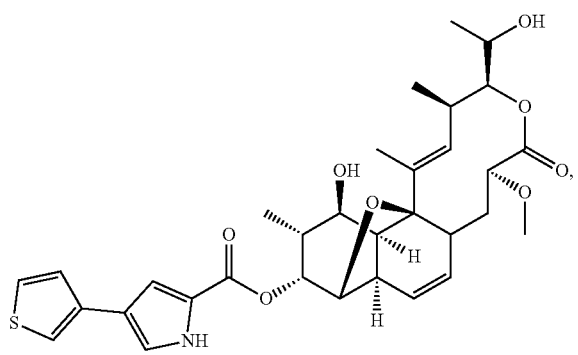
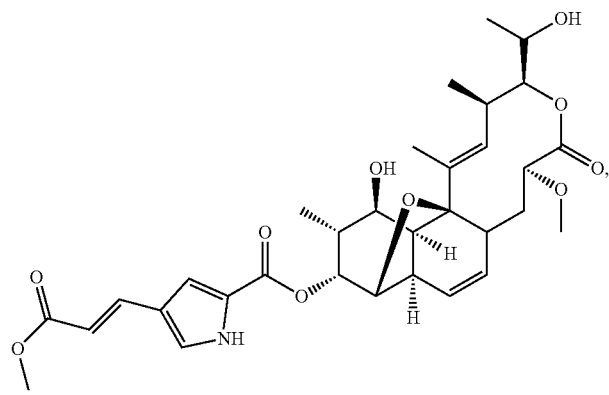
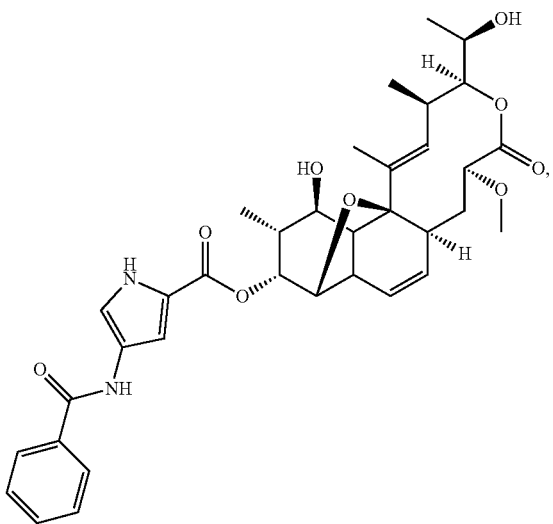

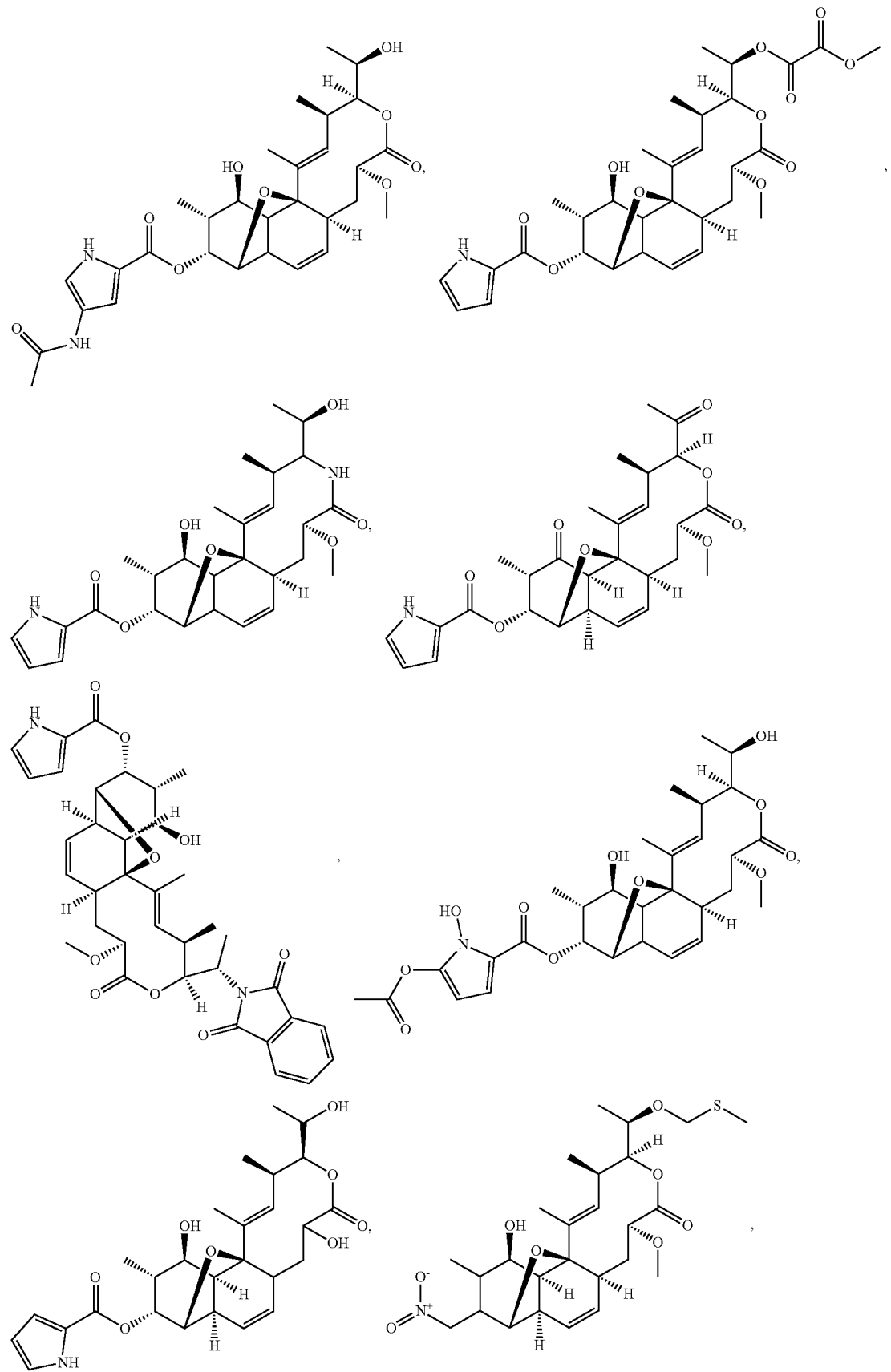

309
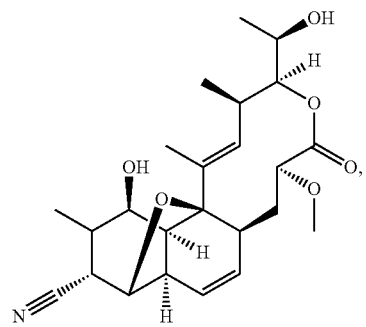
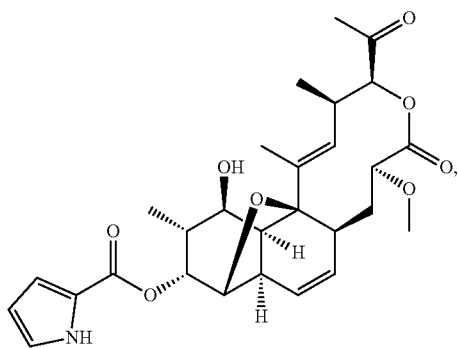
310
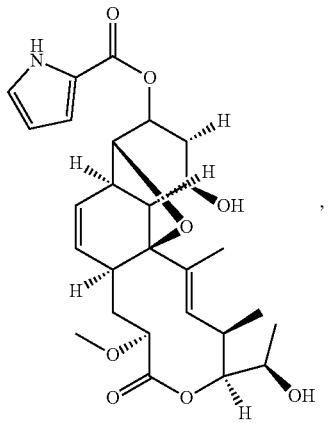
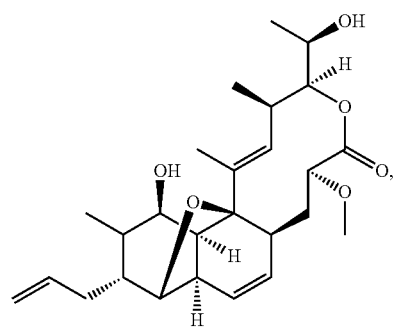
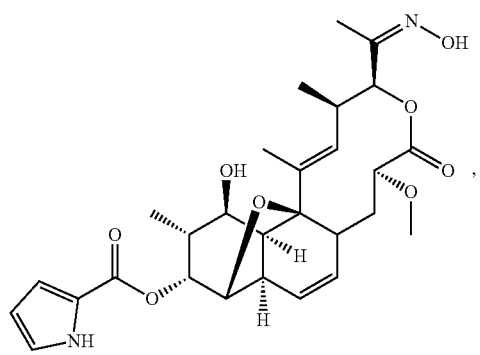
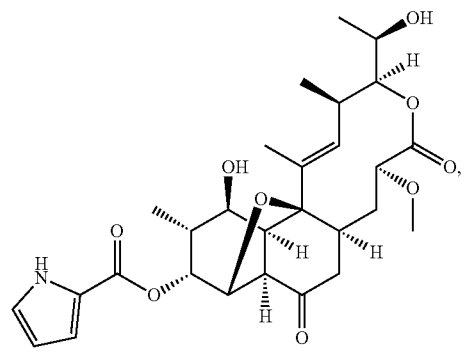
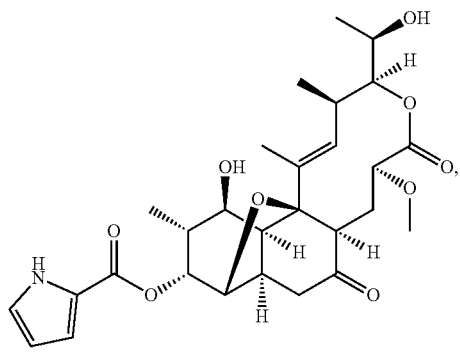
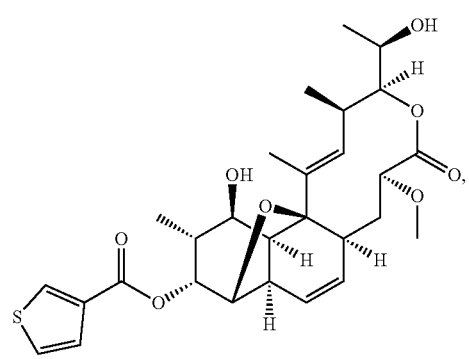
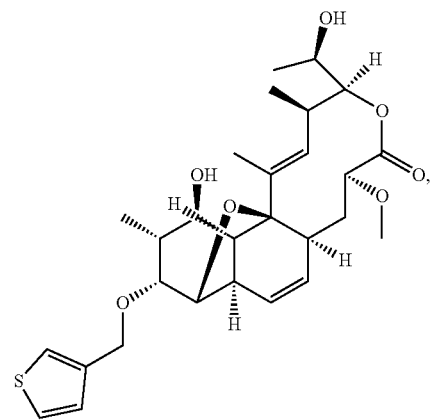

311
312
-continued
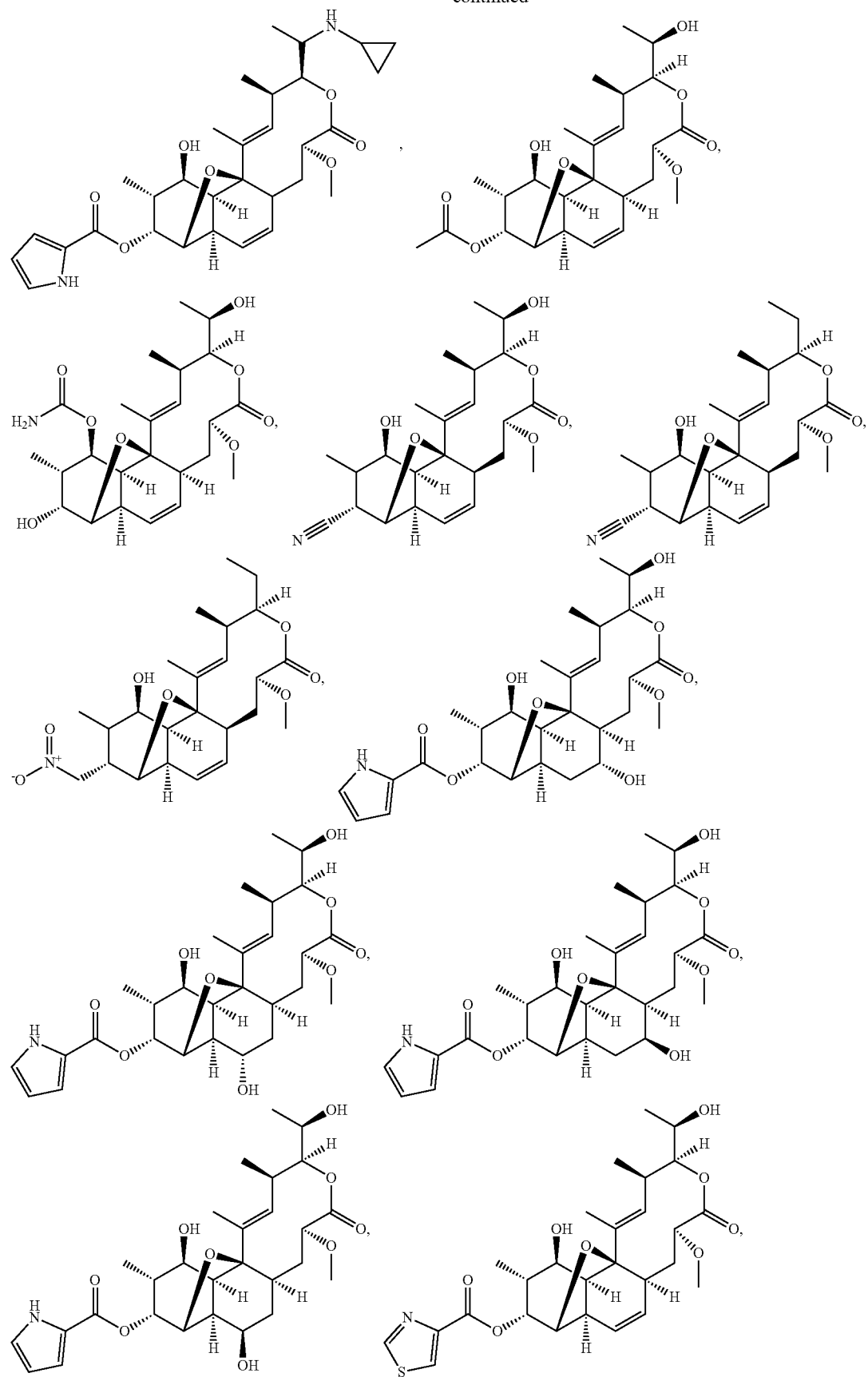

313
314
-continued
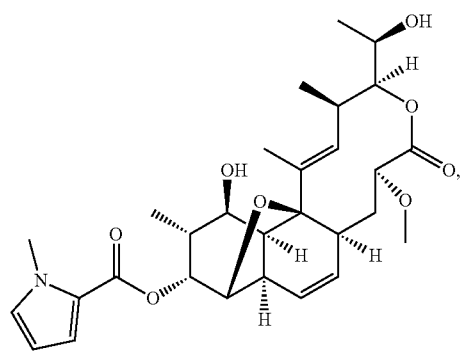
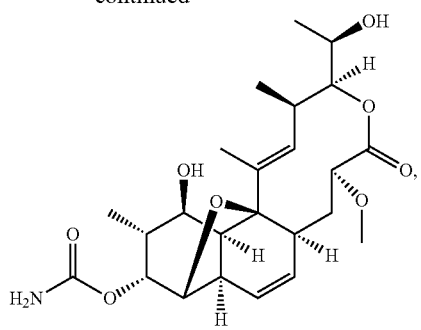
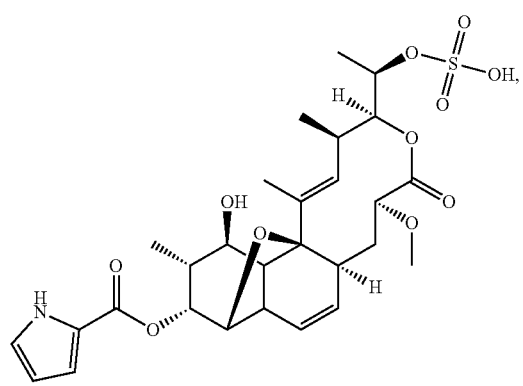
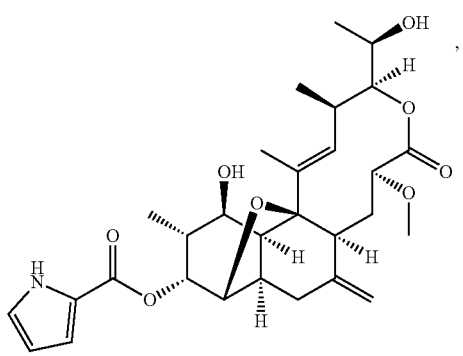
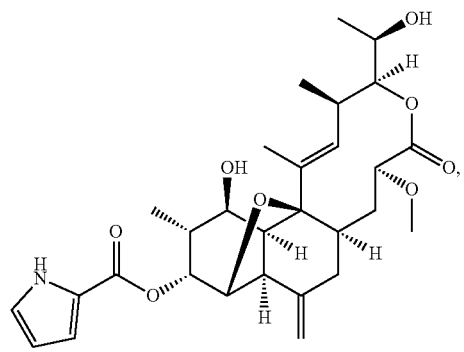
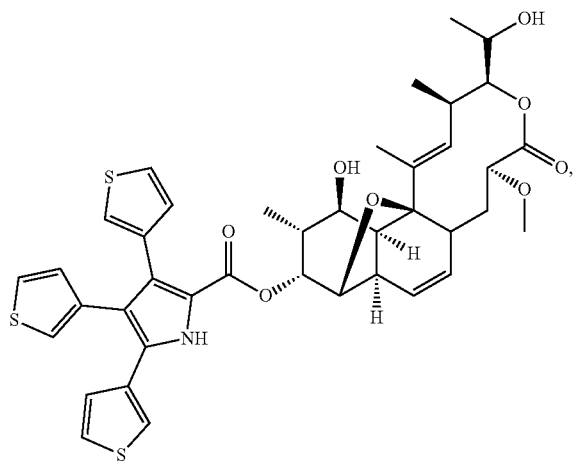
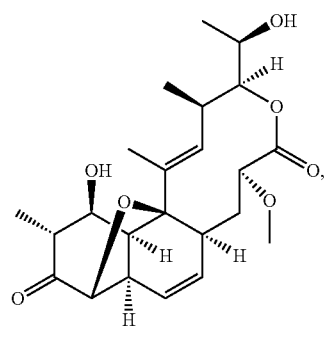
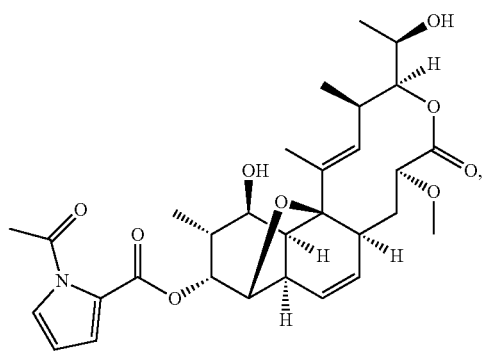

315
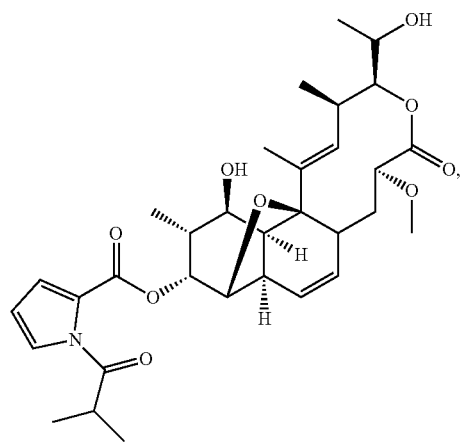
316
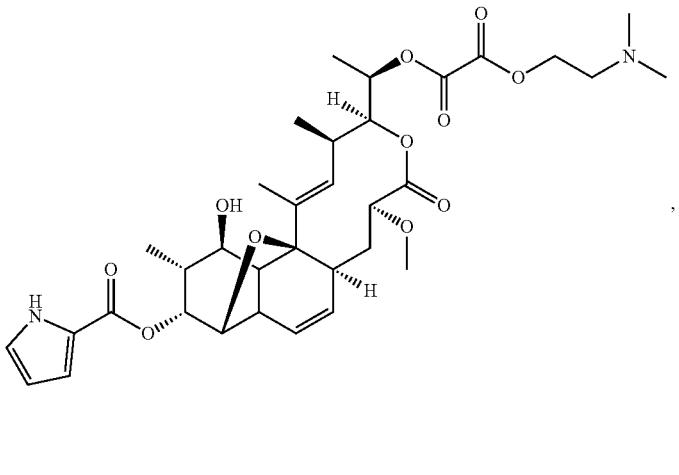
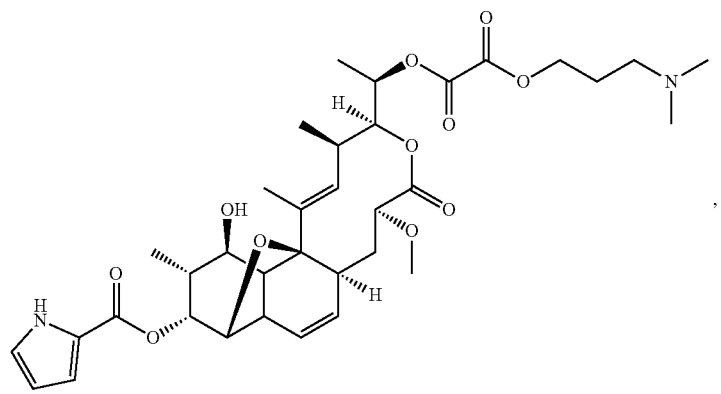
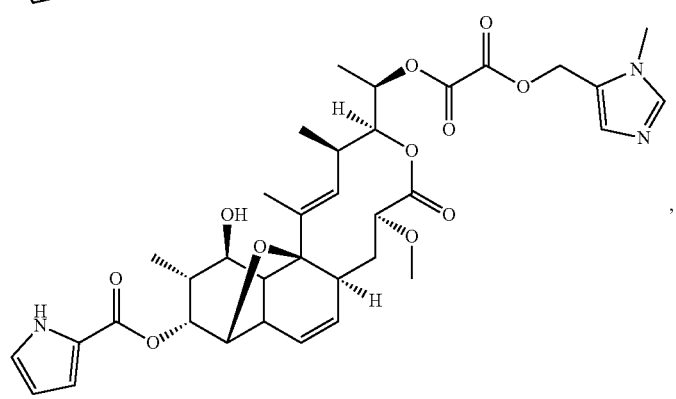
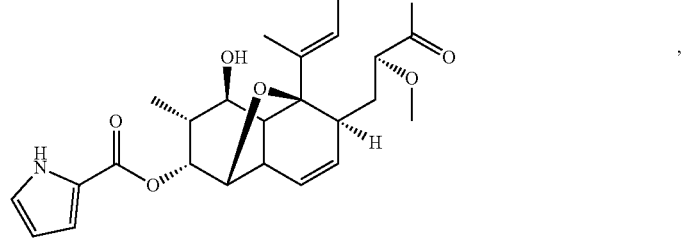

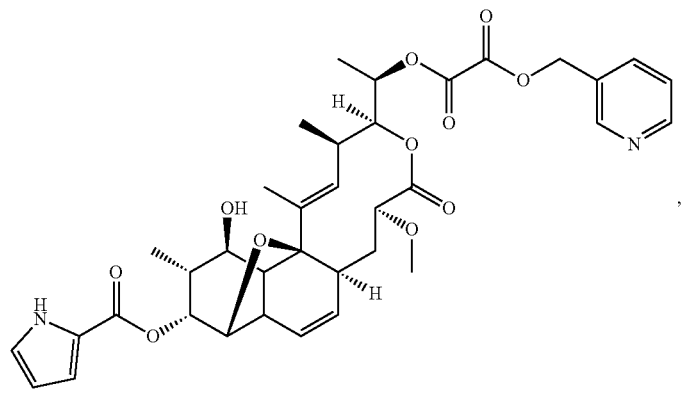
,
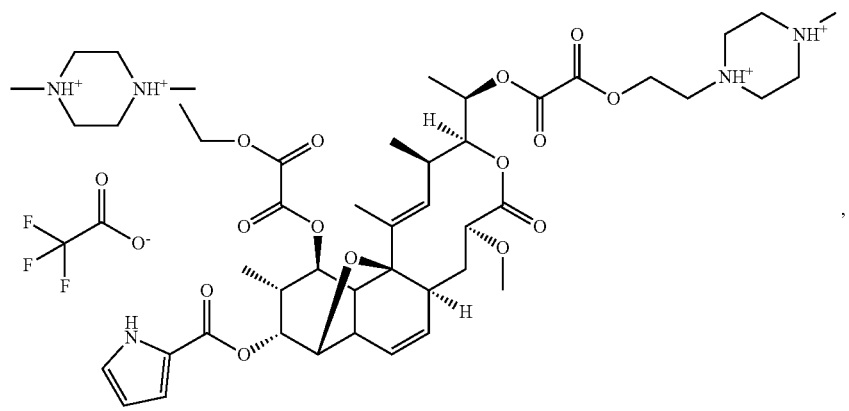
,
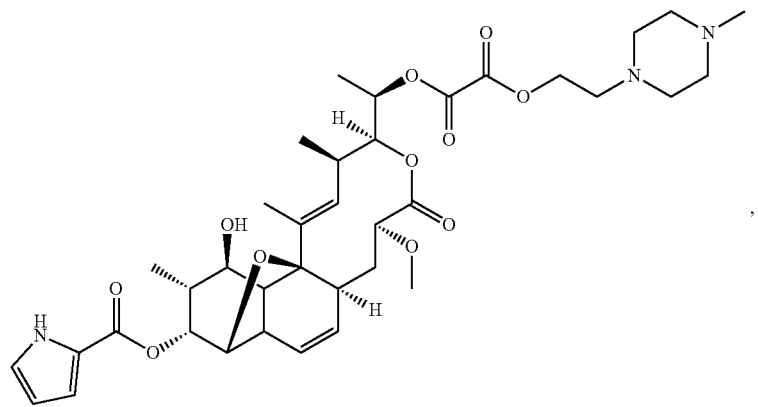
,
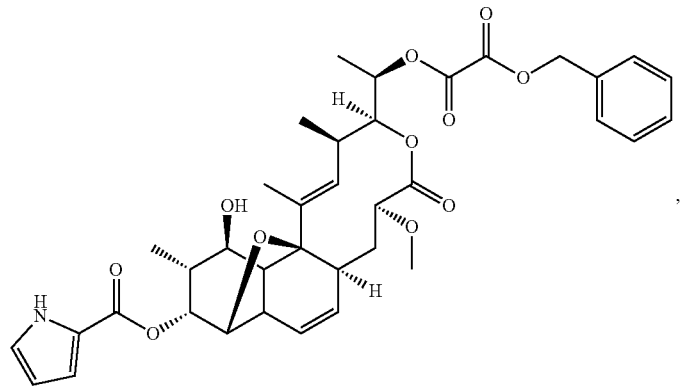
,

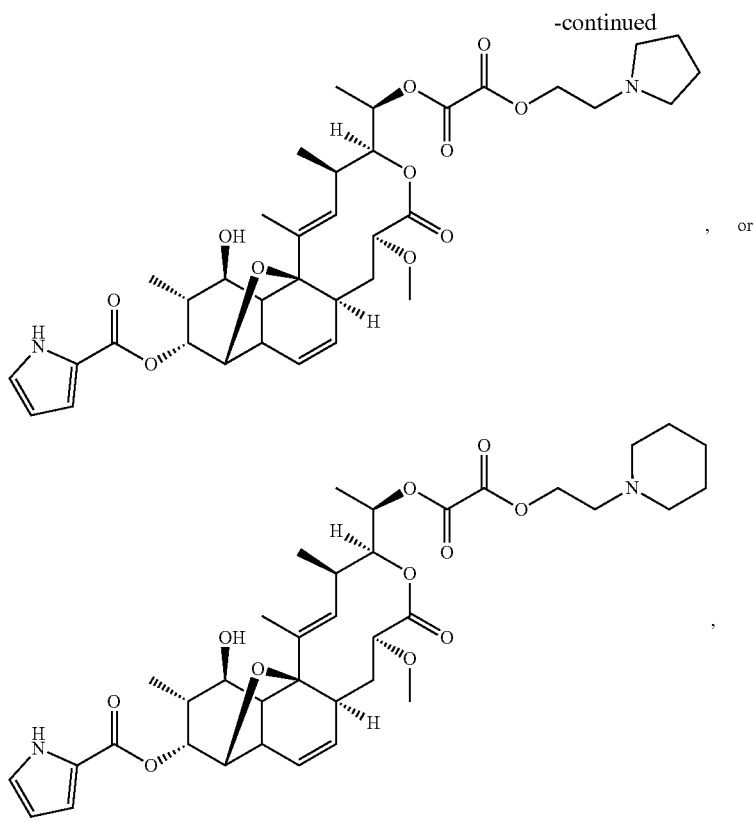

, or

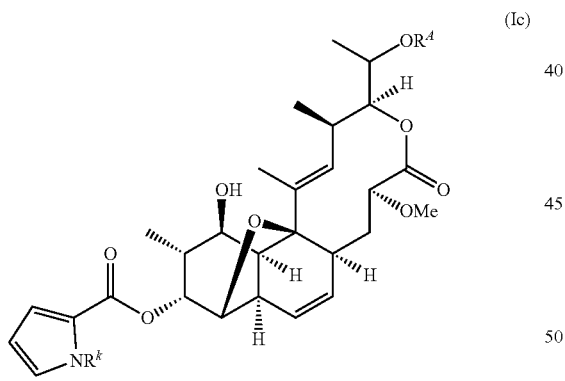

, or a pharmaceutically acceptable salt thereof.

11. The compound of claim 1, which has the formula (Ic)

or a pharmaceutically acceptable salt thereof,
wherein
$R^A$ is H, $C_{1-6}$alkyl, $C_{2-6}$alkenyl, $C_{3-6}$cycloalkyl, —C(=O)$C_{1-6}$alkyl, —C(=O)NHR$^g$, —C(=O)OR$^g$, —C(=O)C(=O)NHR$^g$, —C(=O)C(=O)OR$^g$, AryA, HetA, —C(=O)-AryA, or —C(=O)C(=O)-HetA;
wherein
  any alkyl is optionally substituted with one or two substituents independently selected from halogen, —NR$^x$R$^y$, N$^+$R$^x$R$^y$R$^z$, —SCH$_3$, AryA, and HetA; and the alkenyl is optionally substituted with AryA;
$R^b$ is $C_{1-6}$alkyl, $C_{3-6}$cycloalkyl, AryA, or HetA;
$R^g$ is H, $C_{1-8}$alkyl, $C_{3-6}$cycloalkyl, —C(=O)CCl$_3$, —NR$^x$R$^y$, —NHC(=O)NR$^x$R$^y$, —NHC(=O)OCH$_3$, or AryA, wherein the alkyl or cycloalkyl is optionally substituted by 1 to 3 —NR$^x$R$^y$ or —OH substituents or 1 substituent selected from $C_{1-6}$alkoxy, —COOH, —C(=O)NR$^x$R$^y$, —NR$^v$R$^w$, —S(O)$_2$NR$^x$R$^y$, AryA, and HetA;
$R^k$ is H, —CH$_3$, —C(=O)$C_{1-6}$alkyl, —CH=CHC(=O)OCH$_3$ or —OH;
$R^x$, $R^y$ and $R^z$ are independently H or $C_{1-6}$alkyl;
$R^v$ and $R^w$ are $C_{1-6}$alkyl substituted with 1 to 3 —OH substituents;
AryA is
  1) a 4- to 6-membered monocyclic aromatic ring with 0, 1, 2, or 3 ring atoms independently selected from N, N as a quaternary salt, O and S, optionally substituted with 1 to 3 substituents independently selected from halogen, $C_1$-$C_6$ alkyl, $C_1$-$C_6$ hydroxyalkyl, $C_1$-$C_6$ aminoalkyl, $C_1$-$C_6$ alkoxy, cyano, —NH$_2$, —OH, —CH=CHC(=O)O $C_{1-6}$alkyl, —C(=O)R$^b$, —C(=O)NHR$^b$, —C(=O)OR$^b$, —NHC(=O)$C_{1-6}$alkyl, —NHC(=O)-AryB, —NO$_2$, —OC(=O)$C_{1-6}$alkyl, —S(=O)$_2$R$^b$, —(CH2)$_{0-3}$AryB, and —(CH2)$_{0-3}$HetB; or
  2) a 7- to 11-membered bicyclic aromatic ring with 1, 2 or 3 N, or N as a quaternary salt, ring atoms optionally substituted with 1 to 3 substituents independently selected from $C_1$-$C_6$ alkyl, $C_1$-$C_6$ hydroxyalkyl, $C_1$-$C_6$ aminoalkyl, $C_1$-$C_6$ alkoxy, cyano, —NH$_2$, —OH, —C(=O)R$^b$, —C(=O)NHR$^b$, —C(=O)OR$^b$, —S(=O)$_2$R$^b$, —(CH2)$_{0-3}$AryB, and —(CH2)$_{0-3}$HetB;
HetA is
  1) a 4- to 6-membered saturated or monounsaturated monocyclic ring with 1 or 2 heteroatom ring atoms independently selected from N, N as a quaternary salt, O and S, optionally substituted with 1 or 2 substituents independently selected from halogen, $C_1$-$C_6$ alkyl, $C_1$-$C_6$ hydroxyalkyl, $C_1$-$C_6$ aminoalkyl, $C_1$-$C_6$ alkoxy, cyano, —$NH_2$, —OH, —$(CH_2)_{0-1}$C(=O)$NR^b$ —C(=O)$R^b$, —C(=O)$OR^b$, —S(=O)$_2$ $R^b$, —$(CH_2)_{0-3}$AryB, and —$(CH_2)_{0-3}$HetB; or 2) a 7- to 11-membered saturated or monounsaturated bicyclic ring with 1, 2, or 3 heteroatom ring atoms independently selected from N, N as a quaternary salt, O and S, optionally substituted with 1 or 2 substituents independently selected from halogen, $C_1$-$C_6$ alkyl, $C_1$-$C_6$ hydroxyalkyl, $C_1$-$C_6$ aminoalkyl, $C_1$-$C_6$ alkoxy, cyano, —$NH_2$, —OH, —$(CH_2)_{0-1}$—C(=O)$NR^b$, —C(=O)$R^b$, —C(=O)$OR^b$, —S(=O)$_2R^b$, —(CH2)$_{0-3}$AryB, and —(CH2)$_{0-3}$HetB;

AryB is
1) a 4- to 6-membered monocyclic aromatic ring with 0, 1, 2, or 3 ring atoms independently selected from N, N as a quaternary salt, O and S, optionally substituted with 1 to 3 substituents independently selected from halogen, $C_1$-$C_6$ alkyl, $C_1$-$C_6$ hydroxyalkyl, $C_1$-$C_6$ aminoalkyl, $C_1$-$C_6$ alkoxy, cyano, —$NH_2$, —OH, —$(CH_2)_{1-3}$—C(=O)$NR^xR^y$, —$(CH_2)_{1-3}SO_2NR^xR^y$, —CH=CHC(=O)$OC_{1-6}$alkyl, —NHC(=O)$C_{1-6}$alkyl, —$NO_2$, —$N^+(O)OH$, and —OC(=O)$C_{1-6}$alkyl; or 2) a 7- to 11-membered bicyclic aromatic ring with 1, 2 or 3 N, or N as a quaternary salt, ring atoms optionally substituted with 1 to 3 substituents independently selected from $C_1$-$C_6$ alkyl, $C_1$-$C_6$ hydroxyalkyl, $C_1$-$C_6$ aminoalkyl, $C_1$-$C_6$ alkoxy, cyano, —$NH_2$, and —OH;

HetB is
1) a 4- to 6-membered saturated or monounsaturated monocyclic ring with 1 or 2 heteroatom ring atoms independently selected from N, N as a quaternary salt, O and S, optionally substituted with 1 or 2 substituents independently selected from halogen, $C_1$-$C_6$ alkyl, $C_1$-$C_6$ hydroxyalkyl, $C_1$-$C_6$ aminoalkyl, $C_1$-$C_6$ alkoxy, cyano, —$NH_2$, and —OH; or 2) a 7- to 11-membered saturated or monounsaturated bicyclic ring with 1, 2, or 3 heteroatom ring atoms independently selected from N, N as a quaternary salt, O and S, optionally substituted with 1 or 2 substituents independently selected from halogen, $C_1$-$C_6$ alkyl, $C_1$-$C_6$ hydroxyalkyl, $C_1$-$C_6$ aminoalkyl, $C_1$-$C_6$ alkoxy, cyano, —$NH_2$, and —OH.

12. The compound of claim 11, or a pharmaceutically acceptable salt thereof, wherein $R^k$ is H or —C(=O)$C_{1-6}$alkyl.

13. A pharmaceutical composition which comprises a compound of claim 1, or a pharmaceutically acceptable salt thereof, and a pharmaceutically acceptable carrier.

14. A method for inhibiting bacterial DnaE in a subject having a bacterial infection which comprises administering to the subject (i) an effective amount of a compound of claim 1, or a pharmaceutically acceptable salt thereof, or (ii) a pharmaceutical composition according to claim 13.

15. A method for treating a bacterial infection which comprises administering to a subject in need of such treatment (i) a therapeutically effective amount of a compound of claim 1, or a pharmaceutically acceptable salt thereof, or (ii) a pharmaceutical composition according to claim 13.

* * * * *